(12) United States Patent
Beigelman et al.

(10) Patent No.: US 8,772,474 B2
(45) Date of Patent: Jul. 8, 2014

(54) CYCLIC NUCLEOTIDE ANALOGS

(75) Inventors: Leonid Beigelman, San Mateo, CA (US); David Bernard Smith, San Mateo, CA (US); Jerome Deval, Pacifica, CA (US); Vivek Kumar Rajwanshi, Cupertino, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 34 days.

(21) Appl. No.: 13/332,068

(22) Filed: Dec. 20, 2011

(65) Prior Publication Data

US 2012/0165286 A1 Jun. 28, 2012

Related U.S. Application Data

(60) Provisional application No. 61/426,471, filed on Dec. 22, 2010, provisional application No. 61/536,445, filed on Sep. 19, 2011.

(51) Int. Cl.
| | |
|---|---|
| C07H 19/00 | (2006.01) |
| C07H 19/20 | (2006.01) |
| C07H 19/04 | (2006.01) |
| A01N 43/04 | (2006.01) |
| A61K 31/70 | (2006.01) |

(52) U.S. Cl.
USPC .......... 536/26.11; 536/26.12; 536/26.13; 536/26.14; 514/47; 514/51

(58) Field of Classification Search
None
See application file for complete search history.

(56) References Cited

U.S. PATENT DOCUMENTS

| | | | |
|---|---|---|---|
| 4,093,714 | A | 6/1978 | Tolman et al. |
| 5,432,272 | A | 7/1995 | Benner |
| 5,625,056 | A | 4/1997 | Genieser et al. |
| 7,125,855 | B2 | 10/2006 | Bhat et al. |
| 2006/0014689 | A1 | 1/2006 | Vesely |
| 2010/0249068 | A1 | 9/2010 | Beigelman et al. |
| 2010/0297079 | A1 | 11/2010 | Almond et al. |
| 2012/0070411 | A1 | 3/2012 | Beigelman et al. |
| 2012/0070415 | A1 | 3/2012 | Beigelman et al. |
| 2012/0071434 | A1 | 3/2012 | Smith et al. |
| 2013/0164261 | A1 | 6/2013 | Wang et al. |

FOREIGN PATENT DOCUMENTS

| | | |
|---|---|---|
| DE | 4217679 | 12/1993 |
| JP | 2006-248949 | 9/2006 |
| PL | 144 471 | 4/1985 |
| WO | WO 88/03147 | 5/1988 |
| WO | WO 95/06474 | 3/1995 |
| WO | WO 03/104250 | 12/2003 |
| WO | WO 2005/123755 | 12/2005 |
| WO | WO 2007/006544 | 1/2007 |
| WO | WO 2007/027248 | 3/2007 |
| WO | WO 2007/149554 | 12/2007 |
| WO | WO 2008/032103 | 3/2008 |
| WO | WO 2010/020786 | 2/2010 |
| WO | WO 2010/048552 | 4/2010 |
| WO | WO 2010/108140 | 9/2010 |

OTHER PUBLICATIONS

Cancer Vaccines: Pursuing the promise, The Women's Cancers Program at Dana-Farber, internet article, Aug. 16, 2006.*
International Search Report and Written Opinion dated Mar. 21, 2012 for International Application No. PCT/US2011/066249, filed Dec. 20, 2011.
Bajwa et al., "Thymidine nucleoside 3',5'-cyclic phosphoramidites and phosphites. Configuration at phosphorus in trivalent and pentavalent cyclic nucleotides by phosphorus-31 and carbon 13-NMR" *Tet. Lett.* (1978) 5:421-424.
Baraniak, J., "Deoxyribonucleoside cyclic 3',5'-phosphorofluoridates" *Phosphorus, Sulfur and Silicon* (1996) 111:80.
Baraniak et al., "Synthesis of adenosine cyclic 3',5'-phosphorofluoridate (cAMP-F)" *Tet. Lett.* (1995) 36(44):8119-8122.
Baraniak et al., "Ribonucleoside cyclic 3',5'-phosphoramidates: synthesis, stereochemistry, and conversion into ribonucleoside cyclic 3',5'-phosphorothioates and —[$^{18}$O] phosphates" *J. Chem. Soc. Perkin Trans.* 1 (1987) 8:1645-1656, Uploaded in 2 parts.
Boteloho et al., "Inhibition of cAMP-dependent protein kinase by adenosine cyclic 3',5'-phosphorodithioate, a second cAMP antagonist" *J. Bio. Chem.* (Apr. 15, 1988) 263(11):5301-5305.
Carey, Francis, Organic Chemistry, 2nd ed., McGraw Hill, Inc., New York (1992), pp. 328-331.
Cullis, P., "The stereospecific conversion of P-chiral phosphorothioates into[$^{18}$O]*-phosphates" *Tet. Lett.* (1983) 24(50):5677-5680.
De Vroom et al., "Synthesis of ribonucleoside 3,'5'-cyclic phosphorothioate using a modified hydroxybenzotriazole phsophotriester approach" *Recueil Trav. Chim. Pays-Bas* (1987) 106(11):577-580.
Feldwisch et al., "Purification and characterization of a cAMP-binding protein of *Volvox carteri* f. *nagariensis* Iyengar" *Eur. J. Biochem.* (1995) 229(2):480-489.
Gopalakrishnan et al. "A virtual screen approach for thymidine monophosphate kinase inhibitors as antitubercular agents based on docking and pharmacophore models" *J. Chem. Inf. Model.* (2005) 45(4):1101-1008.
Greene, et al., Protective Groups in Organic Synthesis, 3. Ed., John Wiley & Sons, (1999) Cover & Contents pages. Hayakawa et al., "A strategy for the stereoselective preparation of thymidine phosphorothioates with the ® or the (S) configuration of the stereogenic phosphorus atom and their application to the synthesis of oligodeoxyribonucleotides with stereochemically pure phosphate/phosphorothioate chimeric backbone" *Eur. J. Org. Chem.* (2006)17:3834-3844.

(Continued)

*Primary Examiner* — Layla Bland
(74) *Attorney, Agent, or Firm* — Knobbe Martens Olson & Bear LLP

(57) ABSTRACT

Disclosed herein are cyclic nucleotide analogs, methods of synthesizing cyclic nucleotide analogs and methods of treating diseases and/or conditions such as viral infections, cancer, and/or parasitic diseases with cyclic nucleotide analogs.

43 Claims, 36 Drawing Sheets

(56) References Cited

OTHER PUBLICATIONS

Herbert et al., "Structural features of the noncatalytic cGMP binding sites of frog photoreceptor phosphodiesterase using cGMP analogs" *J. Bio. Chem.* (1998) 273(10):5557-5565.

Hung et al., "A new nonhydrolysis reactive cGMP analogue, (Rp)-guanosine-3',5'-cyclic-S-(4-bromo-2,3-dioxobuyl)monophorothoate, which targets the cGMP binding site of human platelet PDE3A" *Bioorg. Chem.* (2008) 36(3):141-147.

Hung et al., "New insights from the structure-function analysis of the catalytic region of human platelet phosphodiesterase 3A: a role for the unique 44 amino acid insert" *J. Bio. Chem.* (Sep. 29, 2006) 281(39):29236-29244.

Hung et al., "A nonhydrolyzable reactive cAMP analogue, (Sp)-8-[(4-bromo-2,3-dioxobutyl)thio]adenosine 3',5'—cyclic S-(methyl)monophosphorothioate, irreversibly inactivates human platelet cGMP-inhibited cAMP phosphodiesterase at micromolar concentrations" *Biochemistry* (2002) 41(9):2962-2969.

Hung et al., "A new nonhydrolyzable reactive cAMP analog, (Sp)-Adenosine-3',5'-cyclic-S-(4-bromo-2,3-dioxobuyl)monophosphorothioate irreversibly inactivates human platelets cGMP-inhibited cAMP phosphodiesterase" *Bioorg. Chem.* (2002) 30(1):16-31.

"IUPAC-IUB Commission on Biochemical Nomenclature Abbreviated Nomenclature of Synthetic Polypeptides (Polymerized Amino Acids)* Revised Recommendations (1971)" Biochemistry. (1972) 11(5):942-944.

Lesiak et al., "A new approach to syntheses of organic phosphoroselenoates and phosphorodiselenoates. Proof of absolute configuration assignment in diastereomers of cTMPS [thymidine cyclic 3',5'-phosphorothioates]"*Polish J. of Chem.* (1979) 53(10):2041-2050.

Lesnikowski et al., "A simple procedure for synthesis of diastereoisomers of thymidine cyclic 3',5'-phosphate derivatives" Nucleic Acids Symposium Series No. 18, Seventh Symposium on the Chemistry of Nucleic Acid Components (Aug. 20-Sep. 5, 1987) :273-276.

Lesnikowski et al., "Some aspects of the electron impact induced fragmentation of diastereoisomeric thymidine cyclic 3',5'-phsophoranilidothioates" *Organic Mass Spectrometry* (1980) 15(9):454-455.

Lin et al., "Novel 3',5'-cyclic nucleotide analog: Adenosine 3',5'-cyclic Boranomonophosphate" *Org. Lett.* (2001) 3(6):795-797.

Mcomie, J. F. W., Protective Groups in Organic Chemistry, Plenum Press, 1973. Cover & Contents pages only.

McMurry, John, Organic Chemistry, 5th ed., Brooks/Cole, Pacific Grove, CA. (2000), Chapter 11.5, pp. 398 and 408.

Misiura et al., "Synthesis, chemical and enzymatic reactivity, and toxicity of dithymidylyl-3',5'-phosphorofluridate and —phosphorothiofluoridate" *Bioorg. Med. Chem.* (2001) 9(6):1525-1532.

Scott et al., "Mapping ligand interactions with the hyperpolarization activated cyclic nucleotide modulated (HCN) ion channel binding domain using a soluble construct" *Biochemistry* (2007) 46(33):9417-9431.

Sopchik et al., "Facile preparation of the individual diastereoisomers of thymidine 3',5'-cyclic phosphorothioate (cTMPS)" *Tet. Lett.* (1981) 22:307-310.

Streitwieser et al., Introduction to Organic Chemistry, 2nd ed., Macmillan Publishing Co. Inc., New York, NY (1981) pp. 169-171.

Sun et al., "Effects of cGMP, cAMP and two other cAMP derivatives on the transcription system of isolated rat liver nuclei" *Chinese Biochemical Journal* (Oct. 1987) 3(5):455-461, √-abs.

Tian et al., "Synthesis of 8-chloroadenosine 3',5'-cyclophosphotriesters and phosphoramidates" *Progress in Natural Science* (Dec. 1994) 4(6):726-731.

Wu et al., "Cyclophosphorylation of adenosine" *Acta Chemica Sinica* (1986) 44(6):635-638, √abs.

Venkatachalam et al. *European Journal of Medicinal Chemistry* (2004) 39:665-683.

* cited by examiner

Figure 1A: HCV Protease Inhibitors

| # | Name | Structure |
|---|---|---|
| 1001 | Telaprevir VX-950 | 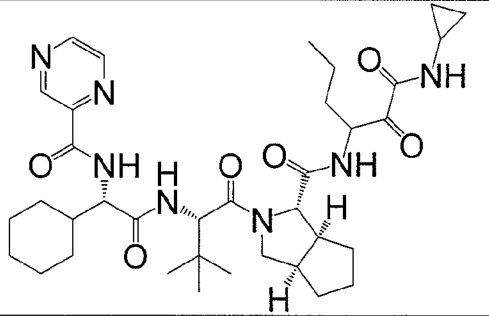 |
| 1002 | MK-5172 | 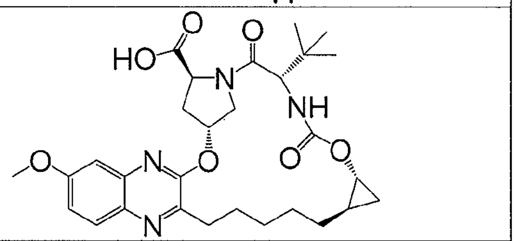 |
| 1003 | ABT-450 | |
| 1004 | BILN-2061 | 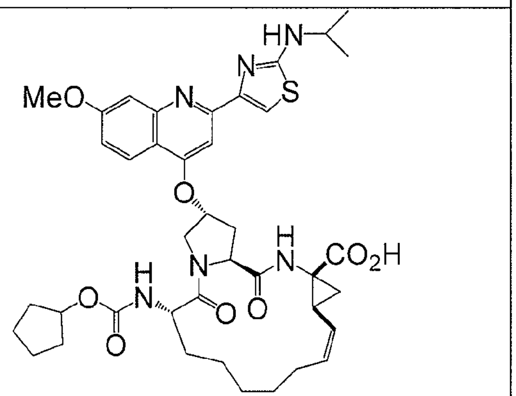 |
| 1005 | BI-201335 | |
| 1006 | BMS-650032 | |
| 1007 | Boceprevir SCH 503034 | |

Figure 1B: HCV Protease Inhibitors

| # | Name | Structure |
|---|---|---|
| 1008 | GS-9256 | |
| 1009 | GS-9451 | |
| 1010 | IDX-320 | |
| 1011 | ACH-1625 | |
| 1012 | ACH-2684 | |
| 1013 | TMC-435<br>TMC-435350 | *(structure shown)* |
| 1014 | Danoprevir<br>ITMN-191<br>RG7227<br>RO5190591 | *(structure shown)* |

Figure 2: HCV Polymerase Inhibitors – Nucleosides, Nucleotides and Analogs Thereof

| # | Name | Structure |
|---|------|-----------|
| 2001 | RG7128 | 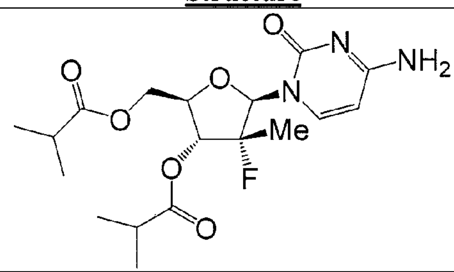 |
| 2002 | PSI-7851 | 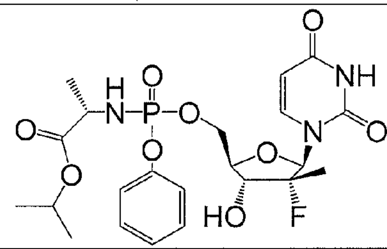 |
| 2003 | PSI-7977 | 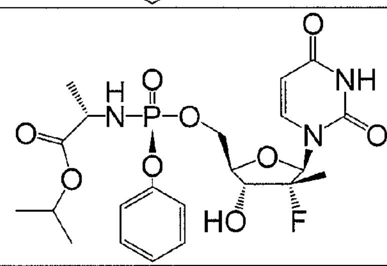 |
| 2004 | INX-189 | 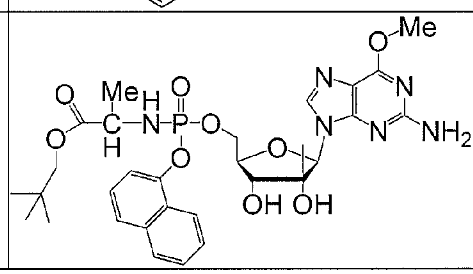 |
| 2005 | PSI-352938 | 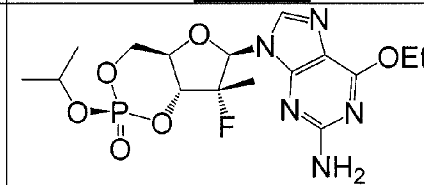 |
| 2006 | 4'-azidouridine and its prodrugs | 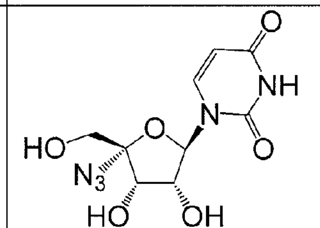 |
| 2007 | PSI-661 | |
| 2008 | GS-6620 | |
| 2009 | IDX-184 | 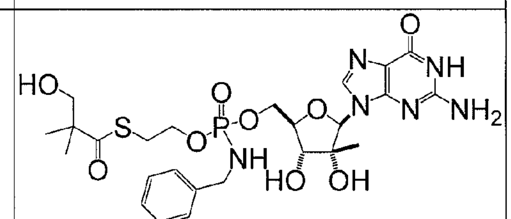 |
| 2010 | TMC649128 | |

Figure 3: HCV Polymerase Inhibitors – Non-Nucleosides

| # | Name | Structure |
|---|---|---|
| 3001 | ABT-333 | |
| 3002 | ANA-598 | |
| 3003 | VX-222<br>S1480<br>VCH-222 | |
| 3004 | HCV-796 | 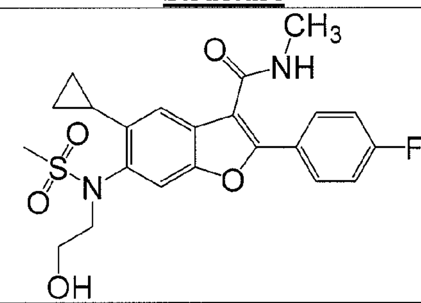 |
| 3005 | BI-207127 | |
| 3006 | GS-9190 | 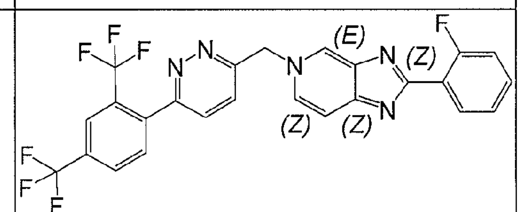 |
| 3007 | Filibuvir<br>PF-00868554 | 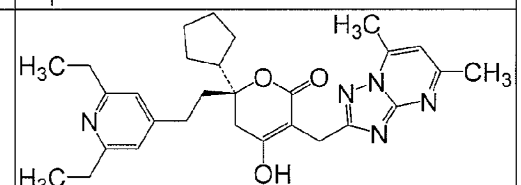 |
| 3008 | VX-497 | 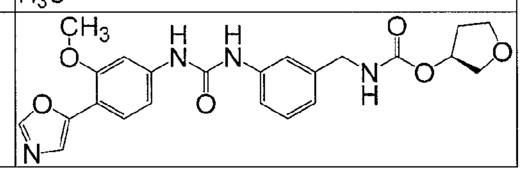 |

Figure 4: NS5A Inhibitors

| # | Name | Structure |
|---|---|---|
| 4001 | BMS-790052 S1482 | (structure shown) |
| 4002 | PPI-461 | |
| 4003 | ACH-2928 | |
| 4004 | GS-5885 | |
| 4005 | BMS-824393 | |

Figure 5: Other Antivirals

| # | Name |
|---|---|
| 5001 | Debio-025 |
| 5002 | MIR-122 |

Figure 6A: Compounds of Formula (CC)

Figure 6B: Compounds of Formula (CC)
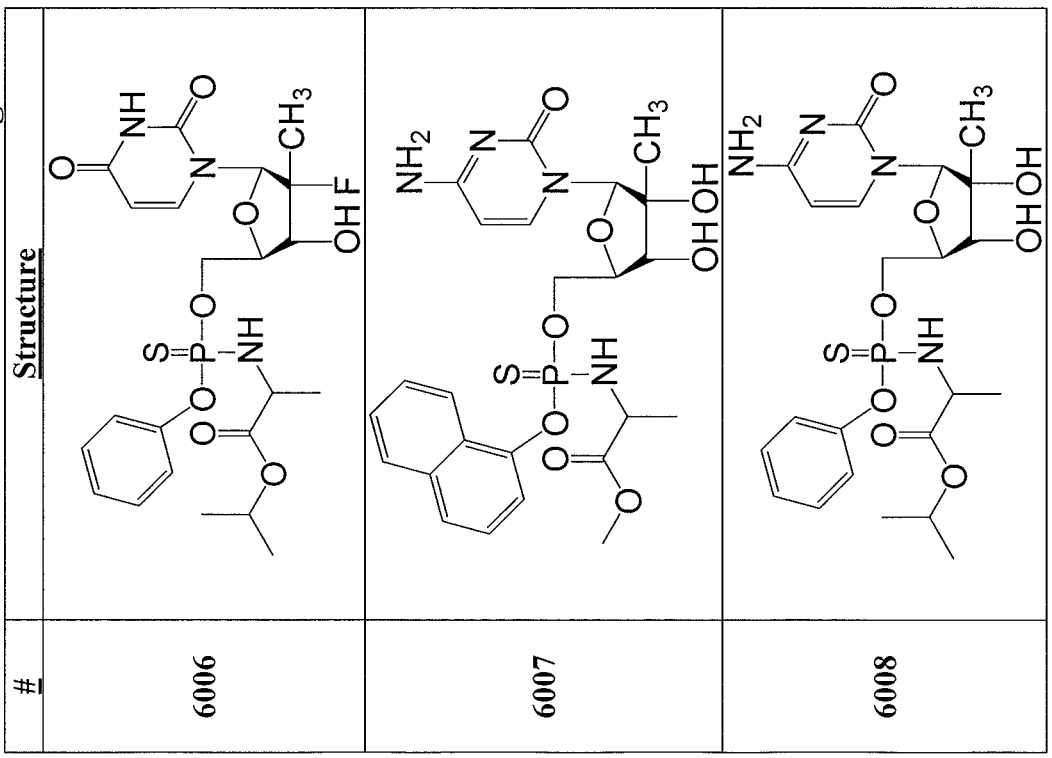
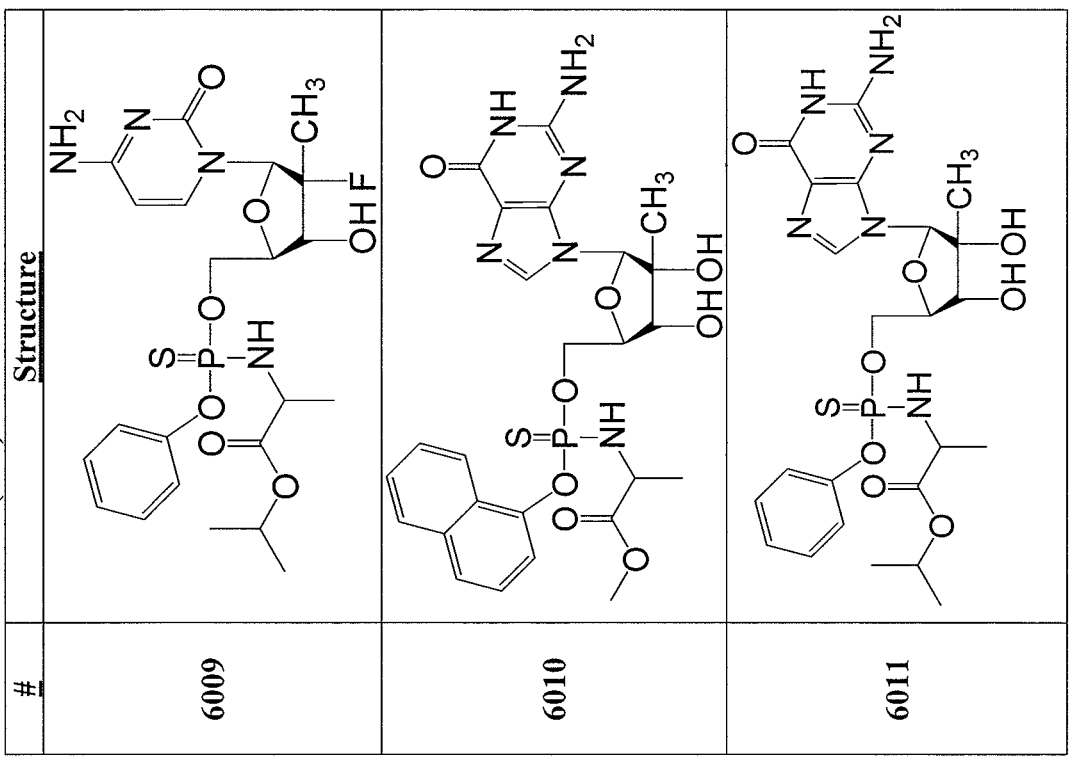

Figure 6C: Compounds of Formula (CC)
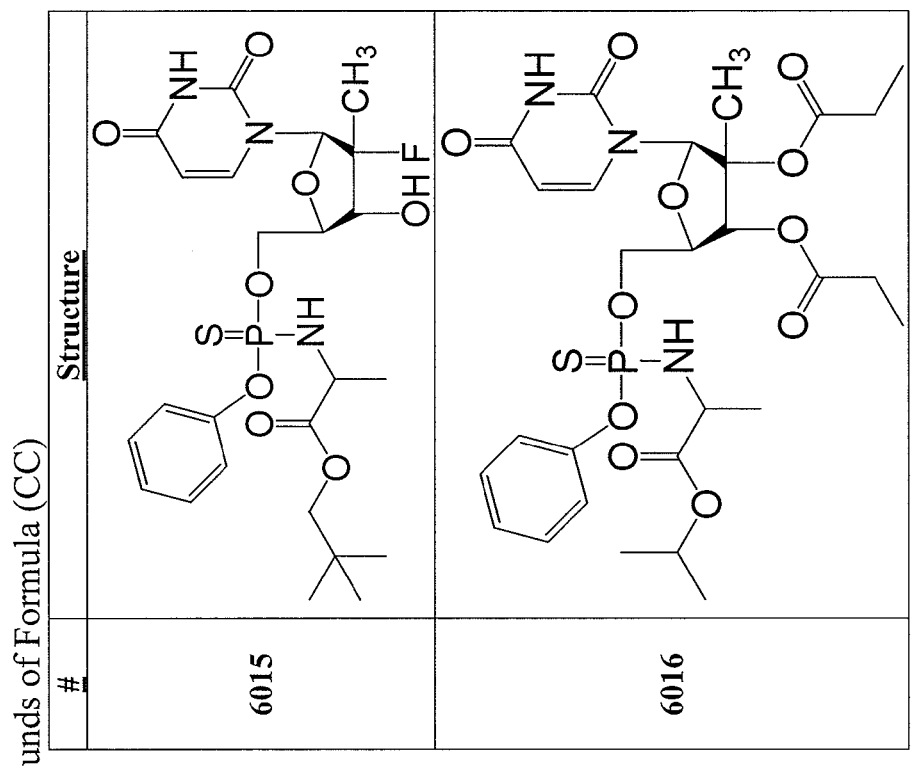
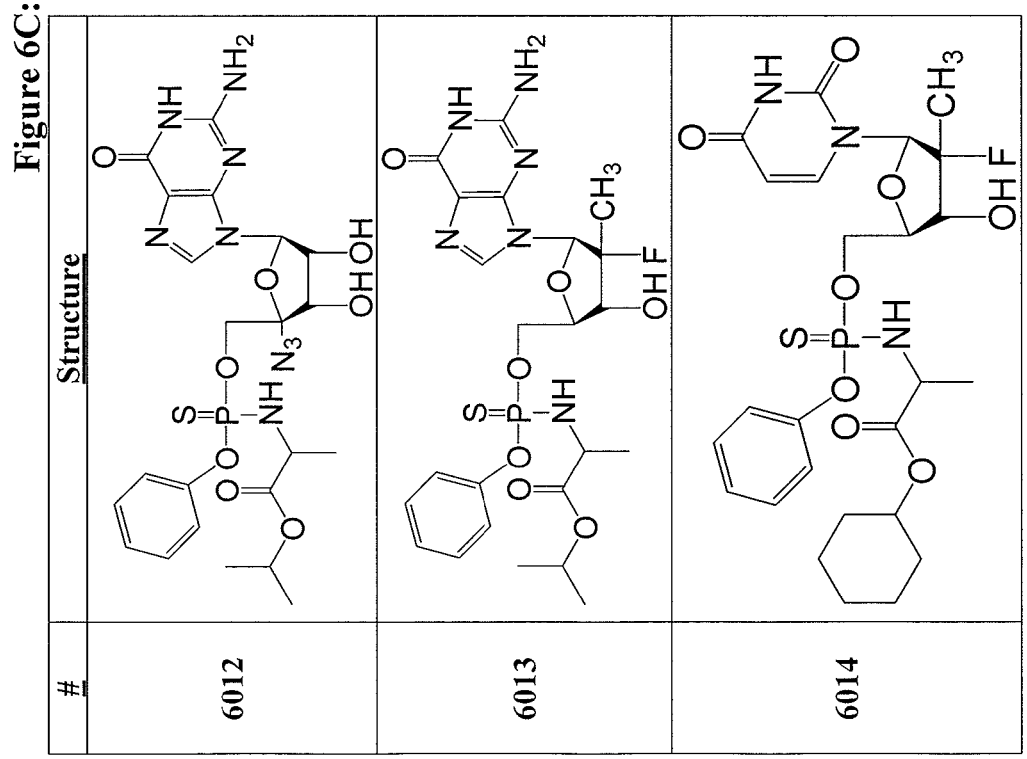

Figure 6D: Compounds of Formula (CC)

Figure 6E: Compounds of Formula (CC)

Figure 6F: Compounds of Formula (CC)

Figure 6G: Compounds of Formula (CC)

| # | Structure |
|---|---|
| 6037 | 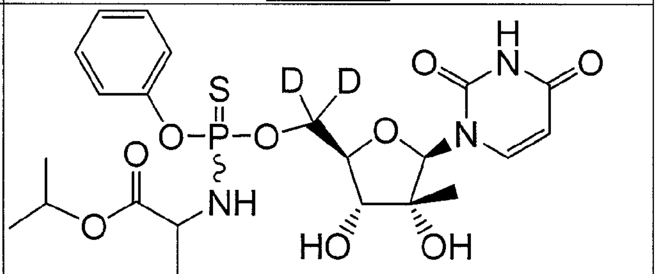 |
| 6038 | 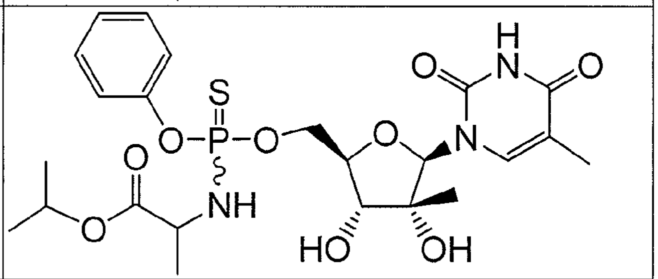 |
| 6039 | 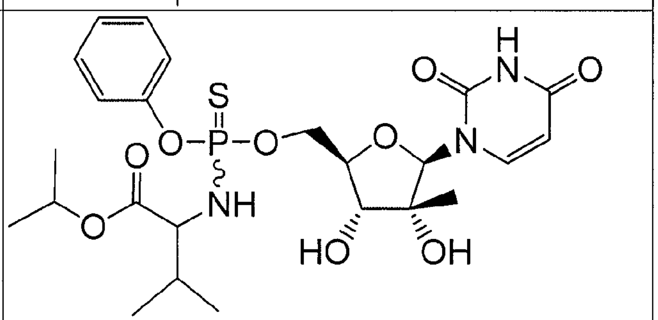 |
| 6040 | |
| 6041 | |
| 6042 | |

Figure 6H: Compounds of Formula (CC)

Figure 6I: Compounds of Formula (CC)
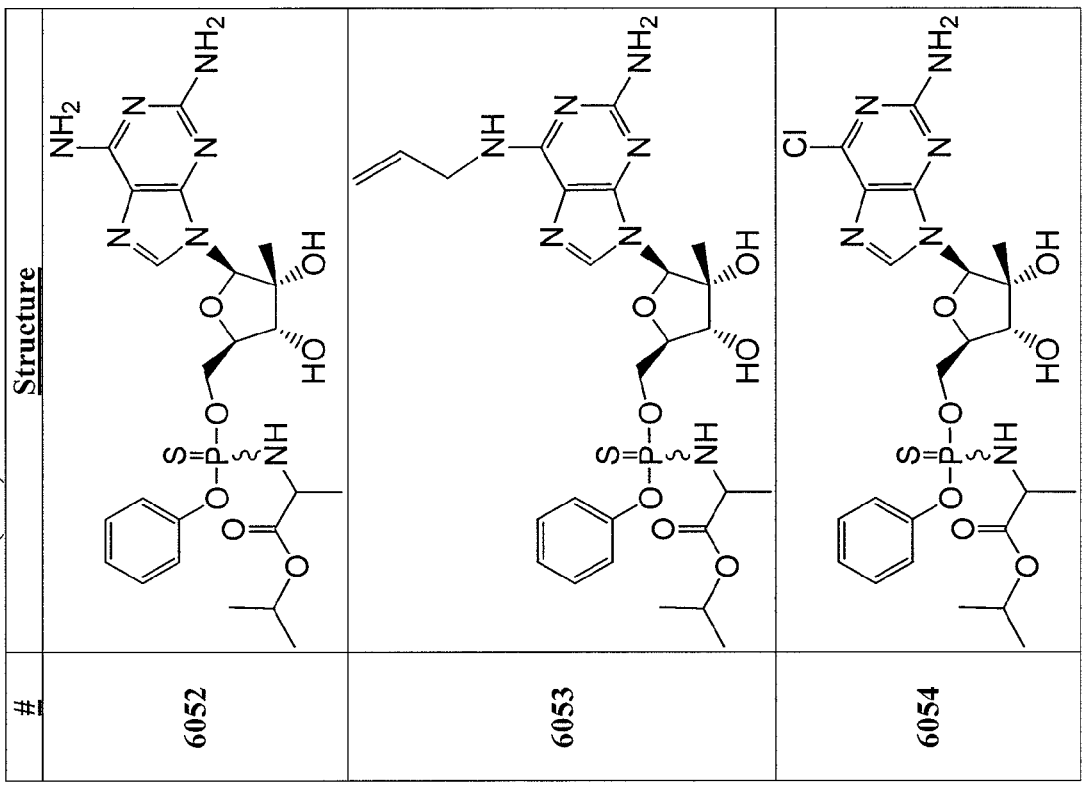
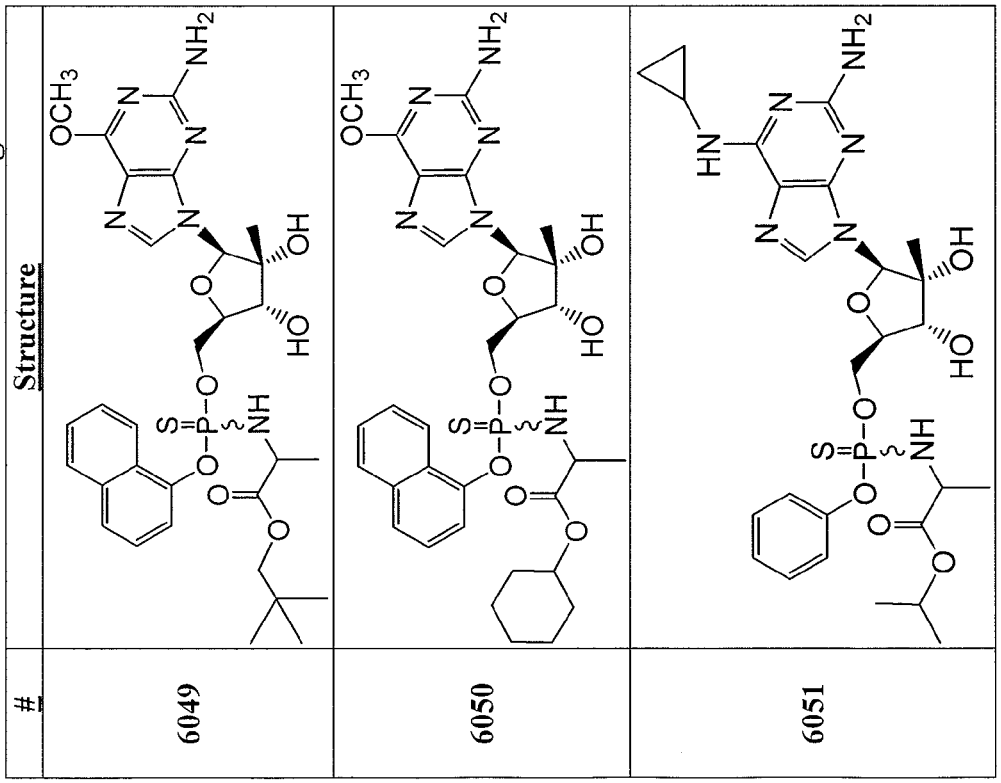

Figure 6J: Compounds of Formula (CC)

Figure 6K: Compounds of Formula (CC)

Figure 6L: Compounds of Formula (CC)

| # | Structure |
|---|---|
| 6067 | (4-fluorophenyl phosphorothioate prodrug of 2'-methyluridine with isopropyl alaninate) |
| 6068 | (2-chlorophenyl phosphorothioate prodrug of 2'-methyluridine with isopropyl alaninate) |
| 6069 | (4-methylphenyl phosphorothioate prodrug of 2'-methyluridine with isopropyl alaninate) |
| 6070 | (4-methoxyphenyl phosphorothioate prodrug of 2'-methyluridine with isopropyl alaninate) |
| 6071 | (quinolin-8-yl phosphorothioate prodrug of 2'-methyluridine with isopropyl alaninate) |
| 6072 | (pyridin-3-yl phosphorothioate prodrug of 2'-methyluridine with isopropyl alaninate) |

Figure 6M: Compounds of Formula (CC)

Figure 7A: Compounds of Formula (AA) and triphosphates thereof

Figure 7B: Compounds of Formula (AA) and triphosphates thereof

| # | Structure |
|---|---|
| 7006 | 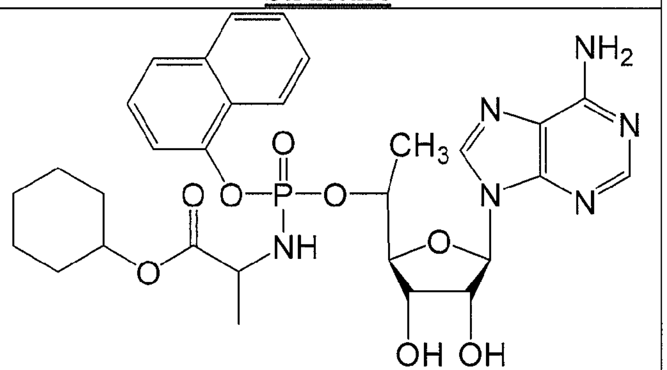 |
| 7007 | 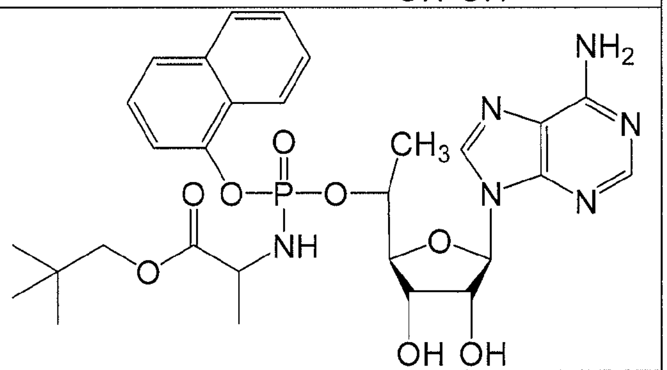 |
| 7008 | 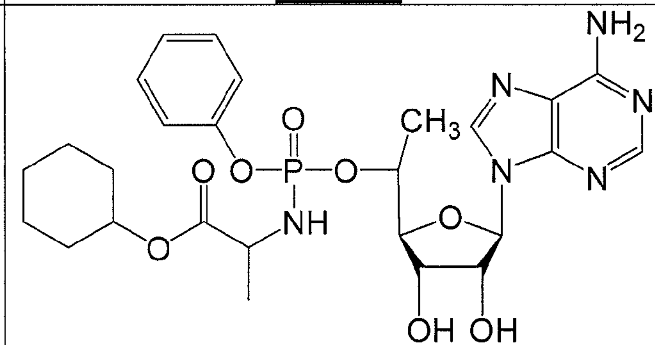 |
| 7009 | 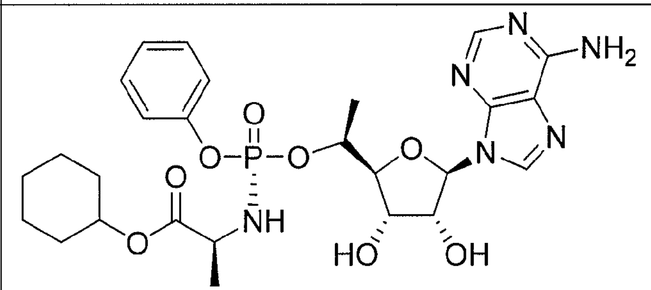 |
| 7010 | 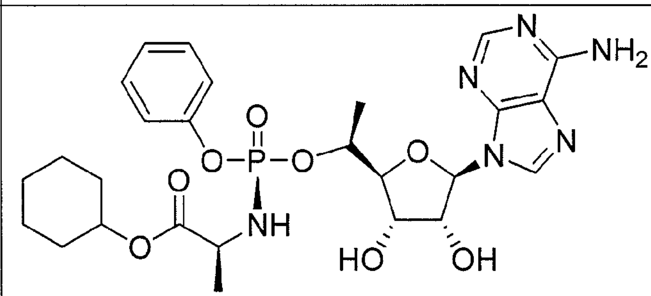 |

Figure 7C: Compounds of Formula (AA) and triphosphates thereof
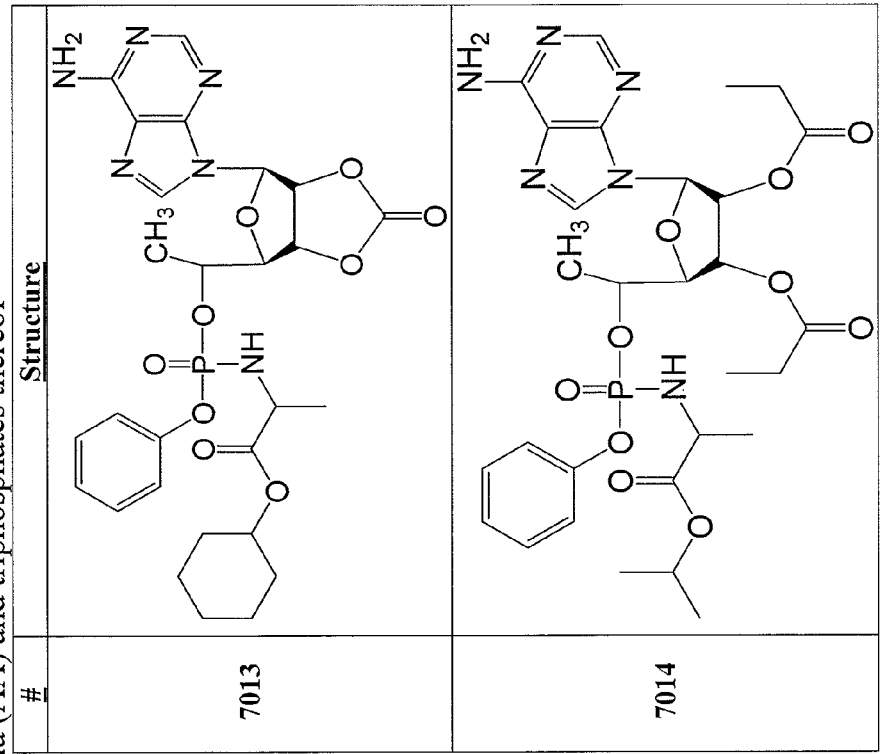
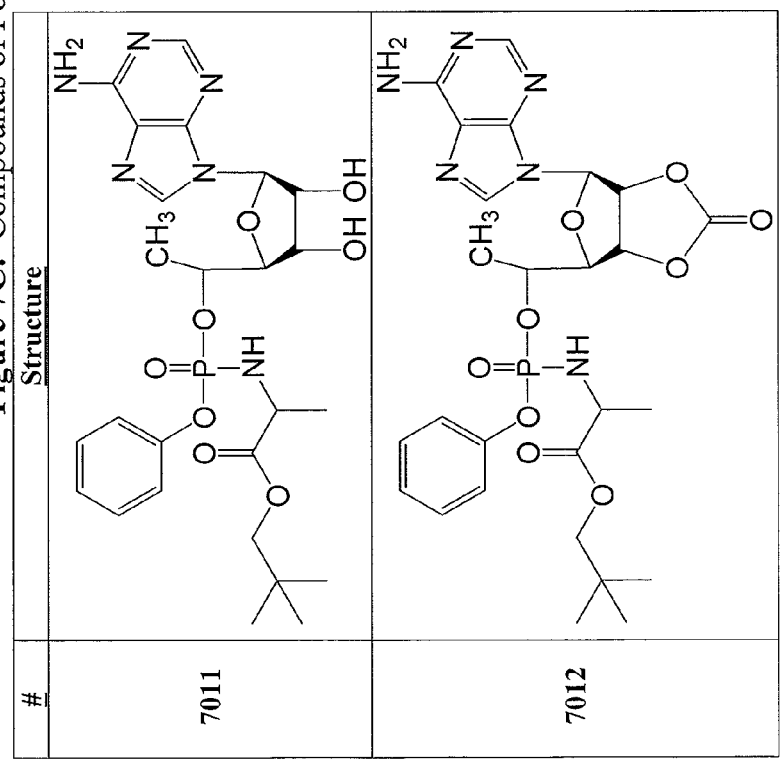

Figure 7D: Compounds of Formula (AA) and triphosphates thereof
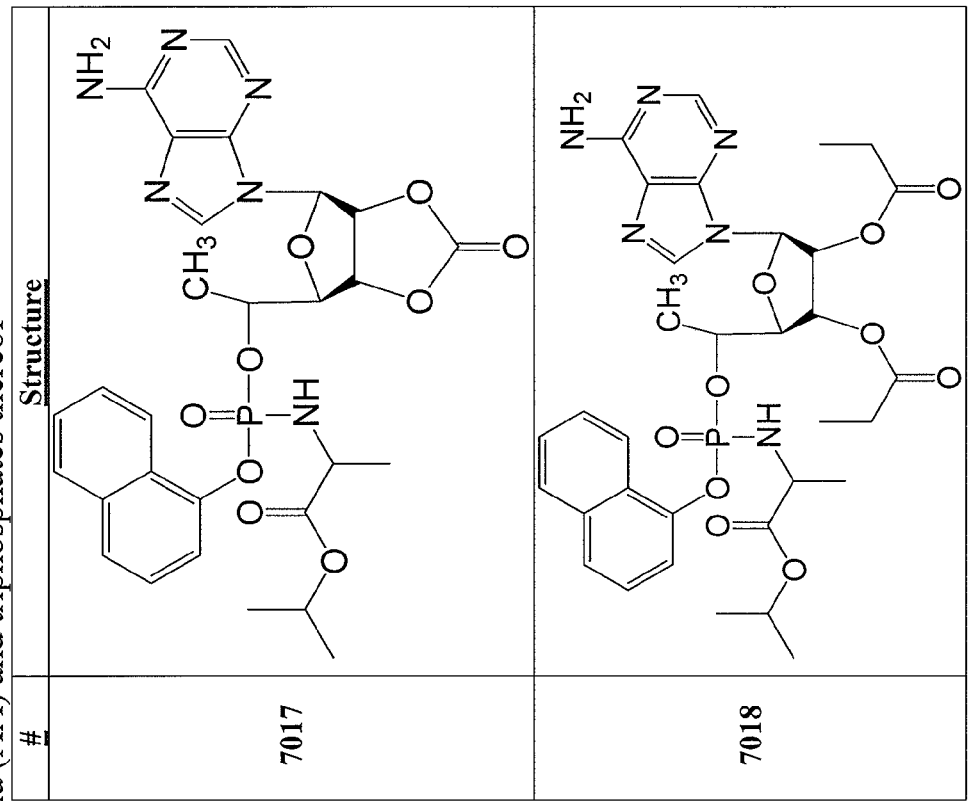
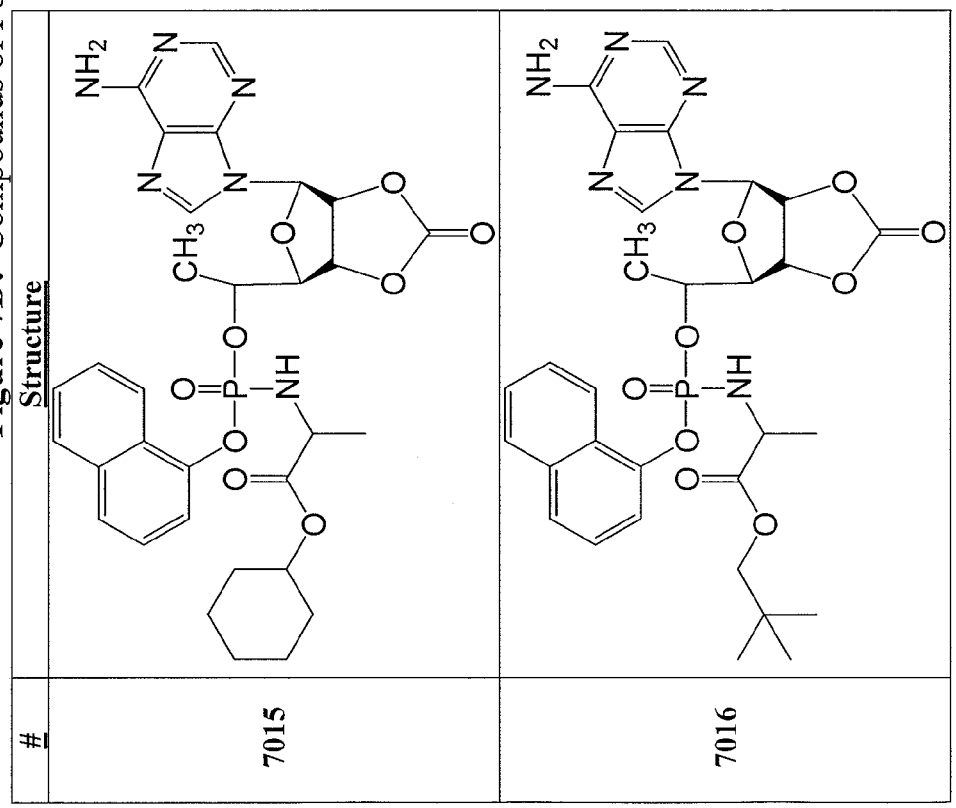

Figure 7E: Compounds of Formula (AA) and triphosphates thereof
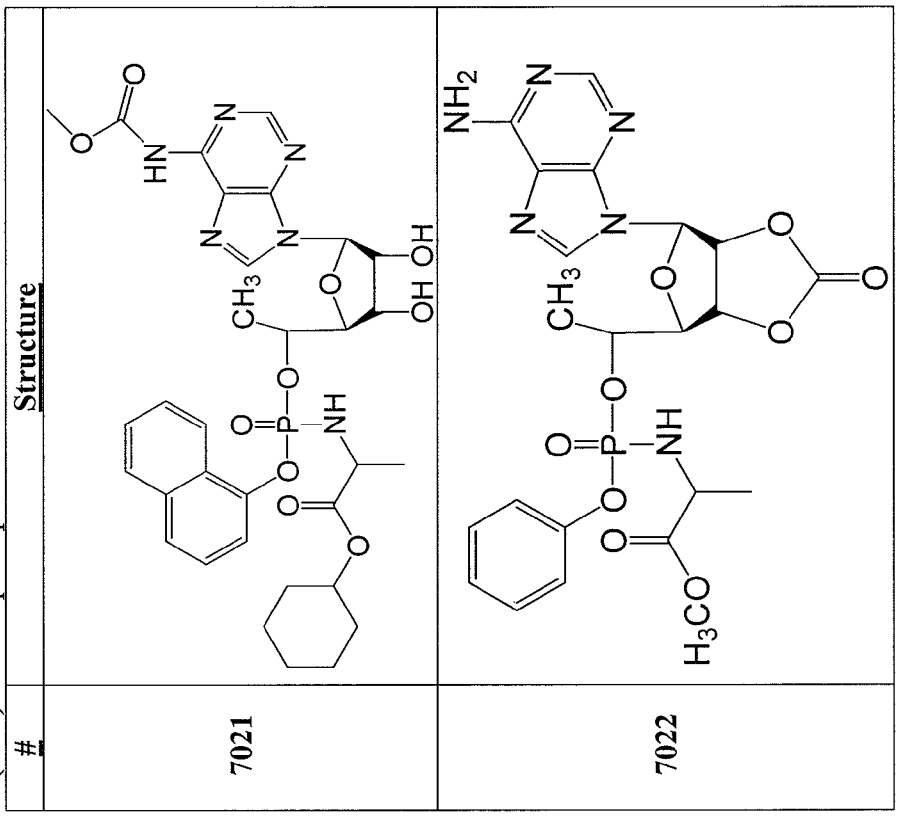
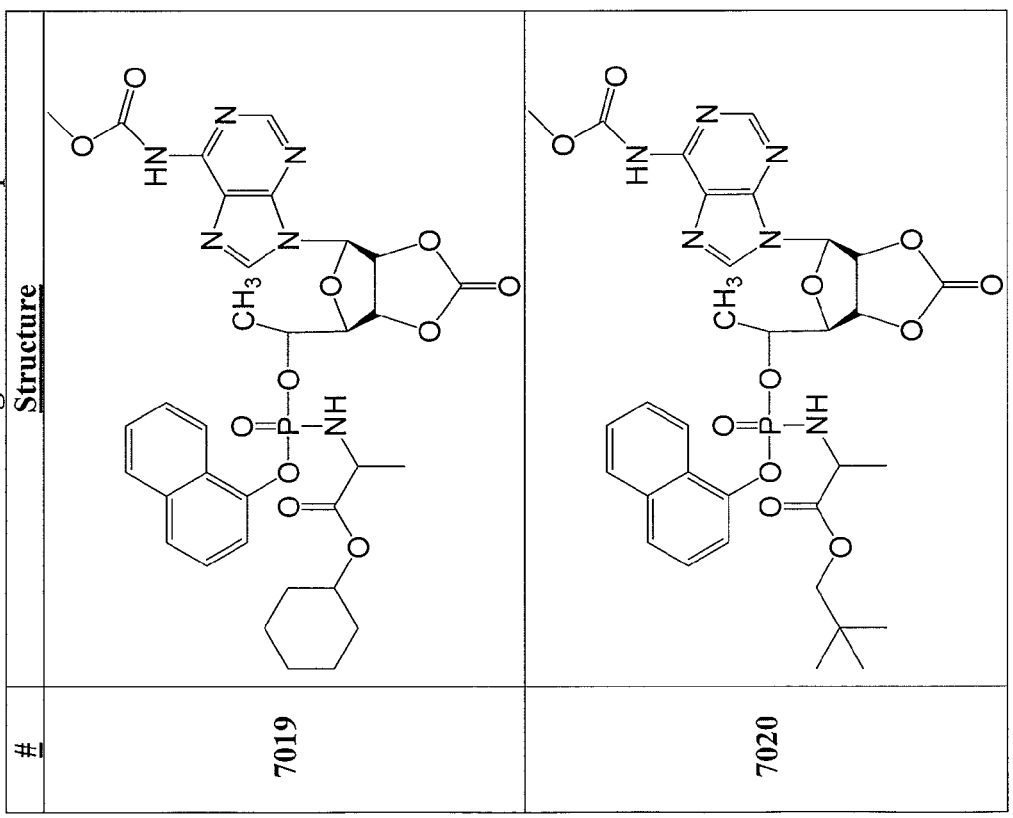

Figure 7F: Compounds of Formula (AA) and triphosphates thereof
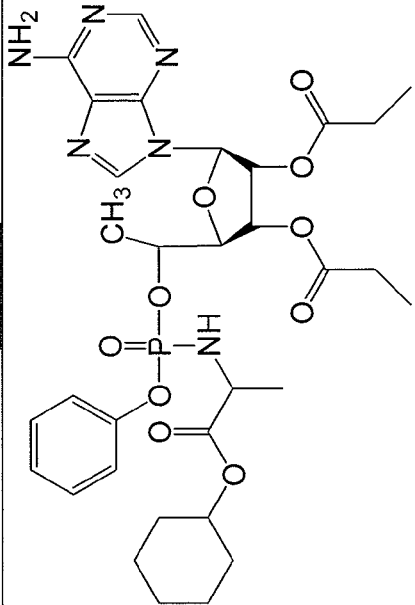
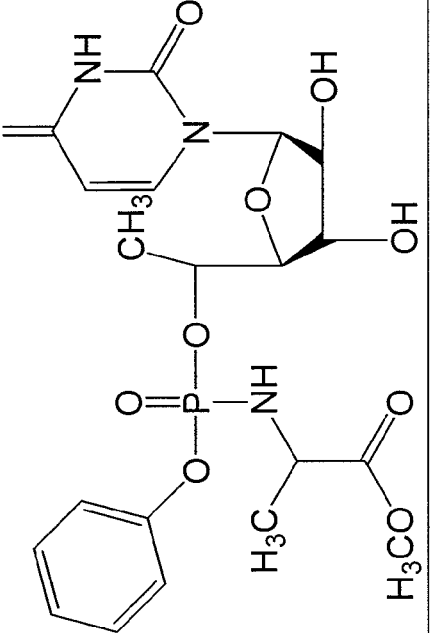
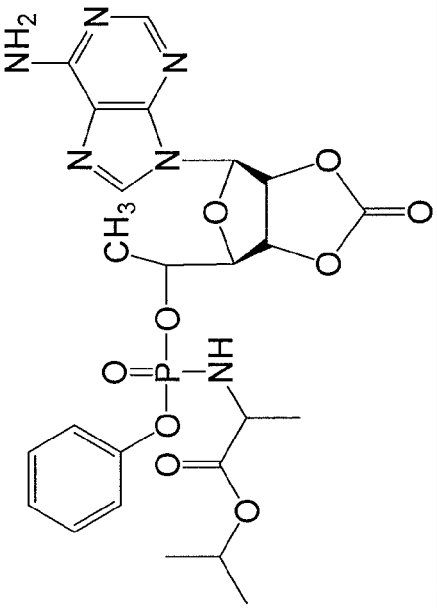
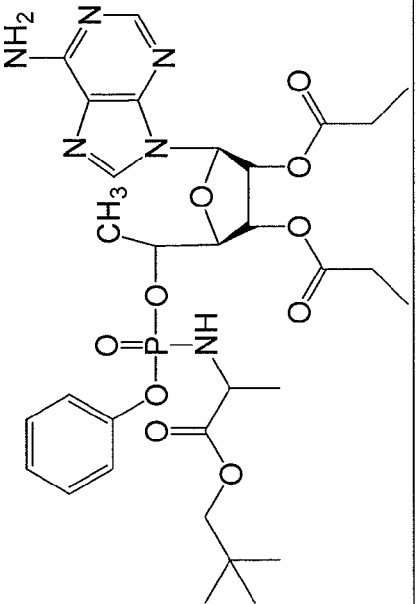

Figure 7G: Compounds of Formula (AA) and triphosphates thereof

| # | Structure |
|---|---|
| 7027 | 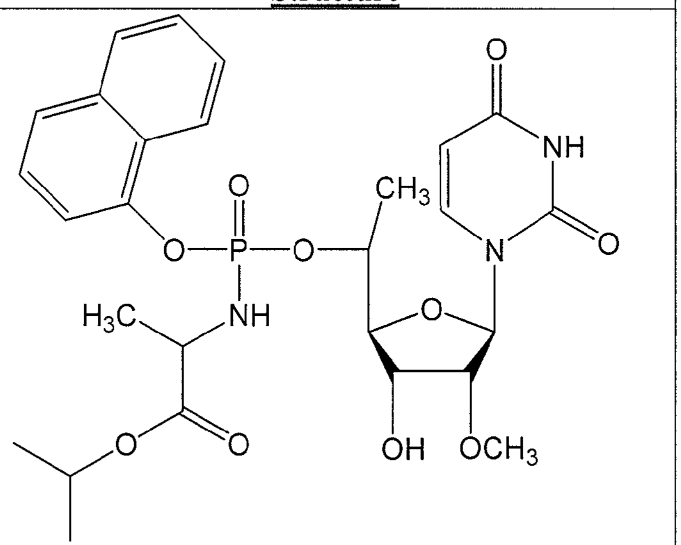 |
| 7028 | 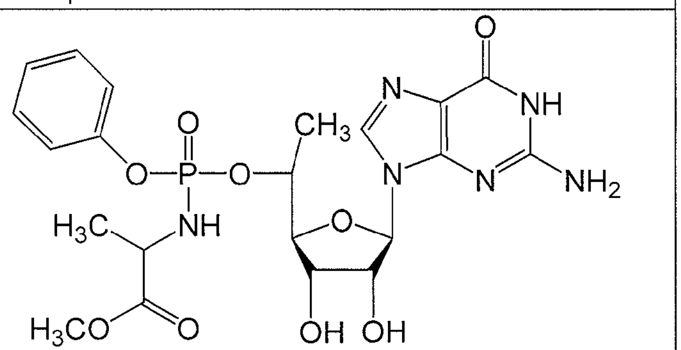 |
| 7029 | |
| 7030 | |

Figure 7H: Compounds of Formula (AA) and triphosphates thereof
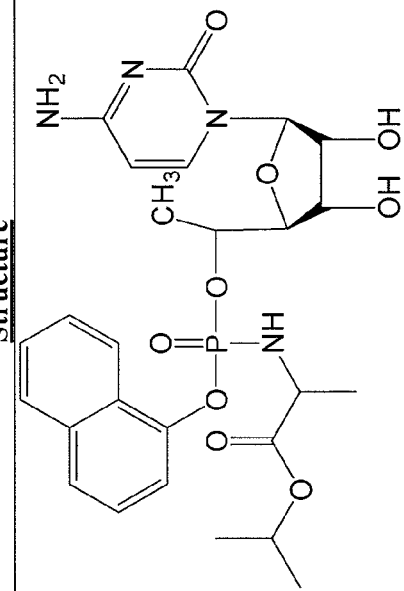
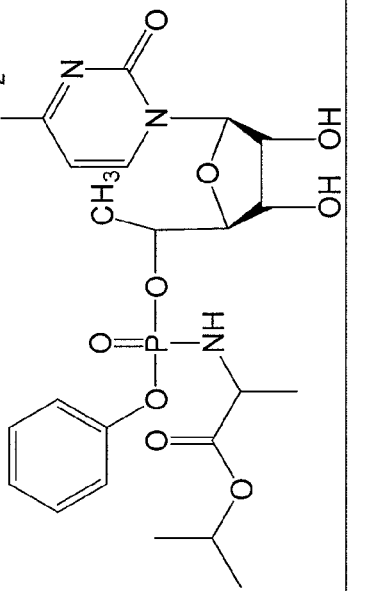
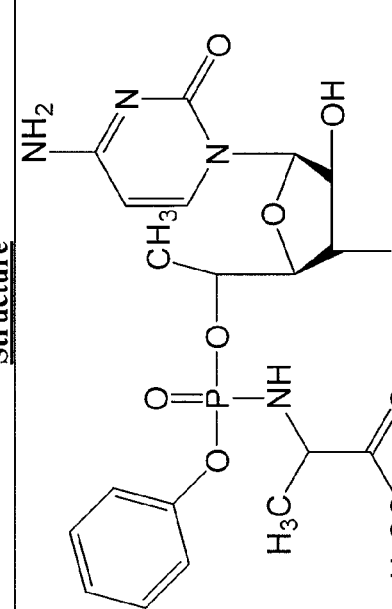
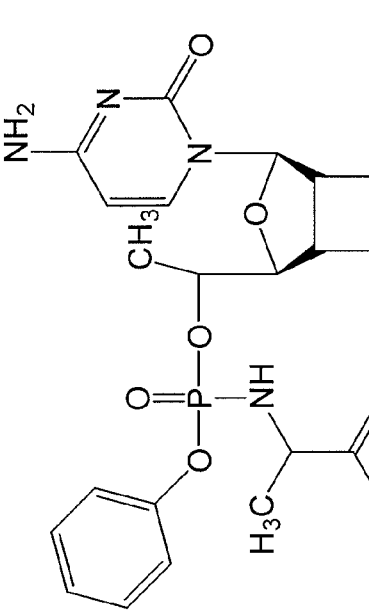

Figure 7I: Compounds of Formula (AA) and triphosphates thereof
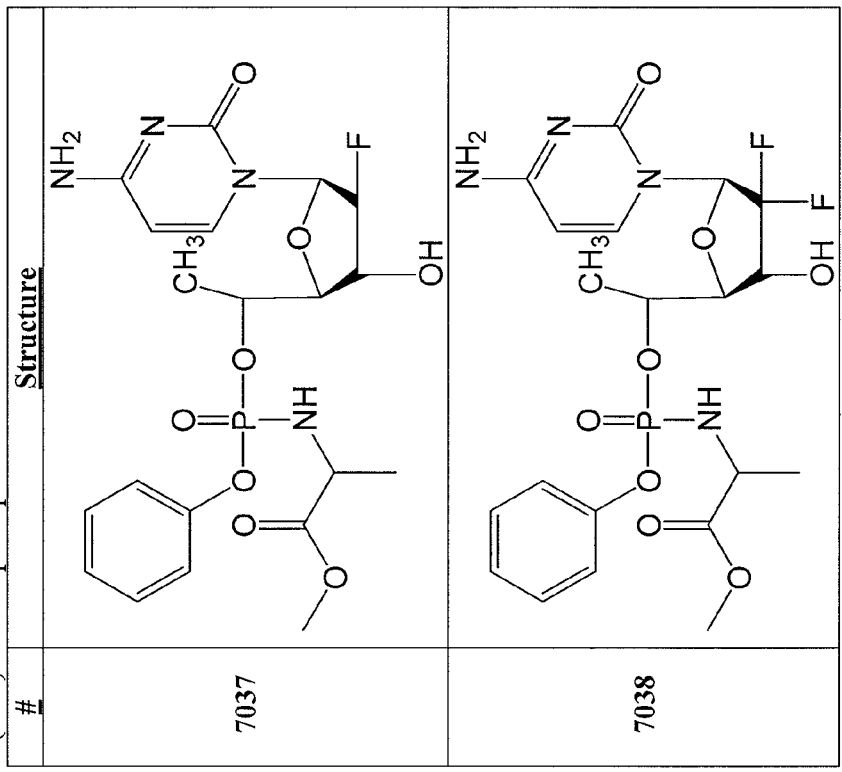
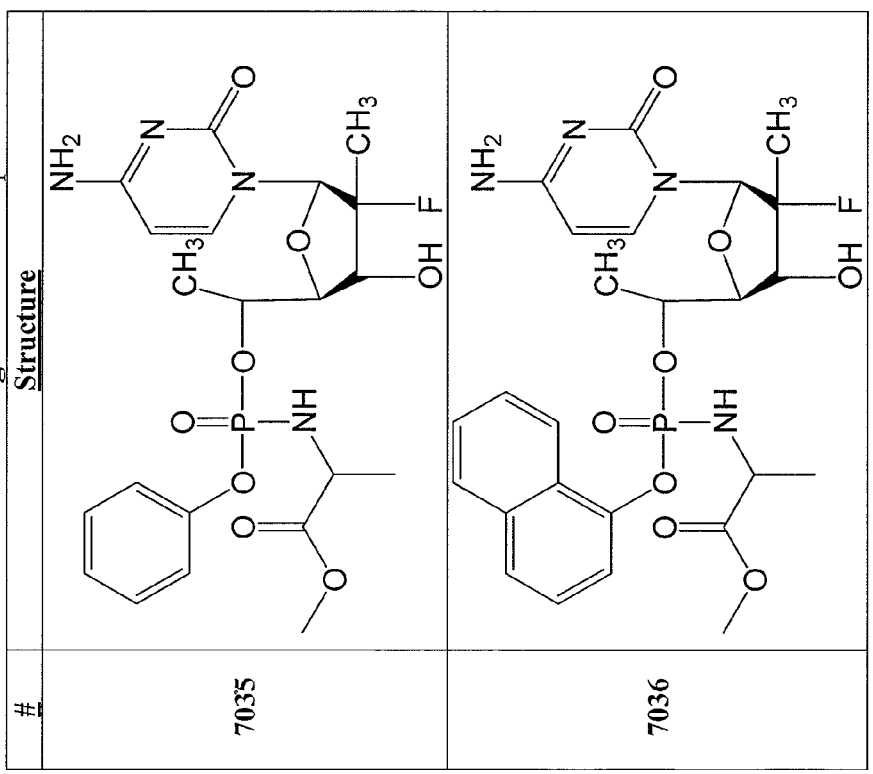

Figure 7J: Compounds of Formula (AA) and triphosphates thereof

| # | Structure |
|---|---|
| 7039 | 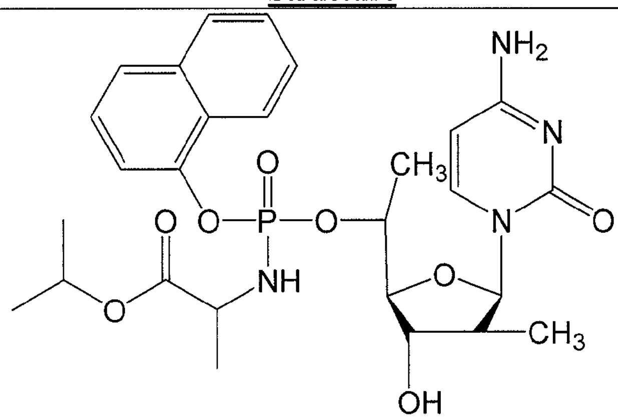 |
| 7040 | 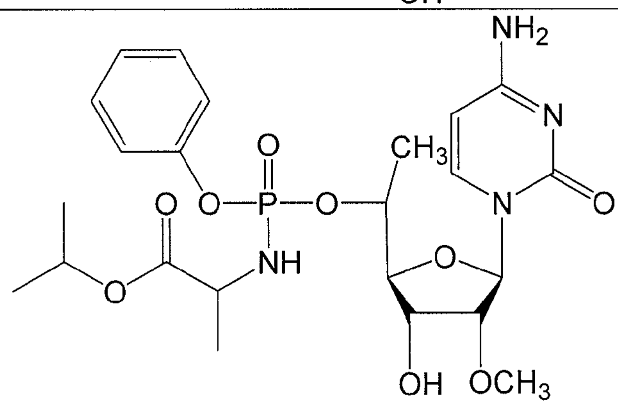 |
| 7041 | |
| 7042 | |

Figure 7K: Compounds of Formula (AA) and triphosphates thereof

Figure 7L: Compounds of Formula (AA) and triphosphates thereof

| # | Structure |
|---|---|
| 7049 | 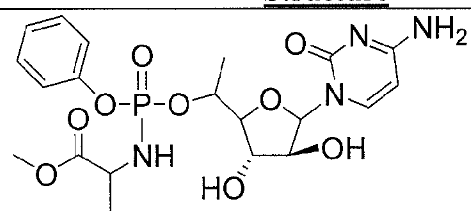 |
| 7050 | 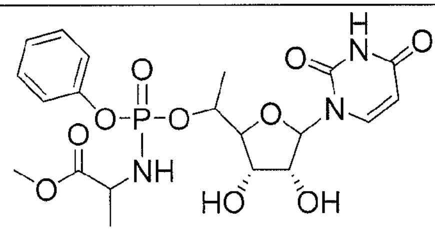 |
| 7051 | 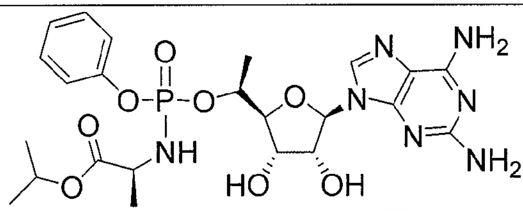 |
| 7052 | 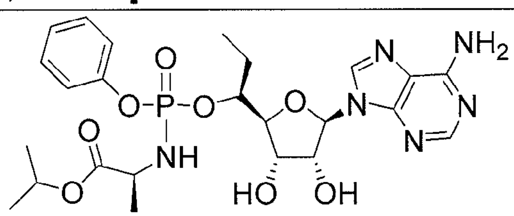 |
| 7053 | |
| 7054 | |
| 7055 | |
| 7056 | |

Figure 7M: Compounds of Formula (AA) and triphosphates thereof

| # | Structure |
|---|---|
| 7057 | 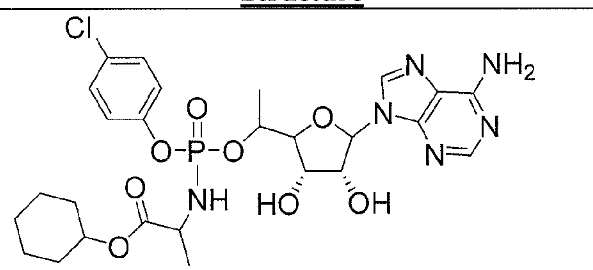 |
| 7058 | 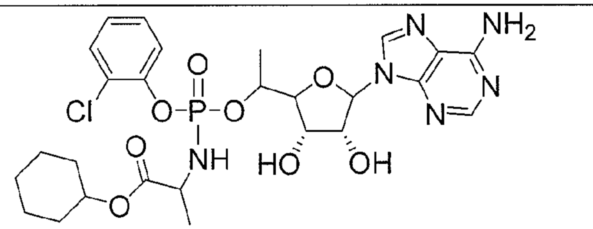 |
| 7059 | 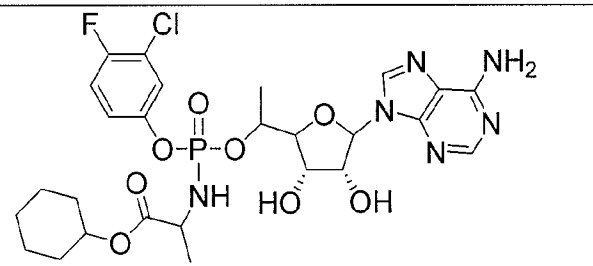 |
| 7060 | 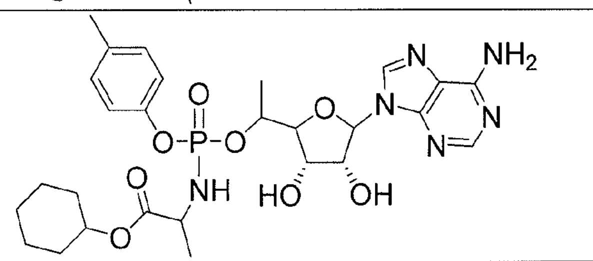 |

| # | Structure |
|---|---|
| 7061 | 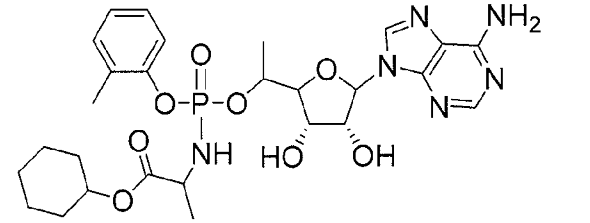 |
| 7062 | 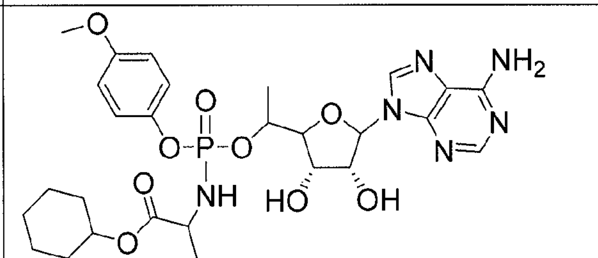 |
| 7063 | 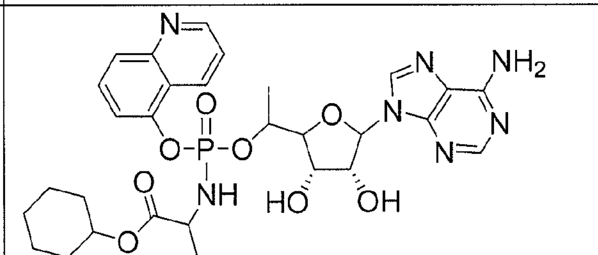 |
| 7064 | 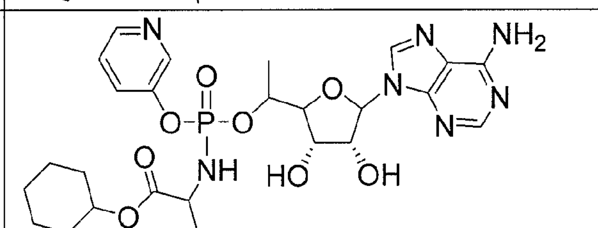 |

Figure 7N: Compounds of Formula (AA) and triphosphates thereof

| # | Structure |
|---|---|
| 7065 | 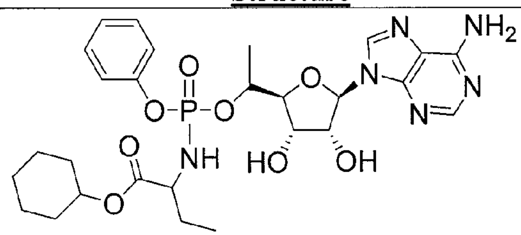 |
| 7066 | 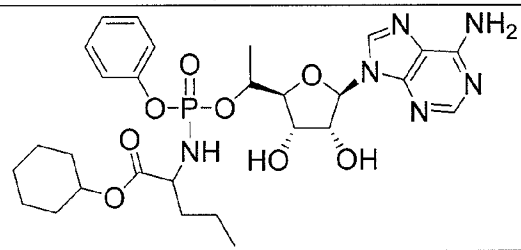 |
| 7067 | 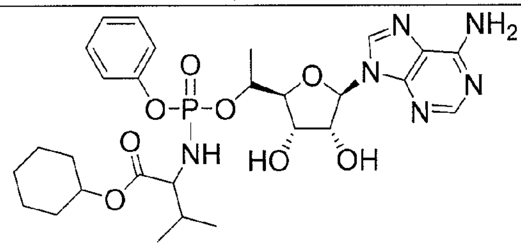 |
| 7068 | 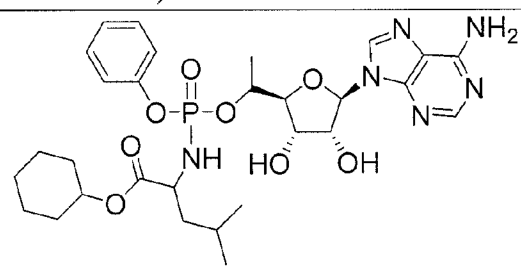 |
| 7069 | |
| 7070 | |
| 7071 | |
| 7072 | |

Figure 7O: Compounds of Formula (AA) and triphosphates thereof

| # | Structure |
|---|---|
| 7073 | (cytosine nucleoside triphosphate analog with 2'-OH, 3'-OH, and 5'-methyl) |
| 7074 | (adenine nucleoside triphosphate analog with 2'-OH, 3'-OH, and 5'-methyl) |
| 7075 | (purine nucleoside triphosphate analog with 2'-OH, 3'-OH, and 5'-methyl) |
| 7076 | (cytosine nucleoside triphosphate analog with 2',2'-difluoro, 3'-OH, and 5'-methyl) |
| 7077 | (cytosine nucleoside triphosphate analog with 2',2'-difluoro, 3'-OH, and 5'-methyl) |

Figure 8A: Compounds of Formula (I)

| # | Structure |
|---|---|
| 8000 | 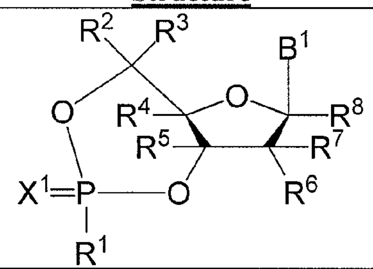 |
| 8001 | 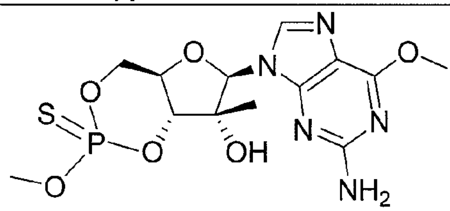 |
| 8002 | 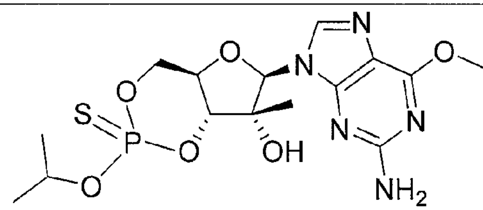 |
| 8003 | 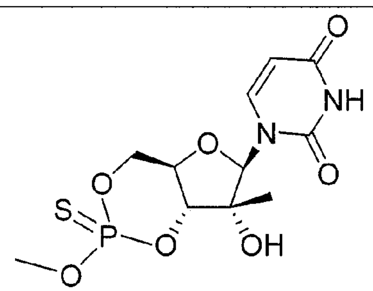 |
| 8004 | 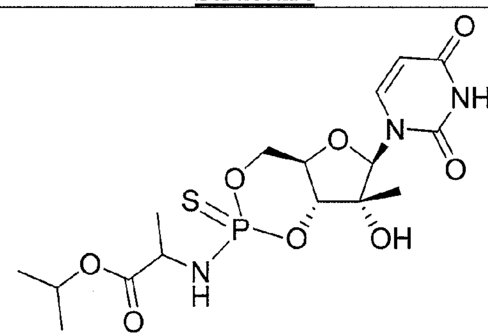 |
| 8005 | 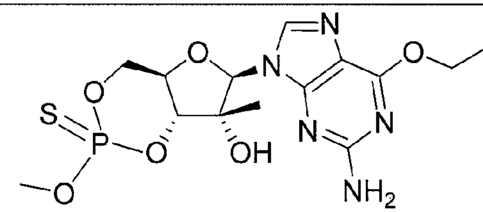 |
| 8006 | 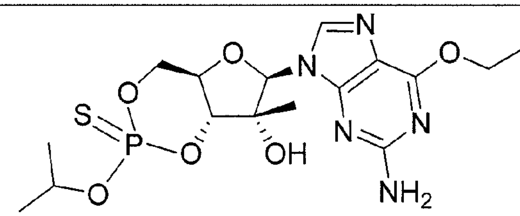 |

Figure 8B: Compounds of Formula (I)

Figure 8C: Compounds of Formula (I)

| # | Structure |
|---|---|
| 8015 | 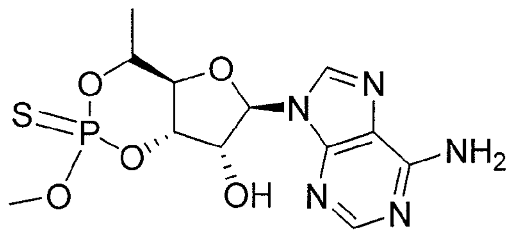 |
| 8016 | |

Figure 9: Formula (DD)

| # | Structure |
|---|---|
| 9000 | 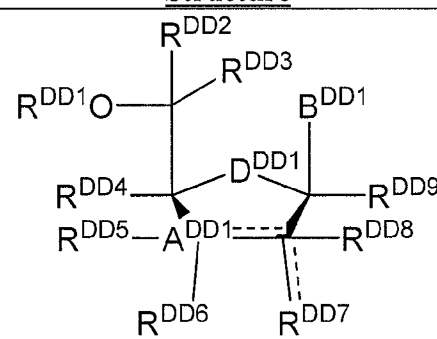 |

CYCLIC NUCLEOTIDE ANALOGS

CROSS-REFERENCE TO RELATED APPLICATIONS

This application claims the benefit of U.S. Provisional Application Nos. 61/536,445, filed Sep. 19, 2011; and 61/426,471, filed Dec. 22, 2010; both of which are incorporated herein by reference in their entirety; including any drawings.

BACKGROUND

1. Field

The present application relates to the fields of chemistry, biochemistry and medicine. More particularly, disclosed herein are cyclic nucleotide analogs, pharmaceutical compositions that include one or more cyclic nucleotide analogs and methods of synthesizing the same. Also disclosed herein are methods of treating diseases and/or conditions with cyclic nucleotide analogs alone or in combination therapy with other agents.

2. Description

Nucleoside analogs are a class of compounds that have been shown to exert antiviral and anticancer activity both in vitro and in vivo, and thus, have been the subject of widespread research for the treatment of viral infections and cancer. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I) or a pharmaceutically acceptable salt thereof.

Some embodiments disclosed herein relate to methods of ameliorating and/or treating a neoplastic disease that can include administering to a subject suffering from the neoplastic disease a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a neoplastic disease. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a neoplastic disease.

Some embodiments disclosed herein relate to methods of inhibiting the growth of a tumor that can include administering to a subject having a tumor a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for inhibiting the growth of a tumor. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for inhibiting the growth of a tumor.

Some embodiments disclosed herein relate to methods of ameliorating and/or treating a viral infection that can include administering to a subject suffering from the viral infection a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a viral infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a viral infection.

Some embodiments disclosed herein relate to methods of ameliorating and/or treating a viral infection that can include contacting a cell infected with the virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for ameliorating and/or treating a viral infection that can include contacting a cell infected with the virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for ameliorating and/or treating a viral infection by contacting a cell infected with the virus with an effective amount of said compound(s).

Some embodiments disclosed herein relate to methods of inhibiting replication of a virus that can include contacting a cell infected with the virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for inhibiting replication of a virus that can include contacting a cell infected with the virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for inhibiting replication of a virus by contacting a cell infected with the virus with an effective amount of said compound(s).

Some embodiments disclosed herein relate to methods of ameliorating and/or treating a parasitic disease that can include administering to a subject suffering from the parasitic disease a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a parasitic disease. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a parasitic disease.

Some embodiments disclosed herein relate to methods of ameliorating and/or treating a viral infection that can include administering to a subject suffering from the viral infection a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, a compound of Formula (CC), and a compound of Formula (DD), or a pharmaceutically acceptable salt or any of the foregoing. Some embodiments disclosed herein relate to methods of ameliorating and/or treating a viral infection that can include contacting a cell infected with the viral infection with a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, a compound of Formula (CC), and a compound of Formula (DD), or a pharmaceutically acceptable salt of any of the foregoing. Some embodiments disclosed herein relate to methods of inhibiting replication of a virus that can include administering to a subject a therapeutically effective amount of a compound described herein or a pharmaceutically acceptable salt thereof (for example, a compound of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, a compound of Formula (CC), and a compound of Formula (DD), or a pharmaceutically acceptable salt of any of the foregoing. In some embodiments, the agent can be a compound, or a pharmaceutically acceptable salt thereof, selected from Compound 1001-1014, 2001-2010, 3001-3008, 4001-4005, 5001-5002, 6000-6078, 7000-7077 or 9000, or a pharmaceutical composition that includes one or more of the aforementioned compounds, or pharmaceutically acceptable salt thereof. In some embodiments, the method can include administering a second agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, a compound of Formula (CC), and a compound of Formula (DD), or a pharmaceutically acceptable salt of any of the foregoing. In some embodiments, the viral infection can be HCV.

BRIEF DESCRIPTION OF THE DRAWINGS

FIGS. 1A-1B show example HCV protease inhibitors.
FIG. 2 shows example nucleoside HCV polymerase inhibitors.
FIG. 3 shows example non-nucleoside HCV polymerase inhibitors.
FIG. 4 shows example NS5A inhibitors.
FIG. 5 shows example other antivirals.
FIGS. 6A-6M show example compounds of Formula (CC).
FIGS. 7A-7O show example compounds of Formula (AA), and triphosphates thereof.
FIGS. 8A-8C show example compounds of Formula (I).
FIG. 9 shows Formula (DD).

DETAILED DESCRIPTION

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{1A}$, $R^{2A}$, $R^{3A}$, $R^{3B}$, $R^{4A}$, $R^{5A}$, $R^{6A}$, $R^{7A}$, and $R^{8A}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^{18}$ and $R^{19}$ of an —C($R^{18}$)($R^{19}$)— group are indicated to be "taken together," it means that they are covalently bonded to one another to form a ring:

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino and a di-substituted amino group, and protected derivatives thereof.

As used herein, "$C_a$ to $C_b$," in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$), and butylene ($—CH_2CH_2CH_2CH_2—$). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys are methoxy, ethoxy, n-propoxy, 1-methylethoxy (isopropoxy), n-butoxy, iso-butoxy, sec-butoxy, tert-butoxy, and the like. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

As used herein, "aryloxy" and "arylthio" refers to RO— and RS—, in which R is an aryl, such as, but not limited to, phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2—$" group wherein each X is a halogen.

A "trihalomethanesulfonamido" group refers to an "$X_3CS(O)_2N(R_A)—$" group wherein each X is a halogen, and $R_A$ hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a $—NH_2$ group.
As used herein, the term "hydroxy" refers to a —OH group.
A "cyano" group refers to a "—CN" group.
The term "azido" as used herein refers to a $—N_3$ group.
The term "allenyl" as used herein refers to a $R_2C=C=CR—$ group in which each R can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl.

An "isocyanato" group refers to a "—NCO" group.
A "thiocyanato" group refers to a "—CNS" group.
An "isothiocyanato" group refers to an "—NCS" group.
A "mercapto" group refers to an "—SH" group.
A "carbonyl" group refers to a C=O group.
An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

An "N-sulfonamido" group refers to a "$RSO_2N(R_A)—$" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

An "O-carbamyl" group refers to a "—$OC(=O)N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

An "O-thiocarbamyl" group refers to a "—OC(=S)—N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

A "C-amido" group refers to a "—C(=O)N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl) alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g., 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, benzyl-O—C(=O)—, and naphthyl-O—C(=O)—. N-linked amino acid ester derivatives can be substituted or unsubstituted.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W.

Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g., methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry,* 2d ed., Francis Carey (1992), pages 328-331; Introduction to *Organic Chemistry,* 2d ed., Andrew Streitwieser and Clayton Heathcock (1981), pages 169-171; and *Organic Chemistry,* $5^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as a hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as di cyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred, 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of phosphate groups are intended to be included. Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Some embodiments disclosed herein relate to a compound of Formula (I) or a pharmaceutically acceptable salt thereof:

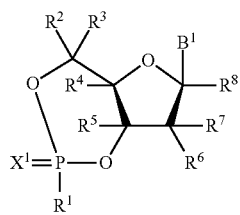

wherein: $B^1$ can be an optionally substituted heterocyclic base or an optionally substituted heterocyclic base with a protected amino group; $X^1$ can be O (oxygen) or S (sulfur); $R^1$ can be selected from —$Z^1$—$R^9$, an optionally substituted N-linked amino acid and an optionally substituted N-linked amino acid ester derivative; $Z^1$ can be selected from O (oxygen), S (sulfur) and N($R^{10}$); $R^2$ and $R^3$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^2$ and $R^3$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^4$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^5$ can be hydrogen or an optionally substituted $C_1$-6 alkyl; $R^6$ can be selected from hydrogen, halogen, azido, amino, cyano, an optionally substituted $C_{1-6}$ alkyl, —$OR^{11}$ and —OC(=O)$R^{12}$; $R^7$ can be selected from hydrogen, halogen, azido, cyano, an optionally substituted $C_{1-6}$ alkyl, —$OR^{13}$ and —OC(=O)$R^{14}$; $R^8$ can be selected from hydrogen, halogen, azido, cyano, an optionally substituted $C_{1-6}$ alkyl, —$OR^{15}$ and —OC(=O)$R^{16}$; $R^9$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl), an optionally substituted heterocyclyl ($C_{1-6}$ alkyl), and Formula (II); $R^{10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl); $R^{11}$, $R^{13}$ and $R^{15}$ can be independently hydrogen or an optionally substituted $C_{1-6}$ alkyl; $R^{12}$, $R^{14}$ and $R^{16}$ can be independently an optionally substituted $C_{1-6}$ alkyl or an optionally substituted $C_{3-6}$ cycloalkyl; and Formula (II) can be:

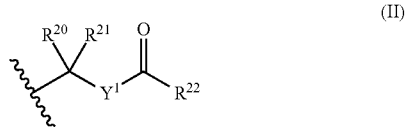

wherein: $R^{20}$ and $R^{21}$ can be independently selected from a hydrogen, an optionally substituted $C_{1-24}$ alkyl and an optionally substituted aryl; $R^{22}$ can be selected from a hydrogen, an optionally substituted $C_{1-24}$ alkyl, an optionally substituted aryl, an optionally substituted —O—$C_{1-24}$ alkyl and an optionally substituted —O-aryl; and $Y^1$ can be O (oxygen) or S (sulfur).

In some embodiments, a compound of Formula (I) cannot have a structure selected from:

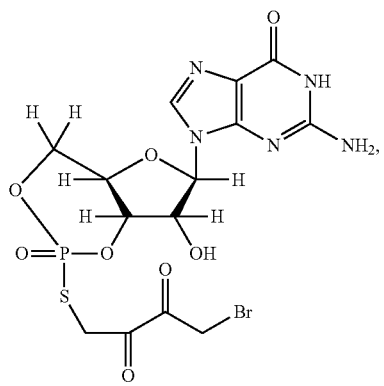
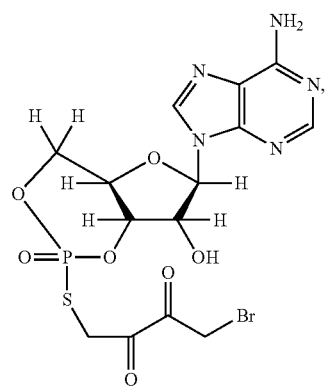
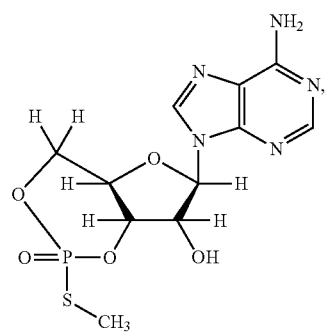
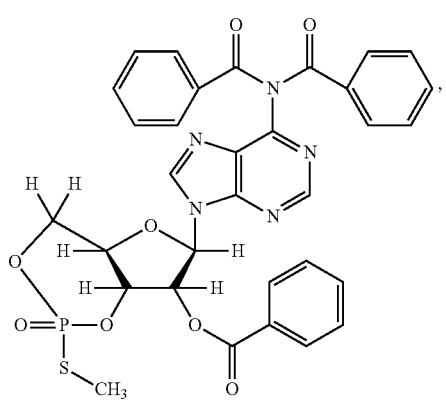
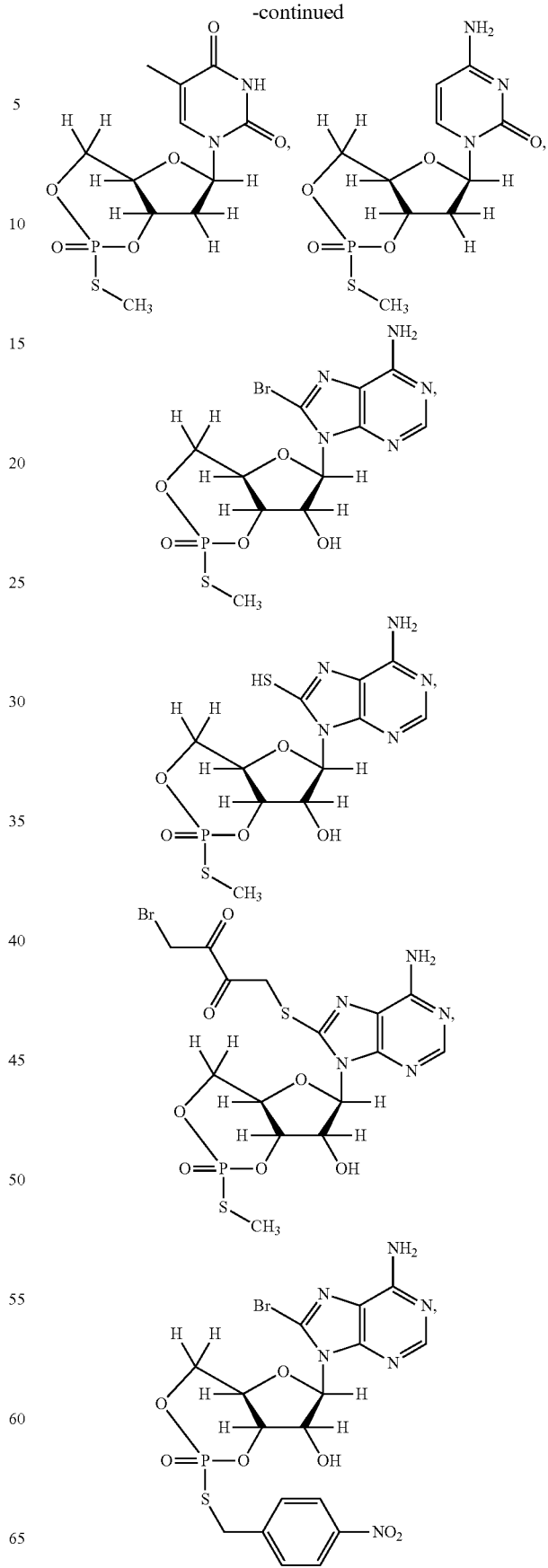

17
-continued
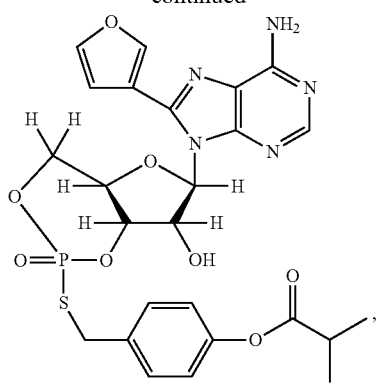
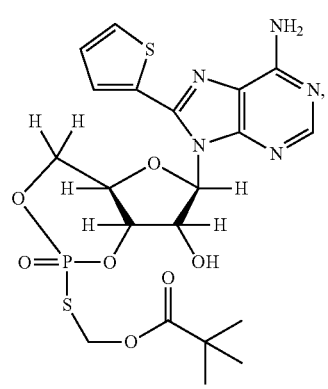
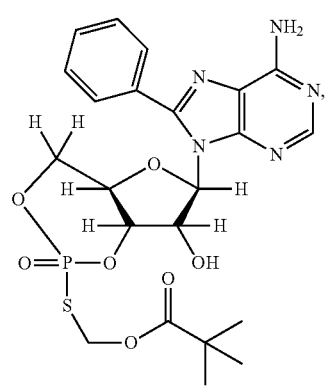
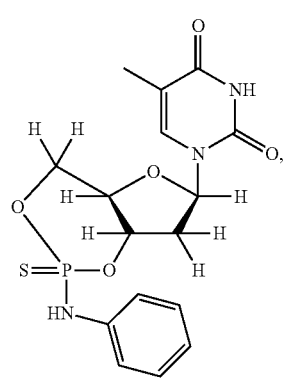
18
-continued
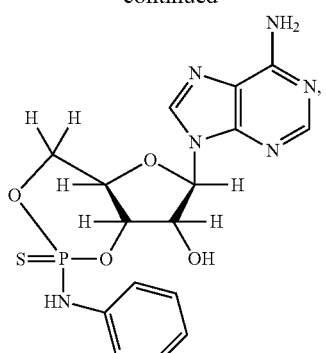
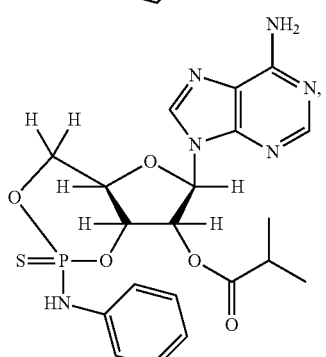
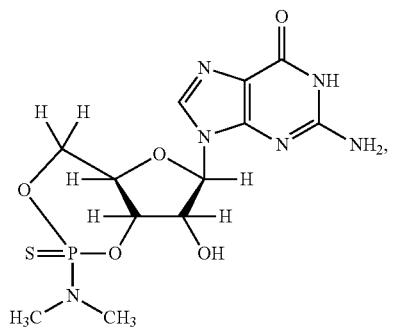
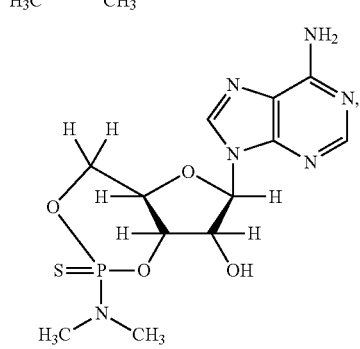
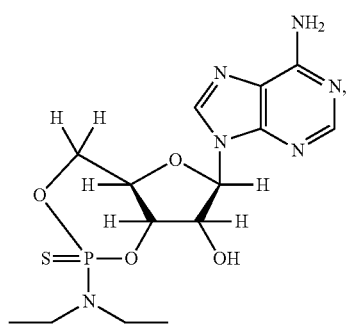

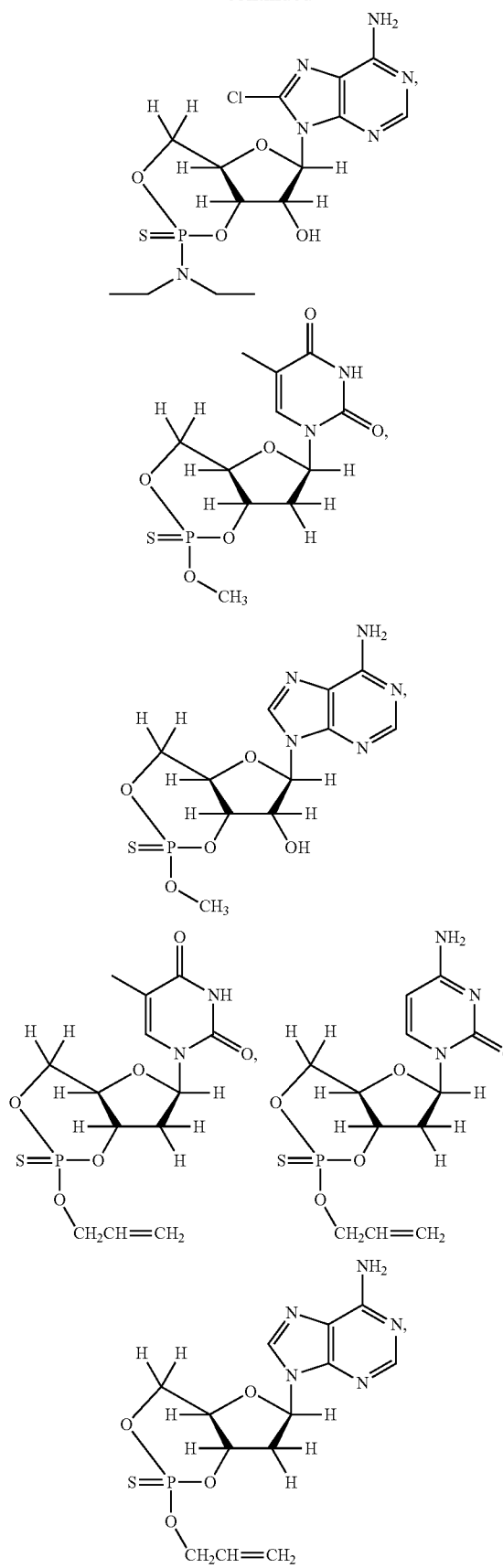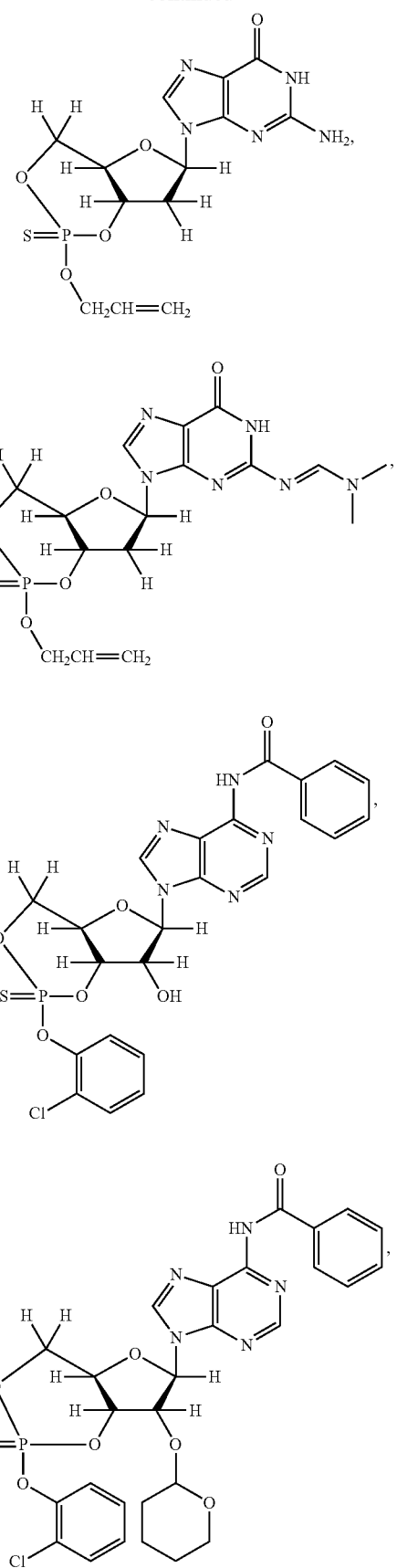

21
-continued
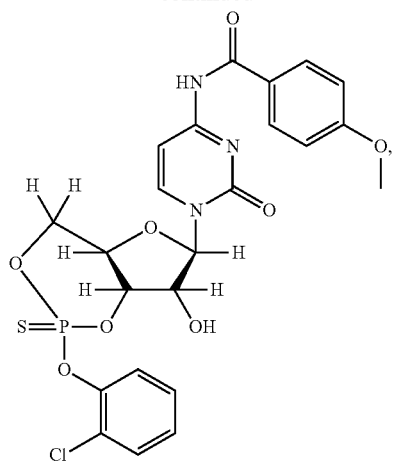
22
-continued
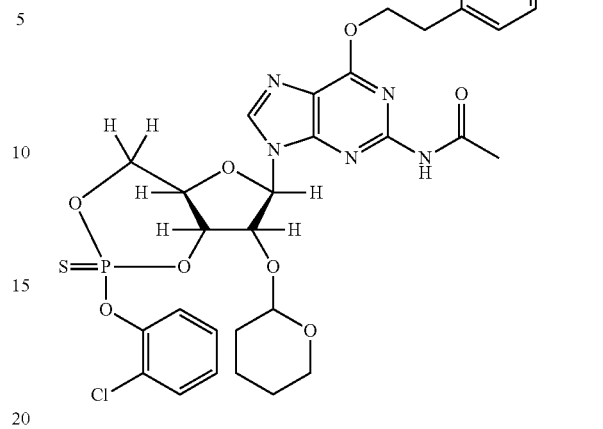
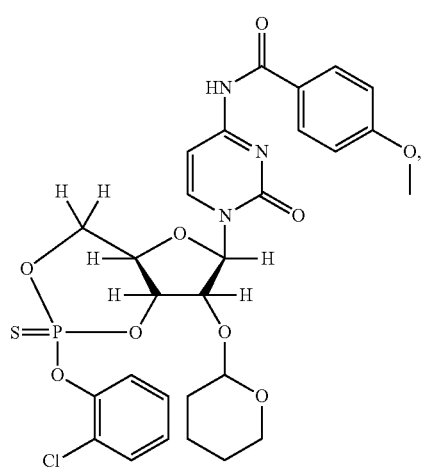
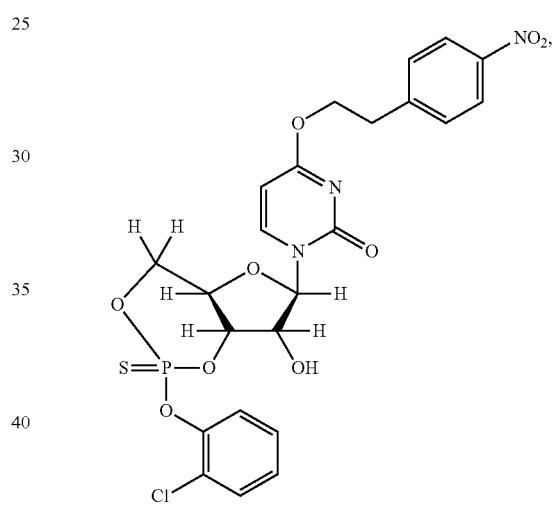
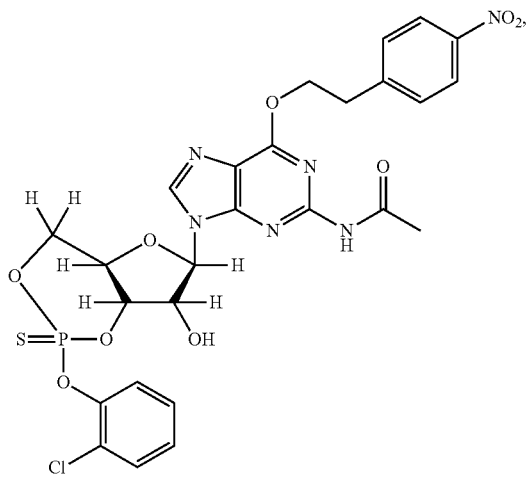
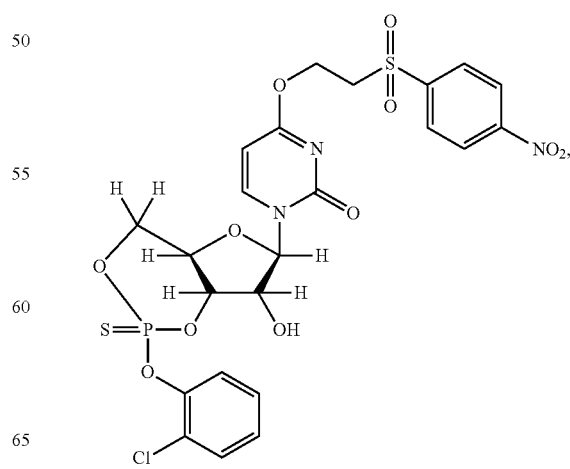

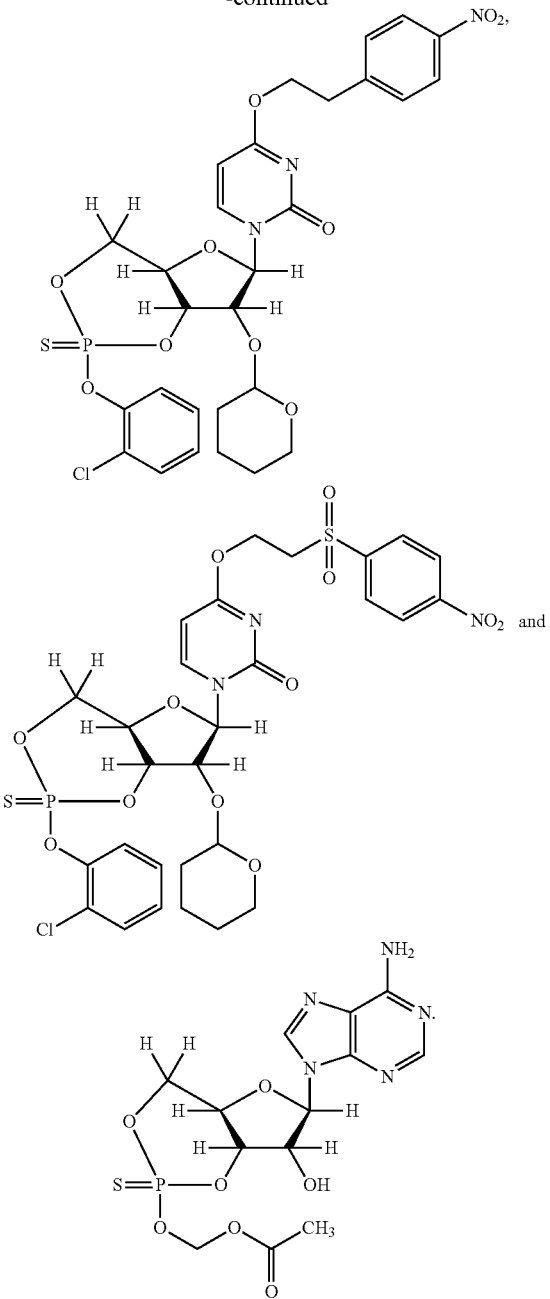

In some embodiments, when $X^1$ is S (sulfur), $R^1$ is —$Z^1$—$R^9$, $Z^1$ is $N(R^{10})$ and $R^{10}$ is hydrogen, then $R^9$ cannot be an optionally substituted phenyl. In some embodiments, when $X^1$ is S (sulfur), $Z^1$ is $N(R^{10})$ and $R^{10}$ is hydrogen, then $R^9$ cannot be an unsubstituted aryl, for example an unsubstituted phenyl. In other embodiments, when $X^1$ is S (sulfur), $R^1$ is —$Z^1$—$R^9$ and $Z^1$ is $N(R^{10})$, then $R^9$ and $R^{10}$ cannot both be methyl or ethyl. In some embodiments, when $X^1$ is S (sulfur), $R^1$ is —$Z^1$—$R^9$ and $Z^1$ is $N(R^{10})$, then $R^9$ and $R^{10}$ cannot both be an unsubstituted $C_{1-4}$ alkyl. In some embodiments, when $X^1$ is S (sulfur), $R^1$ is —$Z^1$—$R^9$ and $Z^1$ is $N(R^{10})$, then $R^9$ and $R^{10}$ cannot both be an optionally substituted $C_{1-4}$ alkyl. In some embodiments, when $X^1$ is S (sulfur), $R^1$ is —$Z^1$—$R^9$ and $Z^1$ is $N(R^{10})$, then $R^9$ and $R^{10}$ cannot both be an unsubstituted alkyl. In some embodiments, when $X^1$ is S (sulfur), $R^1$ is —$Z^1$—$R^9$ and $Z^1$ is $N(R^{10})$, then $R^9$ and $R^{10}$ cannot both be an optionally substituted alkyl.

In some embodiments, when $X^1$ is S (sulfur), $R^1$ is —$Z^1$—$R^9$ and $Z^1$ is O (oxygen), then $R^9$ cannot be methyl. In some embodiments, when $X^1$ is S (sulfur), $R^1$ is —$Z^1$—$R^9$ and $Z^1$ is O (oxygen), then $R^9$ cannot be an unsubstituted alkyl, for example an unsubstituted $C_{1-4}$ alkyl. In some embodiments, when $X^1$ is S (sulfur), $R^1$ is —$Z^1$—$R^9$ and $Z^1$ is O (oxygen), then $R^9$ cannot be an optionally substituted alkyl, for example an optionally substituted $C_{1-4}$ alkyl. In other embodiments, when $X^1$ is S (sulfur), $R^1$ is —$Z^1$—$R^9$ and $Z^1$ is O (oxygen), then $R^9$ cannot be —$CH_2$—OC(=O)—($C_{1-4}$ alkyl), such as —$CH_2$—OC(=O)$CH_3$ or —$CH_2$—OC(=O)C($CH_3$). In some embodiments, when $X^1$ is S (sulfur), $R^1$ is —$Z^1$—$R^9$ and $Z^1$ is O (oxygen), then $R^9$ cannot be —$CH_2$—OC(=O)—O—($C_{1-6}$ alkyl), such as —$CH_2$—OC(=O)—O—isopropyl. In still other embodiments, when $X^1$ is S (sulfur), $R^1$ is —$Z^1$—$R^9$ and $Z^1$ is O (oxygen), then $R^9$ cannot be —$CH_2CH=CH_2$. In some embodiments, when $X^1$ is S (sulfur), $R^1$ is —$Z^1$—$R^9$ and $Z^1$ is O (oxygen), then $R^9$ cannot be an unsubstituted $C_{1-4}$ alkenyl. In some embodiments, when $X^1$ is S (sulfur), $R^1$ is —$Z^1$—$R^9$ and $Z^1$ is O (oxygen), then $R^9$ cannot be an unsubstituted alkenyl. In other embodiments, when $X^1$ is S (sulfur), $R^1$ is —$Z^1$—$R^9$ and $Z^1$ is O (oxygen), then $R^9$ cannot be 2-chlorophenyl. In some embodiments, when $X^1$ is S (sulfur), $R^1$ is —$Z^1$—$R^9$ and $Z^1$ is O (oxygen), then $R^9$ cannot be an optionally substituted aryl, such as an unsubstituted or substituted phenyl.

In some embodiments, when $X^1$ is O (oxygen), $R^1$ is —$Z^1$—$R^9$, $Z^1$ is $N(R^{10})$ and $R^{10}$ is hydrogen, then $R^9$ cannot be an optionally substituted phenyl. In some embodiments, when $X^1$ is O (oxygen), $R^1$ is —$Z^1$—$R^9$, $Z^1$ is $N(R^{10})$ and $R^{10}$ is hydrogen, then $R^9$ cannot be an optionally substituted aryl, such as an unsubstituted or substituted phenyl. In other embodiments, when $X^1$ is O (oxygen), $R^1$ is —$Z^1$—$R^9$, $Z^1$ is $N(R^{10})$ and $R^{10}$ is hydrogen, then $R^9$ cannot be an optionally substituted benzyl. In some embodiments, when $X^1$ is O (oxygen), $R^1$ is —$Z^1$—$R^9$, $Z^1$ is $N(R^{10})$ and $R^{10}$ is hydrogen, then $R^9$ cannot be an unsubstituted aryl($C_{1-6}$ alkyl). In still other embodiments, when $X^1$ is O (oxygen), $R^1$ is —$Z^1$—$R^9$, $Z^1$ is $N(R^{10})$ and $R^{10}$ is hydrogen, then $R^9$ cannot be a substituted aryl($C_{1-6}$ alkyl). In yet still other embodiments, when $X^1$ is O (oxygen), $R^1$ is —$Z^1$—$R^9$ and $Z^1$ is $N(R^{10})$, then $R^9$ and $R^{10}$ cannot be an unsubstituted $C_{1-4}$ alkyl. Examples of $C_{1-4}$ alkyls are described herein. In some embodiments, when $X^1$ is O (oxygen), $R^1$ is —$Z^1$—$R^9$ and $Z^1$ is $N(R^{10})$, then $R^9$ and $R^{10}$ cannot both be an optionally substituted alkyl, such as an optionally substituted $C_{1-4}$ alkyl.

In some embodiments, when $X^1$ is O (oxygen), $R^1$ is —$Z^1$—$R^9$ and $Z^1$ is O (oxygen), then $R^9$ cannot be methyl. In some embodiments, when $X^1$ is O (oxygen), $R^1$ is —$Z^1$—$R^9$ and $Z^1$ is O (oxygen), then $R^9$ cannot be an unsubstituted $C_{1-4}$ alkyl. In some embodiments, when $X^1$ is O (oxygen), $R^1$ is —$Z^1$—$R^9$ and $Z^1$ is O (oxygen), then $R^9$ cannot be an optionally substituted alkyl, such as an optionally substituted $C_{1-4}$ alkyl. In other embodiments, when $X^1$ is O (oxygen), $R^1$ is —$Z^1$—$R^9$ and $Z^1$ is O (oxygen), then $R^9$ cannot be —$CH_2$—OC(=O)—($C_{1-4}$ alkyl), such as —$CH_2$—OC(=O)$CH_3$, or —$CH_2$—OC(=O)C($CH_3$). In some embodiments, when $X^1$ is O (oxygen), $R^1$ is —$Z^1$—$R^9$ and $Z^1$ is O (oxygen), then $R^9$ cannot be —$CH_2$—OC(=O)—O—($C_{1-6}$ alkyl), such as —$CH_2$—OC(=O)—O-isopropyl. In still other embodiments, when $X^1$ is O (oxygen), $R^1$ is —$Z^1$—$R^9$ and $Z^1$ is O (oxygen), then $R^9$ cannot be an optionally substituted phenyl. In some embodiments, when $X^1$ is O (oxygen), $R^1$ is —$Z^1$—$R^9$ and $Z^1$ is O (oxygen), then $R^9$ cannot be an unsubstituted aryl. In yet still other embodiments, when $X^1$ is O (oxygen), $R^1$ is $-Z^1-R^9$ and $Z^1$ is O (oxygen), then $R^9$ cannot be an optionally substituted aryl($C_{1-6}$ alkyl), for example, an optionally substituted benzyl.

In some embodiments, when $X^1$ is O (oxygen), $R^1$ is $-Z^1-R^9$ and $Z^1$ is S (sulfur), then $R^9$ cannot be methyl. In some embodiments, when $X^1$ is O (oxygen), $R^1$ is $-Z^1-R^9$ and $Z^1$ is S (sulfur), then $R^9$ cannot be an unsubstituted $C_{1-4}$ alkyl. Examples of $C_{1-4}$ alkyl groups are described herein. In some embodiments, when $X^1$ is O (oxygen), $R^1$ is $-Z^1-R^9$ and $Z^1$ is S (sulfur), then $R^9$ cannot be an optionally substituted alkyl. In other embodiments, when $X^1$ is O (oxygen), $R^1$ is $-Z^1-R^9$ and $Z^1$ is S (sulfur), then $R^9$ cannot be $-CH_2-C(=O)-C(=O)-CH_2$-halo, such as $-CH_2-C(=O)-C(=O)-CH_2Br$, $-CH_2-C(=O)-C(=O)-CH_2Cl$, $-CH_2-C(=O)-C(=O)-CH_2F$, or $-CH_2-C(=O)-C(=O)-CH_2I$. In other embodiments, when $X^1$ is O (oxygen), $R^1$ is $-Z^1-R^9$ and $Z^1$ is S (sulfur), then $R^9$ cannot be $-CH_2-OC(=O)$-t-butyl, $-CH_2-OC(=O)$-methyl, $-CH_2-OC(=O)(C_{1-6}$ alkyl), $-CH_2-OC(=O)-O$-isopropyl, or $-CH_2-OC(=O)-O-(C_{1-6}$ alkyl). In still other embodiments, when $X^1$ is O (oxygen), $R^1$ is $-Z^1-R^9$ and $Z^1$ is S (sulfur), then $R^9$ cannot be 4-nitro-benzyl or 4-isobutyryloxy-benzyl. In some embodiments, when $X^1$ is O (oxygen), $R^1$ is $-Z^1-R^9$ and $Z^1$ is S (sulfur), then $R^9$ cannot be an optionally substituted aryl($C_{1-6}$ alkyl).

The compound of Formula (I) can have various phosphorous containing groups. For example, the cyclic phosphorous containing group can be a cyclic phosphate, a cyclic phosphorothioate, a cyclic phosphoramidate or a cyclic thiophosphoramidate. In some embodiments, $X^1$ can be O (oxygen). In some embodiments, $X^1$ can be O (oxygen), and $R^1$ can be $-Z^1-R^9$. In some embodiments, $X^1$ can be O (oxygen), $R^1$ can be $-Z^1-R^9$, and $Z^1$ can be O (oxygen). In other embodiments, $X^1$ can be O (oxygen), $R^1$ can be $-Z^1-R^9$, and $Z^1$ can be S (sulfur). In other embodiments, $X^1$ can be O (oxygen), $R^1$ can be $-Z^1-R^9$, and $Z^1$ can be) $N(R^{10})$.

In some embodiments, $X^1$ can be S (sulfur). In some embodiments, $X^1$ can be S (sulfur), and $R^1$ can be $-Z^1-R^9$. In some embodiments, $X^1$ can be S (sulfur), $R^1$ can be $-Z^1-R^9$, and $Z^1$ can be O (oxygen). In other embodiments, $X^1$ can be S (sulfur), $R^1$ can be $-Z^1-R^9$, and $Z^1$ can be S (sulfur). In other embodiments, $X^1$ can be S (sulfur), $R^1$ can be $-Z^1-R^9$, and $Z^1$ can be $N(R^{10})$.

The substituents attached to the 5'-position of a compound of Formula (I) can vary. In some embodiments, $R^2$ and $R^3$ can be the same. In other embodiments, $R^2$ and $R^3$ can be different. In some embodiments, at least one of $R^2$ and $R^3$ can be hydrogen. In other embodiments, both $R^2$ and $R^3$ can be hydrogen. In some embodiments, at least one of $R^2$ and $R^3$ can be selected from of an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl), or $R^2$ and $R^3$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl. In some embodiments, at least one of $R^2$ and $R^3$ cannot be hydrogen. In some embodiments, at least one of $R^2$ and $R^3$ can be an optionally substituted $C_{1-6}$-alkyl; and the other of $R^2$ and $R^3$ can be hydrogen. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, at least one of $R^2$ and $R^3$ can be methyl, and the other of $R^2$ and $R^3$ can be hydrogen. In other embodiments, at least one of $R^2$ and $R^3$ can be an optionally substituted $C_{1-6}$-haloalkyl, and the other of $R^2$ and $R^3$ can be hydrogen. One example of a suitable optionally substituted $C_{1-6}$-haloalkyl is $CF_3$. In some embodiments, when $X^1$ is O (oxygen), and $R^1$ is $-O-R^9$ or $-N(R^{10})-R^9$, then at least one of $R^2$ and $R^3$ can be selected from an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl), or $R^2$ and $R^3$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl. In some embodiments, when $X^1$ is O (oxygen), and $R^1$ is $-O-R^9$ or $-N(R^{19})-R^9$, then at least one of $R^2$ and $R^3$ cannot be hydrogen. In some embodiments, $R^3$, $R^4$, $R^5$ and $R^8$ can each be hydrogen; and $R^2$ can be an optionally substituted $C_{1-6}$ alkyl. Suitable $C_{1-6}$ alkyl groups are described herein. When the substituents attached to the 5'-carbon make the 5'-carbon chiral, in some embodiments, the 5'-carbon can be a (R)-stereocenter. In other embodiments, the 5'-carbon can be an (S)-stereocenter.

Various amino acids derivatives can be used, including those described herein. In some embodiments, $R^1$ can be an optionally substituted N-linked α-amino acid. Suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional suitable amino acids include, but are not limited to, alpha-ethyl-glycine, alpha-propyl-glycine and beta-alanine. In other embodiments, $R^1$ can be an optionally substituted N-linked α-amino acid ester derivative. Various amino acid ester derivatives can be used, including those described herein. For example, $R^1$ can be an ester derivative of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of N-linked amino acid ester derivatives include, but are not limited to, an ester derivative of any of the following amino acids: alpha-ethyl-glycine, alpha-propyl-glycine and beta-alanine.

In some embodiments, $R^1$ can be an ester derivative of alanine. In some embodiments, $R^1$ can be selected from alanine methyl ester, alanine ethyl ester, alanine isopropyl ester, alanine cyclohexyl ester, alanine neopentyl ester, valine isopropyl ester and leucine isopropyl ester. In some embodiments, the optionally substituted N-linked amino acid or the optionally substituted N-linked amino acid ester derivative can be in the L-configuration. In other embodiments, the optionally substituted N-linked amino acid or the optionally substituted N-linked amino acid ester derivative can be in the D-configuration.

In some embodiments, $R^1$ can have the structure

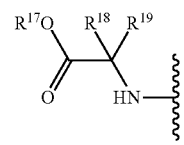

wherein $R^{17}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted $C_{1-6}$, haloalkyl; $R^{18}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{19}$ can be hydrogen or an optionally substituted $C_{1-4}$-alkyl; or $R^{18}$ and $R^{19}$ can be taken together to form an optionally substituted $C_{3-6}$ cycloalkyl.

When $R^1$ has the structure

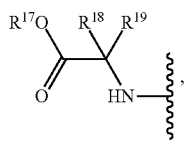

$R^{18}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{18}$ is substituted, $R^{18}$ can be substituted with one or more substituents selected from N-amido, mercapto, alkylthio, an optionally substituted aryl, hydroxy, an optionally substituted heteroaryl, O-carboxy, and amino. In some embodiments, $R^{18}$ can be an unsubstituted $C_{1-6}$-alkyl, such as those described herein. In some embodiments, $R^{18}$ can be methyl.

As to $R^{17}$, in some embodiments, $R^{17}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{17}$ can be methyl or isopropyl. In some embodiments, $R^{17}$ can be ethyl or neopentyl. In other embodiments, $R^{17}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{17}$ can be an optionally substituted cyclohexyl. In still other embodiments, $R^{17}$ can be an optionally substituted aryl, such as phenyl and naphthyl. In yet still other embodiments, $R^{17}$ can be an optionally substituted aryl($C_{1-6}$ alkyl). In some embodiments, $R^{17}$ can be an optionally substituted benzyl. In some embodiments, $R^{17}$ can be an optionally substituted $C_{1-6}$ haloalkyl, for example, $CF_3$.

In some embodiments, $R^{19}$ can be hydrogen. In other embodiments, $R^{19}$ can be an optionally substituted $C_{1-4}$-alkyl, such as methyl, ethyl, n-propyl, isopropyl, n-butyl, isobutyl and tert-butyl. In some embodiments, $R^{19}$ can be methyl. In some embodiments, $R^{18}$ can be hydrogen. In some embodiments, $R^{18}$ and $R^{19}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{18}$ and $R^{19}$, the carbon to which $R^{18}$ and $R^{19}$ are attached may be a chiral center. In some embodiments, the carbon to which $R^{18}$ and $R^{19}$ are attached may be a (R)-chiral center. In other embodiments, the carbon to which $R^{18}$ and $R^{19}$ are attached may be a (S)-chiral center.

As example of a suitable

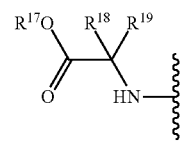

groups include the following:

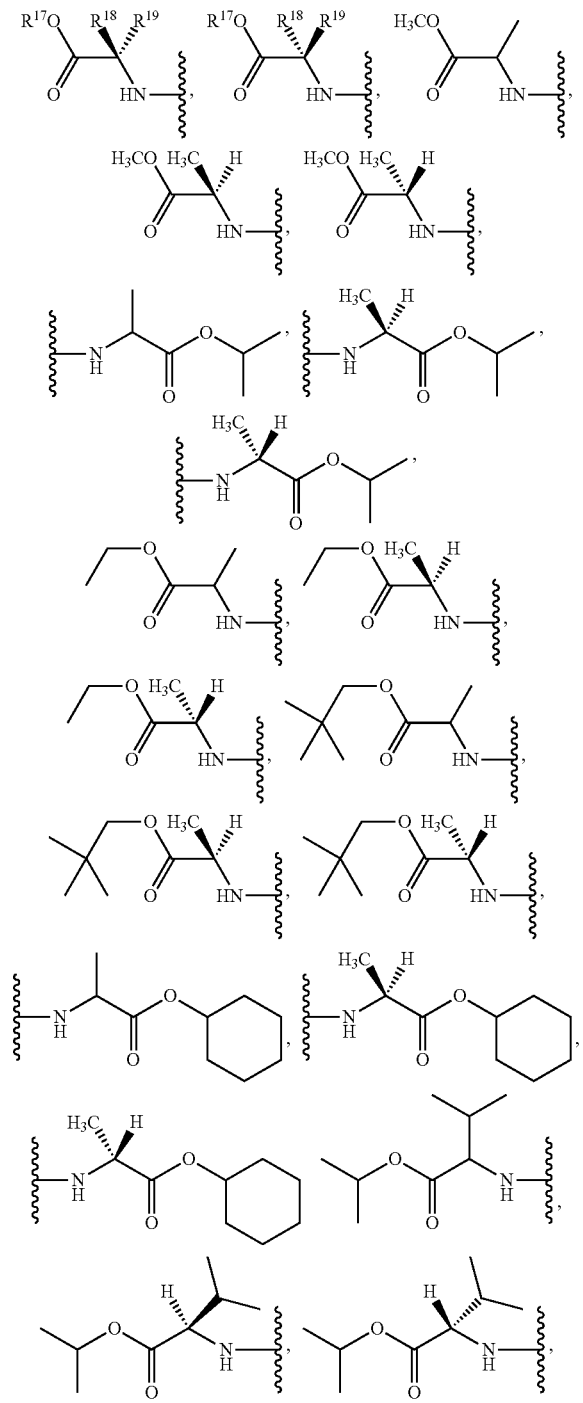

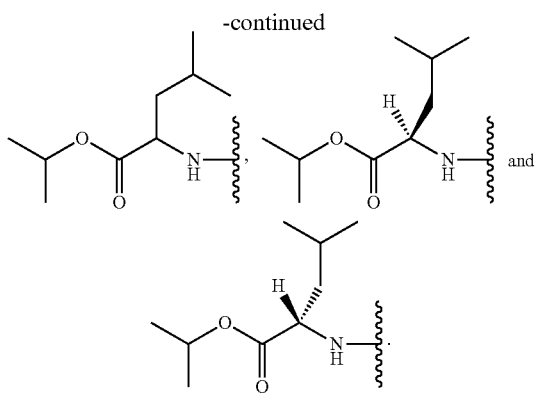

In some embodiments, $R^4$ can be halogen, azido, cyano, an optionally substituted $C_{1-6}$ alkyl, an optionally substituted $C_{2-6}$ alkenyl, an optionally substituted $C_{2-6}$ alkynyl or an optionally substituted allenyl. In some embodiments, $R^4$ can be hydrogen. In other embodiments, $R^4$ can be azido. In other embodiments, $R^4$ can be cyano. In still other embodiments, $R^4$ can be an optionally substituted allenyl. In yet still other embodiments, $R^4$ can be a halogen. In some embodiments, $R^4$ can be fluoro. In other embodiments, $R^4$ can be optionally substituted $C_{1-6}$ alkyl, such as those described herein. In still other embodiments, $R^4$ can be optionally substituted $C_{2-6}$ alkenyl. In yet still other embodiments, $R^4$ can be optionally substituted $C_{2-6}$ alkynyl.

Various substituents can be attached to the 3'-carbon. In some embodiments, $R^5$ can be hydrogen. In other embodiments, $R^5$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained).

The substituents attached to the 2'-carbon can vary. In some embodiments, $R^6$ can be hydrogen. In some embodiments, $R^6$ can be halogen, azido, amino, cyano, an optionally substituted $C_{1-6}$ alkyl, $-OR^{11}$ or $-OC(=O)R^{12}$. In some embodiments, $R^6$ can be halogen. In other embodiments, $R^6$ can be azido. In still other embodiments, $R^6$ can be amino. In yet still other embodiments, $R^6$ can be cyano. In some embodiments, $R^6$ can be an optionally substituted $C_{1-6}$ alkyl. Examples of optionally substituted $C_{1-6}$ alkyl groups include, but are not limited to, methyl, ethyl, n-propyl, isopropyl, n-butyl, isobutyl and tert-butyl. In other embodiments, $R^6$ can be $-OR^{11}$. In some embodiments, when $R^{11}$ is hydrogen, $R^6$ can be a hydroxy group. In other embodiments, when $R^{11}$ is an optionally substituted $C_{1-6}$ alkyl, $R^6$ can be an optionally substituted $C_{1-6}$ alkoxy. Suitable optionally substituted $C_{1-6}$ alkoxy groups are described herein. In some embodiments, $R^6$ can be $-OC(=O)R^{12}$, wherein $R^{12}$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In other embodiments, $R^6$ can be $-OC(=O)R^{12}$, wherein $R^{12}$ can be an optionally substituted $C_{3-6}$ cycloalkyl.

In some embodiments, $R^7$ can be hydrogen. In some embodiments, $R^7$ can be halogen, azido, cyano, an optionally substituted $C_{1-6}$ alkyl, $-OR^{13}$ or $-OC(=O)R^{14}$. In some embodiments, $R^7$ can be halogen. In other embodiments, $R^7$ can be azido. In still other embodiments, $R^7$ can be cyano. In other embodiments, $R^7$ can be an optionally substituted $C_{1-6}$ alkyl. Examples of optionally substituted $C_{1-6}$ alkyl groups include, but are not limited to, methyl, ethyl, n-propyl, isopropyl, n-butyl, isobutyl and tert-butyl. In still other embodiments, $R^7$ can be $-OR^{13}$. When $R^{13}$ is hydrogen, $R^7$ can be hydroxy. Alternatively, when $R^{13}$ is an optionally substituted $C_{1-6}$ alkyl, $R^7$ can be an optionally substituted $C_{1-6}$ alkoxy. Suitable alkoxy groups include methoxy, ethoxy, n-propoxy, isopropoxy, n-butoxy, isobutoxy, tert-butoxy, pentoxy (branched and straight-chained), and hexoxy (branched and straight-chained). In some embodiments, $R^7$ can be $-OC(=O)R^{14}$ in which $R^{14}$ is an optionally substituted $C_{1-6}$ alkyl or an optionally substituted $C_{3-6}$ cycloalkyl. Examples of suitable $C_{1-6}$ alkyl groups are described herein.

In some embodiments, at least one of $R^6$ and $R^7$ can be a halogen. In some embodiments, $R^6$ and $R^7$ can both be a halogen. In other embodiments, $R^6$ can be a halogen and $R^7$ can be an optionally substituted $C_{1-6}$ alkyl, such as those described herein. In still other embodiments, $R^6$ can be a hydroxy and $R^7$ can be an optionally substituted $C_{1-6}$ alkyl, such as those described herein.

In some embodiments, $R^8$ can be hydrogen. In some embodiments, $R^8$ can be halogen, azido, cyano, an optionally substituted $C_{1-6}$ alkyl, $-OR^{15}$ or $-OC(=O)R^{16}$. In some embodiments, $R^8$ can be halogen. In other embodiments, $R^8$ can be azido. In still other embodiments, $R^8$ can be cyano. In other embodiments, $R^8$ can be an optionally substituted $C_{1-6}$ alkyl. Examples of optionally substituted $C_{1-6}$ alkyl groups include, but are not limited to, methyl, ethyl, n-propyl, isopropyl, n-butyl, isobutyl and tert-butyl. In still other embodiments, $R^8$ can be $-OR^{15}$. When $R^{15}$ is hydrogen, $R^8$ can be hydroxy. Alternatively, when $R^{15}$ is an optionally substituted $C_{1-6}$ alkyl, $R^8$ can be an optionally substituted $C_{1-6}$ alkoxy. Suitable alkoxy groups include methoxy, ethoxy, n-propoxy, isopropoxy, n-butoxy, isobutoxy, tert-butoxy, pentoxy (branched and straight-chained), and hexoxy (branched and straight-chained). In some embodiments, $R^8$ can be $-OC(=O)R^{16}$ in which $R^{16}$ is an optionally substituted $C_{1-6}$ alkyl or an optionally substituted $C_{3-6}$ cycloalkyl. Examples of suitable $C_{1-6}$ alkyl groups are described herein.

Those skilled in the art understand that when a hydrogen atom is removed or is absent from an oxygen atom, the oxygen atom can have a negative charge. For example, when $R^6$ is a hydroxy group and the hydrogen is removed or absent, the oxygen atom to which to hydrogen atom was associated with can be Likewise, when $R^7$ or $R^8$ is a hydroxy group and the hydrogen is removed or is absent, the oxygen atom to which to hydrogen atom was associated with can be O$^-$. In some embodiments, $R^2$, $R^3$, $R^4$, $R^5$ and $R^8$ can each be hydrogen.

When $R^1$ is $Z^1-R^9$, the $R^9$ group can vary. In some embodiments, $R^9$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl), an optionally substituted heterocyclyl($C_{1-6}$ alkyl) and Formula (II). In other embodiments, $R^9$ can be selected from an optionally substituted alkynyl, an optionally substituted cycloalkyl, an optionally substituted cycloalkenyl, an optionally substituted heteroaryl, an optionally substituted heterocyclyl, an optionally substituted heteroaryl($C_{1-6}$ alkyl) and an optionally substituted heterocyclyl($C_{1-6}$ alkyl). In some embodiments, $R^9$ can be an optionally substituted alkyl. In some embodiments, $R^9$ can be an optionally substituted $C_{1-6}$ alkyl. Examples of optionally substituted $C_{1-6}$ alkyl groups include, but are not limited to, methyl, ethyl, n-propyl, isopropyl, n-butyl, isobutyl and tert-butyl. In some embodiments, $R^9$ can be an optionally substituted aryl. In some embodiments, $R^9$ can be an optionally substituted phenyl. In some embodiments, $R^9$ can be an optionally substituted aryl($C_{1-6}$ alkyl). In some embodiments, $R^9$ can be benzyl. In some embodiments, $R^9$ can be an optionally substituted cycloalkyl. In some embodiments, $R^9$ can be cyclobutyl, cyclopentyl, or cyclohexyl. In some embodiments, $R^9$ can be —$CH_2$-cyclopropyl. In some embodiments, $R^{10}$ can be hydrogen or an optionally substituted alkyl (for example, an optionally substituted $C_{1-6}$ alkyl).

In some embodiments, $R^9$ can be Formula (II). In some embodiments, $R^{20}$ and $R^{21}$ both can be hydrogen. In some embodiments, $R^{20}$ and $R^{21}$ can each be an optionally substituted $C_{1-24}$ alkyl or an optionally substituted aryl. In some embodiments, at least one of $R^{20}$ and $R^{21}$ can an optionally substituted $C_{1-24}$ alkyl or an optionally substituted aryl, and the other of $R^{20}$ and $R^{21}$ can be hydrogen. In some embodiments, $R^{22}$ can be hydrogen. In some embodiments, $R^{22}$ can be an optionally substituted $C_{1-24}$ alkyl. In some embodiments, $R^{22}$ can be an optionally substituted aryl. In some embodiments, $R^{22}$ can be an optionally substituted —O—$C_{1-24}$ alkyl. In some embodiments, $R^{22}$ can be an optionally substituted —O—$C_{1-6}$ alkyl. Examples of optionally substituted $C_{1-6}$ alkyl groups include, but are not limited to, methyl, ethyl, n-propyl, isopropyl, n-butyl, isobutyl, tert-butyl, pentyl (branched and straight-chained), and hexyl (branched and straight-chained). In some embodiments, $R^{22}$ can be an optionally substituted —O-aryl. In some embodiments, $Y^1$ can be O (oxygen). In some embodiments, $Y^1$ can be S (sulfur). In some embodiments, $R^9$ can be Formula (II), $R^{20}$ and $R^{21}$ both can be hydrogen, $R^{22}$ can be an optionally substituted $C_{1-24}$ alkyl, and $Y^1$ can be O (oxygen). In other embodiments, $R^9$ can be Formula (II), $R^{20}$ and $R^{21}$ both can be hydrogen, $R^{22}$ can be an optionally substituted $C_{1-24}$ alkyl, and $Y^1$ can be S (sulfur). In some embodiments, $R^{20}$ and $R^{21}$ both can be hydrogen, $R^{22}$ can be tert-butyl, and $Y^1$ can be O (oxygen). In other embodiments, $R^{20}$ and $R^{21}$ both can be hydrogen, $R^{22}$ can be tert-butyl, and $Y^1$ can be S (sulfur). In some embodiments, $R^9$ can be pivaloyloxymethyl. In some embodiments, $R^9$ can be isopropyloxycarbonyloxymethyl.

In some embodiments, $R^5$ and $R^8$ can each be hydrogen; and $R^4$ can be azido. In other embodiments, $R^4$, $R^5$, $R^7$ and $R^8$ can each be hydrogen; and $R^6$ can be —OH. In still other embodiments, $R^4$, $R^5$ and $R^8$ can each be hydrogen; and $R^6$ can be halogen. In yet still other embodiments, $R^4$, $R^5$ and $R^8$ can each be hydrogen; and $R^7$ can be an optionally substituted $C_{1-6}$ alkyl. In some embodiments, $R^4$, $R^5$ and $R^8$ can each be hydrogen; $R^6$ can be a halogen; and $R^7$ can be an optionally substituted $C_{1-6}$ alkyl. In other embodiments, $R^4$, $R^5$ and $R^8$ can each be hydrogen; and $R^7$ can be methyl. In still other embodiments, $R^4$, $R^5$ and $R^8$ can each be hydrogen; and $R^7$ can be halogen. In some embodiments, $R^4$, $R^5$ and $R^8$ can each be hydrogen; $R^6$ can be a halogen; and $R^7$ can be a halogen. In yet still other embodiments, $R^4$, $R^5$ and $R^8$ can each be hydrogen; $R^6$ can be —$OR^{11}$; $R^{11}$ can be hydrogen; and $R^7$ can be an optionally substituted $C_{1-6}$ alkyl. In some embodiments, $R^4$, $R^5$ and $R^8$ can each be hydrogen; $R^6$ can be —OH; and $R^7$ can be methyl. In other embodiments, $R^4$, $R^5$ and $R^8$ can each be hydrogen; $R^6$ can be —$OR^{11}$; $R^{11}$ can be hydrogen; and $R^7$ can be halogen. In some of the embodiments of this paragraph, $R^2$ and $R^3$ can both be hydrogen. In some of the embodiments of this paragraph, at least one of $R^2$ and $R^3$ can be an optionally substituted $C_{1-6}$ alkyl; and the other of $R^2$ and $R^3$ can be hydrogen.

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, $B^1$ can be an optionally substituted heterocyclic base or an optionally substituted heterocyclic base with one or more protected amino groups can have one of the following structures:

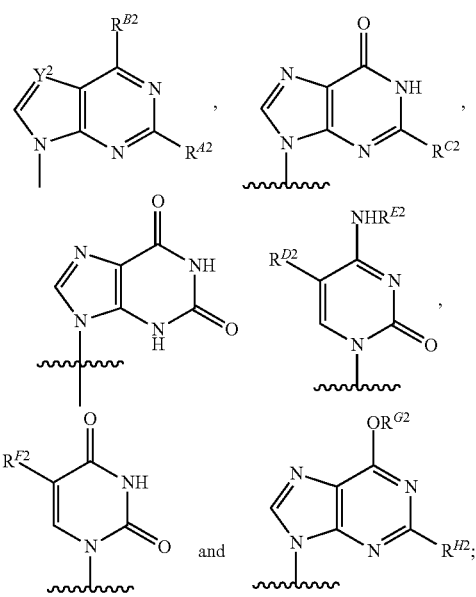

wherein: $R^{A2}$ can be selected from hydrogen, halogen and $NHR^{J2}$, wherein $R^{J2}$ can be selected from hydrogen, —C(=O)$R^{K2}$ and —C(=O)$OR^{L2}$; $R^{B2}$ can be halogen or $NHR^{W2}$, wherein $R^{W2}$ is selected from hydrogen, an optionally substituted $C_{1-6}$ alkyl, an optionally substituted $C_{2-6}$ alkenyl, an optionally substituted $C_{3-8}$ cycloalkyl, —C(=O)$R^{m2}$ and —C(=O)$OR^{N2}$; $R^{C2}$ can be hydrogen or $NHR^{O2}$, wherein $R^{O2}$ can be selected from hydrogen, —C(=O)$R^{P2}$ and —C(=O)$OR^{Q2}$; $R^{D2}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{E2}$ can be selected from hydrogen, an optionally substituted $C_{1-6}$ alkyl, an optionally substituted $C_{3-5}$ cycloalkyl, —C(=O)$R^{R2}$ and —C(=O)$OR^{S2}$; $R^{F2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^2$ can be N (nitrogen) or $CR^{12}$, wherein $R^{12}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{G2}$ can be an optionally substituted $C_{1-6}$ alkyl; $R^{H2}$ can be hydrogen or $NHR^{T2}$, wherein $R^{T2}$ can be independently selected from hydrogen, —C(=O)$R^{U2}$ and —C(=O)$OR^{V2}$, and $R^{K2}$, $R^{L2}$, $R^{M2}$, $R^{N2}$, $R^{P2}$, $R^{Q2}$ $R^{R2}$, $R^{S2}$, $R^{U2}$ and $R^{V2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloalkynyl, $C_{6-10}$ aryl, heteroaryl, heterocyclyl, aryl($C_{1-6}$ alkyl), heteroaryl ($C_{1-6}$ alkyl) and heterocyclyl($C_{1-6}$ alkyl). In some embodiments, the structures shown above can be modified by replacing one or more hydrogens with substituents selected from the list of substituents provided for the definition of "substituted."

In some embodiments, $B^1$ can be selected from adenine, guanine, thymine, cytosine and uracil. In some embodiments, $B^1$ can be an optionally substituted

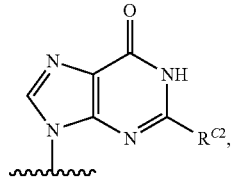

such as

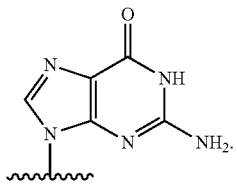 [SMILES: *n1cnc2c(=O)[nH]c(N)nc21]

In still other embodiments, $B^1$ can be

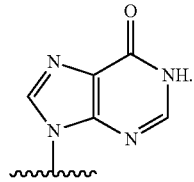 [SMILES: *n1cnc2c(=O)[nH]cnc21]

In yet still other embodiments, $B^1$ can be an optionally substituted

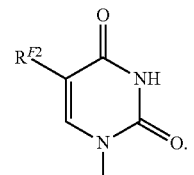

In some embodiments $R^{F2}$ can be hydrogen. In some embodiments, $B^1$ can be

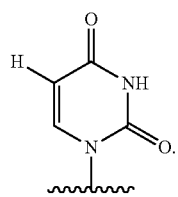

In some embodiments, $B^1$ can be an optionally substituted

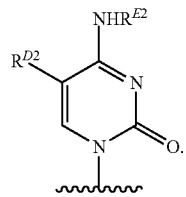

In some embodiments $R^{E2}$ is hydrogen. In some embodiments, $B^1$ can be

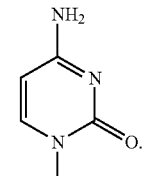

In other embodiments, $B^1$ can be

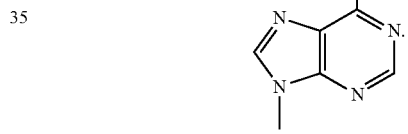

In yet still other embodiments, $B^1$ can be

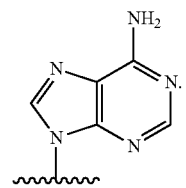 [SMILES: *n1cnc2c(N)ncnc21]

In some embodiments, $B^1$ can be an optionally substituted

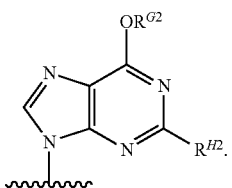

For example, $B^1$ can be wherein $R^{G2}$ can be an optionally substituted $C_{1-4}$ alkyl; and $R^{H2}$ can be $NH_2$. In some embodiments, $R^{G2}$ can be methyl or ethyl.

In some embodiments, when $X^1$ is S (sulfur), $R^1$ is $—Z^1—R^9$ and $Z^1$ is $N(R^{10})$, then $B^1$ can be an optionally substituted cytosine or an optionally substituted uracil. In some embodiments, when $X^1$ is O (oxygen), $R^1$ is $—Z^1—R^9$ and $Z^1$ is S (sulfur), then $B^1$ can be an optionally substituted cytosine.

In some embodiments, if $B^1$ is an optionally substituted guanine, then $R^1$ can be an optionally substituted N-linked amino acid or an optionally substituted N-linked amino acid ester derivative. In other embodiments, if $B^1$ is an optionally substituted guanine and $R^1$ is $—Z^1—R^9$, then $R^9$ can be a substituted alkyl, such as a substituted $C_{1-6}$ alkyl. In still other embodiments, if $B^1$ is an optionally substituted guanine and $R^1$ is $—Z^1—R^9$, then $R^9$ can be a substituted alkenyl. In yet still other embodiments, if $B^1$ is an optionally substituted guanine and $R^1$ is $—Z^1—R^9$, then $R^9$ can be an unsubstituted aryl. In some embodiments, if $B^1$ is an optionally substituted guanine and $R^1$ is $—Z^1—R^9$, then $R^9$ can be Formula (II). In some embodiments, if $B^1$ is an optionally substituted guanine and $R^1$ is $—Z^1—R^9$, then $R^9$ can be Formula (II), wherein $R^{20}$ and $R^{21}$ both can be hydrogen, $R^{22}$ can be an optionally substituted $C_{1-24}$ alkyl, and $Y^1$ can be O (oxygen) or S (sulfur). In some embodiments, if $B^1$ is an optionally substituted guanine and $R^1$ is $—Z^1—R^9$, then $R^9$ can be pivaloyloxymethyl. In some embodiments, if $B^1$ is an optionally substituted guanine and $R^1$ is $—Z^1—R^9$, then $R^9$ can be isopropyloxycarbonyloxymethyl. In some of the embodiments of this paragraph, the optionally substituted guanine can be a protected guanine. In some of the embodiments of this paragraph, $X^1$ is S (sulfur). In some of the embodiments of this paragraph, $X^1$ is O (oxygen).

In some embodiments, if $B^1$ is an optionally substituted uracil, then $R^1$ can be an optionally substituted N-linked amino acid or an optionally substituted N-linked amino acid ester derivative. In other embodiments, if $B^1$ is an optionally substituted uracil and $R^1$ is $—Z^1—R^9$, then $R^9$ can be a substituted alkyl. In still embodiments, if $B^1$ is an optionally substituted uracil and $R^1$ is $—Z^1—R^9$, then $R^9$ can be an unsubstituted aryl. In some embodiments, if $B^1$ is an optionally substituted uracil and $R^1$ is $—Z^1—R^9$, then $R^9$ can be Formula (II). In some embodiments, if $B^1$ is an optionally substituted uracil and $R^1$ is $—Z^1—R^9$, then $R^9$ can be Formula (II), wherein $R^{20}$ and $R^{21}$ both can be hydrogen, $R^{22}$ can be an optionally substituted $C_{1-24}$ alkyl, and $Y^1$ can be O (oxygen) or S (sulfur). In some embodiments, if $B^1$ is an optionally substituted uracil and $R^1$ is $—Z^1—R^9$, then $R^9$ can be pivaloyloxymethyl. In some embodiments, if $B^1$ is an optionally substituted uracil and $R^1$ is $—Z^1—R^9$, then $R^9$ can be isopropyloxycarbonyloxymethyl. In some of the embodiments of this paragraph, the optionally substituted uracil can be a protected uracil. In some of the embodiments of this paragraph, $X^1$ is S (sulfur). In some of the embodiments of this paragraph, $X^1$ is O (oxygen).

In some embodiments, if $B^1$ is an optionally substituted thymine, then $R^1$ can be an optionally substituted N-linked amino acid or an optionally substituted N-linked amino acid ester derivative. In other embodiments, if $B^1$ is an optionally substituted thymine and $R^1$ is $—Z^1—R^9$, then $R^9$ can be a substituted alkyl. In still other embodiments, if $B^1$ is an optionally substituted thymine and $R^1$ is $—Z^1—R^9$, then $R^9$ can be a substituted alkenyl. In yet still other embodiments, if $B^1$ is an optionally substituted thymine and $R^1$ is $—Z^1—R^9$, then $R^9$ can be a substituted aryl. In some embodiments, if $B^1$ is an optionally substituted thymine and $R^1$ is $—Z^1—R^9$, then $R^9$ can be Formula (II). In some embodiments, if $B^1$ is an optionally substituted thymine and $R^1$ is $—Z^1—R^9$, then $R^9$ can be Formula (II), wherein $R^{20}$ and $R^{21}$ both can be hydrogen, $R^{22}$ can be an optionally substituted $C_{1-24}$ alkyl, and $Y^1$ can be O (oxygen) or S (sulfur). In some embodiments, if $B^1$ is an optionally substituted thymine and $R^1$ is $—Z^1—R^9$, then $R^9$ can be pivaloyloxymethyl. In some embodiments, if $B^1$ is an optionally substituted thymine and $R^1$ is $—Z^1—R^9$, then $R^9$ can be isopropyloxycarbonyloxymethyl. In some of the embodiments of this paragraph, the optionally substituted thymine can be a protected thymine. In some of the embodiments of this paragraph, $X^1$ is S (sulfur). In some of the embodiments of this paragraph, $X^1$ is O (oxygen).

In some embodiments, if $B^1$ is an optionally substituted adenine, then $R^1$ can be an optionally substituted N-linked amino acid or an optionally substituted N-linked amino acid ester derivative. In other embodiments, if $B^1$ is an optionally substituted adenine and $R^1$ is $—Z^1—R^9$, then $R^9$ can be a substituted alkyl. In still other embodiments, if $B^1$ is an optionally substituted adenine and $R^1$ is $—Z^1—R^9$, then $R^9$ can be a substituted alkenyl. In some embodiments, if $B^1$ is an optionally substituted adenine and $R^1$ is $—Z^1—R^9$, then $R^9$ can be Formula (II). In some embodiments, if $B^1$ is an optionally substituted adenine and $R^1$ is $—Z^1—R^9$, then $R^9$ can be Formula (II), wherein $R^{20}$ and $R^{21}$ both can be hydrogen, $R^{22}$ can be an optionally substituted $C_{1-24}$ alkyl, and $Y^1$ can be O (oxygen) or S (sulfur). In some embodiments, if $B^1$ is an optionally substituted adenine and $R^1$ is $—Z^1—R^9$, then $R^9$ can be pivaloyloxymethyl. In some embodiments, if $B^1$ is an optionally substituted adenine and $R^1$ is $—Z^1—R^9$, then $R^9$ can be isopropyloxycarbonyloxymethyl. In some of the embodiments of this paragraph, the optionally substituted adenine can be a protected adenine. In some of the embodiments of this paragraph, $X^1$ is S (sulfur). In some of the embodiments of this paragraph, $X^1$ is O (oxygen).

In some embodiments, if $B^1$ is an optionally substituted cytosine, then $R^1$ can be an optionally substituted N-linked amino acid or an optionally substituted N-linked amino acid ester derivative. In other embodiments, if $B^1$ is an optionally substituted cytosine and $R^1$ is $—Z^1—R^9$, then $R^9$ can be a substituted alkyl. In still other embodiments, if $B^1$ is an optionally substituted cytosine and $R^1$ is $—Z^1—R^9$, then $R^9$ can be a substituted alkenyl. In yet still other embodiments, if $B^1$ is an optionally substituted cytosine and $R^1$ is $—Z^1—R^9$, then $R^9$ can be a substituted aryl. In some embodiments, if $B^1$ is an optionally substituted cytosine and $R^1$ is $—Z^1—R^9$, then $R^9$ can be Formula (II). In some embodiments, if $B^1$ is an optionally substituted cytosine and $R^1$ is $—Z^1—R^9$, then $R^9$ can be Formula (II), wherein $R^{20}$ and $R^{21}$ both can be hydrogen, $R^{22}$ can be an optionally substituted $C_{1-24}$ alkyl, and $Y^1$ can be O (oxygen) or S (sulfur). In some embodiments, if $B^1$ is an optionally substituted cytosine and $R^1$ is $—Z^1—R^9$, then $R^9$ can be pivaloyloxymethyl. In some embodiments, if $B^1$ is an optionally substituted cytosine and $R^1$ is $—Z^1—R^9$, then $R^9$ can be isopropyloxycarbonyloxymethyl. In some of the embodiments of this paragraph, the optionally substituted cytosine can be a protected cytosine. In some of the embodiments of this paragraph, $X^1$ is S (sulfur). In some of the embodiments of this paragraph, $X^1$ is O (oxygen).

In some embodiments, $R^4$ cannot be hydrogen. In some embodiments, $R^5$ cannot be hydrogen. In some embodiments, $R^6$ cannot be hydrogen. In some embodiments, $R^6$ cannot be a hydroxy group. In other embodiments, when $R^6$ is —OC(=O)$R^{12}$, then $R^{12}$ cannot be —CH—(CH$_3$)$_2$. In still other embodiments, when $R^6$ is —OC(=O)$R^{12}$, then $R^{12}$ cannot be an optionally substituted alkyl, for example, a substituted $C_{1-4}$ alkyl or an unsubstituted $C_{1-4}$ alkyl. In some embodiments, $R^7$ cannot be hydrogen. In some embodiments, $R^8$ cannot be hydrogen. In some embodiments, $R^9$ cannot be an optionally substituted alkyl, such as a substituted or unsubstituted $C_{1-4}$ alkyl. In other embodiments, $R^9$ cannot be an optionally substituted alkenyl, for example —CH$_2$CH=CH$_2$. In still other embodiments, $R^9$ cannot be an optionally substituted aryl, such as an optionally substituted phenyl. In yet still other embodiments, $R^9$ cannot be an optionally substituted aryl($C_{1-6}$ alkyl), such as an optionally substituted benzyl. In some embodiments, $R^9$ cannot be —CH$_2$—OC(=O)CH$_3$, —CH$_2$—OC(=O)-t-butyl, —CH$_2$—OC(=O)($C_{1-6}$ alkyl), —CH$_2$—OC(=O)—O-isopropyl, or —CH$_2$—OC(=O)—O—($C_{1-6}$ alkyl). In some embodiments, $B^1$ cannot be an optionally substituted such as

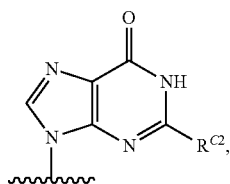

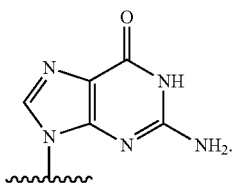 [SMILES: *n1cnc2c(=O)[nH]c(N)nc21]

In some embodiments, $B^1$ cannot be an optionally substituted

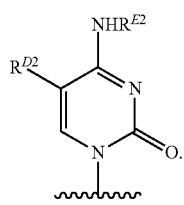

In some embodiments, $B^1$ cannot be an optionally substituted

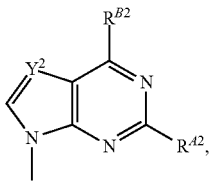

such as

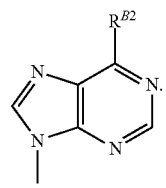

In some embodiments, $B^1$ cannot be an optionally substituted

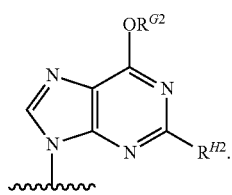

In some embodiments, $B^1$ cannot be a dimethylformamide protected guanine or a 2-(nitrophenyl)ethyl protected guanine. In other embodiments, $B^1$ cannot be an acyl protected guanine. In still other embodiments, $B^1$ cannot be a 2-(nitrophenyl)ethyl protected uracil. In some embodiments, $B^1$ cannot be a 2-(nitrophenyl)sulfonylethyl protected uracil. In yet still other embodiments, $B^1$ cannot be a benzoyl protected adenine. In some embodiments, $B^1$ cannot be an anisoyl protected cytosine. In some embodiments, if $B^1$ is an optionally substituted guanine and $R^1$ is —$Z^1$—$R^9$, then $R^9$ cannot be methyl, —CH$_2$CH=CH$_2$, 2-chlorophenyl or —CH$_2$—C(=O)—C(=O)—CH$_2$-halo, such as —CH$_2$—C(=O)—C(=O)—CH$_2$Br, —CH$_2$—C(=O)—C(=O)—CH$_2$Cl, —CH$_2$—C(=O)—C(=O)—CH$_2$F, or —CH$_2$—C(=O)—C(=O)—CH$_2$I. In some embodiments, if $B^1$ is an optionally substituted uracil and $R^1$ is —$Z^1$—$R^9$, then $R^9$ cannot be methyl or 2-chlorophenyl. In some embodiments, if $B^1$ is an optionally substituted thymine and $R^1$ is —$Z^1$—$R^9$, then $R^9$ cannot be methyl or —CH$_2$CH=CH$_2$. In other embodiments, if $B^1$ is an optionally substituted thymine and $R^1$ is —$Z^1$—$R^9$, then $R^9$ cannot be an optionally substituted phenyl. In yet still other embodiments, if is an optionally substituted adenine and $R^1$ is —$Z^1$—$R^9$, then $R^9$ cannot be methyl or ethyl. In some embodiments, if $B^1$ is an optionally substituted adenine and $R^1$ is —$Z^1$—$R^9$, then $R^9$ cannot be —CH$_2$CH=CH$_2$. In other embodiments, if $B^1$ is an optionally substituted adenine and $R^1$ is —$Z^1$—$R^9$, then $R^9$ cannot be phenyl. In some embodiments, if $B^1$ is an optionally substituted adenine and $R^1$ is —$Z^1$—$R^9$, then $R^9$ cannot be 2-chlorophenyl, 4-nitrobenzyl or 4-isobutyryloxy-benzyl. In other embodiments, if $B^1$ is an optionally substituted adenine and $R^1$ is —$Z^1$—$R^9$, then $R^9$ cannot be —CH$_2$—C(=O)—C(=O)—CH$_2$-halo, such as —CH$_2$—C(=O)—C(=O)—CH$_2$Br, —$C_{1-12}$—C(=O)—C(=O)—CH$_2$Cl, —CH$_2$—C(=O)—C(=O)—CH$_2$F, or —CH$_2$—C(=O)—C(=O)—CH$_2$I. In other embodiments, if $B^1$ is an optionally substituted adenine and $R^1$ is $-Z^1-R^9$, then $R^9$ cannot be $-CH_2-OC(=O)CH_3$, $-CH_2-OC(=O)C(CH_3)_3$, $-CH_2-OC(=O)(C_{1-6}$ alkyl), $-CH_2-OC(=O)-O$-isopropyl, or $-CH_2-C(=O)-O-(C_{1-6}$ alkyl).

Depending upon the substituents attached to the phosphorus atom, the phosphorus atom can be a chiral center. In some embodiments, the phosphorus can be a (R)-stereocenter. In other embodiments, the phosphorus can be a (S)-stereocenter.

In some embodiments, a compound of Formula (I) can be a single diastereomer. In other embodiments, a compound of Formula (I) can be a mixture of diastereomers. In some embodiments, a compound of Formula (I) can be a 1:1 mixture of two diastereomers. In some embodiments, a compound of Formula (I) can be diasteriometrically enriched (for example, one diastereomer can be present at a concentration of >55%, ≥75%, ≥80%, ≥90%, ≥95%, ≥98%, or ≥99% as compared to the total concentration of the other diastereomers).

Some embodiments of $R^1$ of a compound of Formula (I), or a pharmaceutically acceptable salt thereof, are provided in Table 1. Tables 2-3 provide the structures of the variables aa01-aa11 and es01-es14, respectively. For example, the first entry in Table 1 is "aa01,es01," which corresponds to a compound of Formula (I), wherein $R^1$ is

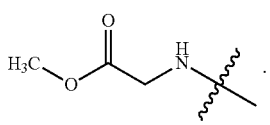 [SMILES: *NCC(=O)OC]

TABLE 1

| $R^1, R_\alpha$ | $R^1, R_\alpha$ | $R^1, R_\alpha$ | $R^1, R_\alpha$ | $R^1, R_\alpha$ | $R^1, R_\alpha$ |
|---|---|---|---|---|---|
| aa01, es01 | aa02, es01 | aa03, es01 | aa04, es01 | aa05, es01 | aa06, es09 |
| aa01, es02 | aa02, es02 | aa03, es02 | aa04, es02 | aa05, es02 | aa06, es10 |
| aa01, es03 | aa02, es03 | aa03, es03 | aa04, es03 | aa05, es03 | aa06, es11 |
| aa01, es04 | aa02, es04 | aa03, es04 | aa04, es04 | aa05, es04 | aa06, es12 |
| aa01, es05 | aa02, es05 | aa03, es05 | aa04, es05 | aa05, es05 | aa07, es09 |
| aa01, es06 | aa02, es06 | aa03, es06 | aa04, es06 | aa05, es06 | aa07, es10 |
| aa01, es07 | aa02, es07 | aa03, es07 | aa04, es07 | aa05, es07 | aa07, es11 |
| aa01, es08 | aa02, es08 | aa03, es08 | aa04, es08 | aa05, es08 | aa07, es12 |
| aa01, es09 | aa02, es09 | aa03, es09 | aa04, es09 | aa05, es09 | aa08, es09 |
| aa01, es10 | aa02, es10 | aa03, es10 | aa04, es10 | aa05, es10 | aa08, es10 |
| aa01, es11 | aa02, es11 | aa03, es11 | aa04, es11 | aa05, es11 | aa08, es11 |
| aa01, es12 | aa02, es12 | aa03, es12 | aa04, es12 | aa05, es12 | aa08, es12 |
| aa06, es01 | aa07, es01 | aa08, es01 | aa09, es01 | aa10, es01 | aa09, es09 |
| aa06, es02 | aa07, es02 | aa08, es02 | aa09, es02 | aa10, es02 | aa09, es10 |
| aa06, es03 | aa07, es03 | aa08, es03 | aa09, es03 | aa10, es03 | aa09, es11 |
| aa06, es04 | aa07, es04 | aa08, es04 | aa09, es04 | aa10, es04 | aa09, es12 |
| aa06, es05 | aa07, es05 | aa08, es05 | aa09, es05 | aa10, es05 | aa10, es09 |
| aa06, es06 | aa07, es06 | aa08, es06 | aa09, es06 | aa10, es06 | aa10, es10 |
| aa06, es07 | aa07, es07 | aa08, es07 | aa09, es07 | aa10, es07 | aa10, es11 |
| aa06, es08 | aa07, es08 | aa08, es08 | aa09, es08 | aa10, es08 | aa10, es12 |

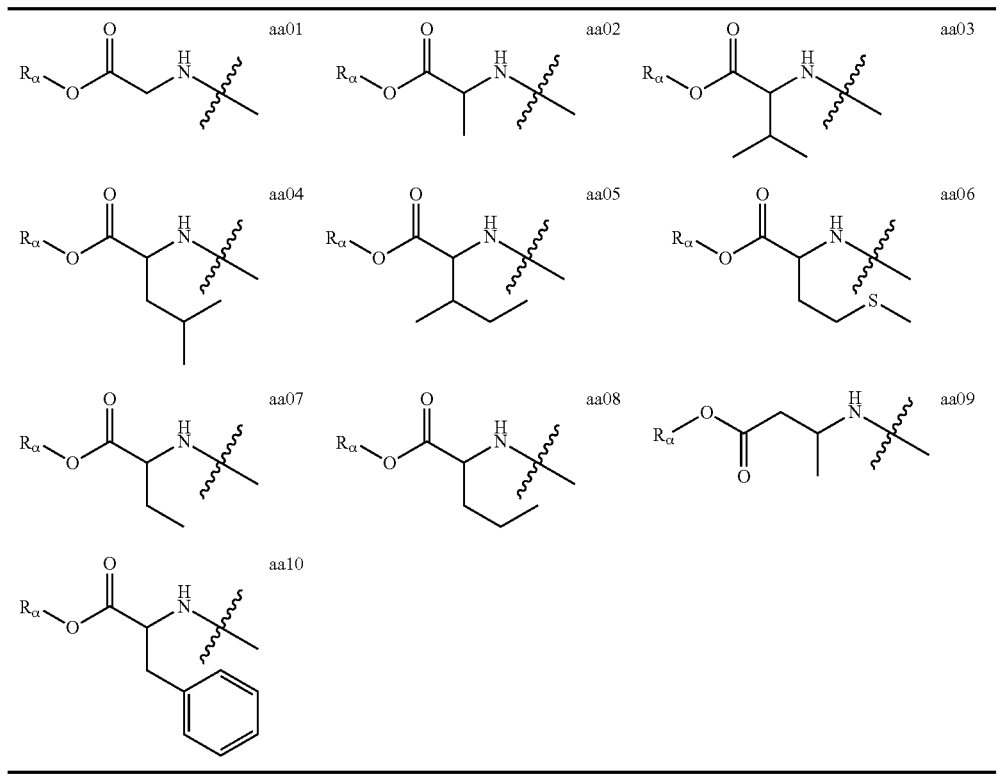

TABLE 2

TABLE 3

| es01 | $R_\alpha$ = methyl | es02 | $R_\alpha$ = ethyl | es03 | $R_\alpha$ = isopropyl |
|---|---|---|---|---|---|
| es04 | $R_\alpha$ = propyl | es05 | $R_\alpha$ = cyclohexyl | es06 | $R_\alpha$ = cyclopentyl |
| es07 | $R_\alpha$ = cyclobutyl | es08 | $R_\alpha$ = cyclopropyl | es09 | $R_\alpha$ = benzyl |
| es11 | $R_\alpha$ = neopentyl | es10 | $R_\alpha$ = t-butyl | es12 | $R_\alpha$ = hydrogen |

Examples of compounds of Formula (I) include, but are not limited to the following:

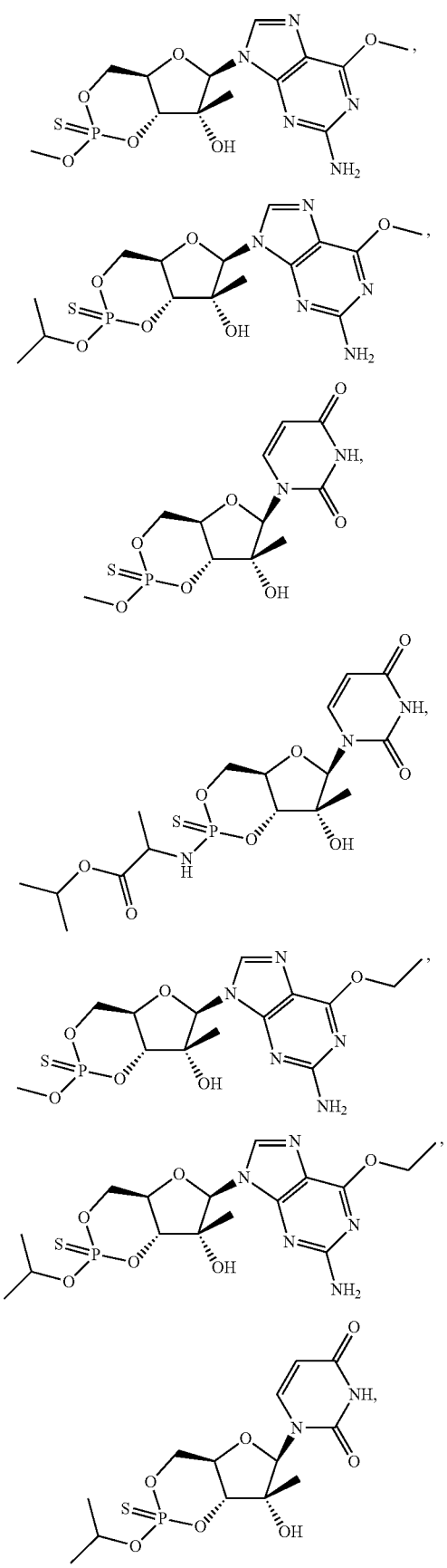
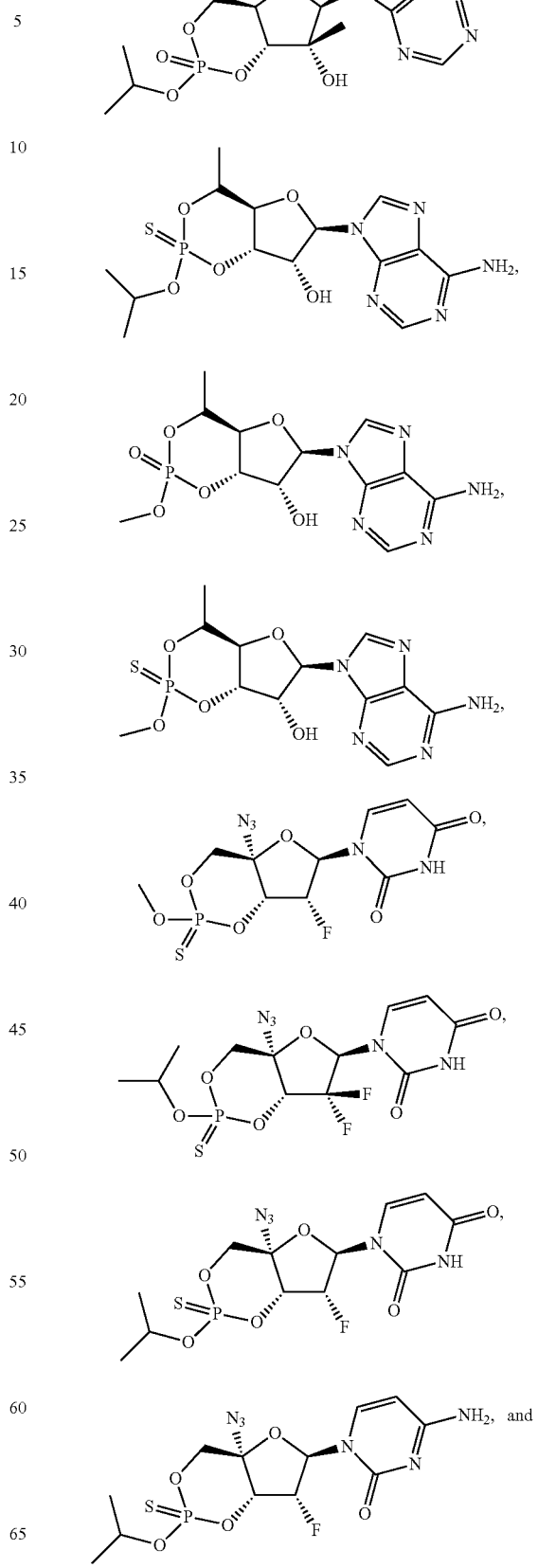

-continued

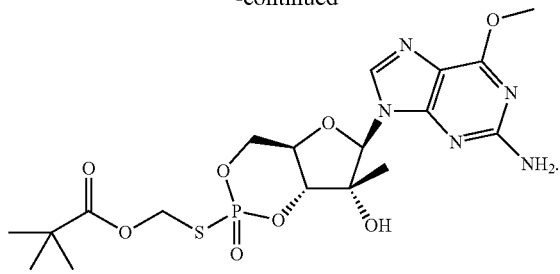

Synthesis

Compounds of Formula (I), and those described herein may be prepared in various ways. General synthetic routes to the compound of Formula (I), and some examples of starting materials used to synthesize the compounds of Formula (I) are shown in Schemes 1 and 2, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1:

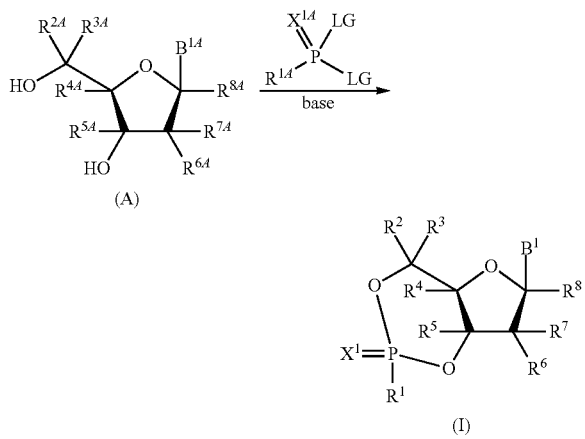

One method for forming a compound of Formula (I) is shown in Scheme 1. In Scheme 1, $R^{1A}$, $R^{2A}$, $R^{3A}$, $R^{4A}$, $R^{5A}$, $R^{6A}$, $R^{7A}$, $R^{8A}$, $X^{1A}$ and $B^{1A}$ can be the same as $R^1$, $R^2$, $R^3$, $R^4$, $R^5$, $R^6$, $R^7$, $R^8$, $X^1$ and $B^1$ as described herein for Formula (I); and each LG can be a leaving group, such as a halogen or a sulfonate ester. As shown in Scheme 1, a nucleoside with a hydroxy group attached to the 3'-carbon and a hydroxy group attached to 5'-carbon can be reacted with a compound having the formula, $R^{1A}P(=X^{1A})(LG)_2$, in the presence of a base, to produce a compound of Formula (I). Suitable bases are known to those skilled in the art. For example, the base can be an amine base, such as an alkylamine (including mono-, di- and tri-alkylamines (e.g., triethylamine)), optionally substituted pyridines (e.g., collidine) and optionally substituted imidazoles (e.g., N-methylimidazole)).

Scheme 2:

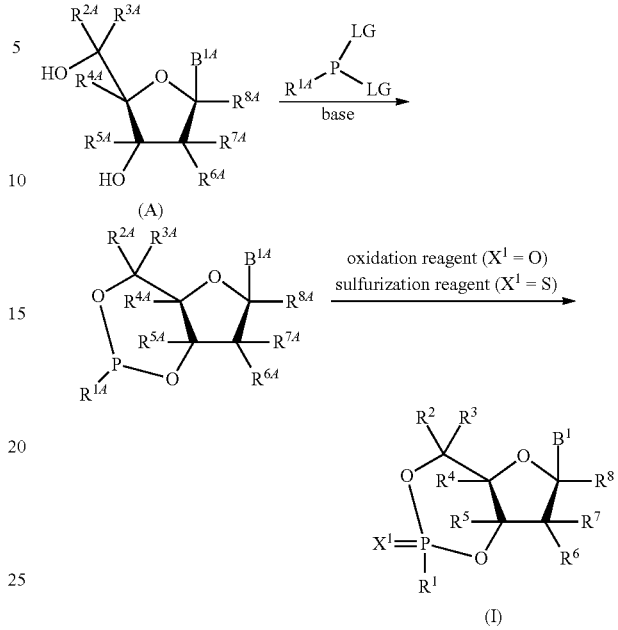

Another method for forming a compound of Formula (I) is shown in Scheme 2. In Scheme 2, $R^{1A}$, $R^{2A}$, $R^{3A}$, $R^{4A}$, $R^{5A}$, $R^{6A}$, $R^{7A}$, $R^{8A}$, $X^{1A}$ and $B^{1A}$ can be the same as $R^1$, $R^2$, $R^3$, $R^4$, $R^5$, $R^6$, $R^7$, $R^8$, $X^1$ and $B^1$ as described herein for Formula (I); and each LG can be a leaving group, such as a halogen or a sulfonate ester. As illustrated in Scheme 2, a compound having a hydroxy group attached to the 3'-carbon and a hydroxy group attached to the 5'-carbon can be reacted with a compound having the formula, $R^{1A}P(LG)_2$, in the presence of a base, to produce a phosphite compound. Suitable bases are known to those skilled in the art and described herein. The phosphorus can then be oxidized to phosphorus(V) using a suitable oxidizing agent, to produce a compound of Formula (I) where $X^1$ is O (oxygen). Alternatively, the phosphite compound can be reacted with a sulfurization reagent to produce a compound of Formula (I) where $X^1$ is S (sulfur). Suitable oxidizing and sulfurization agents are known to those skilled in the art. For example, the oxidation can be carried out using iodine as the oxidizing agent and water as the oxygen donor. Suitable sulfurization agents include, but are not limited to, elemental sulfur, Lawesson's reagent, cyclooctasulfur, 3H-1, 2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

Any —NH, $NH_2$ and/or keto groups present on $B^{1A}$, for example, when $B^{1A}$ is an optionally substituted heterocyclic base, can be protected with one or more suitable protecting groups. Examples of suitable protecting groups include triarylmethyl groups, (2-nitrophenyl)ethyl groups, acyl groups, and dialkylformamidine groups. To reduce the formation of side products, one or more the groups attached to the pentose ring can be protected with one or more suitable protecting groups. As an example, if $R^{4A}$, $R^{5A}$, $R^{6A}$, $R^{7A}$ and/or $R^{8A}$ is/are hydroxy group(s), the hydroxy group(s) can be protected with suitable protecting groups, such as triarylmethyl and/or silyl groups. Examples of triarylmethyl groups include but are not limited to, trityl, monomethoxytrityl (MMTr), 4,4'-dimethoxytrityl (DMTr), 4,4',4"-trimethoxytrityl (TMTr), 4,4',4"-tris- (benzoyloxy)trityl (TBTr), 4,4',4"-tris (4,5-dichlorophthalimido) trityl (CPTr), 4,4',4"-tris (levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr) and 4,4'-di-3,5-hexadienoxytrityl. Examples of silyl groups include, but are not limited to, trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl. Alternatively, at least two of $R^{4A}$, $R^{5A}$, $R^{6A}$, $R^{7A}$ and $R^{8A}$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy)propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal.

The chirality of the 5'-carbon of compounds of Formulae (A) and/or (I) can be inverted using methods known to the skilled in the art. For example, the oxygen attached to the 5'-carbon can be oxidized, for example to an aldehyde for a compound of Formula (A) or ketone for a compound of Formula (I), using a suitable oxidizing agent. The aldehyde and/or ketone can then be reduced using a suitable reducing agent. Examples of suitable reducing agents include, but are not limited to, $NaH$, $LiH$, $NaBH_4$, $LiAlH_4$ and $CaH_2$. Suitable oxidizing and reducing agents are known to those skilled in the art. Examples of suitable oxidizing agents and conditions are described herein.

In some embodiments, $R^6$, $R^7$ and/or $R^8$ can be $-OC(=O)R^{11}$, $-OC(=O)R^{13}$, and $-OC(=O)R^{15}$, respectively. The $-OC(=O)R^{11}$, $-OC(=O)R^{13}$, and $-OC(=O)R^{15}$ groups can be formed at the 1' and 2'-positions using various methods known to those skilled in the art. As an example, a compound of Formula (I), wherein $R^6$ and $R^8$ are both hydroxy groups, can be treated with an alkyl anhydride (e.g., acetic anhydride and propionic anhydride) or an alkyl acid chloride (e.g., acetochloride). If desired, a catalyst can be used to facilitate the reaction. An example of suitable catalyst is 4-dimethylaminopyridine (DMAP). Alternatively, the $-OC(=O)R^{11}$ and $-OC(=O)R^{15}$ groups can be formed at the 1' and 2'-positions by reacting an alkyl acid (e.g., acetic acid and propionic acid) in the presences of a carbodiimide or a coupling reagent. Examples of carbodiimides include, but are not limited to, N,N-dicyclohexylcarbodiimide (DCC), N,N'-diisopropylcarbodiimide (DIC) and 1-ethyl-3-(3-dimethylaminopropyl)carbodiimide (EDC).

As described herein, $B^{1A}$ can include a carbamate and/or an amide. Those skilled in the art know methods for forming a carbamate and/or an amide on $B^{1A}$. In some embodiments, the carbamate can be formed using 1,1'-carbonyldiimidazole and an alcohol.

During the synthesis of any of the compounds described herein, if desired, any hydroxy groups attached to the pentose ring, and any $-NH$, $NH_2$ and/or keto groups present on the $B^{1A}$ can be protected with one or more suitable protecting groups. Suitable protecting groups are described herein. Those skilled in the art will appreciate that groups attached to the pentose ring and any $-NH$, $NH_2$ and/or keto groups present on the $B^{1A}$ can be protected with various protecting groups, and any protecting groups present can be exchanged for other protecting groups. The selection and exchange of the protecting groups is within the skill of those of ordinary skill in the art. Any protecting group(s) can also be removed by methods known in the art, for example, with an acid (e.g., a mineral or an organic acid), a base or a fluoride source.

In some embodiments, neutralizing the charge on the phosphate group may facilitate the penetration of the cell membrane by a compound of Formula (I), or a pharmaceutically acceptable salt thereof, by making the compound more lipophilic compared to a nucleotide having a comparable structure with one or more charges present on the phosphate. Once absorbed and taken inside the cell, the groups attached to the phosphate can be easily removed by esterases, proteases or other enzymes. In some embodiments, the groups attached to the phosphate can be removed by simple hydrolysis. Inside the cell, the monophosphate or mono-thiophosphate thus released may then be metabolized by cellular enzymes to the diphosphate or the active triphosphate, or the α-thiodiphosphate or the active α-thiotriphosphate, respectively. Furthermore, in some embodiments, varying the substituents on a cyclic nucleotide analog compound described herein, such as compound of Formula (I), can help maintain the efficacy of such compounds by reducing undesirable effects, such as isomerization.

In some embodiments, a compound of Formula (I), or a pharmaceutically acceptable salt thereof, can act as a chain terminator of HCV replication. For example, incorporation of a compound of Formula (I) containing a moiety at the 2'-carbon position can terminate further elongation of the RNA chain of HCV. For example, a compound of Formula (I) can contain a 2'-carbon modification wherein $R^7$ is a non-hydrogen group selected from halogen or an optionally substituted $C_{1-6}$ alkyl.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. In some embodiments, a compound of Formula (I), or a pharmaceutically acceptable salt thereof, can have improved properties. A non-limiting list of example properties include, but are not limited to, increased biological half life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formula (I), or a pharmaceutically acceptable salt thereof, can have more potent antiviral activity (for example, a lower $IC_{50}$ in an HCV replicon assay) as compared to the current standard of care.

Additionally, in some embodiments, the presence of a phosphorothioate, phosphoramidate or phosphorothioamidate in a compound of Formula (I) can increase the stability of the compound by inhibiting its degradation. Also, in some embodiments, the presence of a phosphorothioate, phosphoramidate or phosphorothioamidate can make the compound more resistant to cleavage in vivo and provide sustained, extended efficacy. In some embodiments, a phosphorothioate, phosphoramidate or phosphorothioamidate can facilitate the penetration of the cell membrane by a compound of Formula (I) by making the compound more lipophilic.

Pharmaceutical Compositions

Some embodiments described herein relates to a pharmaceutical composition, that can include a therapeutically effective amount of one or more compounds described herein (e.g., a compound of Formula (I), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments disclosed herein relate to a method of treating and/or ameliorating a disease or condition that can include administering to a subject a therapeutically effective amount of one or more compounds described herein, such as a compound of Formula (I), or a pharmaceutically acceptable salt thereof, or a pharmaceutical composition that includes a compound described herein, or a pharmaceutically acceptable salt thereof.

Some embodiments disclosed herein relate to a method of ameliorating or treating a neoplastic disease that can include administering to a subject suffering from a neoplastic disease a therapeutically effective amount of one or more compounds described herein (e.g., a compound of Formula (I), or a pharmaceutically acceptable salt thereof), or a pharmaceutical composition that includes a compound described herein, or a pharmaceutically acceptable salt thereof. In some embodiments, the neoplastic disease can be cancer. In some embodiments, the neoplastic disease can be a tumor such as a solid tumor. In some embodiments, the neoplastic disease can be leukemia. Exemplary leukemias include, but are not limited to, acute lymphoblastic leukemia (ALL), acute myeloid leukemia (AML) and juvenile myelomonocytic leukemia (JMML).

Some embodiments disclosed herein relate to a method of inhibiting the growth of a tumor that can include administering to a subject having a tumor a therapeutically effective amount of one or more compounds described herein (for example, a compound of Formula (I)), or a pharmaceutical composition that includes one or more compounds described herein, or a pharmaceutically acceptable salt thereof.

Other embodiments disclosed herein relates to a method of ameliorating or treating a viral infection that can include administering to a subject suffering from a viral infection a therapeutically effective amount of one or more compounds described herein (for example, a compound of Formula (I)), or a pharmaceutical composition that includes one or more compounds described herein, or a pharmaceutically acceptable salt thereof. In some embodiments, the viral infection can be caused by a virus selected from an adenovirus, an Alphaviridae, an Arbovirus, an Astrovirus, a Bunyaviridae, a Coronaviridae, a Filoviridae, a Flaviviridae, a Hepadnaviridae, a Herpesviridae, an Alphaherpesvirinae, a Betaherpesvirinae, a Gammaherpesvirinae, a Norwalk Virus, an Astroviridae, a Caliciviridae, an Orthomyxoviridae, a Paramyxoviridae, a ParamyxoViruses, a Rubulavirus, a Morbillivirus, a Papovaviridae, a Parvoviridae, a Picornaviridae, an Aphthoviridae, a Cardioviridae, an Enteroviridae, a Coxsackie virus, a Polio Virus, a Rhinoviridae, a Phycodnaviridae, a Poxyiridae, a Reoviridae, a Rotavirus, a Retroviridae, an A-Type Retrovirus, an Immunodeficiency Virus, a Leukemia Viruses, an Avian Sarcoma Viruses, a Rhabdoviruses, a Rubiviridae, a Togaviridae an Arenaviridae and/or a Bornaviridae. In some embodiments, the viral infection can be a hepatitis C viral (HCV) infection. In other embodiments, the viral infection can be influenza. In still other embodiments, the viral infection can be HIV.

Some embodiments disclosed herein relate to methods of ameliorating and/or treating a viral infection that can include contacting a cell infected with the virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a viral infection that can include contacting a cell infected with the virus with an effective amount of said compound(s). Still other embodiments described herein relate to one or more compounds described herein, or a pharmaceutically acceptable salt of a compound described herein, that can be used for ameliorating and/or treating a viral infection by contacting a cell infected with the virus with an effective amount of said compound(s). In some embodiments, the compound can be a compound of Formula (I), or a pharmaceutical acceptable salt thereof. In other embodiments, the compound can be a mono-, di- and/or tri-phosphate of a compound of Formula (I), or a pharmaceutically acceptable salt of the foregoing. In some embodiments, the virus can be a HCV virus.

Some embodiments disclosed herein relate to methods of inhibiting replication of a virus that can include contacting a cell infected with the virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a virus that can include contacting a cell infected with the virus with an effective amount of said compound(s). Still other embodiments described herein relate to a compound described herein, or a pharmaceutically acceptable salt of a compound described herein, that can be used for inhibiting replication of a virus by contacting a cell infected with the virus with an effective amount of said compound(s). In some embodiments, the compound can be a compound of Formula (I), or a pharmaceutical acceptable salt thereof. In other embodiments, the compound can be a mono-, di- and/or tri-phosphate of a compound of Formula (I), or a pharmaceutically acceptable salt of the foregoing. In some embodiments, the virus can be a HCV virus.

HCV is an enveloped positive strand RNA virus in the Flaviviridae family. There are various nonstructural proteins of HCV, such as NS2, NS3, NS4, NS4A, NS4B, NS5A, and NS5B. NS5B is believed to be an RNA-dependent RNA polymerase involved in the replication of HCV RNA.

Some embodiments described herein relate to a method of inhibiting NS5B polymerase activity that can include contacting a cell (for example, a cell infected with HCV) with an effective amount of a compound of Formula (I), or a pharmaceutical acceptable salt thereof. Some embodiments described herein relate to a method of inhibiting NS5B polymerase activity that can include administering a cell (for example, a cell infected with HCV) with an effective amount of a compound of Formula (I), or a pharmaceutical acceptable salt thereof. In some embodiments, a compound of Formula (I), or a pharmaceutically acceptable salt thereof, can inhibit a RNA dependent RNA polymerase. In some embodiments, a compound of Formula (I), or a pharmaceutically acceptable salt thereof, can inhibit a HCV polymerase (for example, NS5B polymerase).

Some embodiments described herein relate to a method of treating HCV infection in a subject suffering from a HCV infection that can include administering to the subject an effective amount of a compound of Formula (I), or a pharmaceutical acceptable salt thereof, or a pharmaceutical composition that includes an effective amount of a compound of Formula (I), or a pharmaceutical acceptable salt thereof. Some embodiments described herein relate to a method of treating a condition selected from liver fibrosis, liver cirrhosis, and liver cancer in a subject suffering from one or more of the aforementioned liver conditions that can include administering to the subject an effective amount of a compound or a pharmaceutical composition described herein (for example, a compound of Formula (I), or a pharmaceutical acceptable salt thereof). One cause of liver fibrosis, liver cirrhosis, and/or liver cancer can be a HCV infection. Some embodiments described herein relate to a method of increasing liver function in a subject having a HCV infection that can include administering to the subject an effective amount of a compound or a pharmaceutical composition described herein (for example, a compound of Formula (I), or a pharmaceutical acceptable salt thereof). Also contemplated is a method for reducing or eliminating further virus-caused liver damage in a subject having an HCV infection by administering to the subject an effective amount of a compound or a pharmaceutical composition described herein (for example, a compound of Formula (I), or a pharmaceutical acceptable salt thereof). In some embodiments, this method can include slowing or halting the progression of liver disease. In other embodiments, the course of the disease can be reversed, and stasis or improvement in liver function is contemplated.

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4-e; 5a; 6a; 7a-7b; 8a-8b; 9a; 10a; and 11a). In some embodiments, an effective amount of a compound of Formula (I), or a pharmaceutical acceptable salt thereof, or a pharmaceutical composition that includes an effective amount of a compound of Formula (I), or a pharmaceutical acceptable salt thereof, can be effective to treat at least one genotype of HCV. In some embodiments, a compound described herein (for example, a compound of Formula (I), or a pharmaceutical acceptable salt thereof) can be effective to treat all 11 genotypes of HCV. In some embodiments, a compound described herein (for example, a compound of Formula (I), or a pharmaceutical acceptable salt thereof) can be effective to treat 3 or more, 5 or more, 7 or more, or 9 or more genotypes of HCV. In some embodiments, a compound of Formula (I), or a pharmaceutical acceptable salt thereof can be more effective against a larger number of HCV genotypes than the standard of care. In some embodiments, a compound of Formula (I), or a pharmaceutical acceptable salt thereof, can be more effective against a particular HCV genotype than the standard of care (such as genotype 1, 2, 3, 4, 5 and/or 6).

Various indicators for determining the effectiveness of a method for treating a HCV infection are known to those skilled in the art. Examples of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase, and/or other indicator of disease response. Similarly, successful therapy with an effective amount of a compound or a pharmaceutical composition described herein (for example, a compound of Formula (I), or a pharmaceutical acceptable salt thereof) can reduce the incidence of liver cancer in HCV infected subjects.

In some embodiments, an effective amount of a compound of Formula (I), or a pharmaceutically acceptable salt thereof, is an amount that is effective to reduce viral titers to undetectable levels, for example, to about 1000 to about 5000, to about 500 to about 1000, or to about 100 to about 500 genome copies/mL serum. In some embodiments, an effective amount of a compound of Formula (I), or a pharmaceutically acceptable salt thereof, is an amount that is effective to reduce viral load compared to the viral load before administration of the compound of Formula (I), or a pharmaceutically acceptable salt thereof. For example, wherein the viral load is measured before administration of the compound of Formula (I), or a pharmaceutically acceptable salt thereof, and again after completion of the treatment regime with the compound of Formula (I), or a pharmaceutically acceptable salt thereof (for example, 1 month after completion). In some embodiments, an effective amount of a compound of Formula (I), or a pharmaceutically acceptable salt thereof, can be an amount that is effective to reduce viral load to lower than about 100 genome copies/mL serum. In some embodiments, an effective amount of a compound of Formula (I), or a pharmaceutically acceptable salt thereof, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of the compound of Formula (I), or a pharmaceutically acceptable salt thereof. For example, the viral load can be measured before administration of the compound of Formula (I), or a pharmaceutically acceptable salt thereof, and again after completion of the treatment regime with the compound of Formula (I), or a pharmaceutically acceptable salt thereof (for example, 1 month after completion).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of HCV relative to pre-treatment levels in a subject, as determined after completion of the treatment regime (for example 1 month after completion). In some embodiments, a compound of Formula (I), or a pharmaceutically acceptable salt thereof, can result in a reduction of the replication of HCV relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of HCV replication in the range of 1 to 1.5 log, 1.5 log to 2 log, 2 log to 2.5 log, 2.5 to 3 log, 3 log to 3.5 log or 3.5 to 4 log more reduction of HCV replication compared to the reduction of HCV reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of a compound of Formula (I), or a pharmaceutically acceptable salt thereof, is an amount that is effective to achieve a sustained viral response, for example, non-detectable or substantially non-detectable HCV RNA (e.g., less than about 500, less than about 400, less than about 200, or less than about 100 genome copies per milliliter serum) is found in the subject's serum for a period of at least about one month, at least about two months, at least about three months, at least about four months, at least about five months, or at least about six months following cessation of therapy.

In some embodiments, a therapeutically effective amount of a compound of Formula (I), or a pharmaceutically acceptable salt thereof, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of example markers includes measuring the levels of serum alanine aminotransferase (ALT), asparatate aminotransferacse (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51

IU/L, TBIL in the range of 0.3-1.9 mg/dL is considered normal. In some embodiments, an effective amount of a compound of Formula (I), or a pharmaceutically acceptable salt thereof, can be an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a compound of Formula (I), or a pharmaceutically acceptable salt thereof, can be administered to a treatment failure subject suffering from HCV. In some embodiments, a compound of Formula (I), or a pharmaceutically acceptable salt thereof, can be administered to a non-responder subject suffering from HCV. In some embodiments, a compound of Formula (I), or a pharmaceutically acceptable salt thereof, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an HCV strain that is resistant to one or more different anti-HCV agents. In some embodiments, development of resistant HCV strains is delayed when a subject is treated with a compound of Formula (I), or a pharmaceutically acceptable salt thereof, compared to the development of HCV strains resistant to other HCV drugs.

In some embodiments, an effective amount of a compound of Formula (I), or a pharmaceutically acceptable salt thereof, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a compound of Formula (I), or a pharmaceutically acceptable salt thereof, can be provided to a subject that is hypersensitive to interferon and/or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formula (I), or a pharmaceutically acceptable salt thereof, can be administered to a subject experiencing viral load rebound, or can prevent such viral load rebound when used to treat the subject.

The standard of care for treating HCV has been associated with several side effects (adverse events). In some embodiments, a compound of Formula (I), or a pharmaceutically acceptable salt thereof, can decrease the number and/or severity of a side effect that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of apetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formula (I), or a pharmaceutically acceptable salt thereof, can be provided to a subject that discontinued a HCV therapy because of one or more adverse effects or side effects associated with one or more other HCV agents.

Table 4 provides some embodiments of the percentage improvement obtained using a compound of Formula (I), or a pharmaceutically acceptable salt thereof, as compared to the standard of care. Examples include the following: in some embodiments, a compound of Formula (I), or a pharmaceutically acceptable salt thereof, results in a percentage of non-responders that is 10% less than the percentage of non-responders receiving the standard of care; in some embodiments, a compound of Formula (I), or a pharmaceutically acceptable salt thereof, results in a number of side effects that is in the range of about 10% to about 30% less than compared to the number of side effects experienced by a subject receiving the standard of care; and in some embodiments, a compound of Formula (I), or a pharmaceutically acceptable salt thereof, results in a severity of a side effect (such as one of those described herein) that is 25% less than compared to the severity of the same side effect experienced by a subject receiving the standard of care. Methods of quantifying the severity of a side effect are known to those skilled in the art.

TABLE 4

| Percentage of non-responders | Percentage of relapsers | Percentage of resistance | Percentage of viral load rebound | Number of side effects | Severity of side effects |
| --- | --- | --- | --- | --- | --- |
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

Yet still other embodiments disclosed herein relate to a method of ameliorating or treating a parasitic disease that can include administering to a subject suffering from a parasitic disease a therapeutically effective amount of one or more compounds described herein (for example, a compound of Formula (I)), or a pharmaceutical composition that includes one or more compounds described herein. In some embodiments, the parasite disease can be Chagas' disease.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a HCV infection. In some embodiments, the total time of the treatment regime with a compound of Formula (I), or a pharmaceutically acceptable salt thereof, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s). Examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, agents currently used in a conventional standard of care for treating HCV, HCV protease inhibitors, HCV polymerase inhibitors, NS5A inhibitors, other antiviral compounds, compounds of Formula (AA) (including mono-, di, and/or tri-phosphates of Formula (AA), pharmaceutically acceptable salts and pharmaceutical compositions that can include a compound of Formula (AA), mono-, di- and/or tri-phosphates thereof, or a pharmaceutically acceptable salt of the foregoing), compounds of Formula (CC) (including pharmaceutically acceptable salts and pharmaceutical compositions that can include a compound of Formula (CC), or a pharmaceutically acceptable salt thereof), compounds of Formula (DD) (including pharmaceutically acceptable salts and pharmaceutical compositions that can include a compound of Formula (DD), or a pharmaceutically acceptable salt thereof), and/or combinations thereof. In some embodiments, a compound of Formula (I), or a pharmaceutically acceptable salt thereof, or a pharmaceutical composition that includes a compound of Formula (I), or a pharmaceutically acceptable salt thereof, can be used with one, two, three or more additional agents described herein. A non-limiting list of examples of combinations of a compound of Formula (I), or a pharmaceutically acceptable salt thereof, or a pharmaceutical composition that includes a compound of Formula (I), or a pharmaceutically acceptable salt thereof, is provided in Tables A, B, C and D.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, or Pegylated interferon-alpha-2b (brand name PEG-INTRON®) and ribavirin. As another example, a compound disclosed herein can be used in combination with oseltamivir (TAMIFLU®) or zanamivin (RELENZA®) for treating an influenza infection.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HCV, a compound of Formula (I), or a pharmaceutically acceptable salt thereof, or a pharmaceutical composition that includes a compound of Formula (I), or a pharmaceutically acceptable salt thereof, can be used in place of ribavirin.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435, ITMN-191 (DANOPREVIR®) and/or a combination thereof. A non-limiting list of example HCV protease inhibitors includes the compounds numbered 1001-1014 in FIGS. 1A-1B.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, INX-189, PSI-352938, PSI-661, 4'-azidouridine (including known prodrugs of 4'-azidouridine), GS-6620, IDX-184 and TMC649128, and/or combinations thereof. A non-limiting list of example nucleoside inhibitors includes compounds numbered 2001-2010 in FIG. 2. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside inhibitors includes the compounds numbered 3001-3008 in FIG. 3.

In some embodiments, a compound of Formula (I), or a pharmaceutically acceptable salt thereof, or a pharmaceutical composition that includes a compound of Formula (I), or a pharmaceutically acceptable salt thereof, can be used in combination with a NS5A inhibitor. A non-limiting list of example NS5A inhibitors include BMS-790052, PPI-461, ACH-2928, GS-5885, BMS-824393 and/or combinations thereof. A non-limiting list of example NS5A inhibitors includes the compounds numbered 4001-4005 in FIG. 4.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, Debio-025, MIR-122 and/or combinations thereof. A non-limiting list of example other antiviral compounds includes the compounds numbered 5001-5002 in FIG. 5.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (AA), mono-, di- and/or tri-phosphate thereof, or a pharmaceutically acceptable salt of the foregoing, or a pharmaceutical composition that includes a compound of Formula (AA), mono-, di- and/or tri-phosphate thereof, or a pharmaceutically acceptable salt of the foregoing (see, U.S. application Ser. No. 13/236,450, filed Sep. 19, 2011, and U.S. Provisional Application Nos. 61/385,425, filed Sep. 22, 2010, and 61/426,467, filed Dec. 22, 2010, the contents of which are incorporated by reference in their

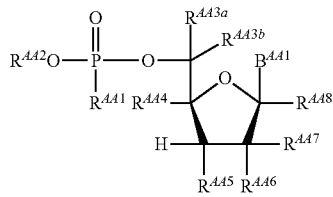

Formula (AA)

wherein $B^{AA1}$ can be an optionally substituted heterocyclic base or an optionally substituted heterocyclic base with a protected amino group; $R^{AA1}$ can be an optionally substituted N-linked amino acid or an optionally substituted N-linked amino acid ester derivative; $R^1$ be selected from an optionally substituted aryl, an optionally substituted heteroaryl and an optionally substituted heterocyclyl; $R^{AA3a}$ and $R^{AA3b}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl), provided that at least one of $R^{AA3a}$ and $R^{AA3b}$ is not hydrogen; or $R^{AA3a}$ and $R^{AA3b}$ can be taken together to form a group selected from an optionally substituted $C_{3-6}$ cycloalkyl, an optionally substituted $C_{3-6}$ cycloalkenyl, an optionally substituted $C_{3-6}$ aryl, and an optionally substituted $C_{3-6}$ heteroaryl; $R^{AA4}$ can be hydrogen; $R^{AA5}$ can be selected from hydrogen, $-OR^{AA9}$ and $-OC(=O)R^{AA10}$; $R^{AA6}$ can be selected from hydrogen, halogen, $-OR^{AA11}$ and $-OC(=O)R^{AA12}$; or $R^{AA5}$ and $R^{AA6}$ can be both oxygen atoms and linked together by a carbonyl group; $R^{AA7}$ can be selected from hydrogen, halogen, an optionally substituted $C_{1-6}$ alkyl, $-OR^{AA13}$ and $-OC(=O)R^{AA14}$; $R^{AA8}$ can be hydrogen or an optionally substituted $C_{1-6}$ alkyl; $R^{AA9}$, $R^{AA11}$ and $R^{AA13}$ can be independently selected from hydrogen and an optionally substituted $C_{1-6}$ alkyl; and $R^{AA10}$, $R^{AA12}$ and $R^{AA14}$ can be independently selected from an optionally substituted $C_{1-6}$ alkyl and an optionally substituted $C_{3-6}$ cycloalkyl. A non-limiting list of examples of compounds of Formula (AA), and phosphates thereof, includes the compounds numbered 7000-7077 in FIGS. 7A-7O. In some embodiments, Formula (AA) cannot be compound 7044, 7045, 7046, 7047, 7048, 7049, 7050, 7072, 7073, 7074, 7075, 7076 or 7077.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (CC), or a pharmaceutically acceptable salt thereof, or a pharmaceutical composition that includes a compound of Formula (CC), or a pharmaceutically acceptable salt thereof (see, U.S. application Ser. No. 13/236,435, filed Sep. 19, 2011, and U.S. Provisional Application Nos. 61/385,363, filed Sep. 22, 2010, and 61/426,461, filed Dec. 22, 2010, the contents of which are incorporated by reference in their entireties):

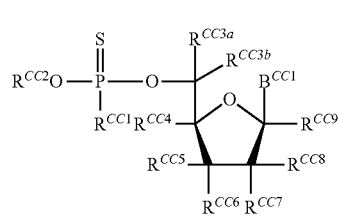

Formula (CC)

wherein $B^{CC1}$ can be an optionally substituted heterocyclic base or an optionally substituted heterocyclic base with a protected amino group; $R^{CC1}$ can be selected from O⁻, OH, an optionally substituted N-linked amino acid and an optionally substituted N-linked amino acid ester derivative; $R^{CC2}$ can be selected from an optionally substituted aryl, an optionally substituted heteroaryl, an optionally substituted heterocyclyl and

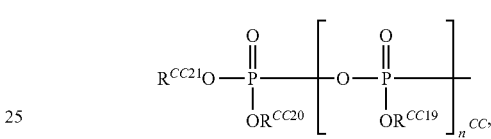

wherein $R^{CC19}$, $R^{CC20}$ and $R^{CC21}$ can be independently absent or hydrogen, and $n^{CC}$ can be 0 or 1; provided that when $R^{CC1}$ is O⁻ or OH, then $R^{CC2}$ is

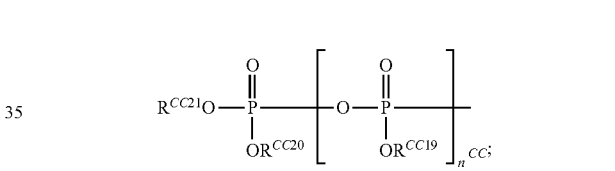

$R^{CC3a}$ and $R^{CC3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{CC3a}$ and $R^{CC3b}$ can be taken together to form an optionally substituted $C_{3-6}$ cycloalkyl; $R^{CC4}$ can be selected from hydrogen, azido, an optionally substituted $C_{1-6}$ alkyl, an optionally substituted $C_{2-6}$ alkenyl and an optionally substituted $C_{2-6}$ alkynyl; $R^{CC5}$ can be selected from hydrogen, halogen, azido, cyano, an optionally substituted $C_{1-6}$ alkyl, $-OR^{CC10}$ and $-OC(=O)R^{CC11}$; $R^{CC6}$ can be selected from hydrogen, halogen, azido, cyano, an optionally substituted $C_{1-6}$ alkyl, $-OR^{CC12}$ and $-OC(=O)R^{CC13}$; $R^{CC7}$ can be selected from hydrogen, halogen, azido, cyano, an optionally substituted $C_{1-6}$ alkyl, $-OR^{CC14}$ and $-OC(=O)R^{CC15}$; or $R^{CC6}$ and $R^{CC7}$ can be both oxygen atoms and linked together by a carbonyl group; $R^{CC8}$ can be selected from hydrogen, halogen, azido, cyano, an optionally substituted $C_{1-6}$ alkyl, $-OR^{CC16}$ and $-OC(=O)R^{CC17}$; $R^{CC9}$ can be selected from hydrogen, azido, cyano, an optionally substituted $C_{1-6}$ alkyl and $-OR^{CC18}$; $R^{CC10}$, $R^{CC12}$, $R^{CC14}$, $R^{CC16}$ and $R^{CC18}$ can be independently selected from hydrogen and an optionally substituted $C_{1-6}$ alkyl; and $R^{CC11}$, $R^{CC13}$, $R^{CC15}$ and $R^{CC17}$ can be independently selected from an optionally substituted $C_{1-6}$ alkyl and an optionally substituted $C_{3-6}$ cycloalkyl. In some embodiments, when $R^{CC3a}$, $R^{CC3b}$, $R^{CC4}$, $R^{CC5}$, $R^{CC7}$, $R^{CC8}$ and $R^{CC9}$ are all hydrogen, then $R^{CC6}$ is not azido. In some embodiments, $R^{CC2}$ cannot be

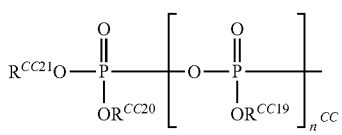

when $R^{CC3a}$ is hydrogen, $R^{CC3b}$ is hydrogen, $R^{CC4}$ is H, $R^{CC5}$ is OH or H, $R^{CC6}$ is hydrogen, OH, or —OC(=O)CH$_3$, $R^{CC7}$ is hydrogen, OH, OCH$_3$ or —OC(=O)CH$_3$, $R^{CC8}$ is hydrogen, OH or OCH$_3$, $R^{CC9}$ is H and $B^{CC1}$ is an optionally substituted adenine, an optionally substituted guanine, an optionally substituted uracil or an optionally substituted hypoxanthine. In some embodiments, $R^{CC2}$ cannot be

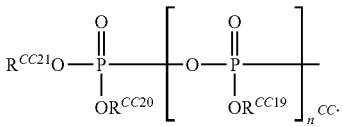

A non-limiting list of examples of compounds of Formula (CC) includes the compounds numbered 6000-6078 in FIGS. 6A-6M.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (DD), or a pharmaceutically acceptable salt thereof, or a pharmaceutical composition that includes a compound of Formula (DD), or a pharmaceutically acceptable salt thereof (see, e.g., U.S. Publication No. 2010-0249068, filed Mar. 19, 2010, the contents of which are incorporated by reference in its entirety):

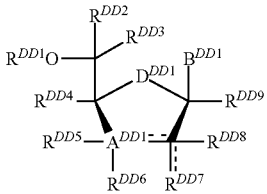

Formula (DD)

wherein each ------ can be independently a double or single bond; $A^{DD1}$ can be selected from C (carbon), O (oxygen) and S (sulfur); $B^{DD1}$ can be an optionally substituted heterocyclic base or a derivative thereof; $D^{DD1}$ can be selected from C=CH$_2$, CH$_2$, O (oxygen), S (sulfur), CHF, and CF$_2$; $R^{DD1}$ can be hydrogen, an optionally substituted alkyl, an optionally substituted cycloalkyl, an optionally substituted aralkyl, dialkylaminoalkylene, alkyl-C(=O)—, aryl-C(=O)—, alkoxyalkyl-C(=O)—, aryloxyalkyl-C(=O)—, alkylsulfonyl, arylsulfonyl, aralkylsulfonyl,

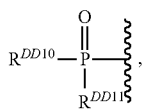

an —O-linked amino acid, diphosphate, triphosphate or derivatives thereof; $R^{DD2}$ and $R^{DD3}$ can be each independently selected from hydrogen, an optionally substituted C$_{1-6}$ alkyl, an optionally substituted C$_{2-6}$ alkenyl, an optionally substituted C$_{2-6}$ alkynyl and an optionally substituted C$_{1-6}$ haloalkyl, provided that at least one of $R^{DD2}$ and $R^{DD3}$ cannot be hydrogen; or $R^{DD2}$ and $R^{DD3}$ are taken together to form a group selected from among C$_{3-6}$ cycloalkyl, C$_{3-6}$ cycloalkenyl, C$_{3-6}$ aryl, and a C$_{3-6}$ heteroaryl; $R^{DD4}$ and $R^{DD9}$ can be independently selected from hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$, —C(=O)NR$^{DDa1}$R$^{DDb1}$, —O—(C=O)R$^{DDa1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted C$_{1-6}$ alkyl, an optionally substituted C$_{2-6}$ alkenyl, an optionally substituted C$_{2-6}$ alkynyl, an optionally substituted aralkyl and an —O-linked amino acid; $R^{DD5}$, $R^{DD6}$ and $R^{DD7}$ can be independently absent or selected from hydrogen, halogen, —NH$_2$, —NHR$^{DDa1}$, NR$^{DDa1}$R$^{DDb1}$, —OR$^{DDa1}$, —SR$^{DDa1}$, CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$, —C(=O)NR$^{DDa1}$R$^{DDb1}$, —O—(C=O)R$^{DDa1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted C$_{1-6}$ alkyl, an optionally substituted C$_{2-6}$ alkenyl, an optionally substituted C$_{2-6}$ alkynyl, an optionally substituted aralkyl and an —O-linked amino acid; or $R^{DD6}$ and $R^{DD7}$ taken together form —O—C(=O)—O—; $R^{DD8}$ can be absent or selected from hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)NR$^{DDa1}$R$^{DDb1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDb1}$, —N(R$^{DDc1}$)—S(=O)$_2$NR$^{DDa1}$R$^{DDb1}$, an optionally substituted C$_{1-6}$ alkyl, an optionally substituted C$_{2-6}$ alkenyl, an optionally substituted C$_{2-6}$ alkynyl, an optionally substituted haloalkyl, an optionally substituted hydroxyalkyl and an —O-linked amino acid, or when the bond to $R^{DD7}$ indicated by ------ is a double bond, then $R^{DD7}$ is a C$_{2-6}$ alkylidene and $R^{DD8}$ is absent; $R^{DDa1}$, $R^{DDb1}$ and $R^{DDc1}$ can be each independently selected from hydrogen, an optionally substituted alkyl, an optionally substituted alkenyl, an optionally substituted alkynyl, an optionally substituted aryl, an optionally substituted heteroaryl, an optionally substituted aralkyl and an optionally substituted heteroaryl(C$_{1-6}$ alkyl); $R^{DD10}$ can be selected from O$^-$, —OH, an optionally substituted aryloxy or aryl-O—,

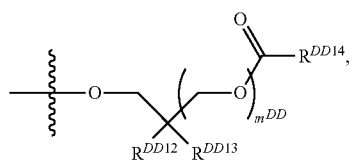

alkyl-C(=O)—O—CH$_2$—O—, alkyl-C(=O)—S—CH$_2$CH$_2$—O— and an —N-linked amino acid; $R^{DD11}$ can be selected from O$^-$, —OH, an optionally substituted aryloxy or aryl-O—,

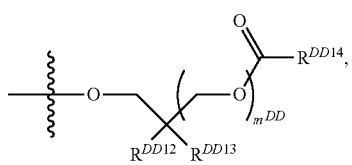

alkyl-C(=O)—O—CH$_2$—O—, alkyl-C(=O)—S—CH$_2$CH$_2$—O— and an —N-linked amino acid; each R$^{DD12}$ and each R$^{DD13}$ can be independently —C≡N or an optionally substituted substituent selected from C$_{1-8}$ organylcarbonyl, C$_{1-8}$ alkoxycarbonyl and C$_{1-8}$ organylaminocarbonyl; each R$^{DD14}$ can be hydrogen or an optionally substituted C$_{1-6}$-alkyl; each m$^{DD}$ can be independently 1 or 2, and if both R$^{DD10}$ and R$^{DD11}$ are

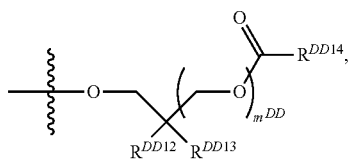

each R$^{DD12}$, each R$^{DD13}$, each R$^{DD14}$ and each m$^{DD}$ can be the same or different. In some embodiments, R$^{DD8}$ can be halogen, —OR$^{DDa1}$, an optionally substituted C$_{1-6}$ alkyl, an optionally substituted C$_{2-6}$ alkenyl, an optionally substituted C$_{2-6}$ alkynyl and an optionally substituted C$_{1-6}$ haloalkyl.

Some embodiments described herein relate to a method of ameliorating or treating a viral infection that can include contacting a cell infected with the viral infection with a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a mono-, di, and/or tri-phosphate thereof, a compound of Formula (CC) and a compound of Formula (DD), or a pharmaceutically acceptable salt of any of the aforementioned compounds.

Some embodiments described herein relate to a method of ameliorating or treating a viral infection that can include administering to a subject suffering from the viral infection a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a mono-, di, and/or tri-phosphate thereof, a compound of Formula (CC) and a compound of Formula (DD), or a pharmaceutically acceptable salt of any of the aforementioned compounds.

Some embodiments described herein relate to a method of inhibiting viral replication of a virus that can include contacting a cell infected with the virus an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a mono-, di, and/or tri-phosphate thereof, a compound of Formula (CC) and a compound of Formula (DD), or a pharmaceutically acceptable salt of any of the aforementioned compounds.

Some embodiments described herein relate to a method of ameliorating or treating a viral infection that can include contacting a cell infected with the viral infection with a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (CC) and a compound of Formula (DD), or a pharmaceutically acceptable salt of any of the aforementioned compounds.

Some embodiments described herein relate to a method of ameliorating or treating a viral infection that can include administering to a subject suffering from the viral infection a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (CC) and a compound of Formula (DD), or a pharmaceutically acceptable salt of any of the aforementioned compounds.

Some embodiments described herein relate to a method of inhibiting viral replication of a virus that can include contacting a cell infected with the virus an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (CC) and a compound of Formula (DD), or a pharmaceutically acceptable salt of any of the aforementioned compounds.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt the thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) in FIGS. 1-7 and 9 (including pharmaceutically acceptable salts and prodrugs thereof) can result in an additive effect. In some embodiments, the combination of a compound of Formula (I), or a pharmaceutically acceptable salt thereof, in combination with one or more additional agent(s) in FIGS. 1-7 and 9 (including pharmaceutically acceptable salts and prodrugs thereof) can result in a synergistic effect. In some embodiments, the combination of a compound of Formula (I), or a pharmaceutically acceptable salt thereof, in combination with one or more additional agent(s) in FIGS. 1-7 and 9 (including pharmaceutically acceptable salts and prodrugs thereof) can result in a strongly synergistic effect. In some embodiments, the combination of a compound of Formula (I), or a pharmaceutically acceptable salt thereof, in combination with one or more additional agent(s) in FIGS. 1-7 and 9 (including pharmaceutically acceptable salts and prodrugs thereof) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) in FIGS. 1-7 and 9 (including pharmaceutically acceptable salts and prodrugs thereof) may be a reduction in the required amount(s) of one or more compounds of FIGS. 1-7 and 9 (including pharmaceutically acceptable salts and prodrugs thereof) that is effective in treating a disease condition disclosed herein (for example, HCV), as compared to the amount required to achieve same therapeutic result when one or more compounds of FIGS. 1-7 and 9 (including pharmaceutically acceptable salts and prodrugs thereof) are administered without a compound of Formula (I), or a pharmaceutically acceptable salt thereof. For example, the amount of a compound in FIGS. 1-7 and 9 (including a pharmaceutically acceptable salt and prodrug thereof), can be less compared to the amount of the compound in FIGS. 1-7 and 9 (including a pharmaceutically acceptable salt and prodrug thereof), needed to achieve the same viral load reduction when administered as a monotherapy. Another potential advantage of utilizing a compound of Formula (I), or a pharmaceutically acceptable salt thereof, in combination with one or more additional agent(s) in FIGS. 1-7 and 9 (including pharmaceutically acceptable salts and prodrugs thereof) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) in FIGS. 1-7 and 9 (including pharmaceutically acceptable salts and prodrugs thereof) may include little to no cross resistance between a compound of Formula (I), or a pharmaceutically acceptable salt thereof, and one or more additional agent(s) in FIGS. 1-7 and 9 (including pharmaceutically acceptable salts and prodrugs thereof) thereof; different routes for elimination of a compound of Formula (I), or a pharmaceutically acceptable salt thereof, and one or more additional agent(s) in FIGS. 1-7 and 9 (including pharmaceutically acceptable salts and prodrugs thereof); little to no overlapping toxicities between a compound of Formula (I), or a pharmaceutically acceptable salt thereof, and one or more additional agent(s) in FIGS. 1-7 and 9 (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) in FIGS. 1-7 and 9 (including pharmaceutically acceptable salts and prodrugs thereof).

A non-limiting list of example combination of compounds of Formula (I), or a pharmaceutically acceptable salt thereof, or a pharmaceutical composition that includes a compound described herein, with one or more additional agent(s) are provided in Tables A, B, C and D. Each numbered X and Y compound in Tables A, B, C and D has a corresponding name and/or structure provided in FIGS. 1 to 9. The numbered compounds in Tables A, B, C and D includes pharmaceutically acceptable salts of the compounds and pharmaceutical compositions containing the compounds or a pharmaceutically acceptable salt thereof. For example, 1001 includes the compound corresponding to 1001, pharmaceutically acceptable salts thereof, and pharmaceutical compositions that include compound 1001 and/or a pharmaceutically acceptable salt thereof. The combinations exemplified in Tables A, B, C and D are designated by the formula X:Y, which represents a combination of a compound X with a compound Y. For example, the combination designated as 1001:8001 in Table A represents a combination of compound 1001 with compound 8001, including pharmaceutically acceptable salts of compound 1001 and/or 8001, and pharmaceutical compositions including compound 1001 and 8001 (including pharmaceutical compositions that include pharmaceutically acceptable salts of compound 1001 and/or compound 8001). Thus, the combination designated as 1001:8001 in Table A represents the combination of Telaprevir (compound 1001, as shown in FIG. 1A) and

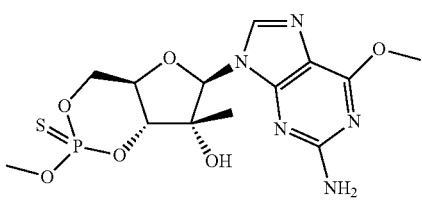

Figure 8B:
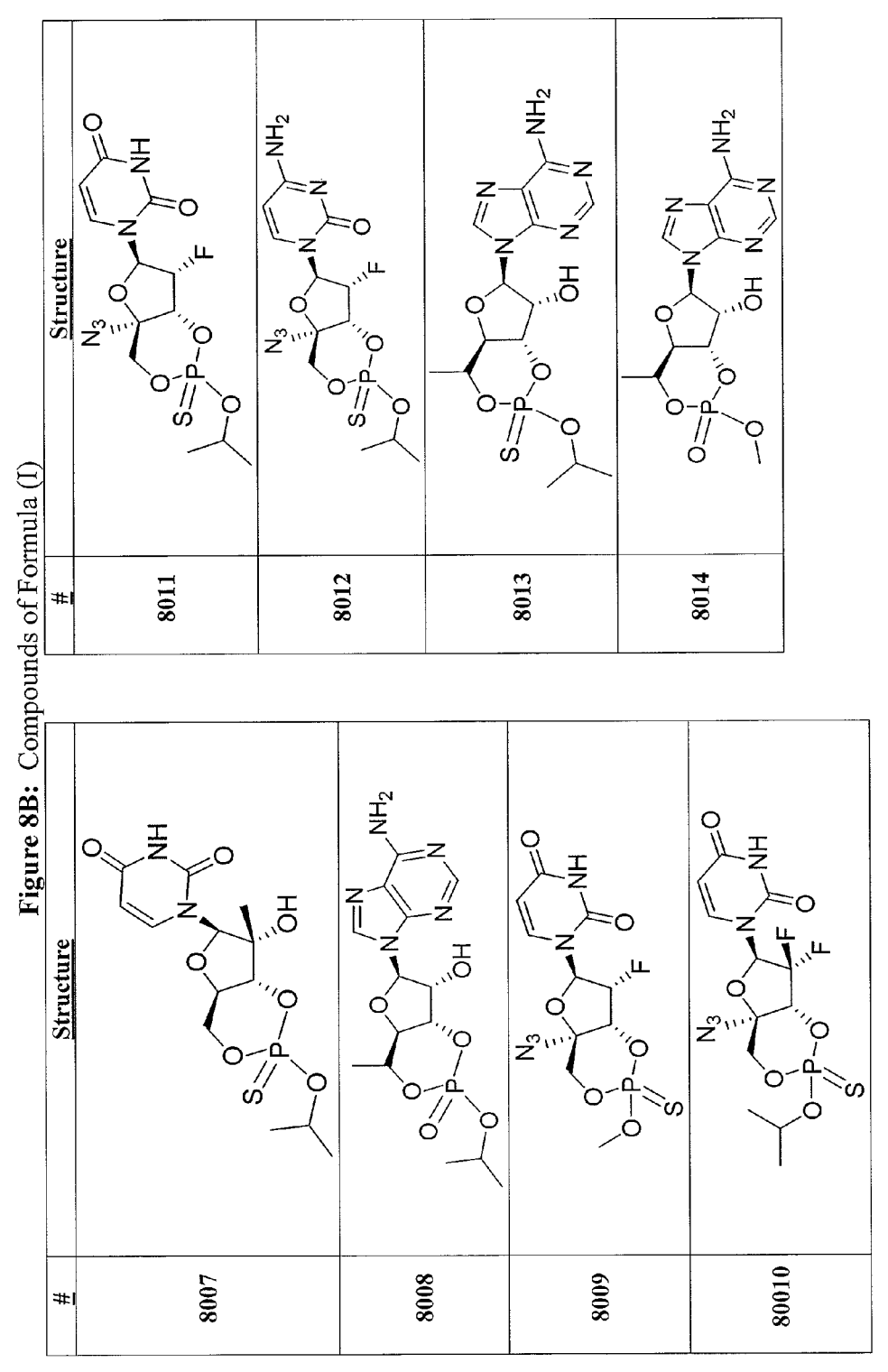

(compound 8001, as shown in FIG. 8A), including pharmaceutically acceptable salts of compound 1001 and/or 8001, and pharmaceutical compositions including compound 1001 and 8001 (including pharmaceutical compositions that include pharmaceutically acceptable salts of compound 1001 and/or compound 8001). Each of the combinations provided in Tables A, B, C and D can be used with one, two, three or more additional agents described herein. In some embodiments described herein, the combination of agents can be used to treat, amerliorate and/or inhibit a virus and/or a viral infection, wherein the virus can be HCV and the viral infection can be an HCV viral infection.

TABLE A

Example combinations of a compound X with a compound Y.
X:Y

1001:8000
1002:8000
1003:8000
1004:8000
1005:8000
1006:8000
1007:8000
1008:8000
1009:8000
1010:8000
1011:8000
1012:8000
1013:8000
1014:8000
2001:8000
2002:8000
2003:8000
2004:8000
2005:8000
2006:8000
2007:8000
2008:8000
2009:8000
2010:8000
3001:8000
3002:8000
3003:8000
3004:8000
3005:8000
3006:8000
3007:8000
3008:8000
4001:8000
4002:8000
4003:8000
4004:8000
4005:8000
5001:8000
5002:8000
1001:8001
1002:8001
1003:8001
1004:8001
1005:8001
1006:8001
1007:8001
1008:8001
1009:8001

TABLE A-continued

Example combinations of a compound X with a compound Y.
X:Y

1010:8001
1011:8001
1012:8001
1013:8001
1014:8001
2001:8001
2002:8001
2003:8001
2004:8001
2005:8001
2006:8001
2007:8001
2008:8001
2009:8001
2010:8001
3001:8001
3002:8001
3003:8001
3004:8001
3005:8001
3006:8001
3007:8001
3008:8001
4001:8001
4002:8001
4003:8001
4004:8001
4005:8001
5001:8001
5002:8001
1001:8002
1002:8002
1003:8002
1004:8002
1005:8002
1006:8002
1007:8002
1008:8002
1009:8002
1010:8002
1011:8002
1012:8002
1013:8002
1014:8002
2001:8002
2002:8002
2003:8002
2004:8002
2005:8002
2006:8002
2007:8002
2008:8002
2009:8002
2010:8002
3001:8002
3002:8002
3003:8002
3004:8002
3005:8002
3006:8002
3007:8002
3008:8002
4001:8002
4002:8002
4003:8002
4004:8002
4005:8002
5001:8002
5002:8002
1001:8003
1002:8003
1003:8003
1004:8003
1005:8003
1006:8003
1007:8003
1008:8003

TABLE A-continued

Example combinations of a compound X with a compound Y.
X:Y

| X:Y |
|---|
| 1009:8003 |
| 1010:8003 |
| 1011:8003 |
| 1012:8003 |
| 1013:8003 |
| 1014:8003 |
| 2001:8003 |
| 2002:8003 |
| 2003:8003 |
| 2004:8003 |
| 2005:8003 |
| 2006:8003 |
| 2007:8003 |
| 2008:8003 |
| 2009:8003 |
| 2010:8003 |
| 3001:8003 |
| 3002:8003 |
| 3003:8003 |
| 3004:8003 |
| 3005:8003 |
| 3006:8003 |
| 3007:8003 |
| 3008:8003 |
| 4001:8003 |
| 4002:8003 |
| 4003:8003 |
| 4004:8003 |
| 4005:8003 |
| 5001:8003 |
| 5002:8003 |
| 1001:8004 |
| 1002:8004 |
| 1003:8004 |
| 1004:8004 |
| 1005:8004 |
| 1006:8004 |
| 1007:8004 |
| 1008:8004 |
| 1009:8004 |
| 1010:8004 |
| 1011:8004 |
| 1012:8004 |
| 1013:8004 |
| 1014:8004 |
| 2001:8004 |
| 2002:8004 |
| 2003:8004 |
| 2004:8004 |
| 2005:8004 |
| 2006:8004 |
| 2007:8004 |
| 2008:8004 |
| 2009:8004 |
| 2010:8004 |
| 3001:8004 |
| 3002:8004 |
| 3003:8004 |
| 3004:8004 |
| 3005:8004 |
| 3006:8004 |
| 3007:8004 |
| 3008:8004 |
| 4001:8004 |
| 4002:8004 |
| 4003:8004 |
| 4004:8004 |
| 4005:8004 |
| 5001:8004 |
| 5002:8004 |
| 1001:8005 |
| 1002:8005 |
| 1003:8005 |
| 1004:8005 |
| 1005:8005 |
| 1006:8005 |
| 1007:8005 |
| 1008:8005 |
| 1009:8005 |
| 1010:8005 |
| 1011:8005 |
| 1012:8005 |
| 1013:8005 |
| 1014:8005 |
| 2001:8005 |
| 2002:8005 |
| 2003:8005 |
| 2004:8005 |
| 2005:8005 |
| 2006:8005 |
| 2007:8005 |
| 2008:8005 |
| 2009:8005 |
| 2010:8005 |
| 3001:8005 |
| 3002:8005 |
| 3003:8005 |
| 3004:8005 |
| 3005:8005 |
| 3006:8005 |
| 3007:8005 |
| 3008:8005 |
| 4001:8005 |
| 4002:8005 |
| 4003:8005 |
| 4004:8005 |
| 4005:8005 |
| 5001:8005 |
| 5002:8005 |
| 1001:8006 |
| 1002:8006 |
| 1003:8006 |
| 1004:8006 |
| 1005:8006 |
| 1006:8006 |
| 1007:8006 |
| 1008:8006 |
| 1009:8006 |
| 1010:8006 |
| 1011:8006 |
| 1012:8006 |
| 1013:8006 |
| 1014:8006 |
| 2001:8006 |
| 2002:8006 |
| 2003:8006 |
| 2004:8006 |
| 2005:8006 |
| 2006:8006 |
| 2007:8006 |
| 2008:8006 |
| 2009:8006 |
| 2010:8006 |
| 3001:8006 |
| 3002:8006 |
| 3003:8006 |
| 3004:8006 |
| 3005:8006 |
| 3006:8006 |
| 3007:8006 |
| 3008:8006 |
| 4001:8006 |
| 4002:8006 |
| 4003:8006 |
| 4004:8006 |
| 4005:8006 |
| 5001:8006 |
| 5002:8006 |
| 1001:8007 |
| 1002:8007 |
| 1003:8007 |
| 1004:8007 |
| 1005:8007 |
| 1006:8007 |

TABLE A-continued

Example combinations of a compound X with a compound Y.
X:Y

| X:Y |
|---|
| 1007:8007 |
| 1008:8007 |
| 1009:8007 |
| 1010:8007 |
| 1011:8007 |
| 1012:8007 |
| 1013:8007 |
| 1014:8007 |
| 2001:8007 |
| 2002:8007 |
| 2003:8007 |
| 2004:8007 |
| 2005:8007 |
| 2006:8007 |
| 2007:8007 |
| 2008:8007 |
| 2009:8007 |
| 2010:8007 |
| 3001:8007 |
| 3002:8007 |
| 3003:8007 |
| 3004:8007 |
| 3005:8007 |
| 3006:8007 |
| 3007:8007 |
| 3008:8007 |
| 4001:8007 |
| 4002:8007 |
| 4003:8007 |
| 4004:8007 |
| 4005:8007 |
| 5001:8007 |
| 5002:8007 |
| 1001:8008 |
| 1002:8008 |
| 1003:8008 |
| 1004:8008 |
| 1005:8008 |
| 1006:8008 |
| 1007:8008 |
| 1008:8008 |
| 1009:8008 |
| 1010:8008 |
| 1011:8008 |
| 1012:8008 |
| 1013:8008 |
| 1014:8008 |
| 2001:8008 |
| 2002:8008 |
| 2003:8008 |
| 2004:8008 |
| 2005:8008 |
| 2006:8008 |
| 2007:8008 |
| 2008:8008 |
| 2009:8008 |
| 2010:8008 |
| 3001:8008 |
| 3002:8008 |
| 3003:8008 |
| 3004:8008 |
| 3005:8008 |
| 3006:8008 |
| 3007:8008 |
| 3008:8008 |
| 4001:8008 |
| 4002:8008 |
| 4003:8008 |
| 4004:8008 |
| 4005:8008 |
| 5001:8008 |
| 5002:8008 |
| 1001:8009 |
| 1002:8009 |
| 1003:8009 |
| 1004:8009 |
| 1005:8009 |
| 1006:8009 |
| 1007:8009 |
| 1008:8009 |
| 1009:8009 |
| 1010:8009 |
| 1011:8009 |
| 1012:8009 |
| 1013:8009 |
| 1014:8009 |
| 2001:8009 |
| 2002:8009 |
| 2003:8009 |
| 2004:8009 |
| 2005:8009 |
| 2006:8009 |
| 2007:8009 |
| 2008:8009 |
| 2009:8009 |
| 2010:8009 |
| 3001:8009 |
| 3002:8009 |
| 3003:8009 |
| 3004:8009 |
| 3005:8009 |
| 3006:8009 |
| 3007:8009 |
| 3008:8009 |
| 4001:8009 |
| 4002:8009 |
| 4003:8009 |
| 4004:8009 |
| 4005:8009 |
| 5001:8009 |
| 5002:8009 |
| 1001:8010 |
| 1002:8010 |
| 1003:8010 |
| 1004:8010 |
| 1005:8010 |
| 1006:8010 |
| 1007:8010 |
| 1008:8010 |
| 1009:8010 |
| 1010:8010 |
| 1011:8010 |
| 1012:8010 |
| 1013:8010 |
| 1014:8010 |
| 2001:8010 |
| 2002:8010 |
| 2003:8010 |
| 2004:8010 |
| 2005:8010 |
| 2006:8010 |
| 2007:8010 |
| 2008:8010 |
| 2009:8010 |
| 2010:8010 |
| 3001:8010 |
| 3002:8010 |
| 3003:8010 |
| 3004:8010 |
| 3005:8010 |
| 3006:8010 |
| 3007:8010 |
| 3008:8010 |
| 4001:8010 |
| 4002:8010 |
| 4003:8010 |
| 4004:8010 |
| 4005:8010 |
| 5001:8010 |
| 5002:8010 |
| 1001:8011 |
| 1002:8011 |
| 1003:8011 |
| 1004:8011 |

TABLE A-continued

Example combinations of a compound X with a compound Y.
X:Y

| X:Y |
|---|
| 1005:8011 |
| 1006:8011 |
| 1007:8011 |
| 1008:8011 |
| 1009:8011 |
| 1010:8011 |
| 1011:8011 |
| 1012:8011 |
| 1013:8011 |
| 1014:8011 |
| 2001:8011 |
| 2002:8011 |
| 2003:8011 |
| 2004:8011 |
| 2005:8011 |
| 2006:8011 |
| 2007:8011 |
| 2008:8011 |
| 2009:8011 |
| 2010:8011 |
| 3001:8011 |
| 3002:8011 |
| 3003:8011 |
| 3004:8011 |
| 3005:8011 |
| 3006:8011 |
| 3007:8011 |
| 3008:8011 |
| 4001:8011 |
| 4002:8011 |
| 4003:8011 |
| 4004:8011 |
| 4005:8011 |
| 5001:8011 |
| 5002:8011 |
| 1001:8012 |
| 1002:8012 |
| 1003:8012 |
| 1004:8012 |
| 1005:8012 |
| 1006:8012 |
| 1007:8012 |
| 1008:8012 |
| 1009:8012 |
| 1010:8012 |
| 1011:8012 |
| 1012:8012 |
| 1013:8012 |
| 1014:8012 |
| 2001:8012 |
| 2002:8012 |
| 2003:8012 |
| 2004:8012 |
| 2005:8012 |
| 2006:8012 |
| 2007:8012 |
| 2008:8012 |
| 2009:8012 |
| 2010:8012 |
| 3001:8012 |
| 3002:8012 |
| 3003:8012 |
| 3004:8012 |
| 3005:8012 |
| 3006:8012 |
| 3007:8012 |
| 3008:8012 |
| 4001:8012 |
| 4002:8012 |
| 4003:8012 |
| 4004:8012 |
| 4005:8012 |
| 5001:8012 |
| 5002:8012 |
| 1001:8013 |
| 1002:8013 |
| 1003:8013 |

TABLE A-continued

Example combinations of a compound X with a compound Y.
X:Y

| X:Y |
|---|
| 1004:8013 |
| 1005:8013 |
| 1006:8013 |
| 1007:8013 |
| 1008:8013 |
| 1009:8013 |
| 1010:8013 |
| 1011:8013 |
| 1012:8013 |
| 1013:8013 |
| 1014:8013 |
| 2001:8013 |
| 2002:8013 |
| 2003:8013 |
| 2004:8013 |
| 2005:8013 |
| 2006:8013 |
| 2007:8013 |
| 2008:8013 |
| 2009:8013 |
| 2010:8013 |
| 3001:8013 |
| 3002:8013 |
| 3003:8013 |
| 3004:8013 |
| 3005:8013 |
| 3006:8013 |
| 3007:8013 |
| 3008:8013 |
| 4001:8013 |
| 4002:8013 |
| 4003:8013 |
| 4004:8013 |
| 4005:8013 |
| 5001:8013 |
| 5002:8013 |
| 1001:8014 |
| 1002:8014 |
| 1003:8014 |
| 1004:8014 |
| 1005:8014 |
| 1006:8014 |
| 1007:8014 |
| 1008:8014 |
| 1009:8014 |
| 1010:8014 |
| 1011:8014 |
| 1012:8014 |
| 1013:8014 |
| 1014:8014 |
| 2001:8014 |
| 2002:8014 |
| 2003:8014 |
| 2004:8014 |
| 2005:8014 |
| 2006:8014 |
| 2007:8014 |
| 2008:8014 |
| 2009:8014 |
| 2010:8014 |
| 3001:8014 |
| 3002:8014 |
| 3003:8014 |
| 3004:8014 |
| 3005:8014 |
| 3006:8014 |
| 3007:8014 |
| 3008:8014 |
| 4001:8014 |
| 4002:8014 |
| 4003:8014 |
| 4004:8014 |
| 4005:8014 |
| 5001:8014 |
| 5002:8014 |
| 1001:8015 |
| 1002:8015 |

TABLE A-continued

Example combinations of a compound X with a compound Y.
X:Y

1003:8015
1004:8015
1005:8015
1006:8015
1007:8015
1008:8015
1009:8015
1010:8015
1011:8015
1012:8015
1013:8015
1014:8015
2001:8015
2002:8015
2003:8015
2004:8015
2005:8015
2006:8015
2007:8015
2008:8015
2009:8015
2010:8015
3001:8015
3002:8015
3003:8015
3004:8015
3005:8015
3006:8015
3007:8015
3008:8015
4001:8015
4002:8015
4003:8015
4004:8015
4005:8015
5001:8015
5002:8015
1001:8016
1002:8016
1003:8016
1004:8016
1005:8016
1006:8016
1007:8016
1008:8016
1009:8016
1010:8016
1011:8016
1012:8016
1013:8016
1014:8016
2001:8016
2002:8016
2003:8016
2004:8016
2005:8016
2006:8016
2007:8016
2008:8016
2009:8016
2010:8016
3001:8016
3002:8016
3003:8016
3004:8016
3005:8016
3006:8016
3007:8016
3008:8016
4001:8016
4002:8016
4003:8016
4004:8016
4005:8016

TABLE A-continued

Example combinations of a compound X with a compound Y.
X:Y

5001:8016
5002:8016

TABLE B

Example combinations of a compound X with a compound Y.
X:Y

8000:7000
8000:7001
8000:7002
8000:7003
8000:7004
8000:7005
8000:7006
8000:7007
8000:7008
8000:7009
8000:7010
8000:7011
8000:7012
8000:7013
8000:7014
8000:7015
8000:7016
8000:7017
8000:7018
8000:7019
8000:7020
8000:7021
8000:7022
8000:7023
8000:7024
8000:7025
8000:7026
8000:7027
8000:7028
8000:7029
8000:7030
8000:7031
8000:7032
8000:7033
8000:7034
8000:7035
8000:7036
8000:7037
8000:7038
8000:7039
8000:7040
8000:7041
8000:7042
8000:7043
8000:7044
8000:7045
8000:7046
8000:7047
8000:7048
8000:7049
8000:7050
8000:7051
8000:7052
8000:7053
8000:7054
8000:7055
8000:7056
8000:7057
8000:7058
8000:7059
8000:7060
8000:7061
8000:7062
8000:7063
8000:7064

TABLE B-continued

Example combinations of a compound X with a compound Y.
X:Y

8000:7065
8000:7066
8000:7067
8000:7068
8000:7069
8000:7070
8000:7071
8000:7072
8000:7073
8000:7074
8000:7075
8000:7076
8000:7077
8001:7000
8001:7001
8001:7002
8001:7003
8001:7004
8001:7005
8001:7006
8001:7007
8001:7008
8001:7009
8001:7010
8001:7011
8001:7012
8001:7013
8001:7014
8001:7015
8001:7016
8001:7017
8001:7018
8001:7019
8001:7020
8001:7021
8001:7022
8001:7023
8001:7024
8001:7025
8001:7026
8001:7027
8001:7028
8001:7029
8001:7030
8001:7031
8001:7032
8001:7033
8001:7034
8001:7035
8001:7036
8001:7037
8001:7038
8001:7039
8001:7040
8001:7041
8001:7042
8001:7043
8001:7044
8001:7045
8001:7046
8001:7047
8001:7048
8001:7049
8001:7050
8001:7051
8001:7052
8001:7053
8001:7054
8001:7055
8001:7056
8001:7057
8001:7058
8001:7059
8001:7060
8001:7061
8001:7062
8001:7063

TABLE B-continued

Example combinations of a compound X with a compound Y.
X:Y

8001:7064
8001:7065
8001:7066
8001:7067
8001:7068
8001:7069
8001:7070
8001:7071
8001:7072
8001:7073
8001:7074
8001:7075
8001:7076
8001:7077
8002:7000
8002:7001
8002:7002
8002:7003
8002:7004
8002:7005
8002:7006
8002:7007
8002:7008
8002:7009
8002:7010
8002:7011
8002:7012
8002:7013
8002:7014
8002:7015
8002:7016
8002:7017
8002:7018
8002:7019
8002:7020
8002:7021
8002:7022
8002:7023
8002:7024
8002:7025
8002:7026
8002:7027
8002:7028
8002:7029
8002:7030
8002:7031
8002:7032
8002:7033
8002:7034
8002:7035
8002:7036
8002:7037
8002:7038
8002:7039
8002:7040
8002:7041
8002:7042
8002:7043
8002:7044
8002:7045
8002:7046
8002:7047
8002:7048
8002:7049
8002:7050
8002:7051
8002:7052
8002:7053
8002:7054
8002:7055
8002:7056
8002:7057
8002:7058
8002:7059
8002:7060
8002:7061
8002:7062

TABLE B-continued

Example combinations of a compound X with a compound Y.
X:Y

8002:7063
8002:7064
8002:7065
8002:7066
8002:7067
8002:7068
8002:7069
8002:7070
8002:7071
8002:7072
8002:7073
8002:7074
8002:7075
8002:7076
8002:7077
8003:7000
8003:7001
8003:7002
8003:7003
8003:7004
8003:7005
8003:7006
8003:7007
8003:7008
8003:7009
8003:7010
8003:7011
8003:7012
8003:7013
8003:7014
8003:7015
8003:7016
8003:7017
8003:7018
8003:7019
8003:7020
8003:7021
8003:7022
8003:7023
8003:7024
8003:7025
8003:7026
8003:7027
8003:7028
8003:7029
8003:7030
8003:7031
8003:7032
8003:7033
8003:7034
8003:7035
8003:7036
8003:7037
8003:7038
8003:7039
8003:7040
8003:7041
8003:7042
8003:7043
8003:7044
8003:7045
8003:7046
8003:7047
8003:7048
8003:7049
8003:7050
8003:7051
8003:7052
8003:7053
8003:7054
8003:7055
8003:7056
8003:7057
8003:7058
8003:7059
8003:7060
8003:7061

TABLE B-continued

Example combinations of a compound X with a compound Y.
X:Y

8003:7062
8003:7063
8003:7064
8003:7065
8003:7066
8003:7067
8003:7068
8003:7069
8003:7070
8003:7071
8003:7072
8003:7073
8003:7074
8003:7075
8003:7076
8003:7077
8004:7000
8004:7001
8004:7002
8004:7003
8004:7004
8004:7005
8004:7006
8004:7007
8004:7008
8004:7009
8004:7010
8004:7011
8004:7012
8004:7013
8004:7014
8004:7015
8004:7016
8004:7017
8004:7018
8004:7019
8004:7020
8004:7021
8004:7022
8004:7023
8004:7024
8004:7025
8004:7026
8004:7027
8004:7028
8004:7029
8004:7030
8004:7031
8004:7032
8004:7033
8004:7034
8004:7035
8004:7036
8004:7037
8004:7038
8004:7039
8004:7040
8004:7041
8004:7042
8004:7043
8004:7044
8004:7045
8004:7046
8004:7047
8004:7048
8004:7049
8004:7050
8004:7051
8004:7052
8004:7053
8004:7054
8004:7055
8004:7056
8004:7057
8004:7058
8004:7059
8004:7060

TABLE B-continued

Example combinations of a compound X with a compound Y.
X:Y

| X:Y |
|---|
| 8004:7061 |
| 8004:7062 |
| 8004:7063 |
| 8004:7064 |
| 8004:7065 |
| 8004:7066 |
| 8004:7067 |
| 8004:7068 |
| 8004:7069 |
| 8004:7070 |
| 8004:7071 |
| 8004:7072 |
| 8004:7073 |
| 8004:7074 |
| 8004:7075 |
| 8004:7076 |
| 8004:7077 |
| 8005:7000 |
| 8005:7001 |
| 8005:7002 |
| 8005:7003 |
| 8005:7004 |
| 8005:7005 |
| 8005:7006 |
| 8005:7007 |
| 8005:7008 |
| 8005:7009 |
| 8005:7010 |
| 8005:7011 |
| 8005:7012 |
| 8005:7013 |
| 8005:7014 |
| 8005:7015 |
| 8005:7016 |
| 8005:7017 |
| 8005:7018 |
| 8005:7019 |
| 8005:7020 |
| 8005:7021 |
| 8005:7022 |
| 8005:7023 |
| 8005:7024 |
| 8005:7025 |
| 8005:7026 |
| 8005:7027 |
| 8005:7028 |
| 8005:7029 |
| 8005:7030 |
| 8005:7031 |
| 8005:7032 |
| 8005:7033 |
| 8005:7034 |
| 8005:7035 |
| 8005:7036 |
| 8005:7037 |
| 8005:7038 |
| 8005:7039 |
| 8005:7040 |
| 8005:7041 |
| 8005:7042 |
| 8005:7043 |
| 8005:7044 |
| 8005:7045 |
| 8005:7046 |
| 8005:7047 |
| 8005:7048 |
| 8005:7049 |
| 8005:7050 |
| 8005:7051 |
| 8005:7052 |
| 8005:7053 |
| 8005:7054 |
| 8005:7055 |
| 8005:7056 |
| 8005:7057 |
| 8005:7058 |
| 8005:7059 |
| 8005:7060 |
| 8005:7061 |
| 8005:7062 |
| 8005:7063 |
| 8005:7064 |
| 8005:7065 |
| 8005:7066 |
| 8005:7067 |
| 8005:7068 |
| 8005:7069 |
| 8005:7070 |
| 8005:7071 |
| 8005:7072 |
| 8005:7073 |
| 8005:7074 |
| 8005:7075 |
| 8005:7076 |
| 8005:7077 |
| 8006:7000 |
| 8006:7001 |
| 8006:7002 |
| 8006:7003 |
| 8006:7004 |
| 8006:7005 |
| 8006:7006 |
| 8006:7007 |
| 8006:7008 |
| 8006:7009 |
| 8006:7010 |
| 8006:7011 |
| 8006:7012 |
| 8006:7013 |
| 8006:7014 |
| 8006:7015 |
| 8006:7016 |
| 8006:7017 |
| 8006:7018 |
| 8006:7019 |
| 8006:7020 |
| 8006:7021 |
| 8006:7022 |
| 8006:7023 |
| 8006:7024 |
| 8006:7025 |
| 8006:7026 |
| 8006:7027 |
| 8006:7028 |
| 8006:7029 |
| 8006:7030 |
| 8006:7031 |
| 8006:7032 |
| 8006:7033 |
| 8006:7034 |
| 8006:7035 |
| 8006:7036 |
| 8006:7037 |
| 8006:7038 |
| 8006:7039 |
| 8006:7040 |
| 8006:7041 |
| 8006:7042 |
| 8006:7043 |
| 8006:7044 |
| 8006:7045 |
| 8006:7046 |
| 8006:7047 |
| 8006:7048 |
| 8006:7049 |
| 8006:7050 |
| 8006:7051 |
| 8006:7052 |
| 8006:7053 |
| 8006:7054 |
| 8006:7055 |
| 8006:7056 |
| 8006:7057 |
| 8006:7058 |

TABLE B-continued

Example combinations of a compound X with a compound Y.
X:Y

8006:7059
8006:7060
8006:7061
8006:7062
8006:7063
8006:7064
8006:7065
8006:7066
8006:7067
8006:7068
8006:7069
8006:7070
8006:7071
8006:7072
8006:7073
8006:7074
8006:7075
8006:7076
8006:7077
8007:7000
8007:7001
8007:7002
8007:7003
8007:7004
8007:7005
8007:7006
8007:7007
8007:7008
8007:7009
8007:7010
8007:7011
8007:7012
8007:7013
8007:7014
8007:7015
8007:7016
8007:7017
8007:7018
8007:7019
8007:7020
8007:7021
8007:7022
8007:7023
8007:7024
8007:7025
8007:7026
8007:7027
8007:7028
8007:7029
8007:7030
8007:7031
8007:7032
8007:7033
8007:7034
8007:7035
8007:7036
8007:7037
8007:7038
8007:7039
8007:7040
8007:7041
8007:7042
8007:7043
8007:7044
8007:7045
8007:7046
8007:7047
8007:7048
8007:7049
8007:7050
8007:7051
8007:7052
8007:7053
8007:7054
8007:7055
8007:7056
8007:7057

TABLE B-continued

Example combinations of a compound X with a compound Y.
X:Y

8007:7058
8007:7059
8007:7060
8007:7061
8007:7062
8007:7063
8007:7064
8007:7065
8007:7066
8007:7067
8007:7068
8007:7069
8007:7070
8007:7071
8007:7072
8007:7073
8007:7074
8007:7075
8007:7076
8007:7077
8008:7000
8008:7001
8008:7002
8008:7003
8008:7004
8008:7005
8008:7006
8008:7007
8008:7008
8008:7009
8008:7010
8008:7011
8008:7012
8008:7013
8008:7014
8008:7015
8008:7016
8008:7017
8008:7018
8008:7019
8008:7020
8008:7021
8008:7022
8008:7023
8008:7024
8008:7025
8008:7026
8008:7027
8008:7028
8008:7029
8008:7030
8008:7031
8008:7032
8008:7033
8008:7034
8008:7035
8008:7036
8008:7037
8008:7038
8008:7039
8008:7040
8008:7041
8008:7042
8008:7043
8008:7044
8008:7045
8008:7046
8008:7047
8008:7048
8008:7049
8008:7050
8008:7051
8008:7052
8008:7053
8008:7054
8008:7055
8008:7056

TABLE B-continued

Example combinations of a compound X with a compound Y.
X:Y

8008:7057
8008:7058
8008:7059
8008:7060
8008:7061
8008:7062
8008:7063
8008:7064
8008:7065
8008:7066
8008:7067
8008:7068
8008:7069
8008:7070
8008:7071
8008:7072
8008:7073
8008:7074
8008:7075
8008:7076
8008:7077
8009:7000
8009:7001
8009:7002
8009:7003
8009:7004
8009:7005
8009:7006
8009:7007
8009:7008
8009:7009
8009:7010
8009:7011
8009:7012
8009:7013
8009:7014
8009:7015
8009:7016
8009:7017
8009:7018
8009:7019
8009:7020
8009:7021
8009:7022
8009:7023
8009:7024
8009:7025
8009:7026
8009:7027
8009:7028
8009:7029
8009:7030
8009:7031
8009:7032
8009:7033
8009:7034
8009:7035
8009:7036
8009:7037
8009:7038
8009:7039
8009:7040
8009:7041
8009:7042
8009:7043
8009:7044
8009:7045
8009:7046
8009:7047
8009:7048
8009:7049
8009:7050
8009:7051
8009:7052
8009:7053
8009:7054
8009:7055

TABLE B-continued

Example combinations of a compound X with a compound Y.
X:Y

8009:7056
8009:7057
8009:7058
8009:7059
8009:7060
8009:7061
8009:7062
8009:7063
8009:7064
8009:7065
8009:7066
8009:7067
8009:7068
8009:7069
8009:7070
8009:7071
8009:7072
8009:7073
8009:7074
8009:7075
8009:7076
8009:7077
8010:7000
8010:7001
8010:7002
8010:7003
8010:7004
8010:7005
8010:7006
8010:7007
8010:7008
8010:7009
8010:7010
8010:7011
8010:7012
8010:7013
8010:7014
8010:7015
8010:7016
8010:7017
8010:7018
8010:7019
8010:7020
8010:7021
8010:7022
8010:7023
8010:7024
8010:7025
8010:7026
8010:7027
8010:7028
8010:7029
8010:7030
8010:7031
8010:7032
8010:7033
8010:7034
8010:7035
8010:7036
8010:7037
8010:7038
8010:7039
8010:7040
8010:7041
8010:7042
8010:7043
8010:7044
8010:7045
8010:7046
8010:7047
8010:7048
8010:7049
8010:7050
8010:7051
8010:7052
8010:7053
8010:7054

TABLE B-continued

Example combinations of a compound X with a compound Y.
X:Y

| X:Y |
|---|
| 8010:7055 |
| 8010:7056 |
| 8010:7057 |
| 8010:7058 |
| 8010:7059 |
| 8010:7060 |
| 8010:7061 |
| 8010:7062 |
| 8010:7063 |
| 8010:7064 |
| 8010:7065 |
| 8010:7066 |
| 8010:7067 |
| 8010:7068 |
| 8010:7069 |
| 8010:7070 |
| 8010:7071 |
| 8010:7072 |
| 8010:7073 |
| 8010:7074 |
| 8010:7075 |
| 8010:7076 |
| 8010:7077 |
| 8011:7000 |
| 8011:7001 |
| 8011:7002 |
| 8011:7003 |
| 8011:7004 |
| 8011:7005 |
| 8011:7006 |
| 8011:7007 |
| 8011:7008 |
| 8011:7009 |
| 8011:7010 |
| 8011:7011 |
| 8011:7012 |
| 8011:7013 |
| 8011:7014 |
| 8011:7015 |
| 8011:7016 |
| 8011:7017 |
| 8011:7018 |
| 8011:7019 |
| 8011:7020 |
| 8011:7021 |
| 8011:7022 |
| 8011:7023 |
| 8011:7024 |
| 8011:7025 |
| 8011:7026 |
| 8011:7027 |
| 8011:7028 |
| 8011:7029 |
| 8011:7030 |
| 8011:7031 |
| 8011:7032 |
| 8011:7033 |
| 8011:7034 |
| 8011:7035 |
| 8011:7036 |
| 8011:7037 |
| 8011:7038 |
| 8011:7039 |
| 8011:7040 |
| 8011:7041 |
| 8011:7042 |
| 8011:7043 |
| 8011:7044 |
| 8011:7045 |
| 8011:7046 |
| 8011:7047 |
| 8011:7048 |
| 8011:7049 |
| 8011:7050 |
| 8011:7051 |
| 8011:7052 |
| 8011:7053 |

TABLE B-continued

Example combinations of a compound X with a compound Y.
X:Y

| X:Y |
|---|
| 8011:7054 |
| 8011:7055 |
| 8011:7056 |
| 8011:7057 |
| 8011:7058 |
| 8011:7059 |
| 8011:7060 |
| 8011:7061 |
| 8011:7062 |
| 8011:7063 |
| 8011:7064 |
| 8011:7065 |
| 8011:7066 |
| 8011:7067 |
| 8011:7068 |
| 8011:7069 |
| 8011:7070 |
| 8011:7071 |
| 8011:7072 |
| 8011:7073 |
| 8011:7074 |
| 8011:7075 |
| 8011:7076 |
| 8011:7077 |
| 8012:7000 |
| 8012:7001 |
| 8012:7002 |
| 8012:7003 |
| 8012:7004 |
| 8012:7005 |
| 8012:7006 |
| 8012:7007 |
| 8012:7008 |
| 8012:7009 |
| 8012:7010 |
| 8012:7011 |
| 8012:7012 |
| 8012:7013 |
| 8012:7014 |
| 8012:7015 |
| 8012:7016 |
| 8012:7017 |
| 8012:7018 |
| 8012:7019 |
| 8012:7020 |
| 8012:7021 |
| 8012:7022 |
| 8012:7023 |
| 8012:7024 |
| 8012:7025 |
| 8012:7026 |
| 8012:7027 |
| 8012:7028 |
| 8012:7029 |
| 8012:7030 |
| 8012:7031 |
| 8012:7032 |
| 8012:7033 |
| 8012:7034 |
| 8012:7035 |
| 8012:7036 |
| 8012:7037 |
| 8012:7038 |
| 8012:7039 |
| 8012:7040 |
| 8012:7041 |
| 8012:7042 |
| 8012:7043 |
| 8012:7044 |
| 8012:7045 |
| 8012:7046 |
| 8012:7047 |
| 8012:7048 |
| 8012:7049 |
| 8012:7050 |
| 8012:7051 |
| 8012:7052 |

TABLE B-continued

Example combinations of a compound X with a compound Y.
X:Y

8012:7053
8012:7054
8012:7055
8012:7056
8012:7057
8012:7058
8012:7059
8012:7060
8012:7061
8012:7062
8012:7063
8012:7064
8012:7065
8012:7066
8012:7067
8012:7068
8012:7069
8012:7070
8012:7071
8012:7072
8012:7073
8012:7074
8012:7075
8012:7076
8012:7077
8013:7000
8013:7001
8013:7002
8013:7003
8013:7004
8013:7005
8013:7006
8013:7007
8013:7008
8013:7009
8013:7010
8013:7011
8013:7012
8013:7013
8013:7014
8013:7015
8013:7016
8013:7017
8013:7018
8013:7019
8013:7020
8013:7021
8013:7022
8013:7023
8013:7024
8013:7025
8013:7026
8013:7027
8013:7028
8013:7029
8013:7030
8013:7031
8013:7032
8013:7033
8013:7034
8013:7035
8013:7036
8013:7037
8013:7038
8013:7039
8013:7040
8013:7041
8013:7042
8013:7043
8013:7044
8013:7045
8013:7046
8013:7047
8013:7048
8013:7049
8013:7050
8013:7051

TABLE B-continued

Example combinations of a compound X with a compound Y.
X:Y

8013:7052
8013:7053
8013:7054
8013:7055
8013:7056
8013:7057
8013:7058
8013:7059
8013:7060
8013:7061
8013:7062
8013:7063
8013:7064
8013:7065
8013:7066
8013:7067
8013:7068
8013:7069
8013:7070
8013:7071
8013:7072
8013:7073
8013:7074
8013:7075
8013:7076
8013:7077
8014:7000
8014:7001
8014:7002
8014:7003
8014:7004
8014:7005
8014:7006
8014:7007
8014:7008
8014:7009
8014:7010
8014:7011
8014:7012
8014:7013
8014:7014
8014:7015
8014:7016
8014:7017
8014:7018
8014:7019
8014:7020
8014:7021
8014:7022
8014:7023
8014:7024
8014:7025
8014:7026
8014:7027
8014:7028
8014:7029
8014:7030
8014:7031
8014:7032
8014:7033
8014:7034
8014:7035
8014:7036
8014:7037
8014:7038
8014:7039
8014:7040
8014:7041
8014:7042
8014:7043
8014:7044
8014:7045
8014:7046
8014:7047
8014:7048
8014:7049
8014:7050

TABLE B-continued

Example combinations of a compound X with a compound Y.
X:Y

| X:Y |
|---|
| 8014:7051 |
| 8014:7052 |
| 8014:7053 |
| 8014:7054 |
| 8014:7055 |
| 8014:7056 |
| 8014:7057 |
| 8014:7058 |
| 8014:7059 |
| 8014:7060 |
| 8014:7061 |
| 8014:7062 |
| 8014:7063 |
| 8014:7064 |
| 8014:7065 |
| 8014:7066 |
| 8014:7067 |
| 8014:7068 |
| 8014:7069 |
| 8014:7070 |
| 8014:7071 |
| 8014:7072 |
| 8014:7073 |
| 8014:7074 |
| 8014:7075 |
| 8014:7076 |
| 8014:7077 |
| 8015:7000 |
| 8015:7001 |
| 8015:7002 |
| 8015:7003 |
| 8015:7004 |
| 8015:7005 |
| 8015:7006 |
| 8015:7007 |
| 8015:7008 |
| 8015:7009 |
| 8015:7010 |
| 8015:7011 |
| 8015:7012 |
| 8015:7013 |
| 8015:7014 |
| 8015:7015 |
| 8015:7016 |
| 8015:7017 |
| 8015:7018 |
| 8015:7019 |
| 8015:7020 |
| 8015:7021 |
| 8015:7022 |
| 8015:7023 |
| 8015:7024 |
| 8015:7025 |
| 8015:7026 |
| 8015:7027 |
| 8015:7028 |
| 8015:7029 |
| 8015:7030 |
| 8015:7031 |
| 8015:7032 |
| 8015:7033 |
| 8015:7034 |
| 8015:7035 |
| 8015:7036 |
| 8015:7037 |
| 8015:7038 |
| 8015:7039 |
| 8015:7040 |
| 8015:7041 |
| 8015:7042 |
| 8015:7043 |
| 8015:7044 |
| 8015:7045 |
| 8015:7046 |
| 8015:7047 |
| 8015:7048 |
| 8015:7049 |

TABLE B-continued

Example combinations of a compound X with a compound Y.
X:Y

| X:Y |
|---|
| 8015:7050 |
| 8015:7051 |
| 8015:7052 |
| 8015:7053 |
| 8015:7054 |
| 8015:7055 |
| 8015:7056 |
| 8015:7057 |
| 8015:7058 |
| 8015:7059 |
| 8015:7060 |
| 8015:7061 |
| 8015:7062 |
| 8015:7063 |
| 8015:7064 |
| 8015:7065 |
| 8015:7066 |
| 8015:7067 |
| 8015:7068 |
| 8015:7069 |
| 8015:7070 |
| 8015:7071 |
| 8015:7072 |
| 8015:7073 |
| 8015:7074 |
| 8015:7075 |
| 8015:7076 |
| 8015:7077 |
| 8016:7000 |
| 8016:7001 |
| 8016:7002 |
| 8016:7003 |
| 8016:7004 |
| 8016:7005 |
| 8016:7006 |
| 8016:7007 |
| 8016:7008 |
| 8016:7009 |
| 8016:7010 |
| 8016:7011 |
| 8016:7012 |
| 8016:7013 |
| 8016:7014 |
| 8016:7015 |
| 8016:7016 |
| 8016:7017 |
| 8016:7018 |
| 8016:7019 |
| 8016:7020 |
| 8016:7021 |
| 8016:7022 |
| 8016:7023 |
| 8016:7024 |
| 8016:7025 |
| 8016:7026 |
| 8016:7027 |
| 8016:7028 |
| 8016:7029 |
| 8016:7030 |
| 8016:7031 |
| 8016:7032 |
| 8016:7033 |
| 8016:7034 |
| 8016:7035 |
| 8016:7036 |
| 8016:7037 |
| 8016:7038 |
| 8016:7039 |
| 8016:7040 |
| 8016:7041 |
| 8016:7042 |
| 8016:7043 |
| 8016:7044 |
| 8016:7045 |
| 8016:7046 |
| 8016:7047 |
| 8016:7048 |

TABLE B-continued

Example combinations of a compound X with a compound Y.
X:Y

8016:7049
8016:7050
8016:7051
8016:7052
8016:7053
8016:7054
8016:7055
8016:7056
8016:7057
8016:7058
8016:7059
8016:7060
8016:7061
8016:7062
8016:7063
8016:7064
8016:7065
8016:7066
8016:7067
8016:7068
8016:7069
8016:7070
8016:7071
8016:7072
8016:7073
8016:7074
8016:7075
8016:7076
8016:7077
—
—

TABLE C

Example combinations of a compound X with a compound Y.
X:Y

6000:8000
6001:8000
6002:8000
6003:8000
6004:8000
6005:8000
6006:8000
6007:8000
6008:8000
6009:8000
6010:8000
6011:8000
6012:8000
6013:8000
6014:8000
6015:8000
6016:8000
6017:8000
6018:8000
6019:8000
6020:8000
6021:8000
6022:8000
6023:8000
6024:8000
6025:8000
6026:8000
6027:8000
6028:8000
6029:8000
6030:8000
6031:8000
6032:8000
6033:8000
6034:8000
6035:8000
6036:8000

TABLE C-continued

Example combinations of a compound X with a compound Y.
X:Y

6037:8000
6038:8000
6039:8000
6040:8000
6041:8000
6042:8000
6043:8000
6044:8000
6045:8000
6046:8000
6047:8000
6048:8000
6049:8000
6050:8000
6051:8000
6052:8000
6053:8000
6054:8000
6055:8000
6056:8000
6057:8000
6058:8000
6059:8000
6060:8000
6061:8000
6062:8000
6063:8000
6064:8000
6065:8000
6066:8000
6067:8000
6068:8000
6069:8000
6070:8000
6071:8000
6072:8000
6073:8000
6074:8000
6075:8000
6076:8000
6077:8000
6078:8000
6000:8001
6001:8001
6002:8001
6003:8001
6004:8001
6005:8001
6006:8001
6007:8001
6008:8001
6009:8001
6010:8001
6011:8001
6012:8001
6013:8001
6014:8001
6015:8001
6016:8001
6017:8001
6018:8001
6019:8001
6020:8001
6021:8001
6022:8001
6023:8001
6024:8001
6025:8001
6026:8001
6027:8001
6028:8001
6029:8001
6030:8001
6031:8001
6032:8001
6033:8001
6034:8001

TABLE C-continued

Example combinations of a compound X with a compound Y.
X:Y

6035:8001
6036:8001
6037:8001
6038:8001
6039:8001
6040:8001
6041:8001
6042:8001
6043:8001
6044:8001
6045:8001
6046:8001
6047:8001
6048:8001
6049:8001
6050:8001
6051:8001
6052:8001
6053:8001
6054:8001
6055:8001
6056:8001
6057:8001
6058:8001
6059:8001
6060:8001
6061:8001
6062:8001
6063:8001
6064:8001
6065:8001
6066:8001
6067:8001
6068:8001
6069:8001
6070:8001
6071:8001
6072:8001
6073:8001
6074:8001
6075:8001
6076:8001
6077:8001
6078:8001
6000:8002
6001:8002
6002:8002
6003:8002
6004:8002
6005:8002
6006:8002
6007:8002
6008:8002
6009:8002
6010:8002
6011:8002
6012:8002
6013:8002
6014:8002
6015:8002
6016:8002
6017:8002
6018:8002
6019:8002
6020:8002
6021:8002
6022:8002
6023:8002
6024:8002
6025:8002
6026:8002
6027:8002
6028:8002
6029:8002
6030:8002
6031:8002
6032:8002

TABLE C-continued

Example combinations of a compound X with a compound Y.
X:Y

6033:8002
6034:8002
6035:8002
6036:8002
6037:8002
6038:8002
6039:8002
6040:8002
6041:8002
6042:8002
6043:8002
6044:8002
6045:8002
6046:8002
6047:8002
6048:8002
6049:8002
6050:8002
6051:8002
6052:8002
6053:8002
6054:8002
6055:8002
6056:8002
6057:8002
6058:8002
6059:8002
6060:8002
6061:8002
6062:8002
6063:8002
6064:8002
6065:8002
6066:8002
6067:8002
6068:8002
6069:8002
6070:8002
6071:8002
6072:8002
6073:8002
6074:8002
6075:8002
6076:8002
6077:8002
6078:8002
6000:8003
6001:8003
6002:8003
6003:8003
6004:8003
6005:8003
6006:8003
6007:8003
6008:8003
6009:8003
6010:8003
6011:8003
6012:8003
6013:8003
6014:8003
6015:8003
6016:8003
6017:8003
6018:8003
6019:8003
6020:8003
6021:8003
6022:8003
6023:8003
6024:8003
6025:8003
6026:8003
6027:8003
6028:8003
6029:8003
6030:8003

TABLE C-continued

Example combinations of a compound X with a compound Y.
X:Y

| X:Y |
|---|
| 6031:8003 |
| 6032:8003 |
| 6033:8003 |
| 6034:8003 |
| 6035:8003 |
| 6036:8003 |
| 6037:8003 |
| 6038:8003 |
| 6039:8003 |
| 6040:8003 |
| 6041:8003 |
| 6042:8003 |
| 6043:8003 |
| 6044:8003 |
| 6045:8003 |
| 6046:8003 |
| 6047:8003 |
| 6048:8003 |
| 6049:8003 |
| 6050:8003 |
| 6051:8003 |
| 6052:8003 |
| 6053:8003 |
| 6054:8003 |
| 6055:8003 |
| 6056:8003 |
| 6057:8003 |
| 6058:8003 |
| 6059:8003 |
| 6060:8003 |
| 6061:8003 |
| 6062:8003 |
| 6063:8003 |
| 6064:8003 |
| 6065:8003 |
| 6066:8003 |
| 6067:8003 |
| 6068:8003 |
| 6069:8003 |
| 6070:8003 |
| 6071:8003 |
| 6072:8003 |
| 6073:8003 |
| 6074:8003 |
| 6075:8003 |
| 6076:8003 |
| 6077:8003 |
| 6078:8003 |
| 6000:8004 |
| 6001:8004 |
| 6002:8004 |
| 6003:8004 |
| 6004:8004 |
| 6005:8004 |
| 6006:8004 |
| 6007:8004 |
| 6008:8004 |
| 6009:8004 |
| 6010:8004 |
| 6011:8004 |
| 6012:8004 |
| 6013:8004 |
| 6014:8004 |
| 6015:8004 |
| 6016:8004 |
| 6017:8004 |
| 6018:8004 |
| 6019:8004 |
| 6020:8004 |
| 6021:8004 |
| 6022:8004 |
| 6023:8004 |
| 6024:8004 |
| 6025:8004 |
| 6026:8004 |
| 6027:8004 |
| 6028:8004 |

TABLE C-continued

Example combinations of a compound X with a compound Y.
X:Y

| X:Y |
|---|
| 6029:8004 |
| 6030:8004 |
| 6031:8004 |
| 6032:8004 |
| 6033:8004 |
| 6034:8004 |
| 6035:8004 |
| 6036:8004 |
| 6037:8004 |
| 6038:8004 |
| 6039:8004 |
| 6040:8004 |
| 6041:8004 |
| 6042:8004 |
| 6043:8004 |
| 6044:8004 |
| 6045:8004 |
| 6046:8004 |
| 6047:8004 |
| 6048:8004 |
| 6049:8004 |
| 6050:8004 |
| 6051:8004 |
| 6052:8004 |
| 6053:8004 |
| 6054:8004 |
| 6055:8004 |
| 6056:8004 |
| 6057:8004 |
| 6058:8004 |
| 6059:8004 |
| 6060:8004 |
| 6061:8004 |
| 6062:8004 |
| 6063:8004 |
| 6064:8004 |
| 6065:8004 |
| 6066:8004 |
| 6067:8004 |
| 6068:8004 |
| 6069:8004 |
| 6070:8004 |
| 6071:8004 |
| 6072:8004 |
| 6073:8004 |
| 6074:8004 |
| 6075:8004 |
| 6076:8004 |
| 6077:8004 |
| 6078:8004 |
| 6000:8005 |
| 6001:8005 |
| 6002:8005 |
| 6003:8005 |
| 6004:8005 |
| 6005:8005 |
| 6006:8005 |
| 6007:8005 |
| 6008:8005 |
| 6009:8005 |
| 6010:8005 |
| 6011:8005 |
| 6012:8005 |
| 6013:8005 |
| 6014:8005 |
| 6015:8005 |
| 6016:8005 |
| 6017:8005 |
| 6018:8005 |
| 6019:8005 |
| 6020:8005 |
| 6021:8005 |
| 6022:8005 |
| 6023:8005 |
| 6024:8005 |
| 6025:8005 |
| 6026:8005 |

TABLE C-continued

Example combinations of a compound X with a compound Y.
X:Y

6027:8005
6028:8005
6029:8005
6030:8005
6031:8005
6032:8005
6033:8005
6034:8005
6035:8005
6036:8005
6037:8005
6038:8005
6039:8005
6040:8005
6041:8005
6042:8005
6043:8005
6044:8005
6045:8005
6046:8005
6047:8005
6048:8005
6049:8005
6050:8005
6051:8005
6052:8005
6053:8005
6054:8005
6055:8005
6056:8005
6057:8005
6058:8005
6059:8005
6060:8005
6061:8005
6062:8005
6063:8005
6064:8005
6065:8005
6066:8005
6067:8005
6068:8005
6069:8005
6070:8005
6071:8005
6072:8005
6073:8005
6074:8005
6075:8005
6076:8005
6077:8005
6078:8005
6000:8006
6001:8006
6002:8006
6003:8006
6004:8006
6005:8006
6006:8006
6007:8006
6008:8006
6009:8006
6010:8006
6011:8006
6012:8006
6013:8006
6014:8006
6015:8006
6016:8006
6017:8006
6018:8006
6019:8006
6020:8006
6021:8006
6022:8006
6023:8006
6024:8006

TABLE C-continued

Example combinations of a compound X with a compound Y.
X:Y

6025:8006
6026:8006
6027:8006
6028:8006
6029:8006
6030:8006
6031:8006
6032:8006
6033:8006
6034:8006
6035:8006
6036:8006
6037:8006
6038:8006
6039:8006
6040:8006
6041:8006
6042:8006
6043:8006
6044:8006
6045:8006
6046:8006
6047:8006
6048:8006
6049:8006
6050:8006
6051:8006
6052:8006
6053:8006
6054:8006
6055:8006
6056:8006
6057:8006
6058:8006
6059:8006
6060:8006
6061:8006
6062:8006
6063:8006
6064:8006
6065:8006
6066:8006
6067:8006
6068:8006
6069:8006
6070:8006
6071:8006
6072:8006
6073:8006
6074:8006
6075:8006
6076:8006
6077:8006
6078:8006
6000:8007
6001:8007
6002:8007
6003:8007
6004:8007
6005:8007
6006:8007
6007:8007
6008:8007
6009:8007
6010:8007
6011:8007
6012:8007
6013:8007
6014:8007
6015:8007
6016:8007
6017:8007
6018:8007
6019:8007
6020:8007
6021:8007
6022:8007

TABLE C-continued

Example combinations of a compound X with a compound Y.
X:Y

6023:8007
6024:8007
6025:8007
6026:8007
6027:8007
6028:8007
6029:8007
6030:8007
6031:8007
6032:8007
6033:8007
6034:8007
6035:8007
6036:8007
6037:8007
6038:8007
6039:8007
6040:8007
6041:8007
6042:8007
6043:8007
6044:8007
6045:8007
6046:8007
6047:8007
6048:8007
6049:8007
6050:8007
6051:8007
6052:8007
6053:8007
6054:8007
6055:8007
6056:8007
6057:8007
6058:8007
6059:8007
6060:8007
6061:8007
6062:8007
6063:8007
6064:8007
6065:8007
6066:8007
6067:8007
6068:8007
6069:8007
6070:8007
6071:8007
6072:8007
6073:8007
6074:8007
6075:8007
6076:8007
6077:8007
6078:8007
6000:8008
6001:8008
6002:8008
6003:8008
6004:8008
6005:8008
6006:8008
6007:8008
6008:8008
6009:8008
6010:8008
6011:8008
6012:8008
6013:8008
6014:8008
6015:8008
6016:8008
6017:8008
6018:8008
6019:8008
6020:8008

TABLE C-continued

Example combinations of a compound X with a compound Y.
X:Y

6021:8008
6022:8008
6023:8008
6024:8008
6025:8008
6026:8008
6027:8008
6028:8008
6029:8008
6030:8008
6031:8008
6032:8008
6033:8008
6034:8008
6035:8008
6036:8008
6037:8008
6038:8008
6039:8008
6040:8008
6041:8008
6042:8008
6043:8008
6044:8008
6045:8008
6046:8008
6047:8008
6048:8008
6049:8008
6050:8008
6051:8008
6052:8008
6053:8008
6054:8008
6055:8008
6056:8008
6057:8008
6058:8008
6059:8008
6060:8008
6061:8008
6062:8008
6063:8008
6064:8008
6065:8008
6066:8008
6067:8008
6068:8008
6069:8008
6070:8008
6071:8008
6072:8008
6073:8008
6074:8008
6075:8008
6076:8008
6077:8008
6078:8008

TABLE D

Example combinations of a compound X with a compound Y.
X:Y

6000:8009
6001:8009
6002:8009
6003:8009
6004:8009
6005:8009
6006:8009
6007:8009
6008:8009
6009:8009

TABLE D-continued

Example combinations of a compound X with a compound Y.
X:Y

6010:8009
6011:8009
6012:8009
6013:8009
6014:8009
6015:8009
6016:8009
6017:8009
6018:8009
6019:8009
6020:8009
6021:8009
6022:8009
6023:8009
6024:8009
6025:8009
6026:8009
6027:8009
6028:8009
6029:8009
6030:8009
6031:8009
6032:8009
6033:8009
6034:8009
6035:8009
6036:8009
6037:8009
6038:8009
6039:8009
6040:8009
6041:8009
6042:8009
6043:8009
6044:8009
6045:8009
6046:8009
6047:8009
6048:8009
6049:8009
6050:8009
6051:8009
6052:8009
6053:8009
6054:8009
6055:8009
6056:8009
6057:8009
6058:8009
6059:8009
6060:8009
6061:8009
6062:8009
6063:8009
6064:8009
6065:8009
6066:8009
6067:8009
6068:8009
6069:8009
6070:8009
6071:8009
6072:8009
6073:8009
6074:8009
6075:8009
6076:8009
6077:8009
6078:8009
6000:8010
6001:8010
6002:8010
6003:8010
6004:8010
6005:8010
6006:8010
6007:8010

TABLE D-continued

Example combinations of a compound X with a compound Y.
X:Y

6008:8010
6009:8010
6010:8010
6011:8010
6012:8010
6013:8010
6014:8010
6015:8010
6016:8010
6017:8010
6018:8010
6019:8010
6020:8010
6021:8010
6022:8010
6023:8010
6024:8010
6025:8010
6026:8010
6027:8010
6028:8010
6029:8010
6030:8010
6031:8010
6032:8010
6033:8010
6034:8010
6035:8010
6036:8010
6037:8010
6038:8010
6039:8010
6040:8010
6041:8010
6042:8010
6043:8010
6044:8010
6045:8010
6046:8010
6047:8010
6048:8010
6049:8010
6050:8010
6051:8010
6052:8010
6053:8010
6054:8010
6055:8010
6056:8010
6057:8010
6058:8010
6059:8010
6060:8010
6061:8010
6062:8010
6063:8010
6064:8010
6065:8010
6066:8010
6067:8010
6068:8010
6069:8010
6070:8010
6071:8010
6072:8010
6073:8010
6074:8010
6075:8010
6076:8010
6077:8010
6078:8010
6000:8011
6001:8011
6002:8011
6003:8011
6004:8011
6005:8011

TABLE D-continued

Example combinations of a compound X with a compound Y.
X:Y

| X:Y |
|---|
| 6006:8011 |
| 6007:8011 |
| 6008:8011 |
| 6009:8011 |
| 6010:8011 |
| 6011:8011 |
| 6012:8011 |
| 6013:8011 |
| 6014:8011 |
| 6015:8011 |
| 6016:8011 |
| 6017:8011 |
| 6018:8011 |
| 6019:8011 |
| 6020:8011 |
| 6021:8011 |
| 6022:8011 |
| 6023:8011 |
| 6024:8011 |
| 6025:8011 |
| 6026:8011 |
| 6027:8011 |
| 6028:8011 |
| 6029:8011 |
| 6030:8011 |
| 6031:8011 |
| 6032:8011 |
| 6033:8011 |
| 6034:8011 |
| 6035:8011 |
| 6036:8011 |
| 6037:8011 |
| 6038:8011 |
| 6039:8011 |
| 6040:8011 |
| 6041:8011 |
| 6042:8011 |
| 6043:8011 |
| 6044:8011 |
| 6045:8011 |
| 6046:8011 |
| 6047:8011 |
| 6048:8011 |
| 6049:8011 |
| 6050:8011 |
| 6051:8011 |
| 6052:8011 |
| 6053:8011 |
| 6054:8011 |
| 6055:8011 |
| 6056:8011 |
| 6057:8011 |
| 6058:8011 |
| 6059:8011 |
| 6060:8011 |
| 6061:8011 |
| 6062:8011 |
| 6063:8011 |
| 6064:8011 |
| 6065:8011 |
| 6066:8011 |
| 6067:8011 |
| 6068:8011 |
| 6069:8011 |
| 6070:8011 |
| 6071:8011 |
| 6072:8011 |
| 6073:8011 |
| 6074:8011 |
| 6075:8011 |
| 6076:8011 |
| 6077:8011 |
| 6078:8011 |
| 6000:8012 |
| 6001:8012 |
| 6002:8012 |
| 6003:8012 |
| 6004:8012 |
| 6005:8012 |
| 6006:8012 |
| 6007:8012 |
| 6008:8012 |
| 6009:8012 |
| 6010:8012 |
| 6011:8012 |
| 6012:8012 |
| 6013:8012 |
| 6014:8012 |
| 6015:8012 |
| 6016:8012 |
| 6017:8012 |
| 6018:8012 |
| 6019:8012 |
| 6020:8012 |
| 6021:8012 |
| 6022:8012 |
| 6023:8012 |
| 6024:8012 |
| 6025:8012 |
| 6026:8012 |
| 6027:8012 |
| 6028:8012 |
| 6029:8012 |
| 6030:8012 |
| 6031:8012 |
| 6032:8012 |
| 6033:8012 |
| 6034:8012 |
| 6035:8012 |
| 6036:8012 |
| 6037:8012 |
| 6038:8012 |
| 6039:8012 |
| 6040:8012 |
| 6041:8012 |
| 6042:8012 |
| 6043:8012 |
| 6044:8012 |
| 6045:8012 |
| 6046:8012 |
| 6047:8012 |
| 6048:8012 |
| 6049:8012 |
| 6050:8012 |
| 6051:8012 |
| 6052:8012 |
| 6053:8012 |
| 6054:8012 |
| 6055:8012 |
| 6056:8012 |
| 6057:8012 |
| 6058:8012 |
| 6059:8012 |
| 6060:8012 |
| 6061:8012 |
| 6062:8012 |
| 6063:8012 |
| 6064:8012 |
| 6065:8012 |
| 6066:8012 |
| 6067:8012 |
| 6068:8012 |
| 6069:8012 |
| 6070:8012 |
| 6071:8012 |
| 6072:8012 |
| 6073:8012 |
| 6074:8012 |
| 6075:8012 |
| 6076:8012 |
| 6077:8012 |
| 6078:8012 |
| 6000:8013 |
| 6001:8013 |

TABLE D-continued

Example combinations of a compound X with a compound Y.
X:Y

| X:Y |
|---|
| 6002:8013 |
| 6003:8013 |
| 6004:8013 |
| 6005:8013 |
| 6006:8013 |
| 6007:8013 |
| 6008:8013 |
| 6009:8013 |
| 6010:8013 |
| 6011:8013 |
| 6012:8013 |
| 6013:8013 |
| 6014:8013 |
| 6015:8013 |
| 6016:8013 |
| 6017:8013 |
| 6018:8013 |
| 6019:8013 |
| 6020:8013 |
| 6021:8013 |
| 6022:8013 |
| 6023:8013 |
| 6024:8013 |
| 6025:8013 |
| 6026:8013 |
| 6027:8013 |
| 6028:8013 |
| 6029:8013 |
| 6030:8013 |
| 6031:8013 |
| 6032:8013 |
| 6033:8013 |
| 6034:8013 |
| 6035:8013 |
| 6036:8013 |
| 6037:8013 |
| 6038:8013 |
| 6039:8013 |
| 6040:8013 |
| 6041:8013 |
| 6042:8013 |
| 6043:8013 |
| 6044:8013 |
| 6045:8013 |
| 6046:8013 |
| 6047:8013 |
| 6048:8013 |
| 6049:8013 |
| 6050:8013 |
| 6051:8013 |
| 6052:8013 |
| 6053:8013 |
| 6054:8013 |
| 6055:8013 |
| 6056:8013 |
| 6057:8013 |
| 6058:8013 |
| 6059:8013 |
| 6060:8013 |
| 6061:8013 |
| 6062:8013 |
| 6063:8013 |
| 6064:8013 |
| 6065:8013 |
| 6066:8013 |
| 6067:8013 |
| 6068:8013 |
| 6069:8013 |
| 6070:8013 |
| 6071:8013 |
| 6072:8013 |
| 6073:8013 |
| 6074:8013 |
| 6075:8013 |
| 6076:8013 |
| 6077:8013 |
| 6078:8013 |

TABLE D-continued

Example combinations of a compound X with a compound Y.
X:Y

| X:Y |
|---|
| 6000:8014 |
| 6001:8014 |
| 6002:8014 |
| 6003:8014 |
| 6004:8014 |
| 6005:8014 |
| 6006:8014 |
| 6007:8014 |
| 6008:8014 |
| 6009:8014 |
| 6010:8014 |
| 6011:8014 |
| 6012:8014 |
| 6013:8014 |
| 6014:8014 |
| 6015:8014 |
| 6016:8014 |
| 6017:8014 |
| 6018:8014 |
| 6019:8014 |
| 6020:8014 |
| 6021:8014 |
| 6022:8014 |
| 6023:8014 |
| 6024:8014 |
| 6025:8014 |
| 6026:8014 |
| 6027:8014 |
| 6028:8014 |
| 6029:8014 |
| 6030:8014 |
| 6031:8014 |
| 6032:8014 |
| 6033:8014 |
| 6034:8014 |
| 6035:8014 |
| 6036:8014 |
| 6037:8014 |
| 6038:8014 |
| 6039:8014 |
| 6040:8014 |
| 6041:8014 |
| 6042:8014 |
| 6043:8014 |
| 6044:8014 |
| 6045:8014 |
| 6046:8014 |
| 6047:8014 |
| 6048:8014 |
| 6049:8014 |
| 6050:8014 |
| 6051:8014 |
| 6052:8014 |
| 6053:8014 |
| 6054:8014 |
| 6055:8014 |
| 6056:8014 |
| 6057:8014 |
| 6058:8014 |
| 6059:8014 |
| 6060:8014 |
| 6061:8014 |
| 6062:8014 |
| 6063:8014 |
| 6064:8014 |
| 6065:8014 |
| 6066:8014 |
| 6067:8014 |
| 6068:8014 |
| 6069:8014 |
| 6070:8014 |
| 6071:8014 |
| 6072:8014 |
| 6073:8014 |
| 6074:8014 |
| 6075:8014 |
| 6076:8014 |

TABLE D-continued

Example combinations of a compound X with a compound Y.
X:Y

| X:Y |
|---|
| 6077:8014 |
| 6078:8014 |
| 6000:8015 |
| 6001:8015 |
| 6002:8015 |
| 6003:8015 |
| 6004:8015 |
| 6005:8015 |
| 6006:8015 |
| 6007:8015 |
| 6008:8015 |
| 6009:8015 |
| 6010:8015 |
| 6011:8015 |
| 6012:8015 |
| 6013:8015 |
| 6014:8015 |
| 6015:8015 |
| 6016:8015 |
| 6017:8015 |
| 6018:8015 |
| 6019:8015 |
| 6020:8015 |
| 6021:8015 |
| 6022:8015 |
| 6023:8015 |
| 6024:8015 |
| 6025:8015 |
| 6026:8015 |
| 6027:8015 |
| 6028:8015 |
| 6029:8015 |
| 6030:8015 |
| 6031:8015 |
| 6032:8015 |
| 6033:8015 |
| 6034:8015 |
| 6035:8015 |
| 6036:8015 |
| 6037:8015 |
| 6038:8015 |
| 6039:8015 |
| 6040:8015 |
| 6041:8015 |
| 6042:8015 |
| 6043:8015 |
| 6044:8015 |
| 6045:8015 |
| 6046:8015 |
| 6047:8015 |
| 6048:8015 |
| 6049:8015 |
| 6050:8015 |
| 6051:8015 |
| 6052:8015 |
| 6053:8015 |
| 6054:8015 |
| 6055:8015 |
| 6056:8015 |
| 6057:8015 |
| 6058:8015 |
| 6059:8015 |
| 6060:8015 |
| 6061:8015 |
| 6062:8015 |
| 6063:8015 |
| 6064:8015 |
| 6065:8015 |
| 6066:8015 |
| 6067:8015 |
| 6068:8015 |
| 6069:8015 |
| 6070:8015 |
| 6071:8015 |
| 6072:8015 |
| 6073:8015 |
| 6074:8015 |

TABLE D-continued

Example combinations of a compound X with a compound Y.
X:Y

| X:Y |
|---|
| 6075:8015 |
| 6076:8015 |
| 6077:8015 |
| 6078:8015 |
| 6000:8016 |
| 6001:8016 |
| 6002:8016 |
| 6003:8016 |
| 6004:8016 |
| 6005:8016 |
| 6006:8016 |
| 6007:8016 |
| 6008:8016 |
| 6009:8016 |
| 6010:8016 |
| 6011:8016 |
| 6012:8016 |
| 6013:8016 |
| 6014:8016 |
| 6015:8016 |
| 6016:8016 |
| 6017:8016 |
| 6018:8016 |
| 6019:8016 |
| 6020:8016 |
| 6021:8016 |
| 6022:8016 |
| 6023:8016 |
| 6024:8016 |
| 6025:8016 |
| 6026:8016 |
| 6027:8016 |
| 6028:8016 |
| 6029:8016 |
| 6030:8016 |
| 6031:8016 |
| 6032:8016 |
| 6033:8016 |
| 6034:8016 |
| 6035:8016 |
| 6036:8016 |
| 6037:8016 |
| 6038:8016 |
| 6039:8016 |
| 6040:8016 |
| 6041:8016 |
| 6042:8016 |
| 6043:8016 |
| 6044:8016 |
| 6045:8016 |
| 6046:8016 |
| 6047:8016 |
| 6048:8016 |
| 6049:8016 |
| 6050:8016 |
| 6051:8016 |
| 6052:8016 |
| 6053:8016 |
| 6054:8016 |
| 6055:8016 |
| 6056:8016 |
| 6057:8016 |
| 6058:8016 |
| 6059:8016 |
| 6060:8016 |
| 6061:8016 |
| 6062:8016 |
| 6063:8016 |
| 6064:8016 |
| 6065:8016 |
| 6066:8016 |
| 6067:8016 |
| 6068:8016 |
| 6069:8016 |
| 6070:8016 |
| 6071:8016 |
| 6072:8016 |

TABLE D-continued

Example combinations of a compound X with a compound Y.
X:Y

6073:8016
6074:8016
6075:8016
6076:8016
6077:8016
6078:8016

EXAMPLES

Additional embodiments are disclosed in further detail in the following examples, which are not in any way intended to limit the scope of the claims.

Example 1

(Rp/Sp) 2'-C-methyl-6-O-methyl-guanosine-3',5'-cyclic-O-methyl phosphorothioate (1a)

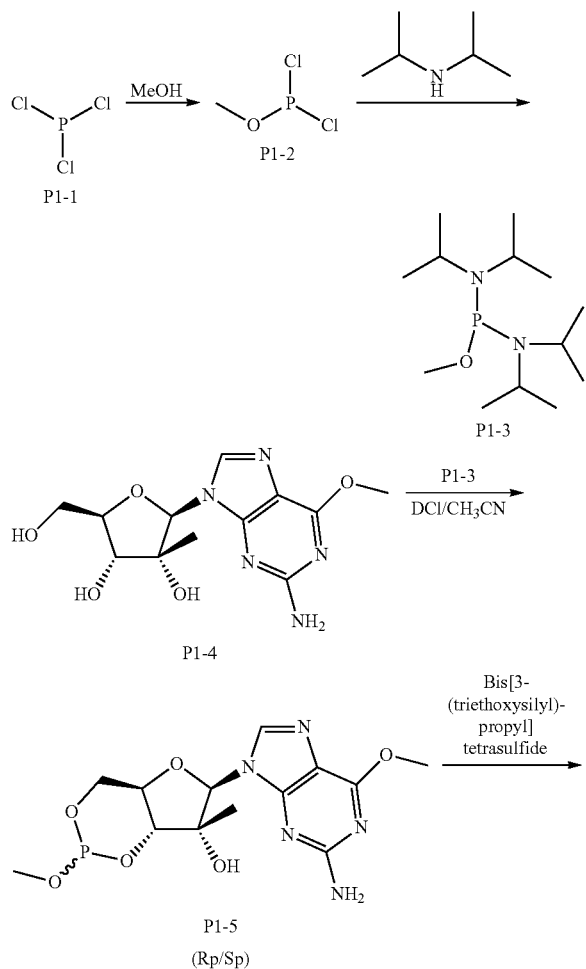
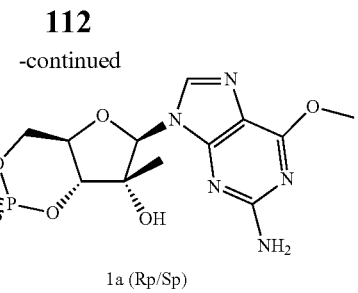

1a (Rp/Sp)

Step 1: Compound of P1-2

To a flask containing P1-1 (20.0 g, 147.3 mmol) was added absolute MeOH (3.78 g, 118 mmol) dropwise over 2 hours at −40° C. The mixture was warmed to room temperature gradually and stirred for another hour. The reaction mixture was distilled to give P1-2 (9.5 g, 61%). $^1$H NMR (CDCl$_3$, 400 MHz) δ 3.90 (d, J=10.4 Hz, 3H). $^{31}$P NMR (CDCl$_3$, 162 MHz) δ180.81.

Step 2: Compound of P1-3

To a solution of P1-2 (9.5 g, 72.0 mmol) in anhydrous ether (200 mL) was added diisopropylamine (43.5 g, 430.8 mmol) dropwise at 0° C. The mixture was stirred at room temperature overnight. The precipitate was filtered and the filtrate was concentrated to give a residue, which was distilled to give P1-3 (6.5 g, 34%) as a colorless oil. $^1$H NMR (CDCl$_3$, 400 MHz) δ 3.42-3.48 (m, 4H), 3.31 (d, J=14.0 Hz, 3H), 1.02-1.11 (m, 27H). $^{31}$P NMR (CDCl$_3$, 162 MHz) δ 130.99.

Step 3: Compound 1a

A 1.0 M solution of 4,5-dicyanoimidazole (DCI) in CH$_3$CN (0.38 mL, 0.38 mmol) was added dropwise into a solution of 2'-C-methyl-6-O-methyl-guanosine (P1-4) (0.2 g, 0.64 mmol) in CH$_3$CN (10 mL) in N$_2$ atmosphere, and stirred at room temperature. After 40 minutes, the reaction mixture was cooled to 0-5° C. using an ice/water bath. A freshly prepared solution of methyl N,N,N',N'-tetraisopropylphosphorodiamidite in dichloromethane (DCM) (221 μl in 0.7 mL DCM, 0.77 mmol) was added. The reaction mixture was allowed to warm to room temperature and was stirred for 2 hours. Additional DCI (50 mg, 0.42 mmol) was added, and the reaction was stirred for 1 h to give a phosphite intermediate. Bis[3-(triethoxysilyl)propyl]tetrasulfide (0.415 mL, 0.77 mmol) was added dropwise to the reaction mixture and the resultant light yellow suspension was stirred for 2 h at room temperature. The reaction mixture was cooled using an ice/water bath, and then diluted with ethyl acetate (EA) (150 mL), washed with saturated NaHCO$_3$ followed by brine, then dried over anhydrous Na$_2$SO$_4$ and concentrated in-vacuo to give a crude product residue which was purified by silica gel (DCM/MeOH; 95:5) to give 37.1 mg as white solid. Further purification by silica gel (DCM/isopropyl alcohol; 94:6) gave 16.9 mg of impure product, which was purified by RP-HPLC (H$_2$O/CH$_3$CN; 0 to 50%, 30 min) to afford compound 1a (8.6 mg) as a white foam after lyophilization. $^1$H NMR (400 MHz, (CD$_3$)$_2$CO, two isomers): δ 1.13 (s, 3H), 3.86 (2s, 3H), 3.71, 3.76 (2d, J=13.6 Hz, 3H), 4.36-4.5 (m, 1H), 4.63-4.71 (m, 3H), 5.09, 5.18 (2s, 1H), 5.85-5.87 (br s, 2H), 6.00 (s, 1H), 7.91, 7.95 (2s, 1H); $^{31}$P NMR ((CD$_3$)$_2$CO, two isomers): δ 65.07 (s), 68.4 (s); MS m/z 404.3 (M+H)$^+$.

Example 2

Preparation of 4'-azido-2'-deoxy-2'-fluorouridine 3',5'-cyclic thiophosphoric acid methyl ester (2a)

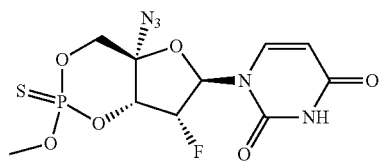

To an ice-cold suspension of 4'-azido-2'-deoxy-2'-fluorouridine (150 mg, 0.52 mmol) in dry pyridine (4 mL) was added tetrazole (0.37 M in MeCN, 4 mL, 1.48 mmol), followed by addition of methyl N,N,N',N'-tetraisopropylphosphordiamidite (204 mg, 0.78 mmol) dropwise over 5 min. The resultant mixture was stirred at the ambient temperature for 16 hours before bis(3-triethoxysilyl)propyl-tetrasulfide (TEST) (0.42 mL, 0.8 mmol) was added. The resulting light yellow suspension was stirred for 3 hours at room temperature. The reaction mixture was cooled down (ice/water bath), and was diluted with EA (100 mL), washed with saturated NaHCO$_3$ and followed by brine, dried over anhydrous Na$_2$SO$_4$ and concentrated in-vacuo to give a crude product residue. The crude product was purified by flash chromatography on silica gel and then further purified on HPLC to give compound 2a (21.2 mg, 11%) as a white solid. $^1$H NMR (CD$_3$OD, 400 MHz) δ 7.69 (d, J=8.0 Hz, 1H), 6.06 (d, J=22.0 Hz, 1H), 5.71 (d, J=8.0 Hz, 1H), 5.67-5.52 (dd, J=55.6 Hz, 5.6 Hz, 1H), 5.35-5.26 (dt, J=25.6 Hz, 4.0 Hz, 1H), 4.66 (m, 2H), 3.85 (d, J=13.6 Hz, 3H). $^{31}$P NMR (CD$_3$OD, 162 MHz) δ62.66. ESI-LCMS: m/z=402 [M+Na]$^+$.

Example 3

Preparation of 4'-azido-2'-deoxy-2'-fluorouridine 3',5'-cyclic thiophosphoric acid isopropyl ester (3a)

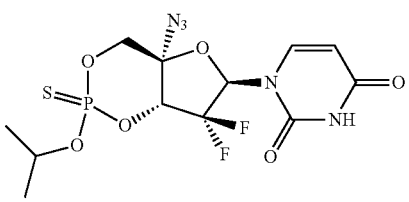

Compound 3a (white solid, 15.5 mg, 7.4%) was prepared using the procedure for preparing compound 2a using 4'-azido-2'-deoxy-2',2'-difluorouridine (150 mg, 0.49 mmol) in place of 4'-azido-2'-deoxy-2'-fluorouridine, and isopropyl N,N,N',N'-tetraisopropylphosphordiamidite (213 mg, 0.74 mmol). $^1$H NMR (CD$_3$OD, 400 MHz) δ7.73 (d, J=6.8 Hz, 1H), 6.35 (br, 1H), 5.77 (d, J=8.0 Hz, 1H), 5.35 (br, 1H), 4.92 (m, 1H), 4.78 (m, 2H), 1.40 (t, 6H). $^{31}$P NMR (CD$_3$OD, 162 MHz) δ58.53. ESI-LCMS: m/z 426 [M+H]$^+$.

Example 4

Preparation of 4'-azido-2'-deoxy-2'-fluorouridine 3',5'-cyclic thiophosphoric acid isopropyl ester (4a)

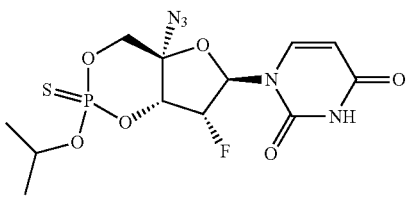

To an ice-cold suspension of 4'-azido-2'-deoxy-2'-fluorouridine (100 mg, 0.35 mmol) in dry pyridine (3 mL) was added tetrazole (0.37 M in MeCN, 3 mL, 1.11 mmol), followed by addition of isopropyl N,N,N',N'-tetraisopropylphosphordiamidite (151 mg, 0.52 mmol) dropwise after 5 min. The resultant mixture was stirred at the ambient temperature for 16 hours before TEST (0.42 mL, 0.8 mmol) was added. The resulting light yellow suspension was stirred for 3 hours at room temperature. The reaction mixture was cooled down (ice/water bath), diluted with EA (100 mL), washed with saturated aqueous NaHCO$_3$ and followed by brine, dried over anhydrous Na$_2$SO$_4$ and concentrated in-vacuo to give a crude product residue. The crude product was purified on silica gel (DCM/MeOH; 95:5) and then further purified on HPLC to give compound 4a (30.5 mg, 21.6%) as a white solid. $^1$H NMR (CD$_3$OD, 400 MHz) δ7.70 (d, J=8.0 Hz, 1H), 6.15 (d, J=22.4 Hz, 1H), 5.71 (d, J=8.0 Hz, 1H), 5.62 (dd, J$_1$=5.2 Hz, J$_2$=55.6 Hz, 1H), 5.38-5.47 (m, 1H), 4.80-4.85 (m, 1H), 4.59-4.71 (m, 2H), 1.39-1.41 (m, 6H); $^{31}$P NMR (CD$_3$OD, 162 MHz) δ 59.36; ESI-LCMS: m/z=430 [M+Na]$^+$.

Example 5

Preparation of 4'-azido-2'-deoxy-2'-fluorocytidine 3',5'-cyclic thiophosphoric acid isopropyl ester (5a)

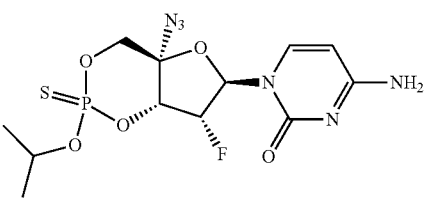

Compound 5a (white solid, 7.2 mg, 8.5%) was prepared using the procedure for preparing compound 4a using 4'-azido-2'-deoxy-2'-fluorocytidine (60 mg, 0.21 mmol) in place of 4'-azido-2'-deoxy-2'-fluorouridine, and isopropyl N,N,N',N'-tetraisopropylphosphordiamidite (92 mg, 0.32 mmol). $^1$H NMR (CD$_3$OD, 400 MHz) δ7.69 (d, J=7.6 Hz, 1H), 5.87-5.93 (m, 2H), 5.58-5.67 (m, 1H), 5.50-5.54 (m, 1H), 4.81-4.84 (m, 1H), 4.62-4.69 (m, 2H), 1.41 (t, J=6.0 Hz, 6H); $^{31}$P NMR (CD$_3$OD, 162 MHz) δ 59.58; ESI-LCMS: m/z 407 [M+H]$^+$.

Example 6

Preparation of 6-(6-Amino-purin-9-yl)-2-isopropoxy-4-methyl-2-oxo-tetrahydro-2l5-furo[3,2-d][1,3,2]dioxaphosphinin-7-ol (6a)

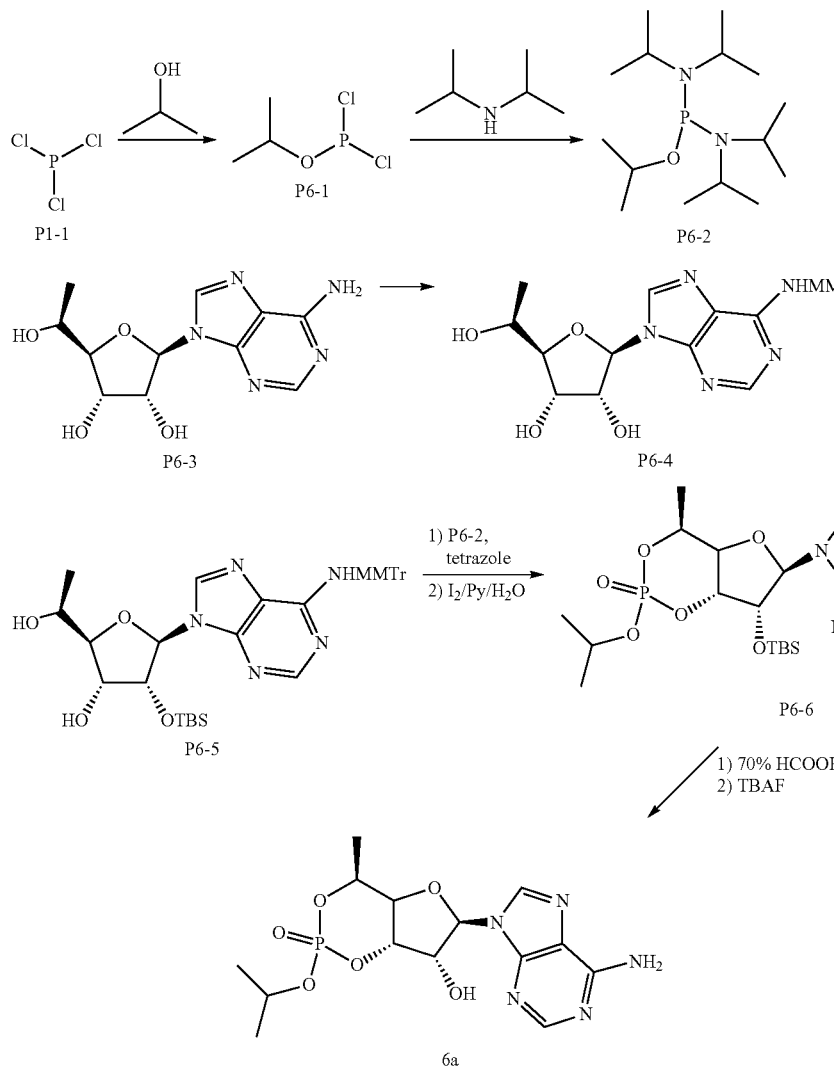

Step 1: Compound P6-1

To a flask containing P1-1 (20.0 g, 147.3 mmol) was added anhydrous i-PrOH (7.1 g, 118 mmol) dropwise over 2 hours at −40° C. The mixture was warmed to room temperature gradually and stirred for another 1 hour. The reaction mixture was distilled under reduced pressure to give pure P6-1 (11.5 g, 61%). $^1$H NMR (CDCl$_3$, 400 MHz) 4.98-5.11 (m, 1H), 1.42 (d, J=3.2 Hz, 6H). $^{31}$P NMR (CDCl$_3$, 162 MHz) δ174.48.

Step 2: Compound P6-2

To a solution of P6-1 (11.5 g, 71.8 mmol) in anhydrous ether (200 mL) was added diisopropylamine (43.5 g, 430.8 mmol) dropwise at 0° C. The mixture was stirred at room temperature overnight. The precipitate was filtered and the filtrate was concentrated to give a residue which was distilled to give P6-2 (8.8 g, 42%) as a colorless oil. $^1$H NMR (CDCl$_3$, 400 MHz) δ3.75-3.79 (m, 1H), 3.44-3.58 (m, 4H), 1.14-1.20 (m, 30H). 1.42 (d, J=3.2 Hz, 6H). $^{31}$P NMR (CDCl$_3$, 162 MHz) δ114.84.

Step 3: 2-(1-Hydroxy-ethyl)-5-(6-{[(4-methoxyphenyl)-diphenyl-methyl]-amino}-purin-9-yl)-tetrahydro-furan-3,4-diol (P6-4)

To a solution of P6-3 (4.5 g, 16 mmol) in dry pyridine (100 mL) was added TMSCl (12.2 g, 113 mmol) at 0° C. The mixture was stirred at room temperature overnight, and then MMTrCl (10.0 g, 32.5 mmol) was added. The mixture was stirred at 4050° C. overnight. NH$_4$OH (300 mL) was added, and the mixture was stirred at 30~40° C. overnight. The mixture was extracted with ethyl acetate and the organic layer was washed with H$_2$O and brine, dried by anhydrous Na$_2$SO$_4$ and filtered. The filtrate was evaporated, and the residue was purified by silica gel column chromatography (DCM:MeOH=100:1 to 30:1) to give P6-4 (5.8 g, 65%) as a brown solid.

Step 4: 4-(tert-Butyl-dimethyl-silanyloxy)-2-(1-hydroxy-ethyl)-5-(6-{[(4-methoxy-phenyl)-diphenyl-methyl]-amino}-purin-9-yl)-tetrahydro-furan-3-ol (P6-5)

To a solution of P6-4 (2.0 g, 3.62 mmol) in dry pyridine (40 mL) was added AgNO$_3$ (1.23 g, 7.24 mmol) and TBSCl (0.709 g, 4.71 mmol) at 0° C. The mixture was stirred at room temperature overnight and then was quenched with water. The solvent was removed under reduced pressure, and the residue was purified by silica gel column chromatography (DCM: MeOH=300:1 to 40:1) to give P6-5 (0.5 g, 20.6%) as a white solid. $^1$H NMR (CDCl$_3$, 400 MHz) δ8.01 (s, 1H), 7.75 (s, 1H), 7.22-7.34 (m, 12H), 7.03 (s, 1H), 6.79 (d, J=8.8 Hz, 1H), 6.25 (d, J=12.0 Hz, 1H), 5.74 (d, J=7.6 Hz, 1H), 5.29 (s, 1H), 5.05 (dd, J$_1$=7.2 Hz, J$_2$=4.8 Hz, 1H), 5.25 (d, J=4.8 Hz, 1H), 4.18 (s, 1H), 3.89 (dd, J$_1$=11.6 Hz, J$_2$=6.4 Hz, 1H), 3.78 (s, 3H), 2.82 (bs, 1H), 1.23 (d, J=6.4 Hz, 3H), 0.91 (s, 1H), 0.79 (s, 9H), 0.08 (s, 2H), −0.19 (s, 3H), −0.42 (s, 3H).

Step 5: {9-[7-(tert-Butyl-dimethyl-silanyloxy)-2-isopropoxy-4-methyl-2-oxo-tetrahydro-2l5-furo[3,2-d][1,3,2]dioxaphosphinin-6-yl]-9H-purin-6-yl}-[(4-methoxy-phenyl)-diphenyl-methyl]-amine (P6-6)

To a solution of P6-5 (310 mg, 0.464 mmol) in dry pyridine (4 mL) was added a solution of tetrazole in MeCN (0.45 M, 4 mL) and P6-2 (197 mg, 0.679 mmol) at 0° C. After stirring at room temperature overnight, a solution of I$_2$ (200 mg, 0.788 mmol) in pyridine (0.6 mL) and H$_2$O (0.2 mL) was added at 0° C. The mixture was stirred at room temperature for 30 min. The reaction was quenched with saturated aqueous Na$_2$S$_2$O$_3$. The solvent was removed, and the residue was purified via silica gel column chromatography (DCM: MeOH=500:1 to 50:1) to give compound P6-6 (190 mg, 53%).

Step 6: Compound 6a

P6-6 (90 mg, 0.116 mmol) was dissolved in 70% formic acid (5 mL) and stirred at room temperature overnight. Tetrabutylammonium fluoride (TBAF) (200 mg, 0.766 mmol) was added, and the mixture was stirred at room temperature for another 30 min. The solvent was removed, and the residue was purified by HPLC (0.1% HCOOH in water and MeCN) to afford compound 6a (9.23 mg, 20.1%) as a white solid. $^1$H NMR (MeOD, 400 MHz) δ 8.21 (s, 1H), 8.18 (s, 1H), 6.01 (s, 1H), 5.80-5.84 (m, 1H), 5.00-5.09 (m, 1H), 4.83-4.85 (m, 1H), 4.79-4.71 (m, 1H), 4.50-4.54 (m, 1H), 1.42-1.50 (m, 9H). $^{31}$P NMR (MeOD, 162 MHz) δ−6.07. LCMS m/z 385.8 (MH$^+$).

Example 7

Preparation of 2-Isopropoxy-6-(6-{[(4-methoxy-phenyl)-diphenyl-methyl]-amino}-purin-9-yl)-4-methyl-2-thioxo-tetrahydro-2l5-furo[3,2-d][1,3,2]dioxaphosphinin-7-ol (7a)

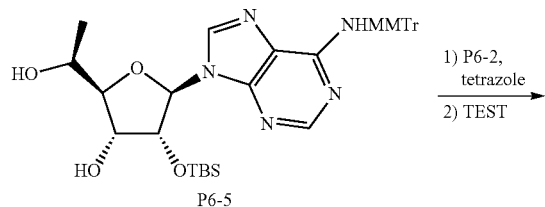

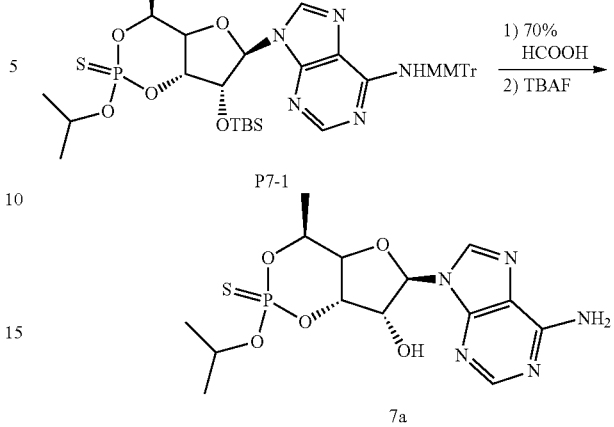

Step 1: {9-[7-(tert-Butyl-dimethyl-silanyloxy)-2-isopropoxy-4-methyl-2-thioxo-tetrahydro-2l5-furo[3,2-d][1,3,2]dioxaphosphinin-6-yl]-9H-purin-6-yl}-[(4-methoxy-phenyl)-diphenyl-methyl]-amine (P7-1)

To a solution of P6-5 (584 mg, 0.876 mmol) in dry pyridine (7.5 mL) was added a solution of 0.45M tetrazole in MeCN (7.5 mL) and P1-3 (381 mg, 1.312 mmol) at 0° C. The mixture was stirred at room temperature overnight and then Bis[3-(triethoxysilyl)propyl]tetrasulfide (TEST) (0.707 mL, 1.312 mmol) at 0° C. The mixture was stirred for another hour. The reaction mixture was concentrated and diluted with ethyl acetate, washed with saturated NaHCO$_3$ and brine, and dried over anhydrous Na$_2$SO$_4$. The organic layer was concentrated, and the residue was purified via silica gel column chromatography (DCM: MeOH=500:1 to 50:1) to give compound P7-1 (105 mg, 15%).

Step 2: Compound 7a

Compound P7-1 (80 mg, 0.102 mmol) was dissolved in 70% formic acid (10 mL) and stirred overnight. The solvent was evaporated, and the residue was dissolved in THF (2 mL). TBAF (162 mg, 0.62 mmol) was added, and the mixture was stirred for 30 min. The solvent was removed, and the residue was purified by preparative HPLC (0.1% HCOOH in water and MeCN) to afford compound 7a (15.81 mg, 36.6%) as a white solid. $^1$H NMR (MeOD, 400 MHz) δ 8.25 (s, 1H), 8.22 (s, 1H), 6.00 (s, 1H), 5.54-5.57 (m, 1H), 5.01-5.06 (m, 1H), 4.69-4.85 (m, 3H), 1.36-1.45 (m, 9H). $^{31}$P NMR (MeOD, 162 MHz) δ62.28, 62.03. LCMS m/z 402.0 (MH$^+$).

Example 8

Preparation of 2-Methoxy-6-(6-{[(4-methoxy-phenyl)-diphenyl-methyl]-amino}-purin-9-yl)-4-methyl-2-oxo-tetrahydro-2l5-furo[3,2-d][1,3,2]dioxaphosphinin-7-ol (8a)

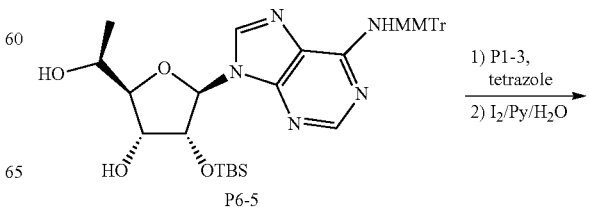

-continued

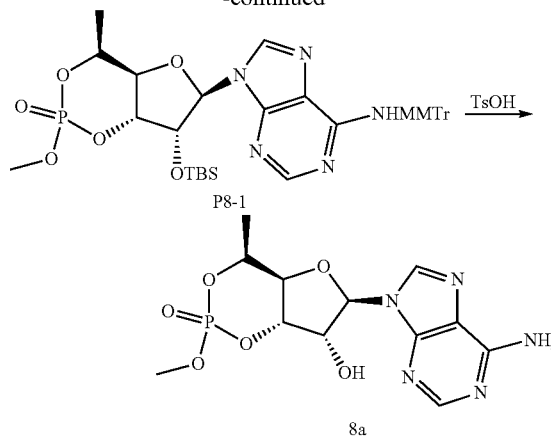

P8-1

TsOH →

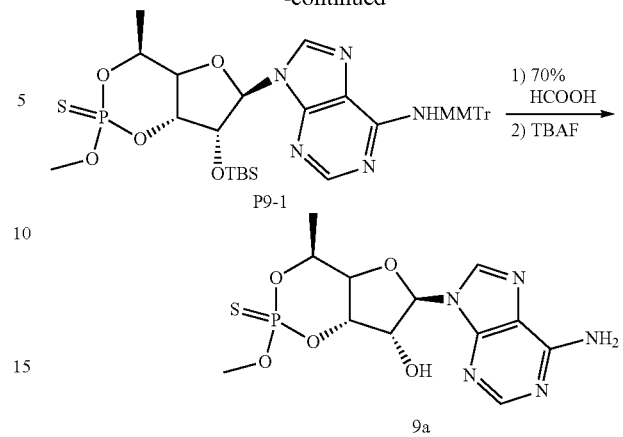

P9-1

1) 70% HCOOH
2) TBAF →

8a

9a

Step 1: {9-[7-(tert-Butyl-dimethyl-silanyloxy)-2-methoxy-4-methyl-2-oxo-tetrahydro-2l5-furo[3,2-d][1,3,2]dioxaphosphinin-6-yl]-9H-purin-6-yl}-[(4-methoxy-phenyl)-diphenyl-methyl]-amine (P8-1)

To a solution of P6-5 (500 mg, 0.750 mmol) in dry pyridine (7 mL) was added a solution of 0.45M tetrazole in MeCN (7 mL) and P1-3 (324 mg, 1.236 mmol) at 0° C. After stirring at room temperature overnight, a solution of $I_2$ (300 mg, 1.182 mmol) in pyridine (0.9 mL) and $H_2O$ (0.3 mL) was added at 0° C. The mixture was stirred at room temperature for 30 min and quenched with saturated aqueous $Na_2S_2O_3$. The solvent was removed, and the residue was purified via silica gel column chromatography (DCM: MeOH=500:1 to 50:1) to give P8-1 (216 mg, 38.8%).

Step 2: Compound 8a

To a solution of P8-1 (216 mg, 0.291 mmol) in DCM (3.2 mL) was added $TsOH.H_2O$ (307 mg, 1.615 mmol). The mixture was warmed to room temperature and stirred overnight. The reaction was quenched with saturated aqueous $Na_2CO_3$. The organic layer was evaporated, and the residue was purified by preparative HPLC (0.1% HCOOH in water and MeCN) to afford compound 8a (10.33 mg, 9.6%) as a white solid. $^1H$ NMR (MeOD, 400 MHz) δ8.24 (s, 1H), 8.23 (s, 1H), 6.04 (s, 1H), 5.66-5.73 (m, 1H), 5.04-5.12 (m, 1H), 4.81-4.84 (m, 1H), 4.52-4.67 (m, 1H), 3.88 (2d, J=11.6 Hz, 3H), 1.43-1.47 (m, 3H). $^{31}P$ NMR (MeOD, 162 MHz) δ 3.59-3.91. LCMS m/z 357.9 (MH+).

Example 9

Preparation of 2-Methoxy-6-(6-{[(4-methoxy-phenyl)-diphenyl-methyl]-amino}-purin-9-yl)-4-methyl-2-thioxo-tetrahydro-2l5-furo[3,2-d][1,3,2]dioxaphosphinin-7-ol (9a)

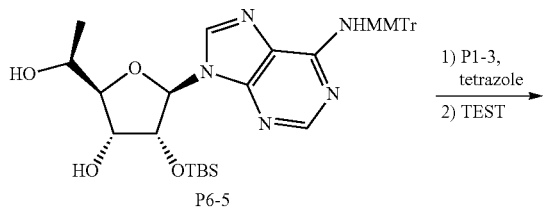

P6-5

1) P1-3, tetrazole
2) TEST →

Step 1: {9-[7-(tert-Butyl-dimethyl-silanyloxy)-2-methoxy-4-methyl-2-thioxo-tetrahydro-2l5-furo[3,2-d][1,3,2]dioxaphosphinin-6-yl]-9H-purin-6-yl}-[(4-methoxy-phenyl)-diphenyl-methyl]-amine(P9-1)

To a solution of P6-5 (190 mg, 0.285 mmol) in dry pyridine (2.5 mL) was added a solution of 0.45M tetrazole in MeCN (2.5 mL) and P1-3 (118 mg, 0.450 mmol) at 0° C. After stirring at room temperature overnight, Bis[3-(triethoxysilyl)propyl]tetrasulfide (TEST) was added (0.194 mL, 0.36 mmol) at 0° C. The mixture was stirred for 1 hour, and the reaction mixture was concentrated, diluted with ethyl acetate, washed with saturated $NaHCO_3$ and brine, and dried over anhydrous $Na_2SO_4$. The organic layer was concentrated, and the residue was purified via a silica gel column chromatography (DCM: MeOH=500:1 to 50:1) to give P9-1 (375 mg, crude).

Step 2: Compound 9a

Compound P9-1 (375 mg, crude) was dissolved in 70% formic acid (10 mL) and stirred overnight. The solvent was evaporated, and the residue was dissolved in THF (10 mL). TBAF (191 mg, 0.73 mmol) was added, and the mixture was stirred for 30 min. The solvent was removed, and the residue was purified by preparative HPLC (0.1% HCOOH in water and MeCN) to afford compound 9a (10.2 mg, 5.5% total yield over steps 1 and 2) as a white solid. $^1H$ NMR (MeOD, 400 MHz) δ8.25 (s, 1H), 8.22 (s, 1H), 6.01 (s, 1H), 5.54-5.65 (m, 1H), 5.03-5.08 (m, 1H), 4.51-4.81 (m, 2H), 3.83 (2d, J=14.0 Hz, 3H), 1.40-1.48 (m, 3H). $^{31}P$ NMR (MeOD, 162 MHz) δ65.09. LCMS m/z 374.0 (MH+).

Example 10

Preparation of 1-(7-Hydroxy-2-methoxy-7-methyl-2-thioxo-tetrahydro-2l5-furo[3,2-d][1,3,2]dioxaphosphinin-6-yl)-1H-pyrimidine-2,4-dione (10a)

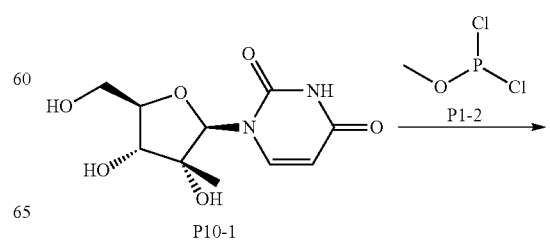

P10-1

P1-2 →

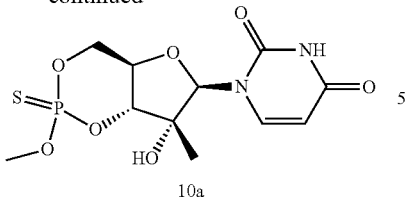

10a

To a solution of P10-1 (320 mg, 1.24 mmol) in dry pyridine (9.0 mL) was added a solution of 0.45 M tetrazole in MeCN (9 mL) and P1-2 (390 mg, 1.49 mmol) at 0° C. The reaction mixture was stirred at room temperature overnight, and bis[3-(triethoxysilyl)propyl]tetrasulfide (803 mg, 1.49 mmol) was then added at 0° C. The mixture was stirred for another hour. The reaction mixture was concentrated and diluted with ethyl acetate, washed with saturated NaHCO$_3$ and brine, and dried over anhydrous Na$_2$SO$_4$. The organic layer was concentrated, and the residue was purified by HPLC (MeCN and 0.1% HCOOH in water) to give compound 10a as a white solid (35 mg, 7.7%). $^1$H NMR (MeOD, 400 MHz) δ7.63-7.65 (d J=8.0 Hz, 1H), 6.07 (s, 1H), 5.75-5.79 (m, 1H), 4.60-4.70 (m, 1H), 4.21-4.46 (m, 1H), 4.10-4.12 (m, 1H), 3.81-3.90 (m, 3H), 1.26 (m, 3H). $^{31}$P NMR (MeOD, 162 MHz) δ64.3, 67.1. ESI-LCMS m/z 350.9 [M+H]$^+$.

Example 11

Preparation of 1-(7-Hydroxy-2-isopropoxy-7-methyl-2-thioxo-tetrahydro-2l5-furo[3,2-d][1,3,2]dioxaphosphinin-6-yl)-1H-pyrimidine-2,4-dione (11a)

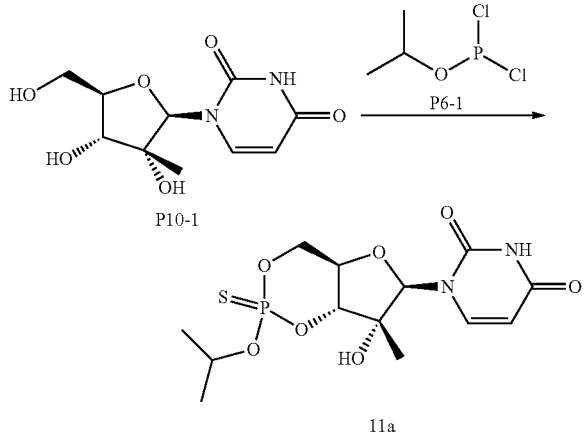

P10-1

11a

To a solution of P10-1 (155 mg, 0.60 mmol) in dry pyridine (4.0 mL) was added a solution of 0.45 M tetrazole in MeCN (3.33 mL) and P6-1 (190 mg, 0.72 mmol) at 0° C. The reaction mixture was stirred at room temperature overnight, and bis[3-(triethoxysilyl)propyl]tetrasulfide (388 mg, 0.72 mmol) was then added at 0° C. The mixture was stirred for another hour. The reaction mixture was concentrated and diluted with ethyl acetate, washed with saturated NaHCO$_3$ and brine, and dried over anhydrous Na$_2$SO$_4$. The organic layer was concentrated, and the residue was purified by HPLC (MeCN and 0.1% HCOOH in water) to give compound 11a as a white solid (21 mg, 9.1%). $^1$H NMR (MeOD, 400 MHz) δ7.61-7.66 (m, 1H), 6.08 (s, 1H), 5.78-5.80 (m, 1H), 4.82-4.97 (m, 1H), 4.61-4.66 (m, 1H), 4.29-4.43 (m, 1H), 4.09-4.23 (m, 1H), 1.37-1.42 (m, 6H), 1.25 (s, 3H). $^{31}$P NMR (MeOD, 162 MHz) δ65.2, 61.3. ESI-LCMS m/z 379.0 [M+H]$^+$.

Example 12

Preparation of 2''-C,O$^6$-Dimethylguanosine 3',5'-cyclic O-pivaloyloxymethyl phosphorothioate (12a)

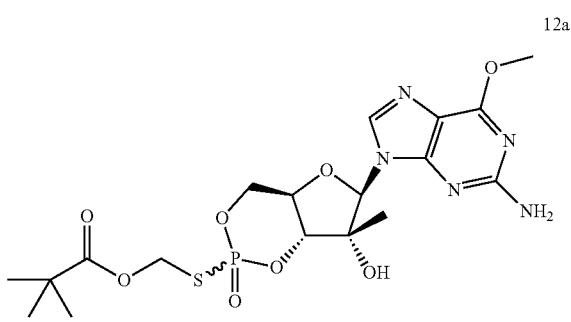

12a

Step 1: Iodomethyl pivalate

Chloromethyl pivalate (1.0 mL, 6.90 mmol) was added to a mixture of NaI (2.08 g, 13.80 mmol) and dry MeCN (10 mL). The reaction mixture was stirred at room temperature overnight in the dark. The mixture was evaporated to dryness. The resulting residue was dissolved in dichloromethane and washed with 5% aqueous NaHSO$_3$ and brine. The organic layer was dried over Na$_2$SO$_4$ and evaporated to dryness. The resulting iodomethyl pivalate was used without further purification in the next step.

Step 2: Compound 12a

N$^2$-(4-Methoxytrityl)-2'-C,O$^6$-dimethylguanosine 3',5'-cyclic phosphorothioate was dissolved in dry MeCN (3 mL) and iodomethyl pivalate (56 mg g, 0.23 mmol) was added. The reaction mixture was stirred for 2.5 hours at room temperature. Saturated aqueous NaHCO$_3$ was added, and the crude product was extracted with dichloromethane. The organic layer was dried over Na$_2$SO$_4$ and evaporated to dryness. The residue was dissolved in 80% aqueous acetic acid (2.0 mL), and the reaction mixture was stirred at room temperature for 20 hours. The reaction mixture was evaporated to dryness, and the resulting residue was coevaporated twice with water. The crude product was purified by silica gel chromatography eluting with dichloromethane containing 10% MeOH. Compound 12a was obtained as white solid in 14% yield (15.0 mg). $^1$H NMR (500 MHz, CD$_3$OD) δ: 7.95 (s, 1H, H8); 5.93 (s, 1H, H1'), 5.58-5.54 (m, 2H, SCH$_2$), 4.80-4.69 (m, 3H, H3', H4', H5''); 4.45 (m, 1H, H5'); 4.06 (s, 3H, OMe); 1.20 (s, 3H, C(Me)$_3$); 1.10 (s, 1H, 2'-Me). $^{13}$C NMR (126 MHz, CD$_3$OD) δ: 177.48 (C=O), 161.50 (C6), 160.22 (C2), 152.66 (C4), 139.14 (C8), 129.34 (C5), 95.15 (C1'), 81.87 (C3'), 76.76 and 76.70 (C2'), 71.00, 70.93, 70.80 and 70.81 (C4' and C5''), 60.23 and 60.20 (SCH$_2$), 52.87 (OMe), 38.52 (spiro C of Piv), 25.85 (C(Me)$_3$), 18.18 (2'-Me). $^{31}$P NMR (202 MHz, CD$_3$OD) δ: 23.13. HR-ESI-MS: [M+H]$^+$ observed 504.1323, calculated 504.1312.

Example 13

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/mL G418.

Determination of anti-HCV Activity

Determination of 50% inhibitory concentration ($EC_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in cell culture media. The compounds were diluted to 10% DMSO with cell culture media, which were used to dose the HCV replicon cells in 96-well format. The final DMSO Concentration was 1%. The HCV replicon cells were incubated at 37° C. for 72 hours. At 72 hours, cells were processed when the cells are still subconfluent. Compounds that reduce the LUC signal are determined by Bright-Glo Luciferase Assay (Promega, Madison, Wis.). % Inhibition was determined for each compound concentration in relation to the control cells (untreated HCV replicon) to calculate the $EC_{50}$.

Compounds of Formula (I) are active in the replicon assay. The antiviral activity of exemplary compounds is shown in Table 5, where 'A' indicates an $EC_{50} < 1$ µM, 'B' indicates an $EC_{50} \geq 1$ µM and <10 µM, and 'C' indicates an $EC_{50} \geq 10$ µM and <100 µM.

TABLE 5

| No. | Compound | $EC_{50}$ |
|---|---|---|
| 1a | | A |
| 8a | | C |
| 10a | | C |
| 11a | | B |
| 12a | | A |

Example 14

Combination of Compounds

Combination Testing

Two or more test compounds are tested in combination with each other using an HCV genotype 1b HCV replicon harbored in Huh7 cells with a stable luciferase (LUC) reporter. Cells are cultured under standard conditions in Dulbecco's modified Eagle's medium (DMEM; Mediatech Inc, Herndon, Va.) containing 10% heat-inactivated fetal bovine serum (FBS; Mediatech Inc, Herndon, Va.) 2 mM L-glutamine, and nonessential amino acids (JRH Biosciences). HCV replicon cells are plated in a 96-well plate at a density of $10^4$ cells per well in DMEM with 10% FBS. On the following day, the culture medium is replaced with DMEM containing either no compound as a control, the test compounds serially diluted in the presence of 2% FBS and 0.5% DMSO, or a combination of one or more test compounds serially diluted in the presence of 2% FBS and 0.5% DMSO. The cells are incubated with no compound as a control, with the test compounds, or the combination of compounds for 72 h. The direct effects of the combination of the test compounds are examined using a luciferase (LUC) based reporter as determined by the Bright-Glo Luciferase Assay (Promega, Madison, Wis.). Dose-response curves are determined for individual compounds and fixed ratio combinations of two or more test compounds.

The effects of test compound combinations are evaluated by two separate methods. In the Loewe additivity model, the experimental replicon data is analyzed by using CalcuSyn (Biosoft, Ferguson, Mo.), a computer program based on the method of Chou and Talalay. The program uses the experimental data to calculate a combination index (CI) value for each experimental combination tested. A CI value of <1 indicates a synergistic effect, a CI value of 1 indicates an additive effect, and a CI value of >1 indicates an antagonistic effect.

The second method that is utilized for evaluating combination effects uses a program called MacSynergy II. MacSynergy II software was kindly provided by Dr. M. Prichard (University of Michigan). The Prichard Model allows for a three-dimensional examination of drug interactions and a calculation of the synergy volume (units: μM²%) generated from running the replicon assay using a checkerboard combination of two or more inhibitors. The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes >100 indicate strong synergistic behavior. Determination of in vitro additive, synergistic and strongly synergistic behavior for combinations of compounds can be of utility in predicting therapeutic benefits for administering the combinations of compounds in vivo to infected patients.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof:

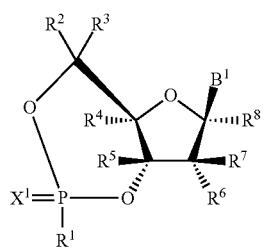

(I)

wherein:
$B^1$ is selected from the group consisting of

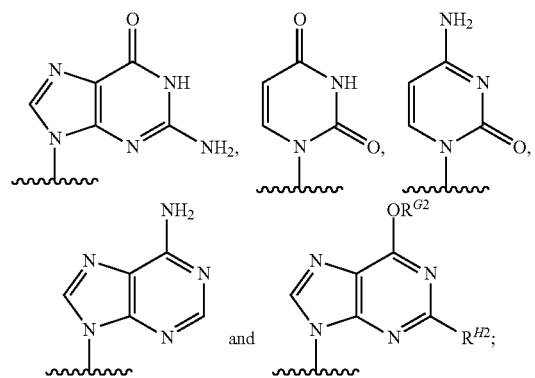

$R^{G2}$ is an unsubstituted $C_{1-6}$ alkyl;
$R^{H2}$ is hydrogen or $NH_2$;

$X^1$ is S (sulfur);

$R^1$ is selected from the group consisting of $-Z^1-R^9$, an optionally substituted N-linked amino acid and an optionally substituted N-linked amino acid ester derivative;

$Z^1$ is selected from the group consisting of O (oxygen), S (sulfur) and)$N(R^{10})$;

$R^2$ and $R^3$ are hydrogen;

$R^4$ is hydrogen or azido;

$R^5$ is hydrogen;

$R^6$ is selected from the group consisting of hydrogen, halogen, $-OR^{11}$ and $-OC(=O)R^{12}$;

$R^7$ is halogen or an optionally substituted $C_{1-6}$ alkyl;

$R^8$ is hydrogen;

$R^9$ is selected from the group consisting of an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl);

$R^{10}$ is hydrogen;

$R^{11}$ is hydrogen or an optionally substituted $C_{1-6}$ alkyl; and $R^{12}$ is an optionally substituted $C_{1-6}$ alkyl or an optionally substituted $C_{3-6}$ cycloalkyl.

2. The compound of claim 1, wherein $R^1$ is $-Z^1-R^9$.

3. The compound of claim 2, wherein $Z^1$ is O.

4. The compound of claim 2, wherein $Z^1$ is $N(R^{10})$.

5. The compound of claim 1, wherein $R^1$ is an optionally substituted N-linked α-amino acid or an optionally substituted N-linked α-amino acid ester derivative.

6. The compound of claim 1, wherein $R^1$ is an optionally substituted N-linked α-amino acid ester derivative.

7. The compound of claim 6, wherein $R^1$ is selected from the group consisting of alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof.

8. The compound of claim 1, wherein $R^1$ has the structure

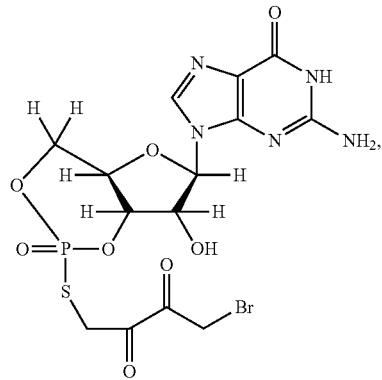

127
-continued
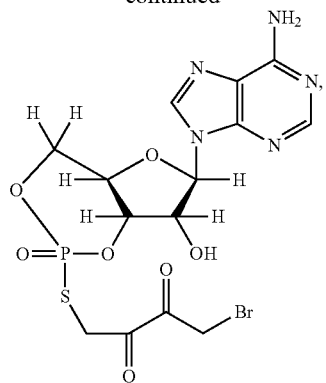
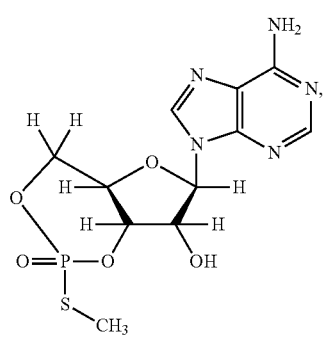
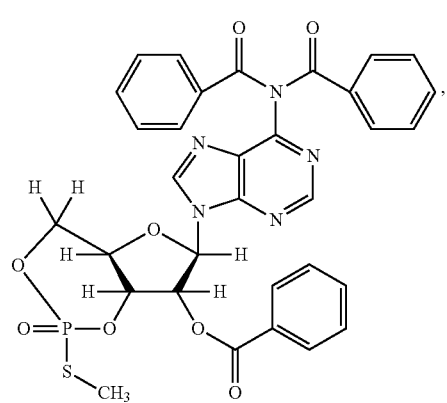
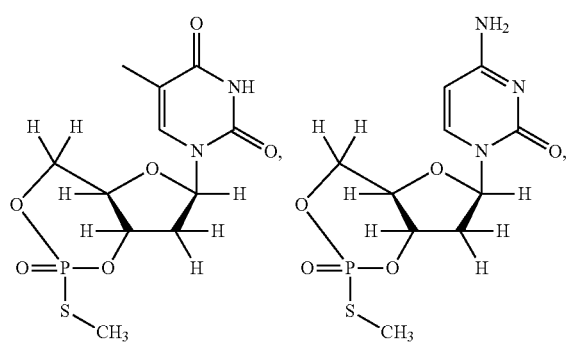
128
-continued
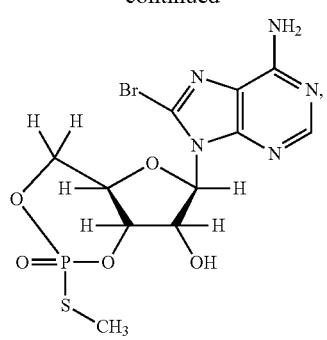
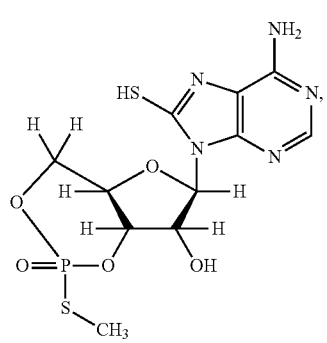
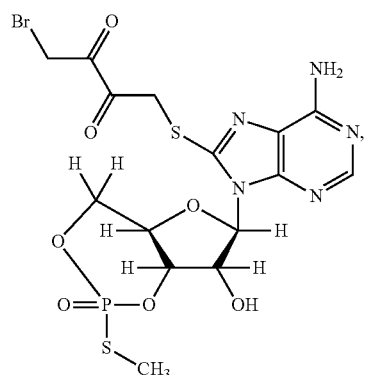
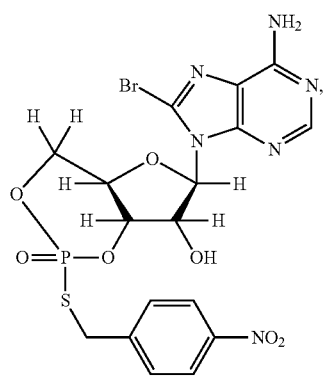

129
-continued
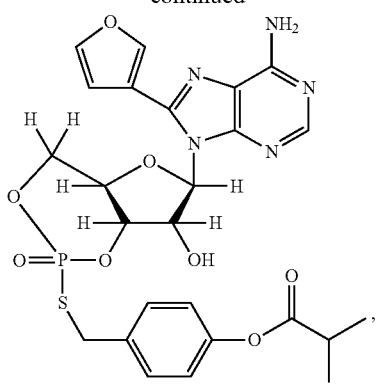
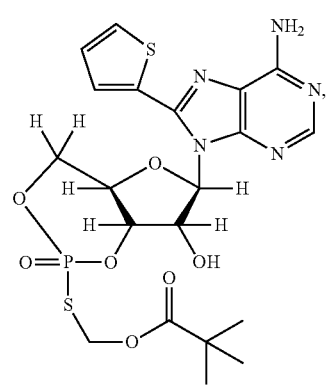
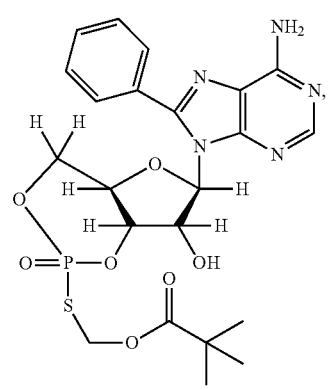
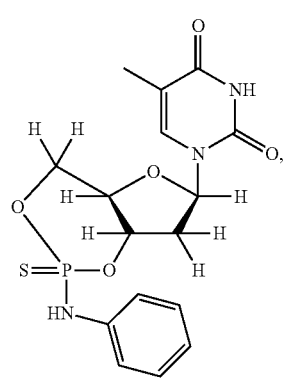
130
-continued
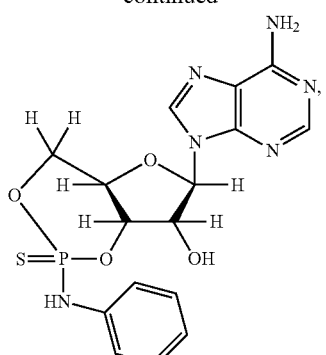
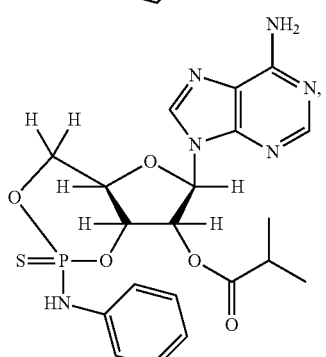
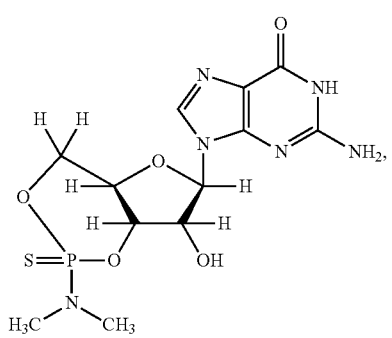
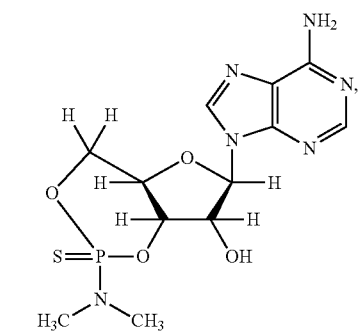
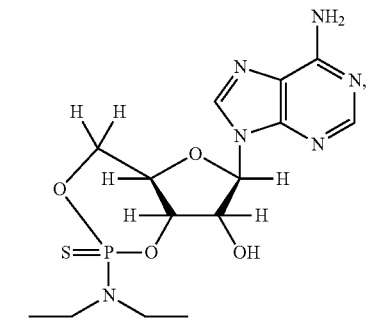

131
-continued
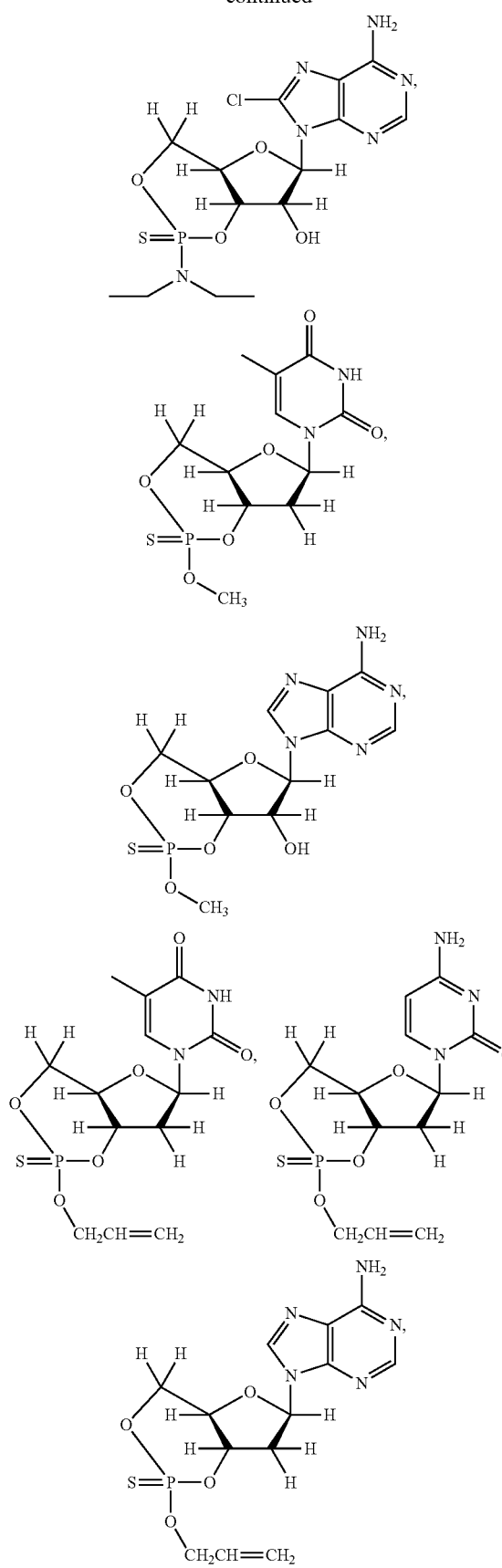
132
-continued
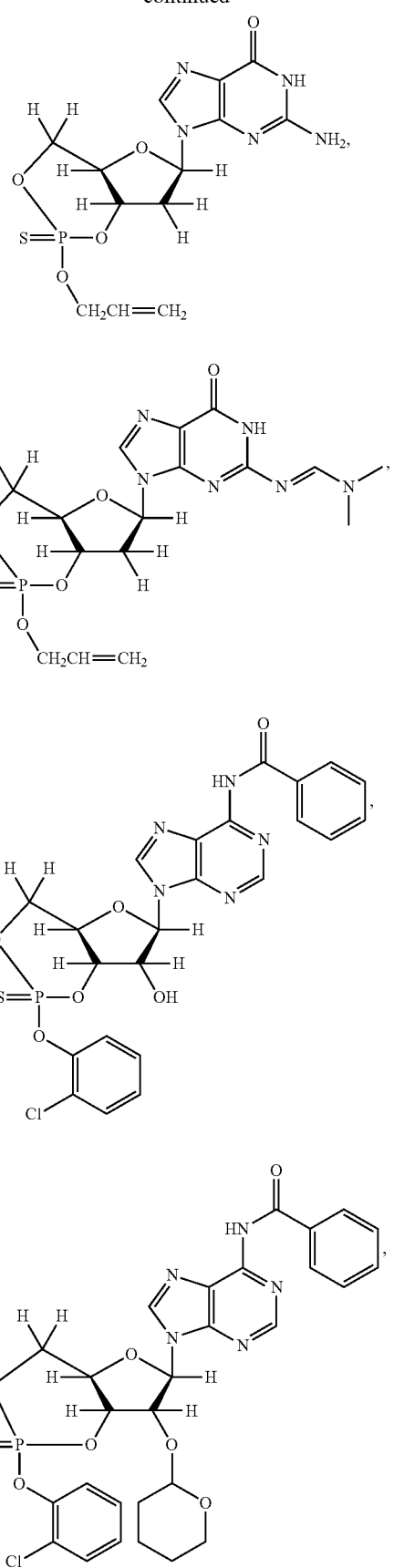

133
-continued
134
-continued
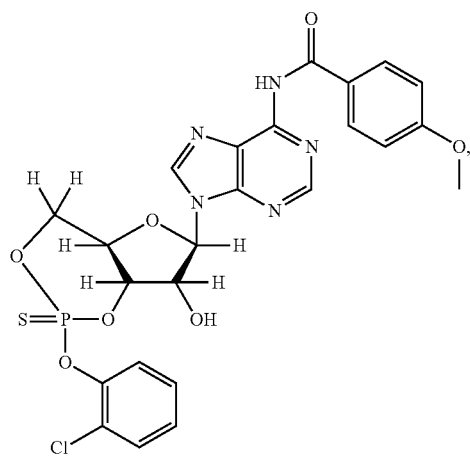
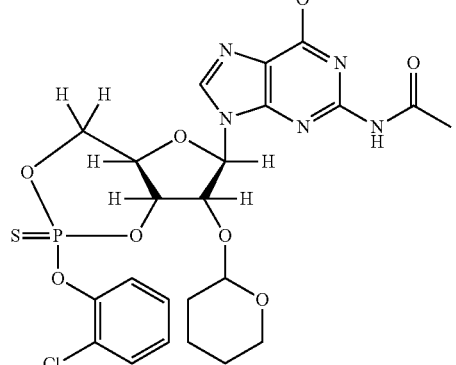
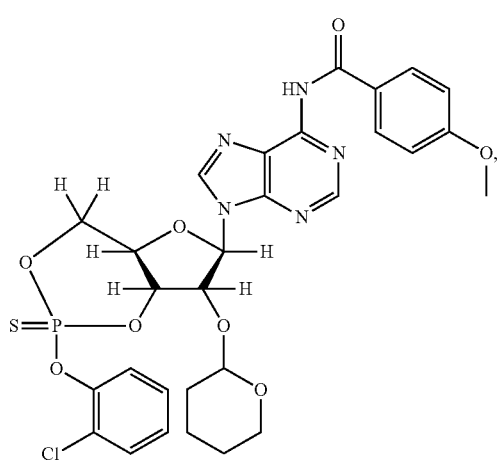
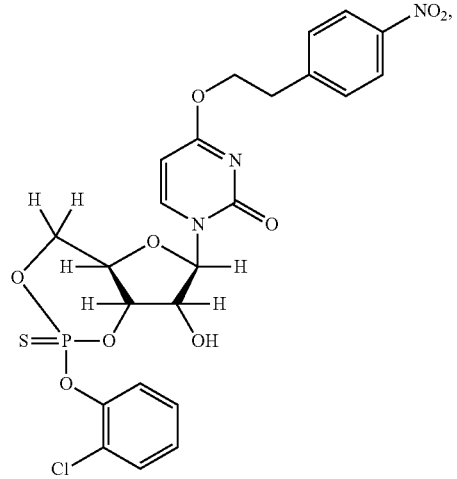
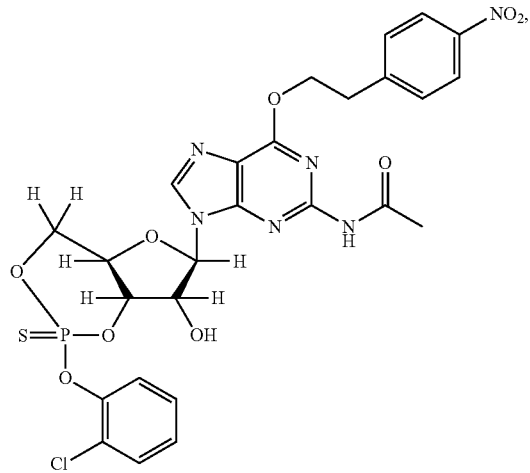
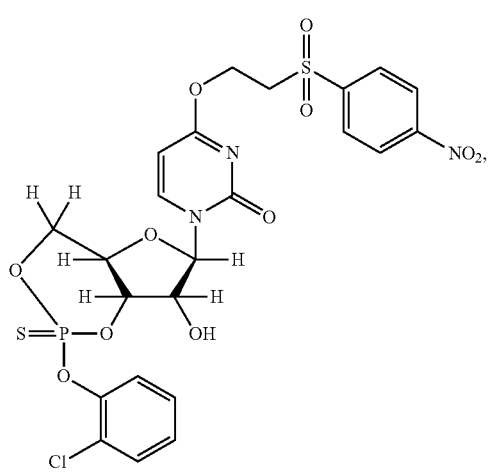

-continued

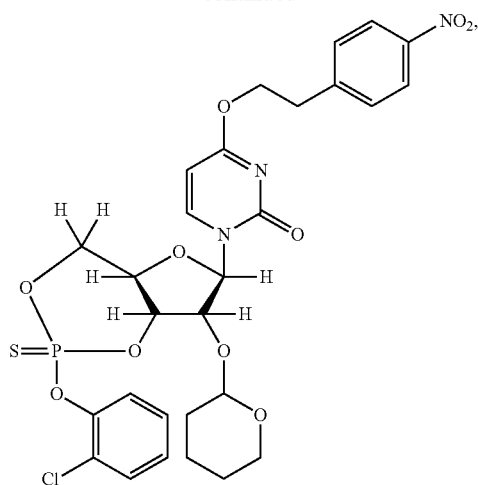

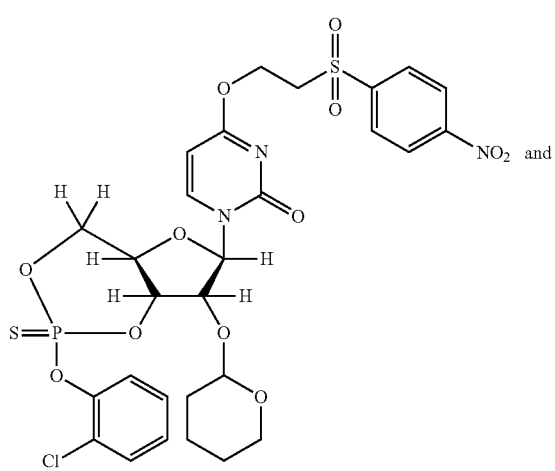

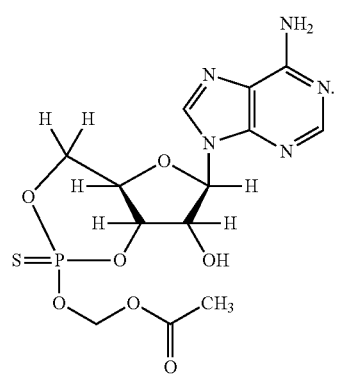

wherein R$^{17}$ is selected from the group consisting of hydrogen, an optionally substituted C$_{1-6}$-alkyl, an optionally substituted C$_{3-6}$ cycloalkyl, an optionally substituted aryl, an optionally substituted aryl(C$_{1-6}$ alkyl) and an optionally substituted C$_{1-6}$ haloalkyl; R$^{18}$ is selected from the group consisting of hydrogen, an optionally substituted C$_{1-6}$ alkyl, an optionally substituted C$_{1-6}$ haloalkyl, an optionally substituted C$_{3-6}$ cycloalkyl, an optionally substituted C$_6$ aryl, an optionally substituted C$_{10}$ aryl and an optionally substituted aryl(C$_{1-6}$ alkyl); and R$^{19}$ is hydrogen or an optionally substituted C$_{1-4}$-alkyl; or R$^{18}$ and R$^{19}$ are taken together to form an optionally substituted C$_{3-6}$ cycloalkyl.

9. The compound of claim 8, wherein R$^{18}$ is an optionally substituted C$_{1-6}$-alkyl.

10. The compound of claim 9, wherein the optionally substituted C$_{1-6}$-alkyl is substituted one or more substituents selected from the group consisting of N-amido, mercapto, alkylthio, an optionally substituted aryl, hydroxy, an optionally substituted heteroaryl, O-carboxy, and amino.

11. The compound claim 8, wherein

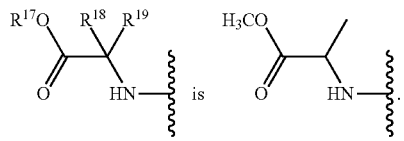

12. The compound of claim 1, wherein R$^6$ is hydrogen or halogen.

13. The compound of claim 1, wherein R$^6$ is —OR$^{11}$.

14. The compound of claim 1, wherein R$^6$ is —OC(=O)R$^{12}$.

15. The compound of claim 1, wherein R$^7$ is an optionally substituted C$_{1-6}$ alkyl.

16. The compound of claim 1, wherein R$^1$ is —Z$^1$—R$^9$, Z$^1$ is O, S or N(R$^{10}$); and R$^9$ is selected from the group consisting of an optionally substituted alkyl, an optionally substituted cycloalkyl, an optionally substituted aryl and an optionally substituted aryl(C$_{1-6}$ alkyl).

17. The compound of claim 16, wherein R$^9$ is an optionally substituted alkyl, an optionally substituted aryl or an optionally substituted aryl(C$_{1-6}$ alkyl).

18. The compound of claim 1, wherein the compound of Formula (I) is selected from the group consisting of:

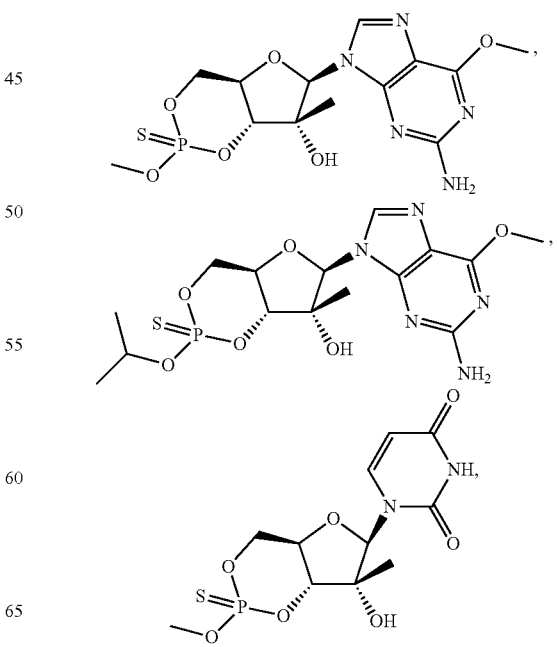

-continued

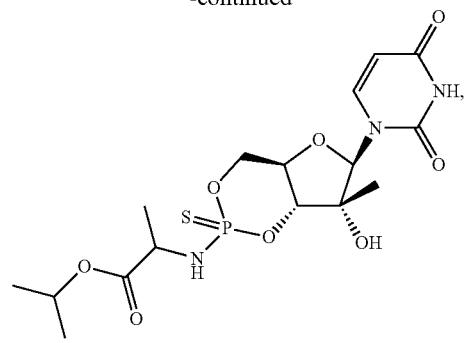

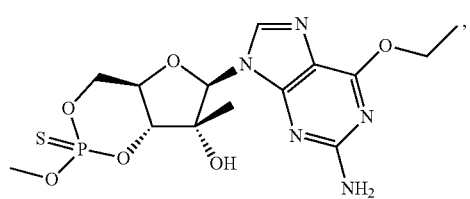

and

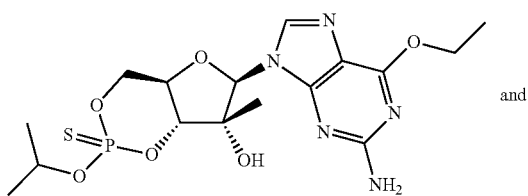

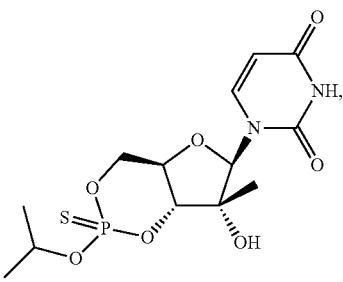

or a pharmaceutical acceptable salt of the foregoing.

19. A pharmaceutical composition comprising a therapeutically effective amount of a compound of claim 1, or a pharmaceutically acceptable salt thereof, and a pharmaceutically acceptable carrier, diluent, excipient or combination thereof.

20. A method of ameliorating or treating a Flaviviridae viral infection comprising administering an effective amount of a compound of claim 1, or a pharmaceutically acceptable salt thereof, to a subject suffering from the Flaviviridae viral infection.

21. A method for ameliorating or treating an HCV infection comprising administering to a subject suffering from an HCV infection an effective amount of a compound of claim 1, or a pharmaceutically acceptable salt thereof.

22. A method for inhibiting NS5B polymerase activity comprising contacting a cell infected with HCV with an effective amount of a compound of claim 1, or a pharmaceutically acceptable salt thereof.

23. A method for ameliorating or treating a Flaviviridae viral infection comprising contacting a cell infected with the Flaviviridae virus with a compound of claim 1, or a pharmaceutically acceptable salt thereof.

24. A method for inhibiting replication of a Flaviviridae virus comprising contacting a cell infected with the Flaviviridae virus with a compound of claim 1, or a pharmaceutically acceptable salt thereof.

25. A method of ameliorating or treating a HCV viral infection comprising contacting a cell infected with HCV with an effective amount of a compound of claim 1, or a pharmaceutically acceptable salt thereof, in combination with one or more agents selected from the group consisting of an interferon, ribavirin, a HCV protease inhibitor, a HCV polymerase inhibitor and a NS5A inhibitor, or a pharmaceutically acceptable salt any of the aforementioned compounds.

26. The method of claim 25, wherein the one or more agents are selected from the group consisting of:

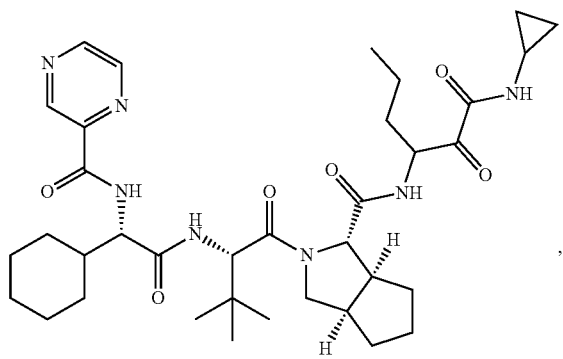

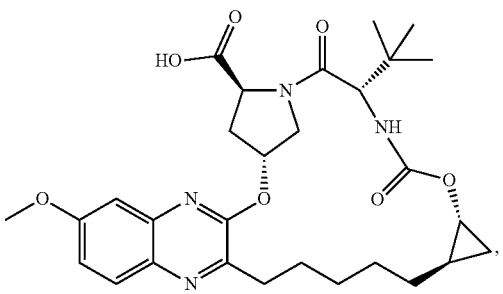

139
-continued
140
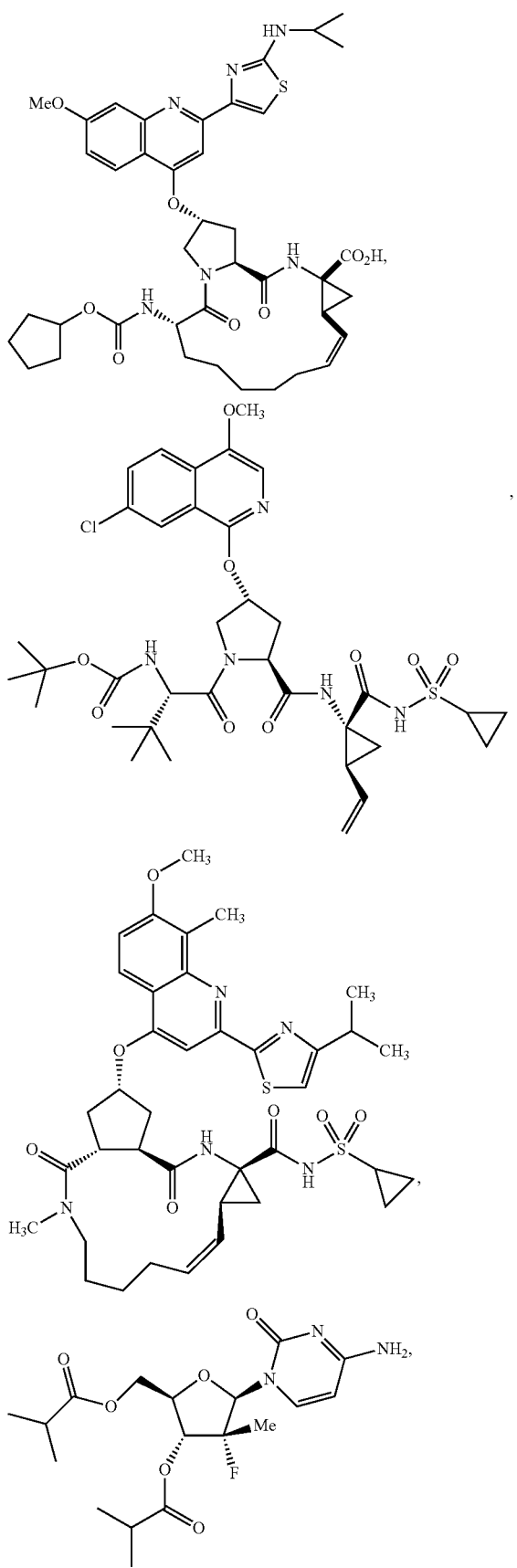
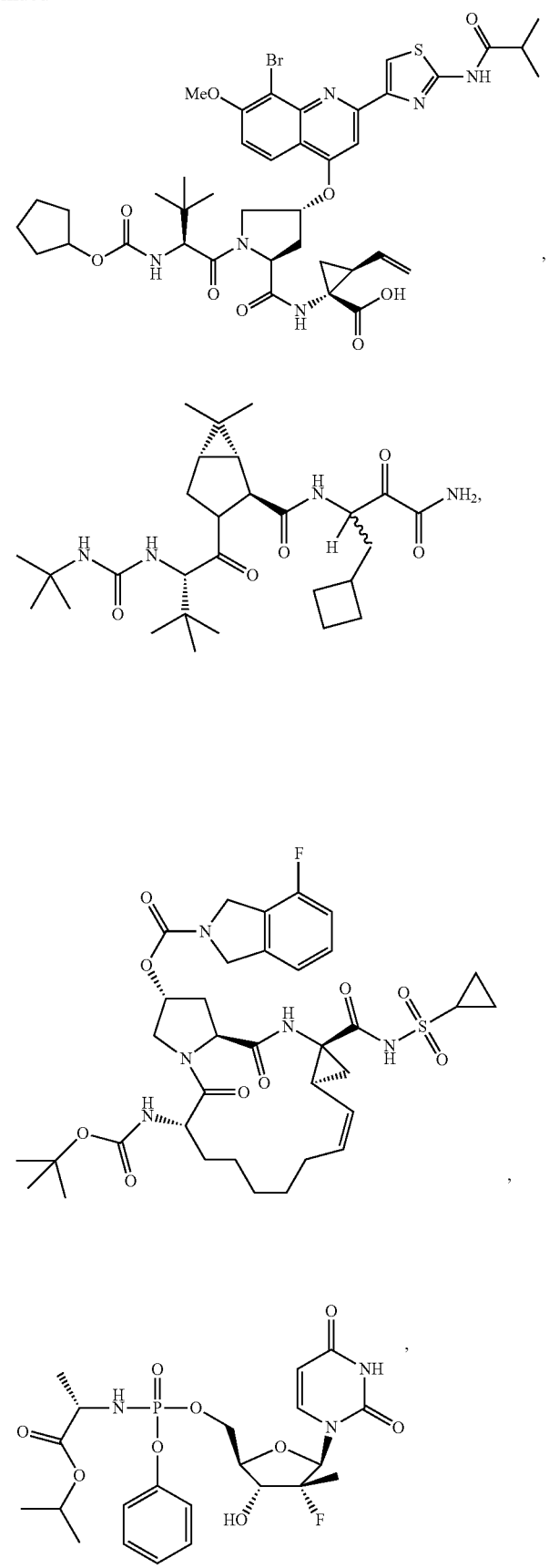

-continued
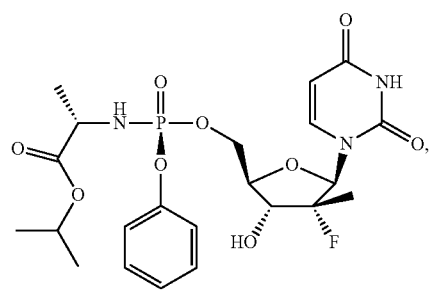
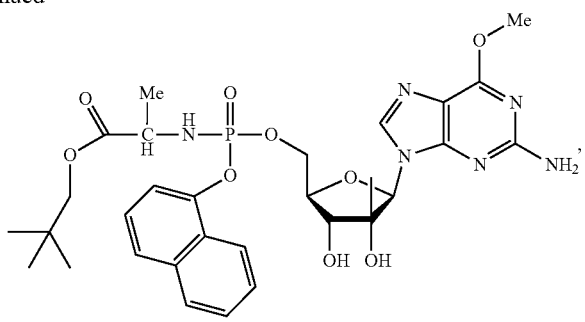
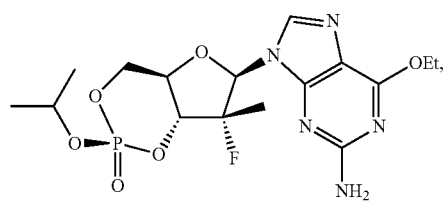
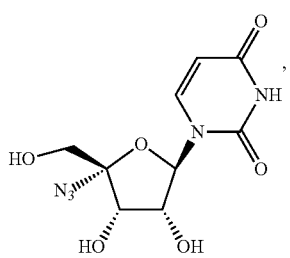
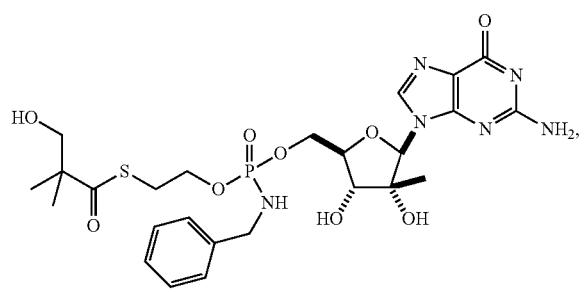
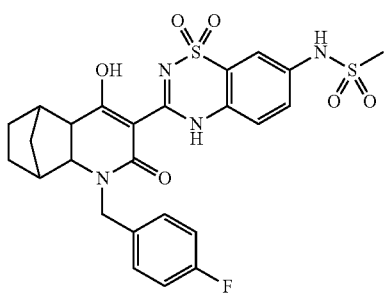
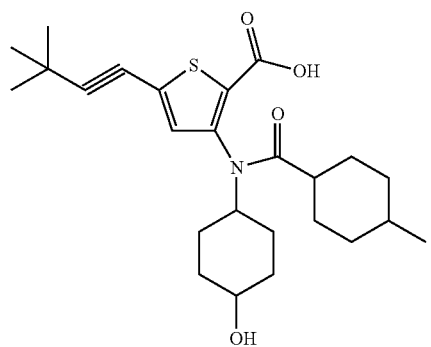
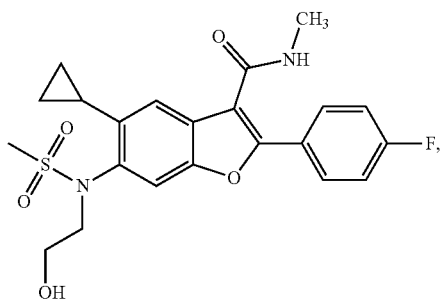
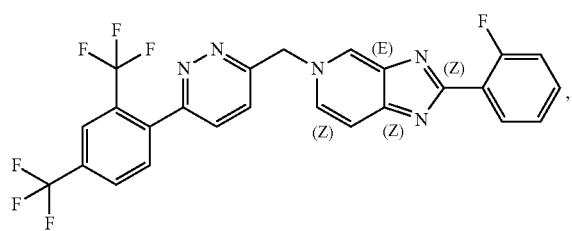
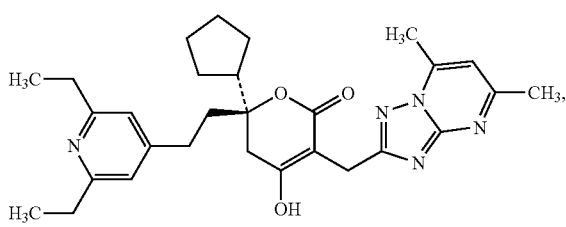
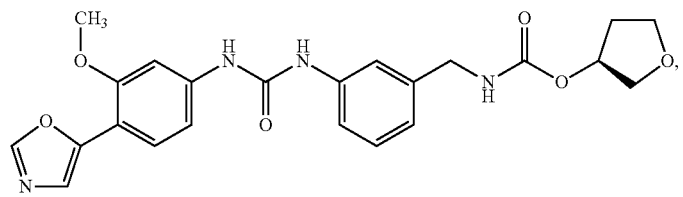

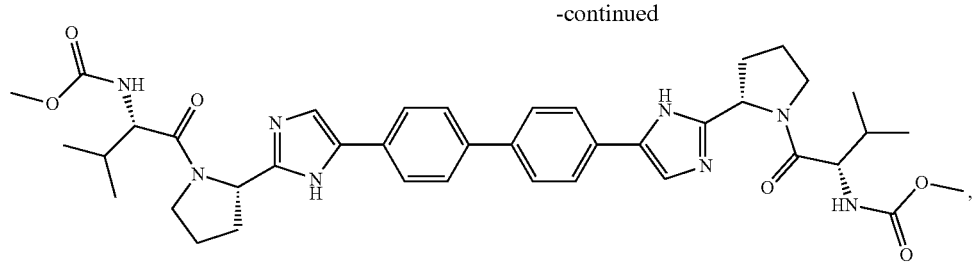
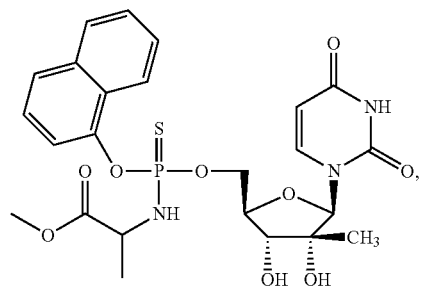 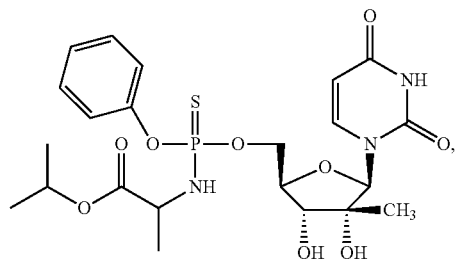
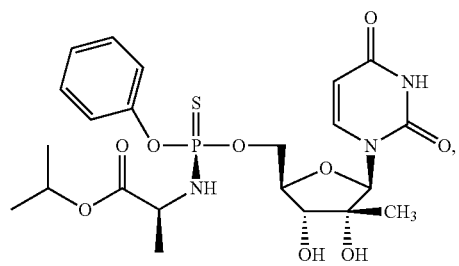 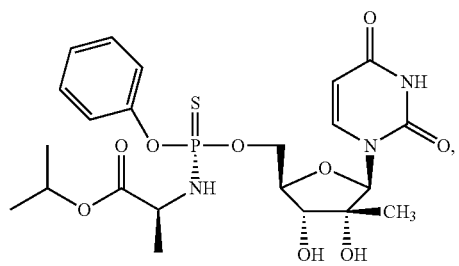
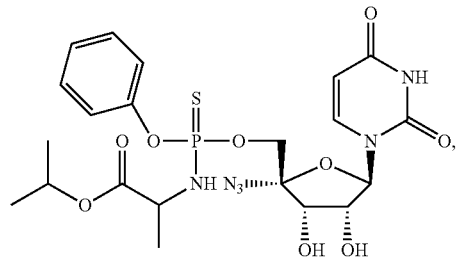 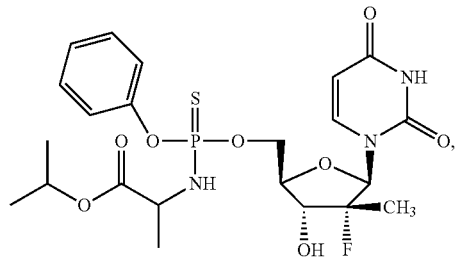
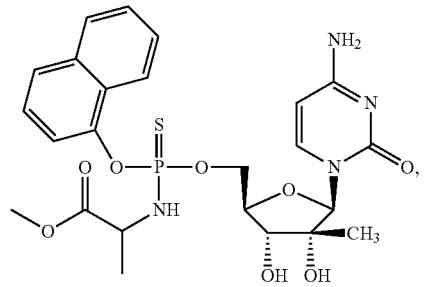 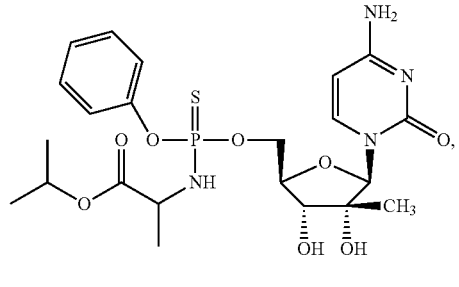
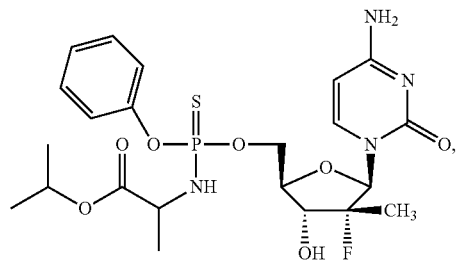 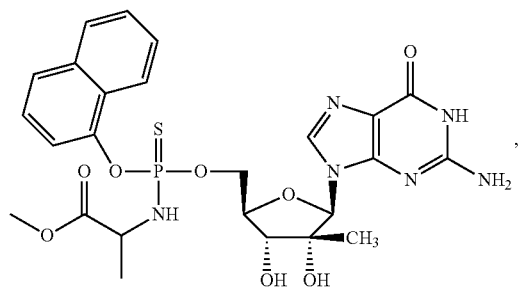

145
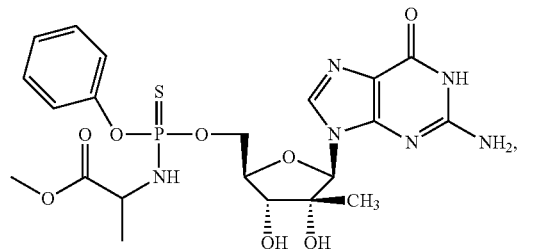
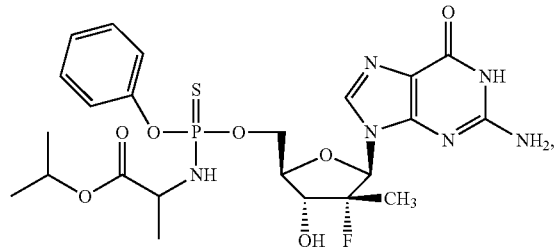
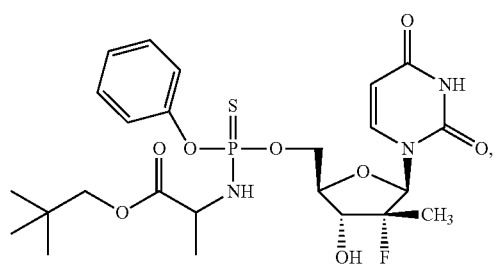
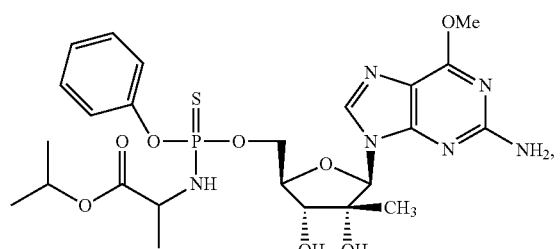
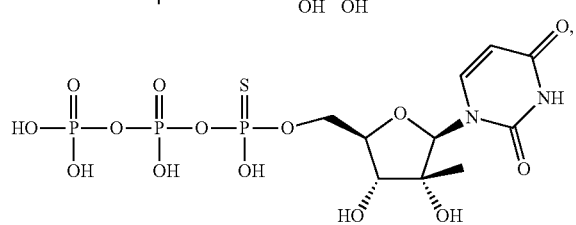
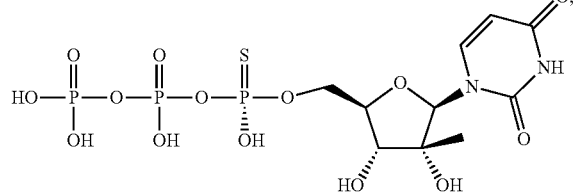
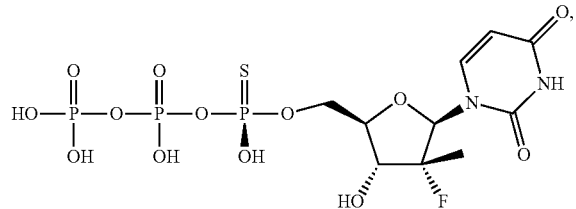
146
-continued
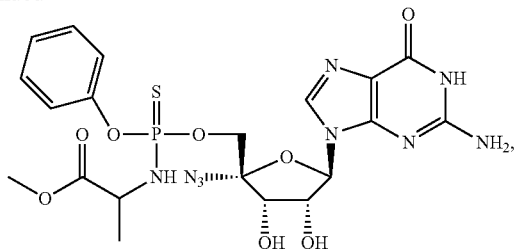
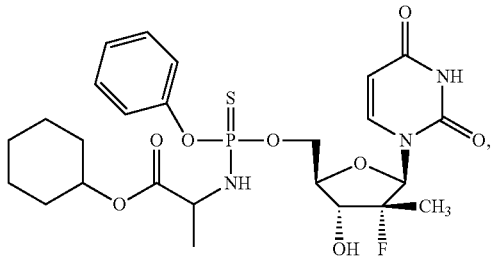
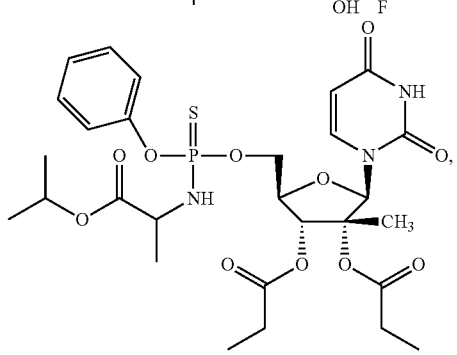
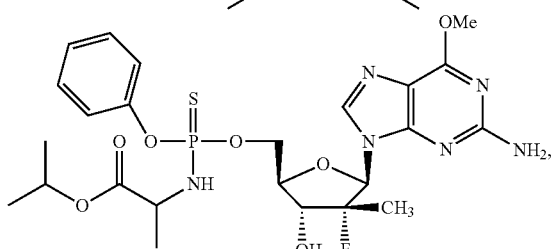
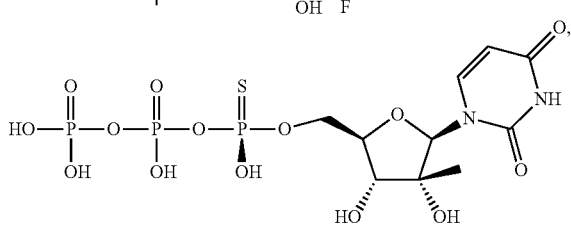
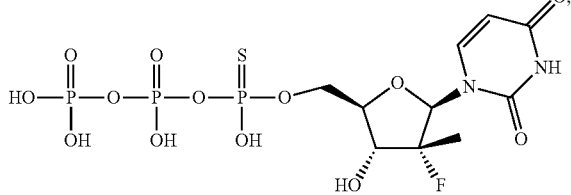
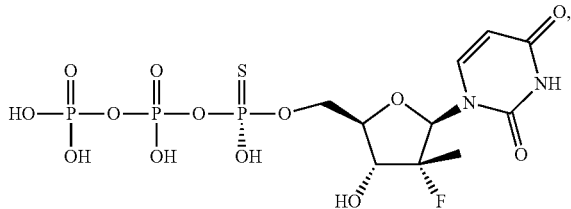

-continued
147
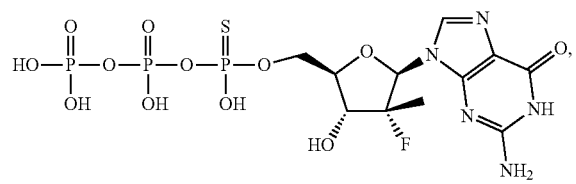
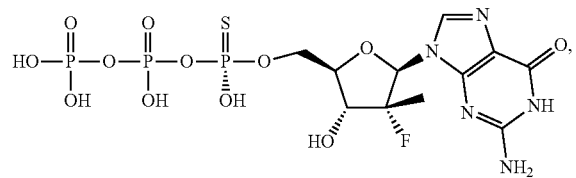
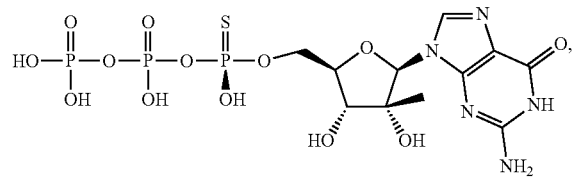
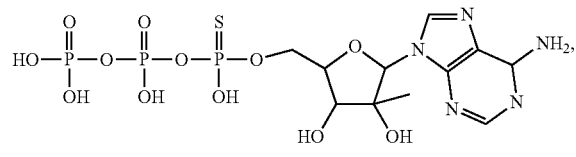
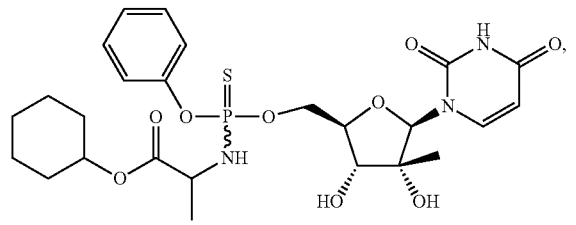
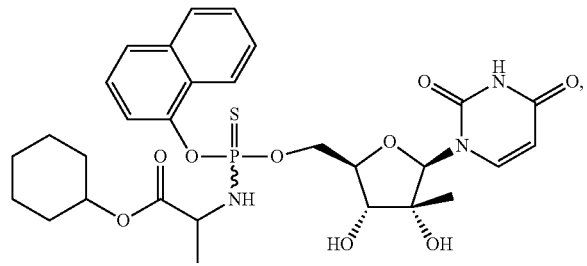
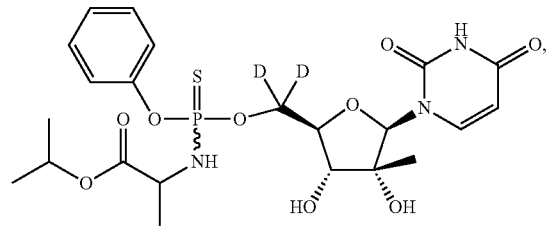
148
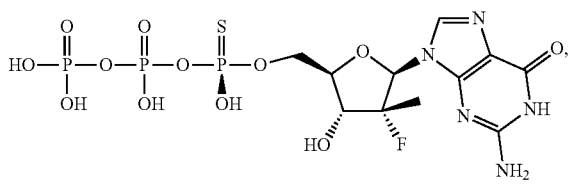
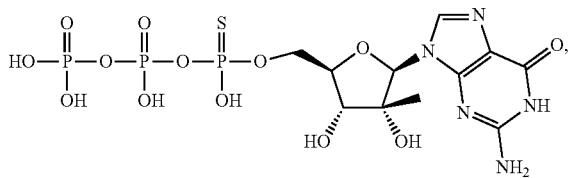
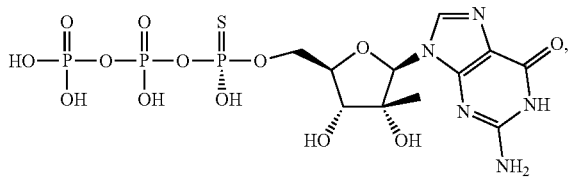
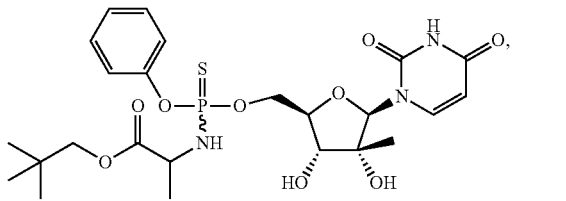
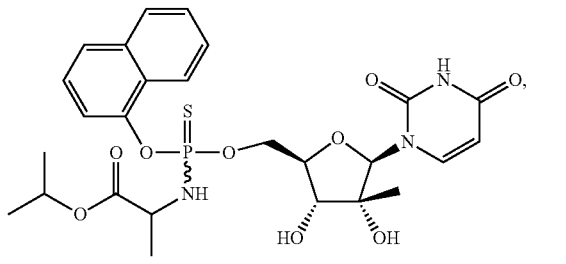
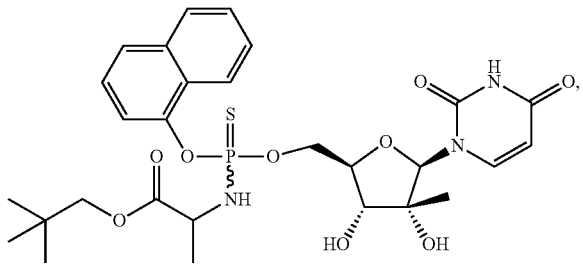
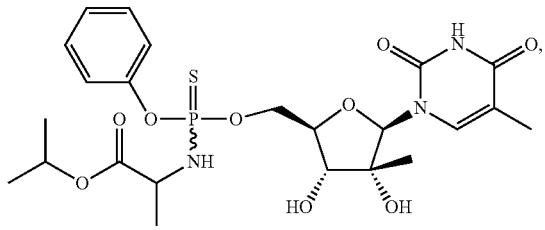

-continued
| 149 | 150 |
|---|---|
| 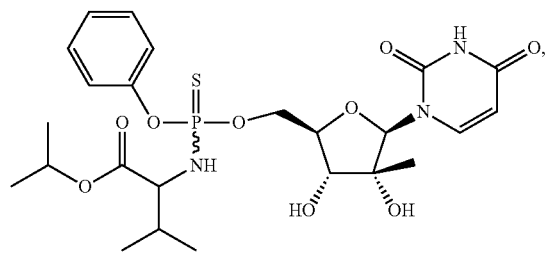 | 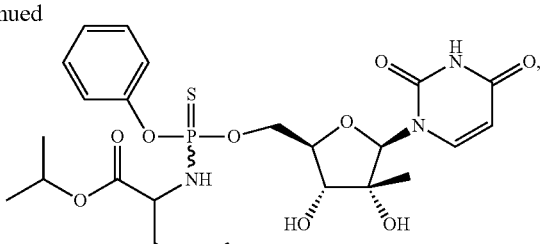 |
| 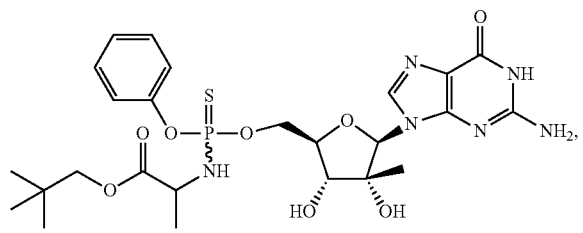 | 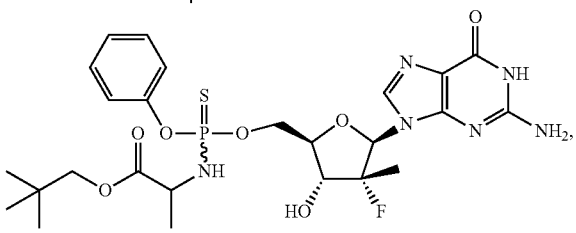 |
| 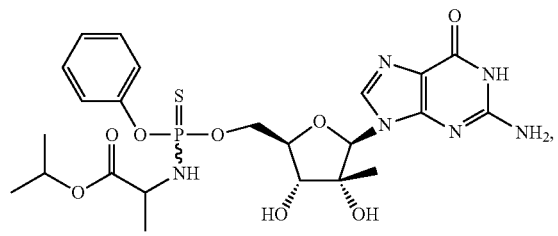 | 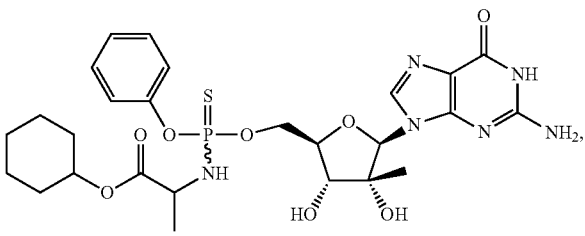 |
| 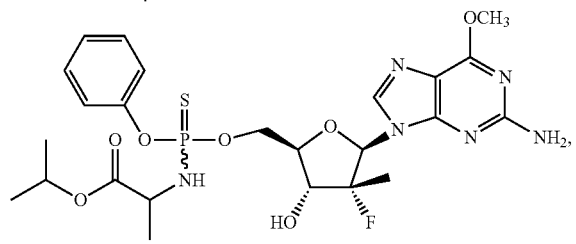 | 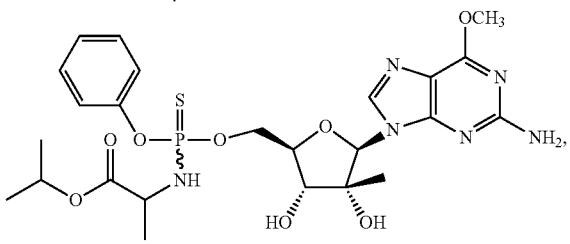 |
| 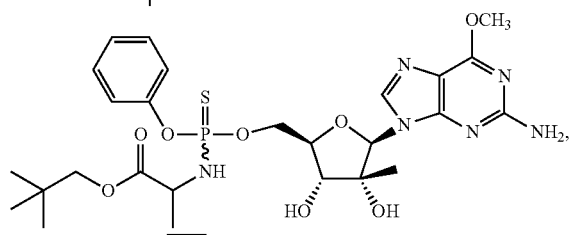 | 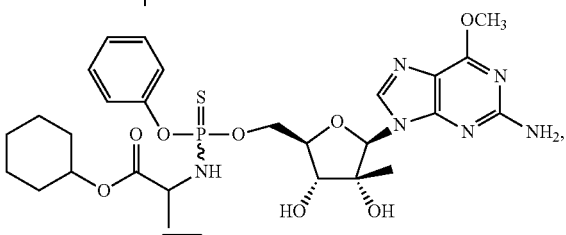 |
| 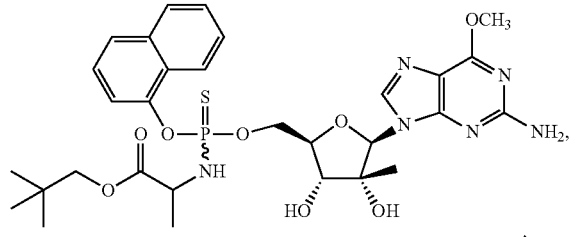 | 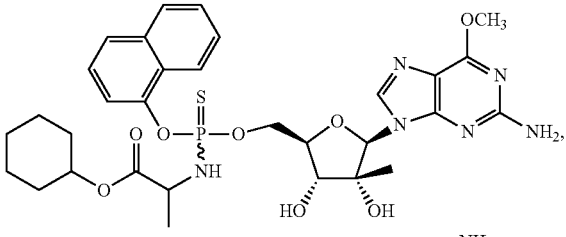 |
| 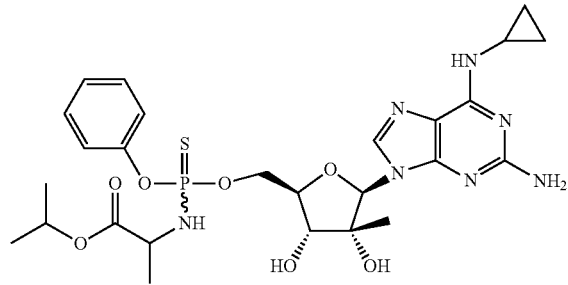 | 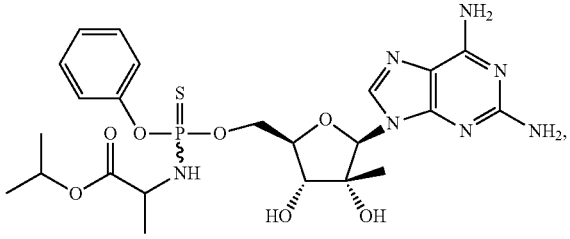 |

151 152
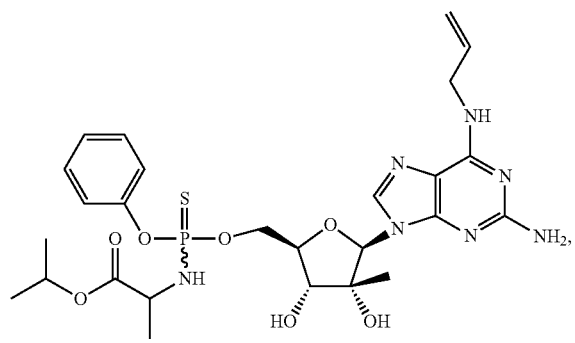 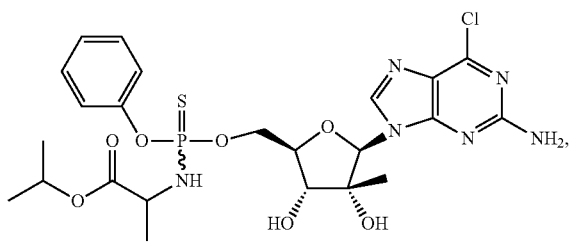
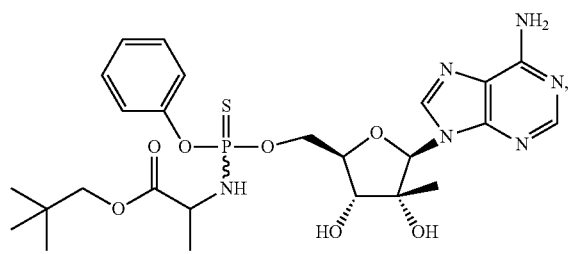 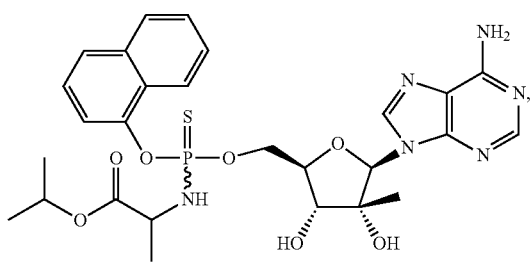
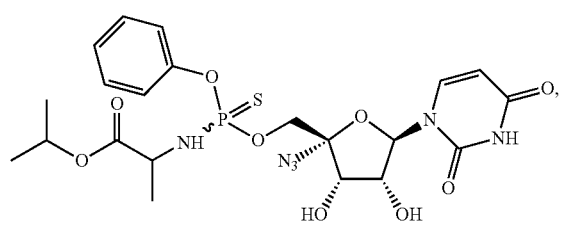 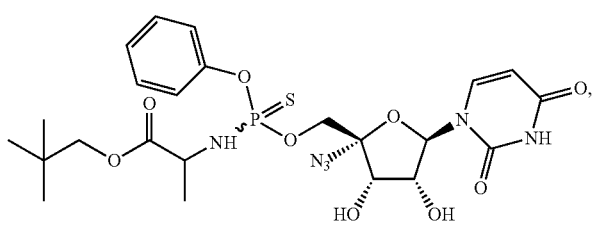
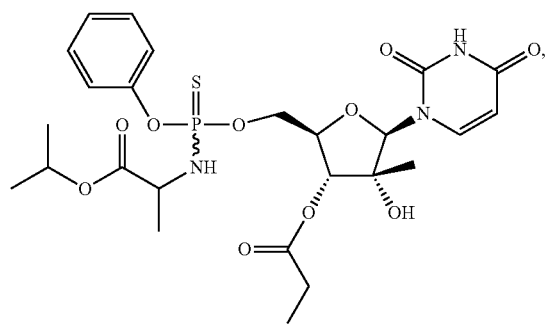 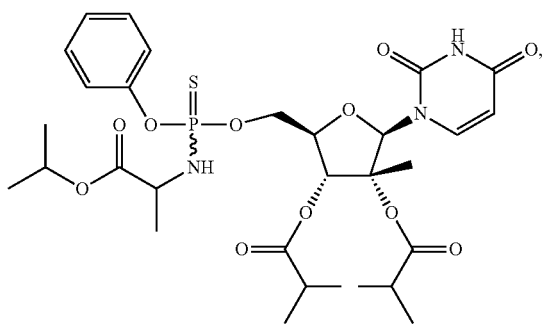
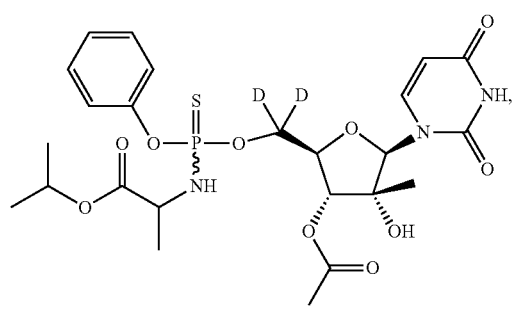 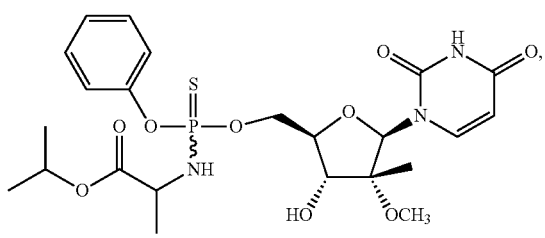

153
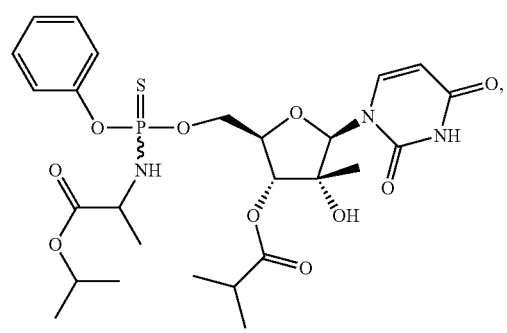
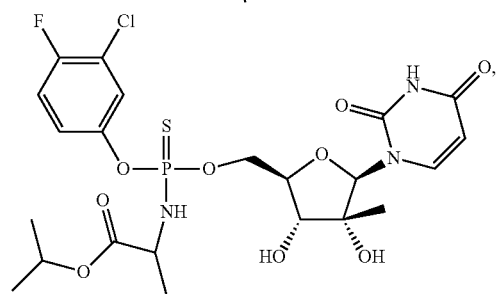
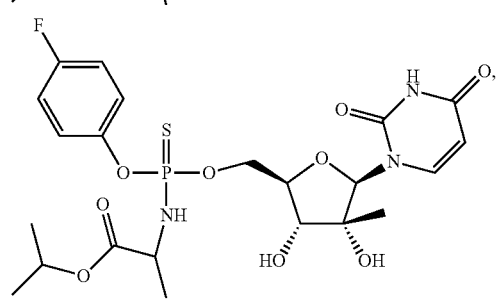
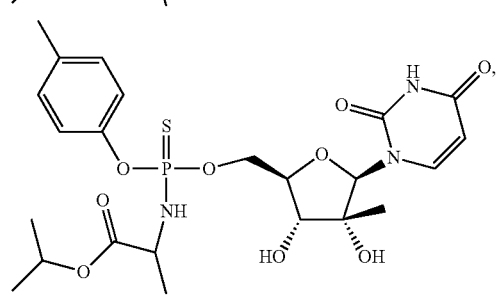
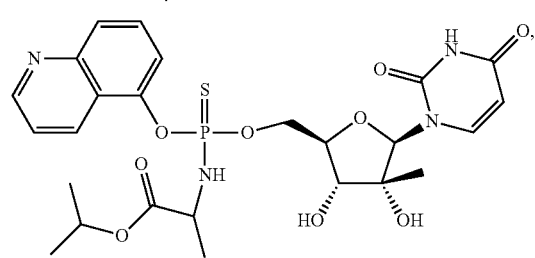
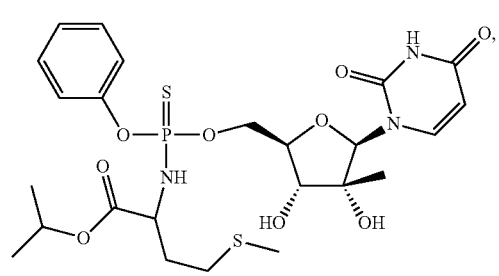
154
-continued
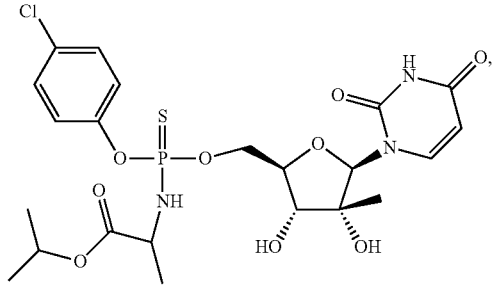
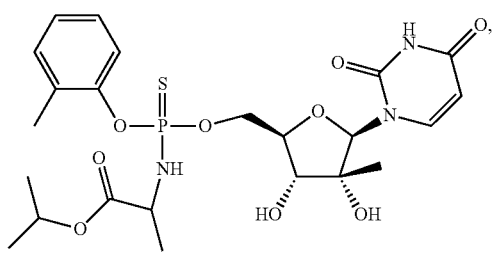
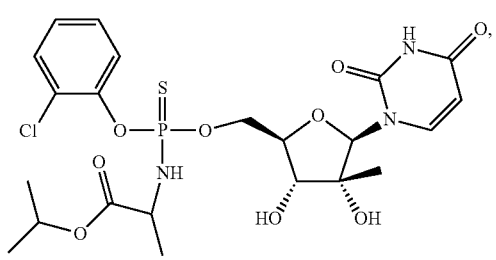
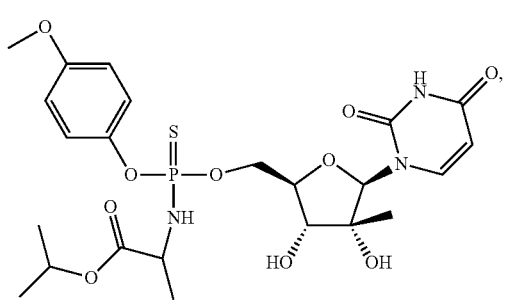
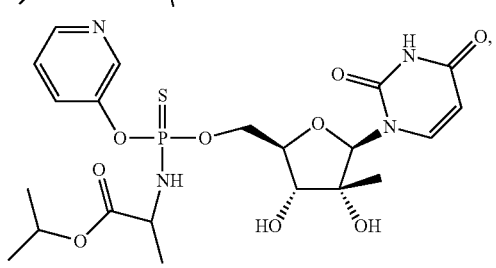
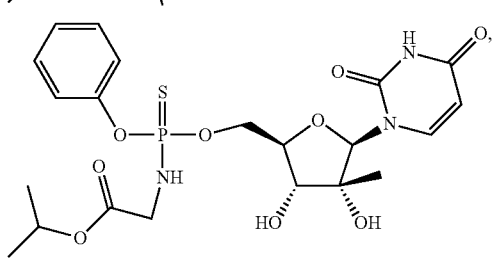

-continued

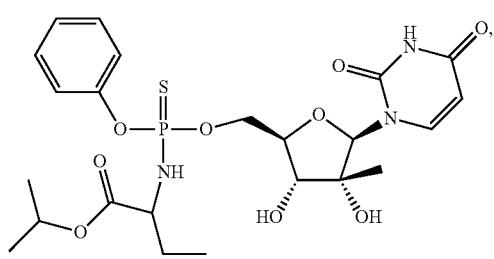

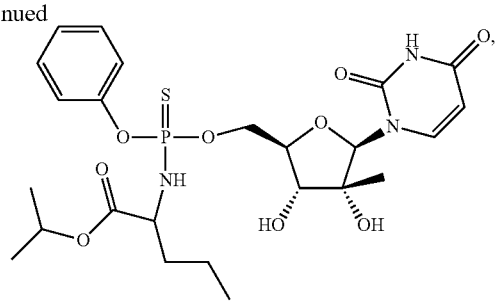

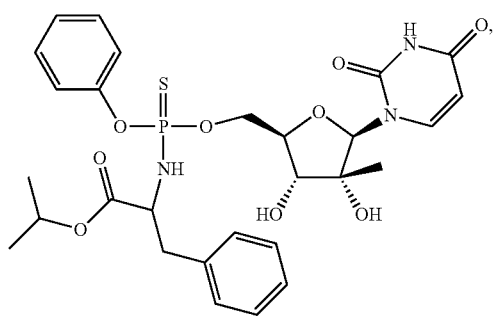

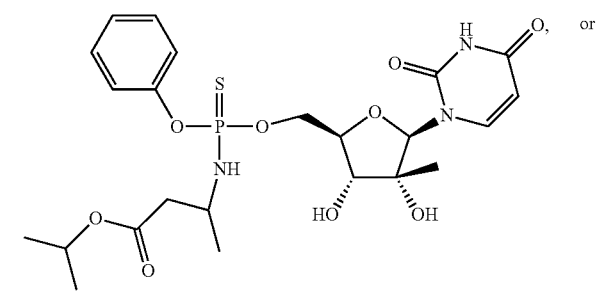

a pharmaceutically acceptable salt of any of the aforementioned compounds.

27. A method of ameliorating or treating a HCV viral infection comprising administering to a subject suffering from HCV an effective amount of a compound of claim 1, or a pharmaceutically acceptable salt thereof, in combination with one or more agents selected from the group consisting of an interferon, ribavirin, a HCV protease inhibitor, a HCV polymerase inhibitor and a NS5A inhibitor, or a pharmaceutically acceptable salt any of the aforementioned compounds.

28. The method of claim 27, wherein the one or more agents are selected from the group consisting of:

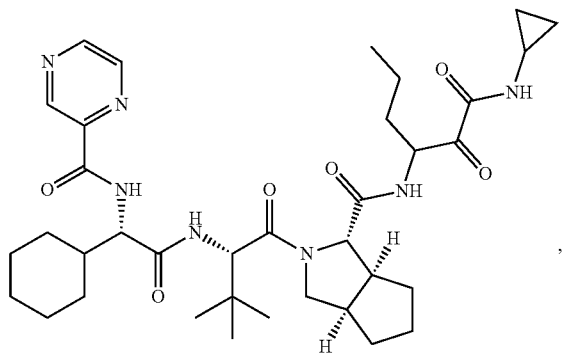

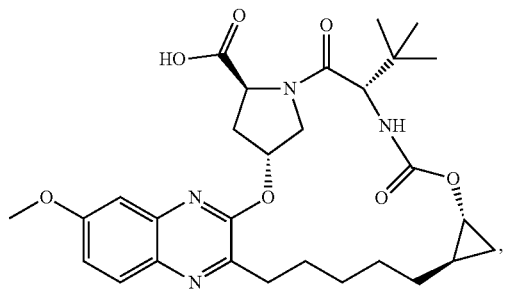

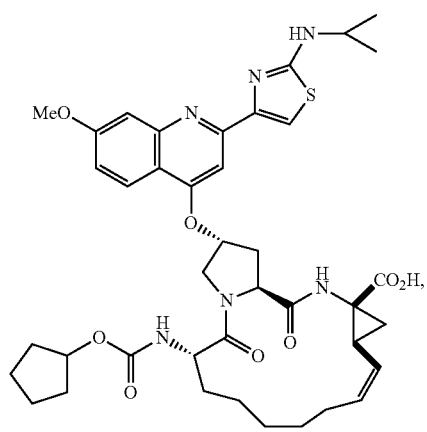

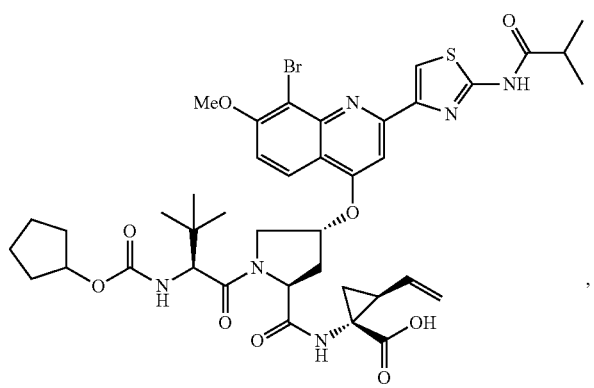

-continued
157
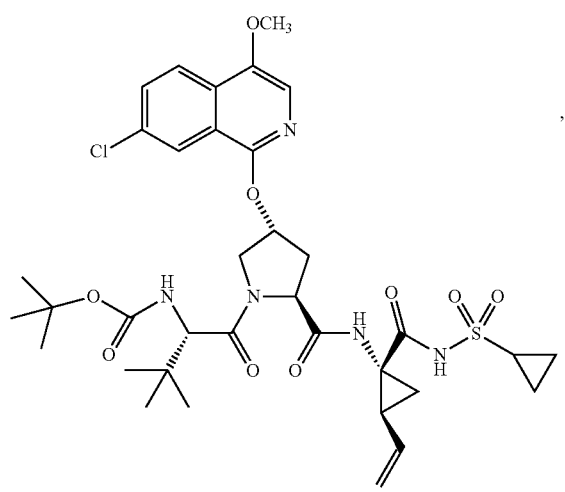
158
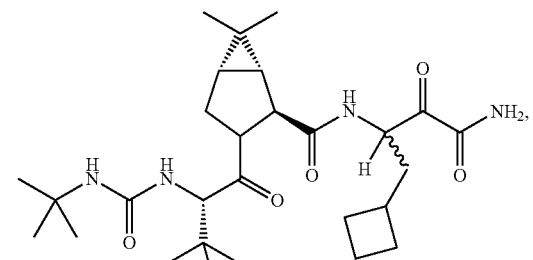,
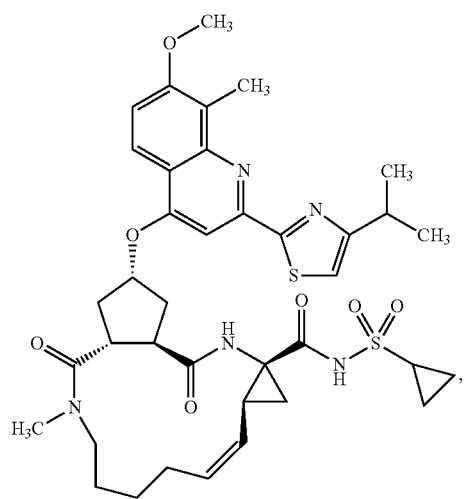,
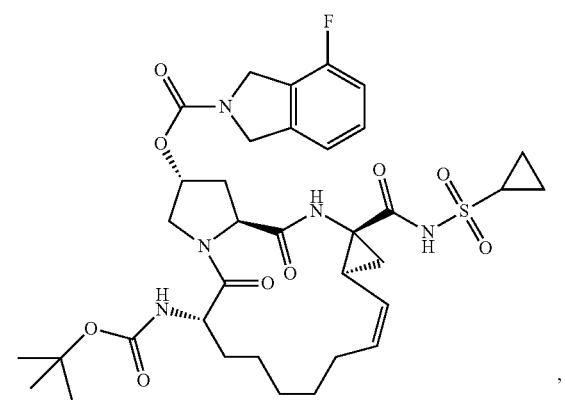,
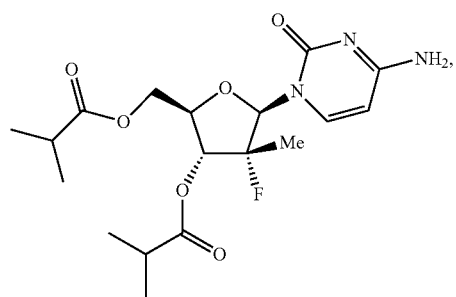,
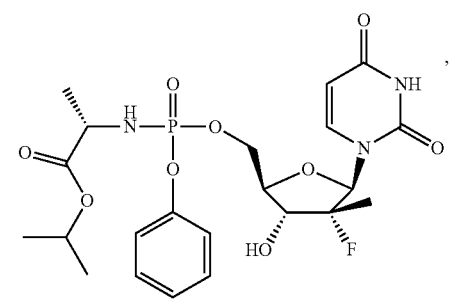,
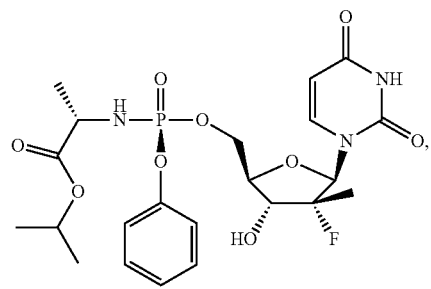,
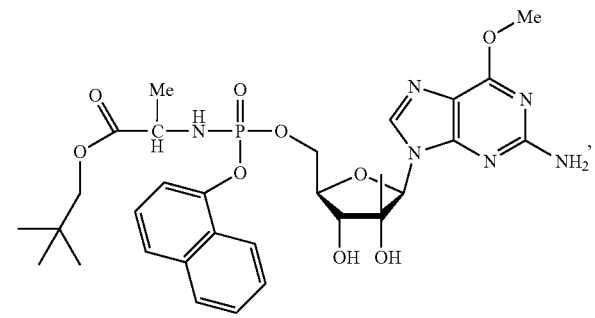,

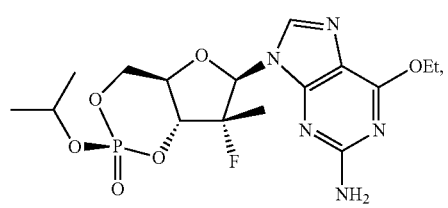
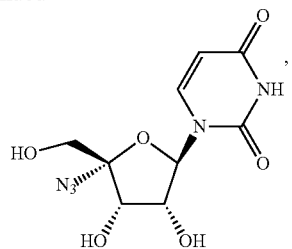
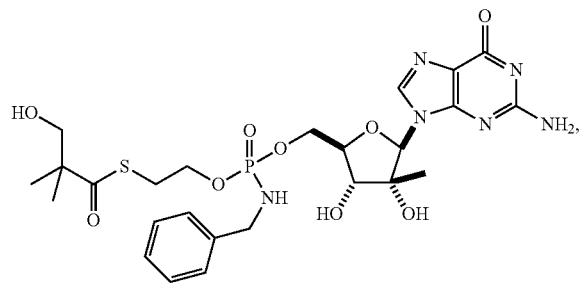
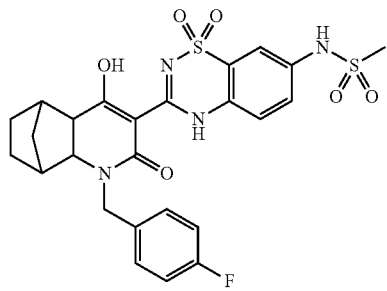
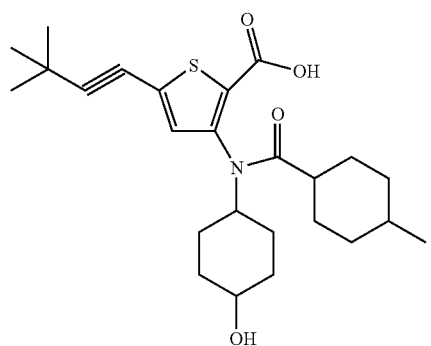
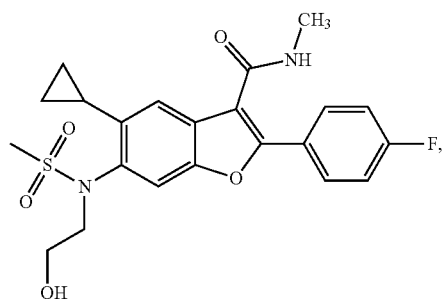
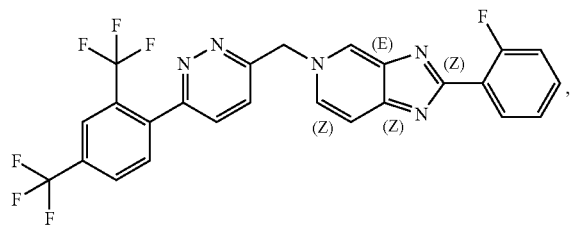
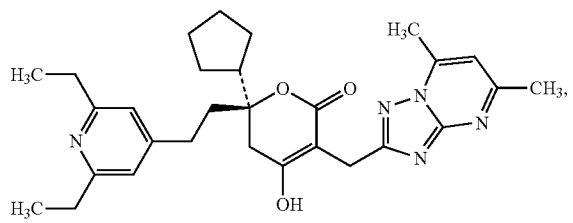
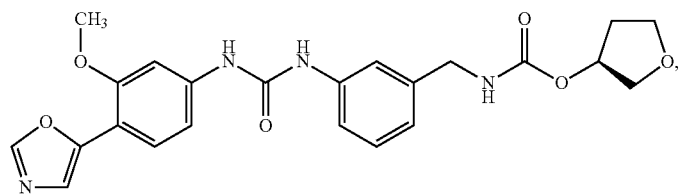
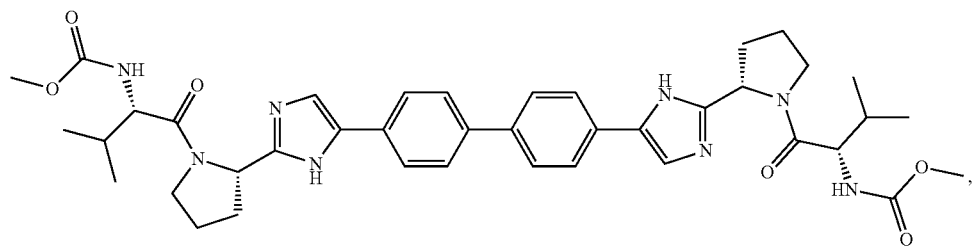

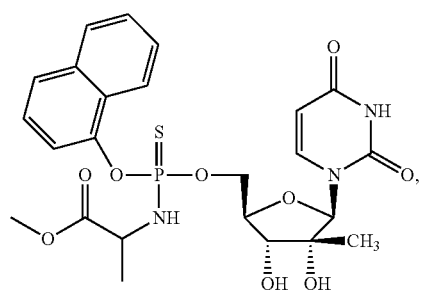
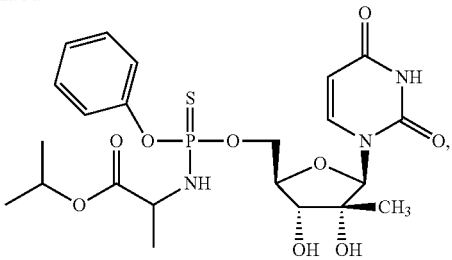
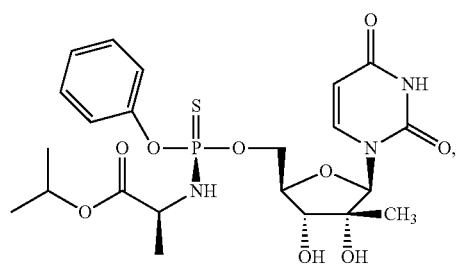
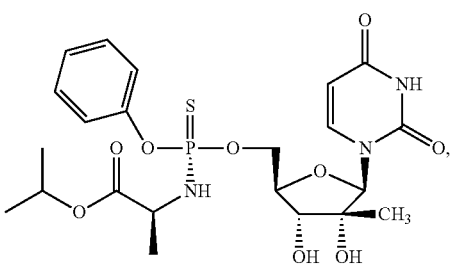
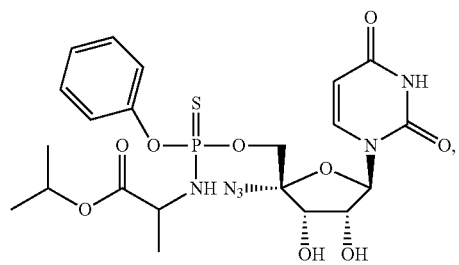
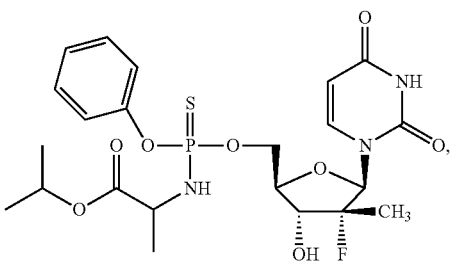
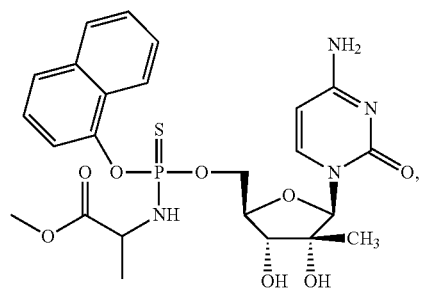
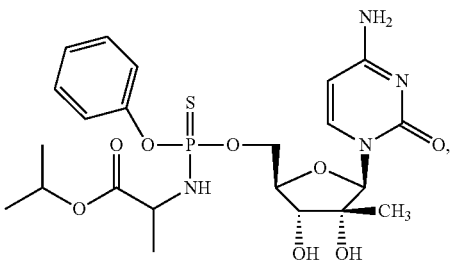
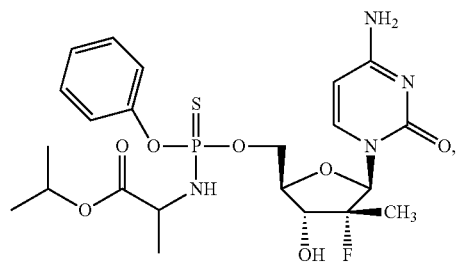
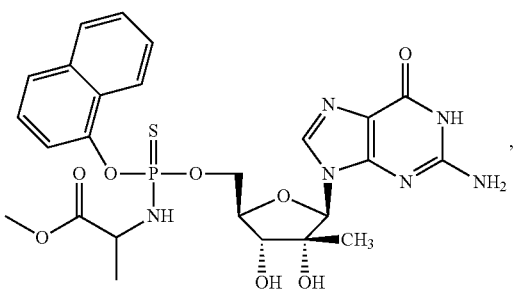
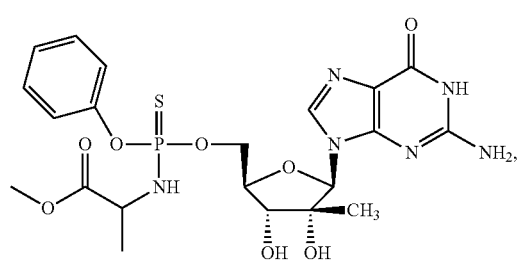
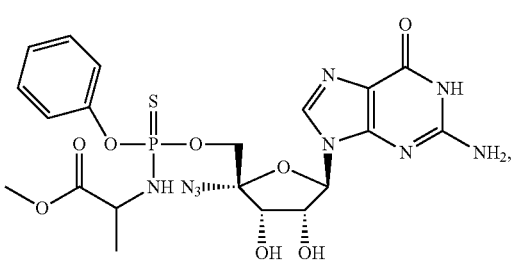

163
-continued
164
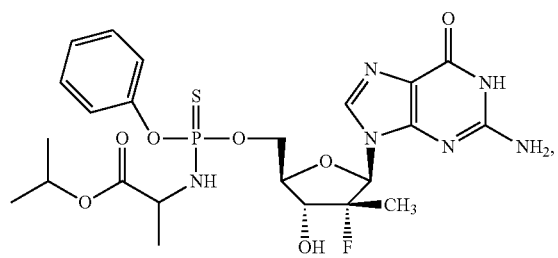
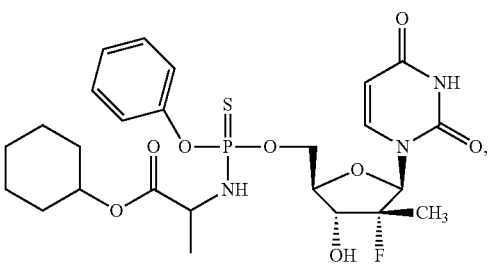
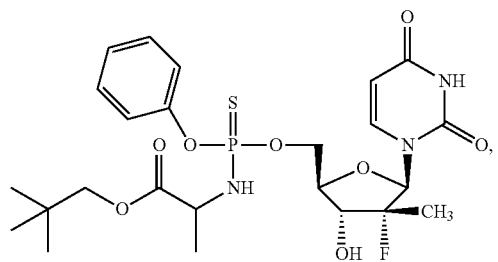
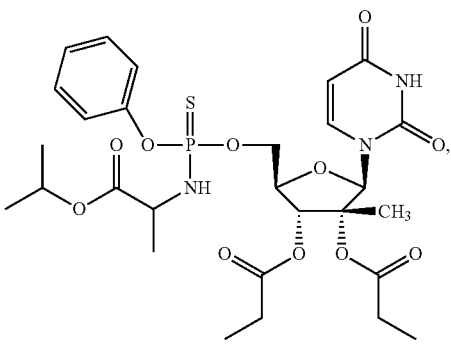
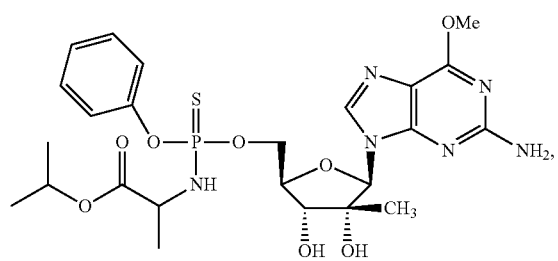
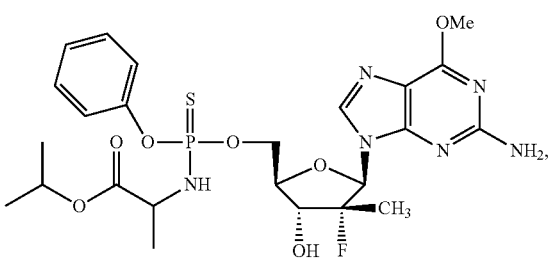
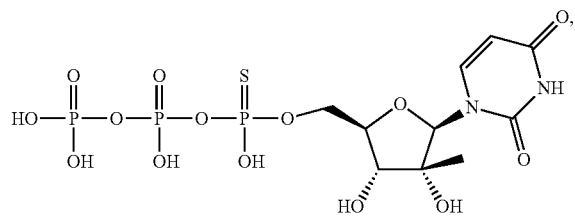
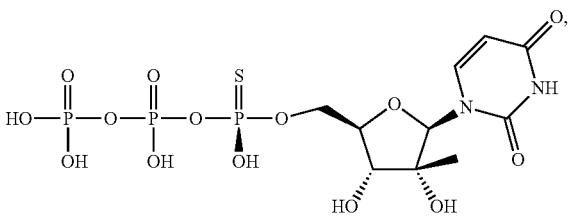
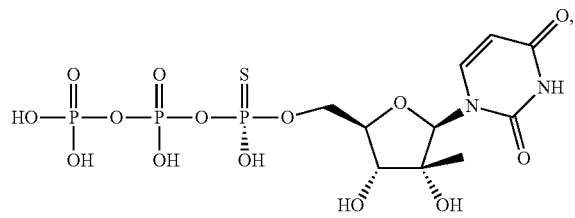
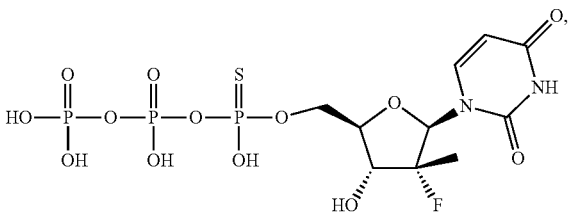
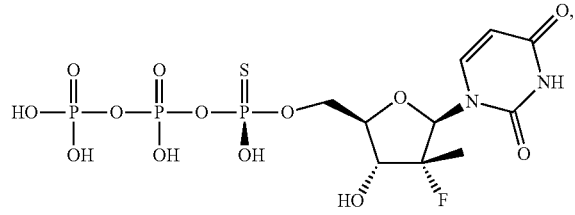
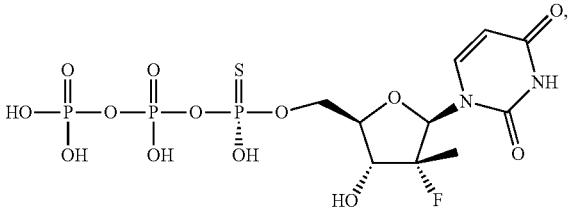
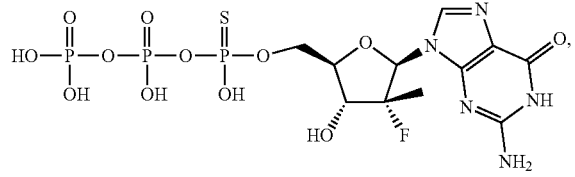
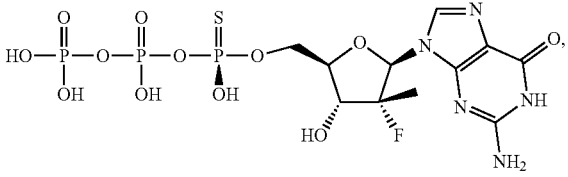

-continued
165
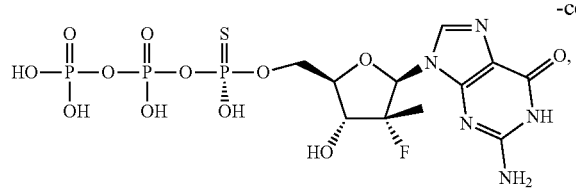
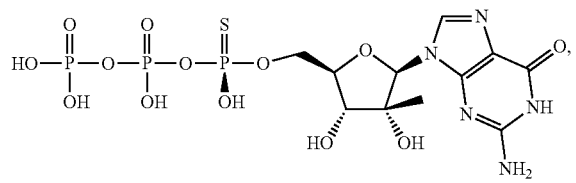
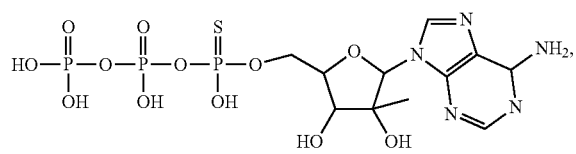
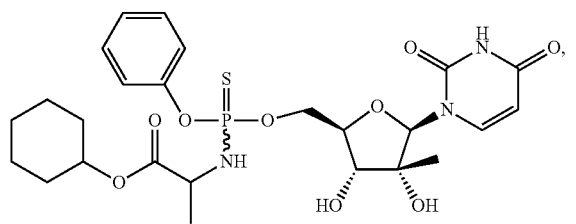
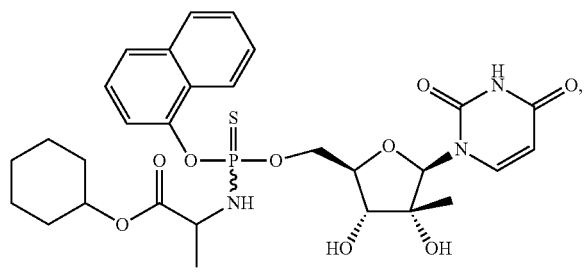
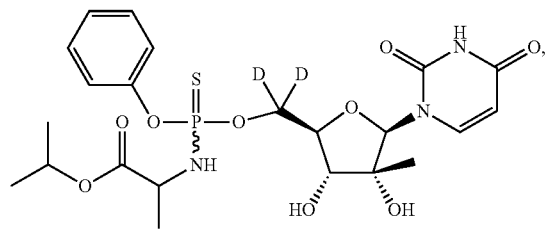
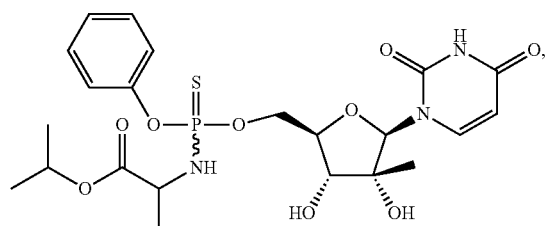
166
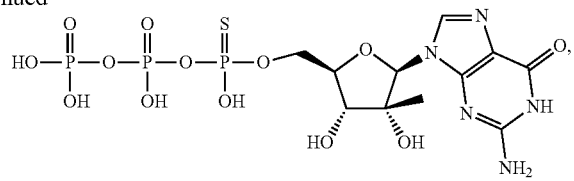
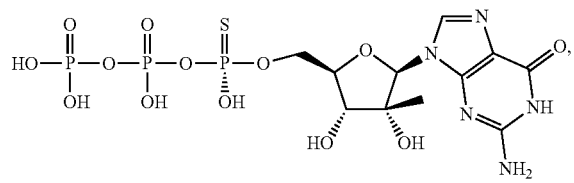
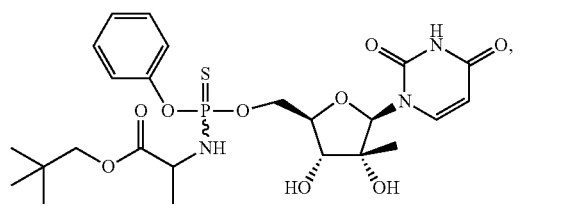
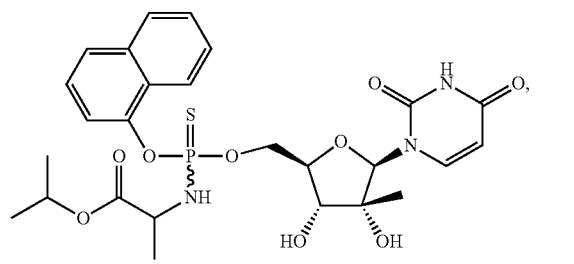
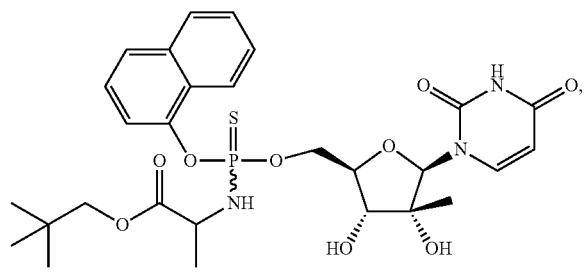
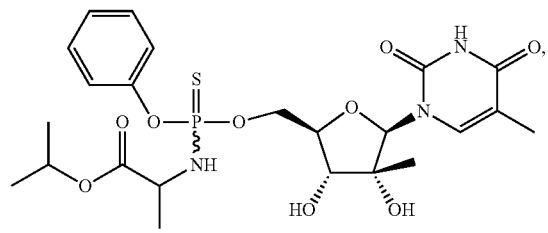
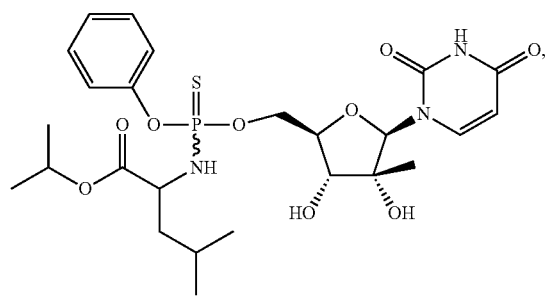

167                                    168
-continued
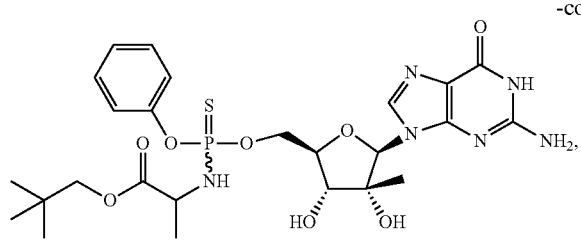 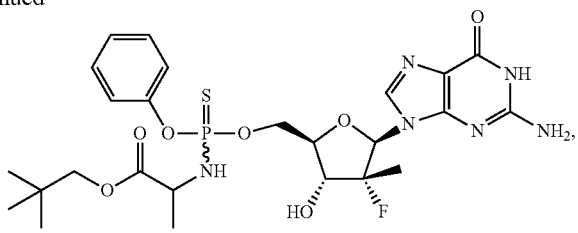
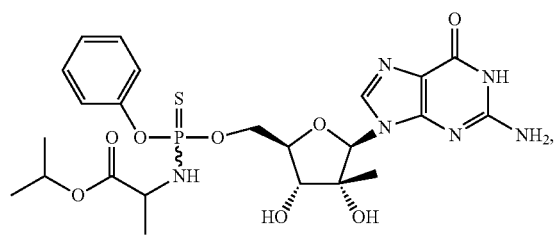 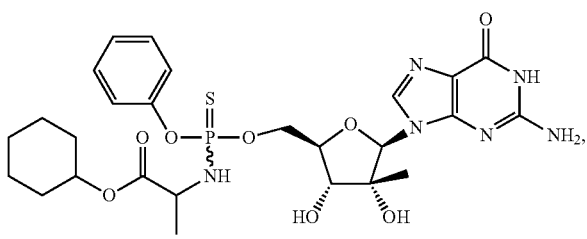
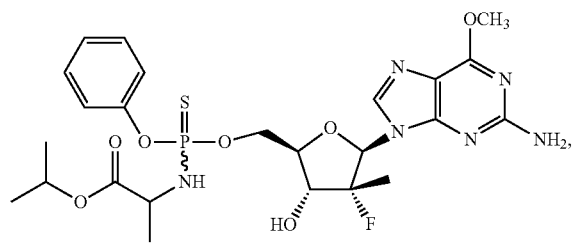 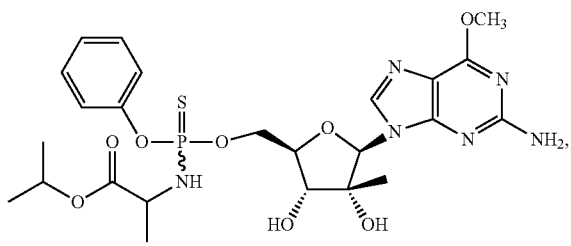
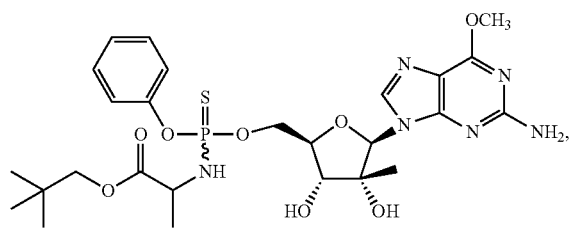 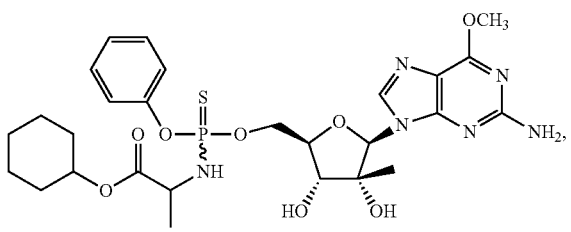
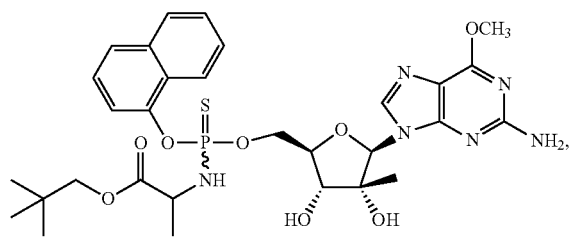 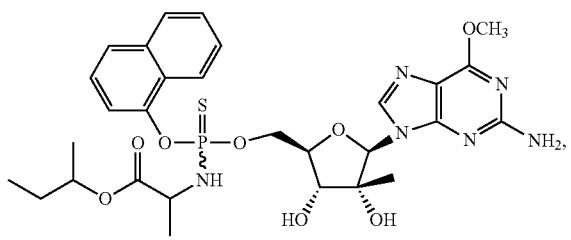
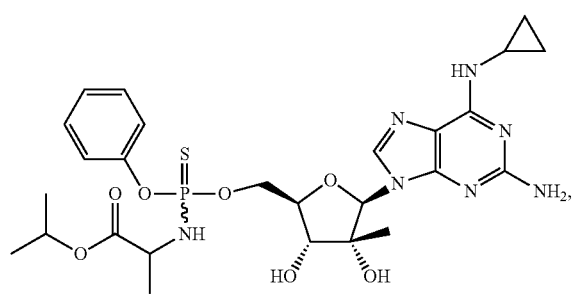 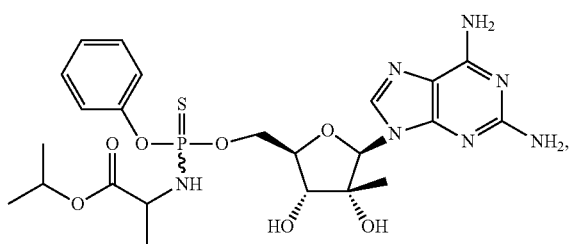

169 170
-continued
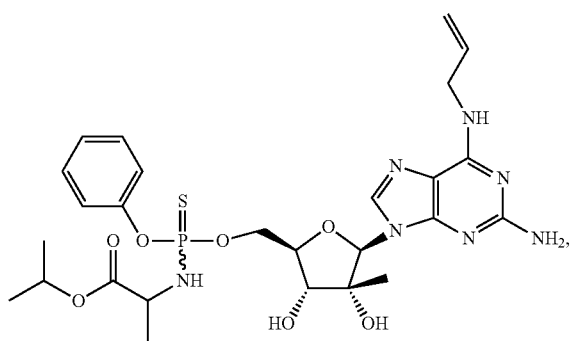 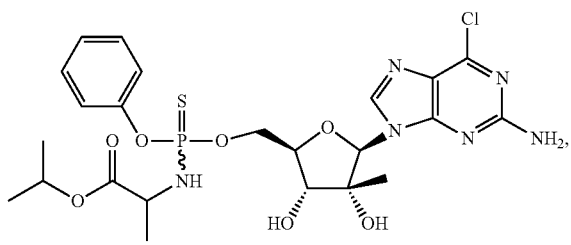
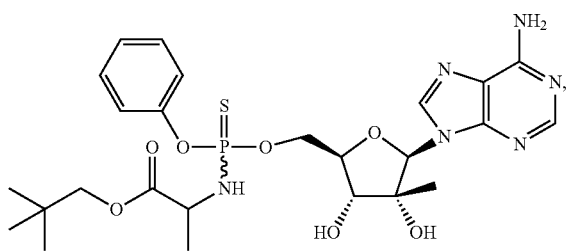 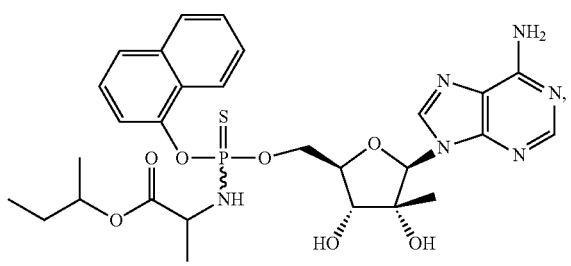
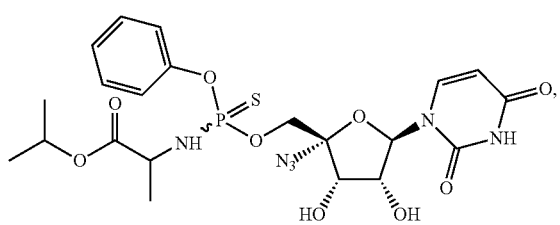 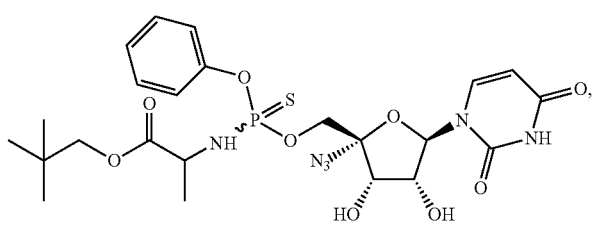
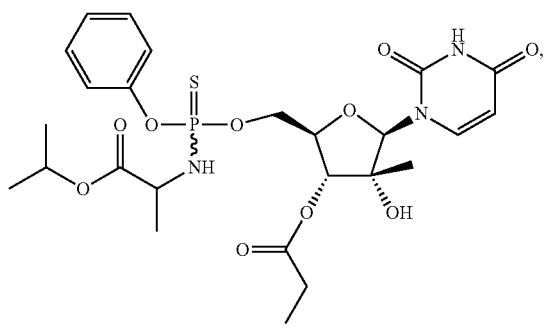 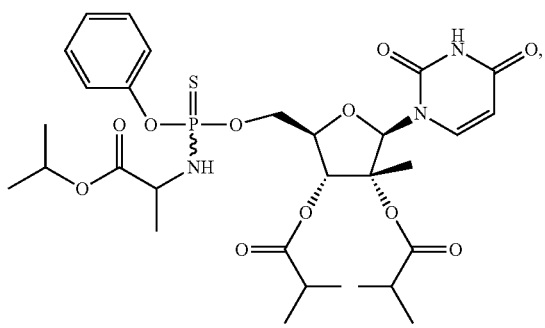
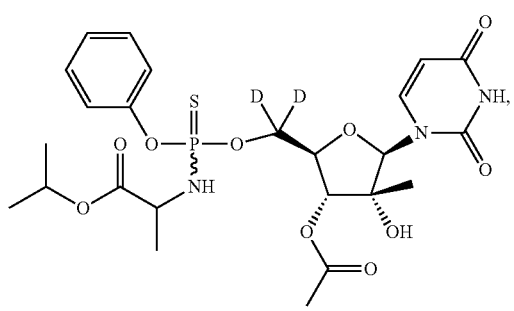 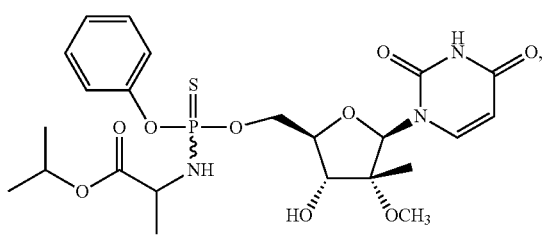

171
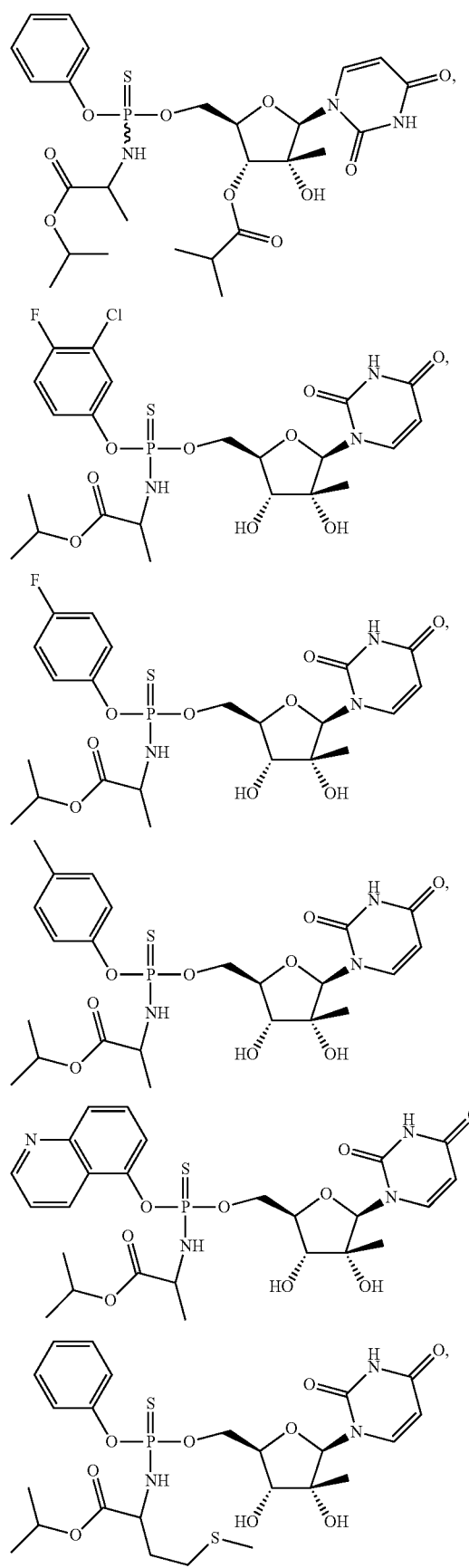
-continued
172
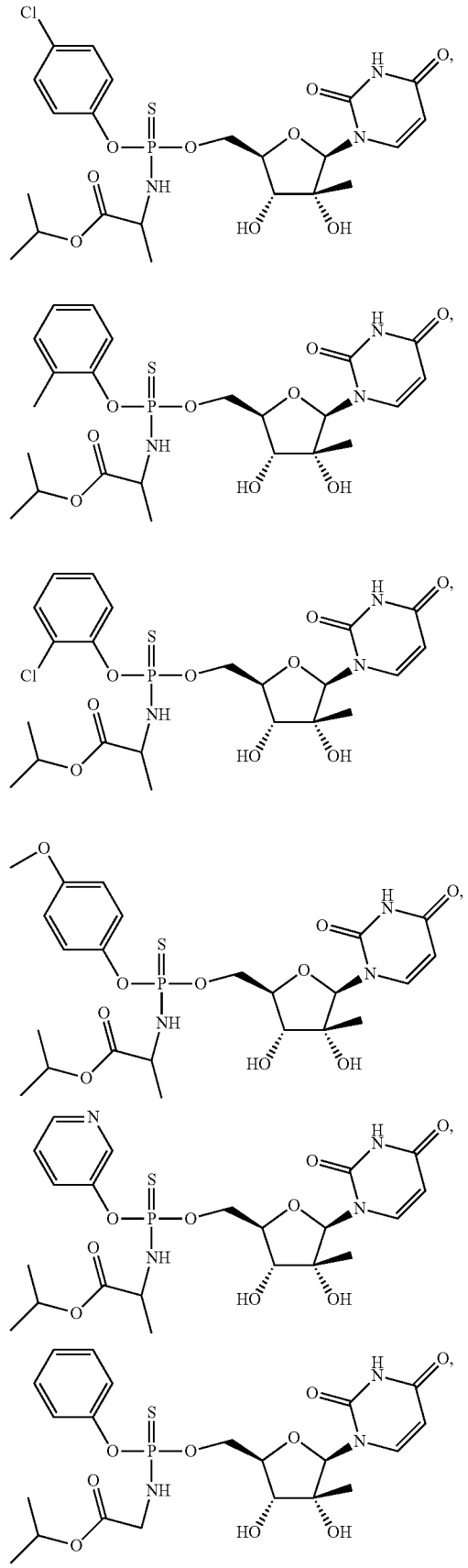

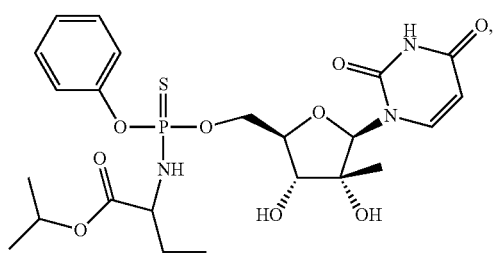

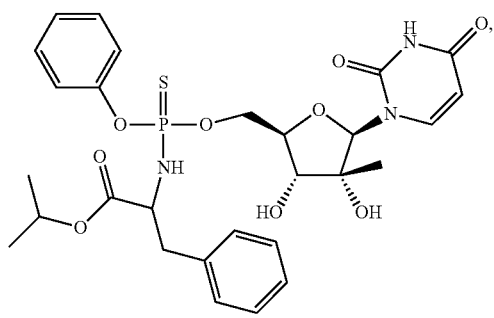

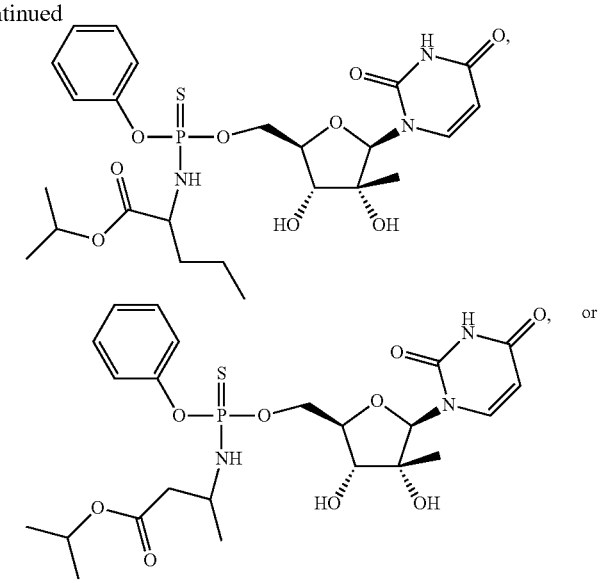

a pharmaceutically acceptable salt of any of the aforementioned compounds.

29. The compound of claim 2, wherein $Z^1$ is S.
30. The compound of claim 13, wherein $R^6$ is —OH.
31. The compound of claim 15, wherein $R^7$ is methyl.
32. The compound of claim 1, wherein $R^6$ is halogen.
33. The compound of claim 1, wherein $B^1$ is

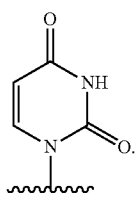 [SMILES: *n1ccc(=O)[nH]c1=O]

34. The compound of claim 33, wherein $Z^1$ is O.
35. The compound of claim 34, wherein $R^6$ is —OH.
36. The compound of claim 35, wherein $R^7$ is methyl.
37. The compound of claim 1, wherein $B^1$ is

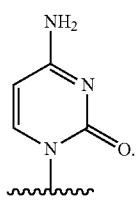 [SMILES: *n1ccc(N)nc1=O]

38. The compound of claim 37, wherein $Z^1$ is O.
39. The compound of claim 38, wherein $R^6$ is —OH.
40. The compound of claim 39, wherein $R^7$ is methyl.

41. The compound of claim 1, wherein $B^1$ is

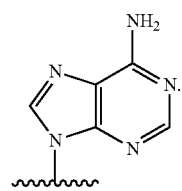

42. The compound of claim 1, wherein $B^1$ is

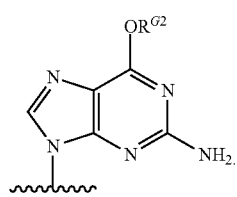

43. The compound of claim 1, wherein the compound is

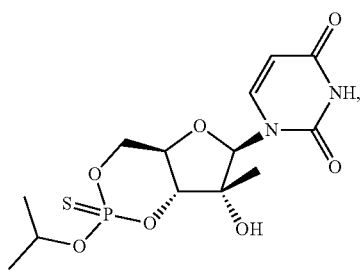

or a pharmaceutically acceptable salt thereof.

* * * * *